(12) United States Patent
Aicher et al.

(10) Patent No.: US 7,713,979 B2
(45) Date of Patent: May 11, 2010

(54) CYCLOALKYL LACTAM DERIVATIVES AS INHIBITORS OF 11-BETA-HYDROXYSTEROID DEHYDROGENASE 1

(75) Inventors: Thomas Daniel Aicher, Superior, CO (US); Mark Joseph Chicarelli, Longmont, CO (US); Ronald Jay Hinklin, Longmont, CO (US); Hongqi Tian, Longmont, CO (US); Owen Brendan Wallace, Zionsville, IN (US); John Gordon Allen, Newbury Park, CA (US); Zhaogen Chen, Shanghai (CN); Thomas Edward Mabry, Indianapolis, IN (US); Jefferson Ray McCowan, Indianapolis, IN (US); Nancy June Snyder, Lizton, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 52 days.

(21) Appl. No.: 11/718,111

(22) PCT Filed: Oct. 26, 2005

(86) PCT No.: PCT/US2005/038369

§ 371 (c)(1),
(2), (4) Date: Apr. 27, 2007

(87) PCT Pub. No.: WO2006/049952

PCT Pub. Date: May 11, 2006

(65) Prior Publication Data

US 2008/0275043 A1    Nov. 6, 2008

Related U.S. Application Data

(60) Provisional application No. 60/623,203, filed on Oct. 29, 2004.

(51) Int. Cl.
 C07D 207/00 (2006.01)
 A61K 31/40 (2006.01)
 A61K 31/497 (2006.01)
 A61K 31/445 (2006.01)
 C07D 211/06 (2006.01)
 C07D 403/00 (2006.01)

(52) U.S. Cl. .................. 514/254.02; 514/326; 514/424; 544/372; 546/226; 548/543

(58) Field of Classification Search ................. 514/424, 514/254.02, 326; 548/543; 546/226; 544/372
See application file for complete search history.

(56) References Cited

FOREIGN PATENT DOCUMENTS

| DE | 812 551 | 9/1951 |
|---|---|---|
| WO | WO 02/26706 | 4/2002 |
| WO | WO 2004/033427 | 4/2004 |
| WO | WO 2004/056744 | 7/2004 |
| WO | WO 2005/108361 | 11/2005 |

OTHER PUBLICATIONS

Konno et al., Electrolytic Partial Fluorination of Organic Compounds 6.1 Highly Regioselective Electrochemical Monofluorination of Aliphatic Nitrogen-Containing Heterocycles, *Tetrahedron Letters*, 1992, pp. 7017-7020, vol. 33, No. 46.

*Primary Examiner*—Golam M. M. Shameem
*Assistant Examiner*—Sun Jae Y Loewe
(74) *Attorney, Agent, or Firm*—Dan L. Wood

(57) ABSTRACT

The present invention discloses compounds of Formula I: (I) having 11beta-HSD type 1 antagonist activity, as well as methods for preparing such compounds. In another embodiment, the invention discloses pharmaceutical compositions comprising compounds of Formula I, as well as the use of the Formula I and compositions as medicaments to treat diabetes, hyperglycemia, obesity, hypertension, hyperlipidemia, Syndrome X, and other conditions associated with hyperglycemia.

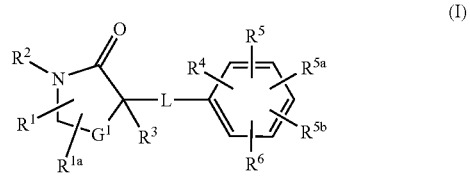

(I)

7 Claims, No Drawings

CYCLOALKYL LACTAM DERIVATIVES AS INHIBITORS OF 11-BETA-HYDROXYSTEROID DEHYDROGENASE 1

This application claims the benefit of U.S. Provisional Patent Application No. 60/623,203, filed Oct. 29, 2004.

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison- with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver, and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin reisistance, resulting in hyperglycemia.

Insulin resistance is primarily due to a receptor signaling defect that is not yet completely understood. Resistance to insulin results in insufficient activation of glucose uptake, diminished oxidation of glucose and storage of glycogen in muscle, inadequate insulin repression of lipolysis in adipose tissue, and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance but have not developed Type 2 diabetes are also at risk of developing "Syndrome X" or "metabolic syndrome". Syndrome X or metabolic syndrome is a condition characterized by insulin resistance, along with abdominal obesisty, hyper insulinemia, high blood pressure, low HDL and High VLDL. These patients, whether or not they develop overt diabetes mellitus, are at increased risk of developing the cardiovascular complications listed above.

Evidence in rodents and humans links 11-beta hydroxysteroid dehydrogenase 1 ("11-β-HSD1") to metabolic syndrome. Evidence suggests that a drug which specifically inhibits 11-β-HSD1 in type 2 obese diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secreation from the beta cells of the islet may also be increased.

There is a continuing need for new methods of treating diabetes and related conditions, such as metabolic syndrome. It is an object of this invention to meet this and other needs.

SUMMARY OF THE INVENTION

The present invention provides a compound structurally represented by formula (I):

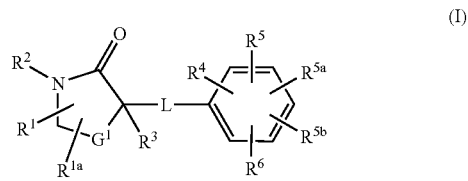

or a pharmaceutically acceptable salt thereof, wherein $G^1$ is methylene or ethylene;

L is a divalent linking group selected from $C_1$-$C_4$ alkylene, —S—, —CH(OH)—, and —O—;

$R^1$ is hydrogen, hydroxy, —($C_1$-$C_4$)alkyl (optionally substituted with one to three halogens), —($C_1$-$C_6$)alkoxy (optionally substituted with one to three halogens), or —$CH_2OR^7$, wherein $R^7$ is hydrogen or —($C_1$-$C_4$)alkyl (optionally substituted with one to three halogens);

$R^{1a}$ is hydrogen or —$CH_3$ (optionally substituted with one to three halogens);

$R^2$ is

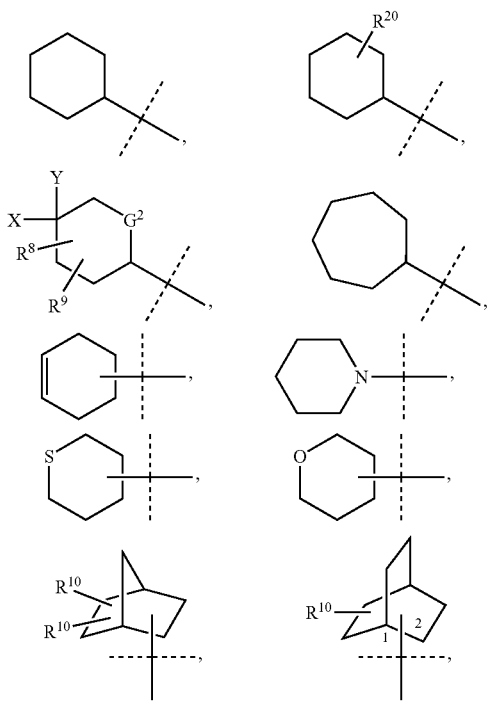

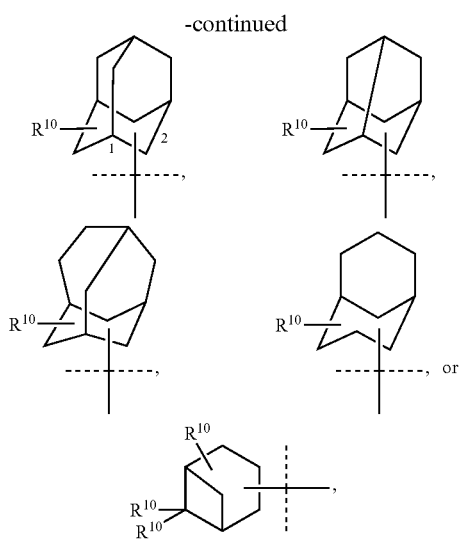

-continued wherein the dashed line represents the point of attachment to the $R^2$ positon in formula I; wherein X is hydrogen, hydroxy, —O—$CH_3$, —$CH_2OH$, or —O—C(O)-phenyl-$NO_2$; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, —($C_1$-$C_4$)alkyl; $R^9$ is independently hydrogen, hydroxy, —($C_1$-$C_4$)alkyl, or phenyl; $R^{10}$ is independently at each occurrence hydrogen, hydroxy, or —($C_1$-$C_4$)alkyl; and $G^2$ is methylene, ethylene, or 1-propylene;

$R^3$ is hydrogen, hydroxyl (provided that when L is —S— or —CH(OH)— then $R^3$ cannot be hydroxy), or —($C_1$-$C_4$) alkyl (optionally substituted with one to three halogens);

$R^4$ and $R^5$ are each independently
hydrogen, hydroxy, —C(O)OH, —($C_1$-$C_4$)alkyl (optionally substituted with one to three halogens), —($C_1$-$C_6$) alkoxy (optionally substituted with one to three halogens), halogen, cyano, —$CF_3$, —$OCF_3$, —($C_1$-$C_4$) alkyl-C(O)OH, —($C_1$-$C_4$)alkyl-C(O)O($C_1$-$C_4$)alkyl, or —($C_1$-$C_4$)alkyl-OH;

$R^{5a}$ and $R^{5b}$ are independently hydrogen or halogen;

$R^6$ is
hydrogen, hydroxy, —($C_1$-$C_4$)alkyl (optionally substituted with one to three halogens), —($C_1$-$C_6$)alkoxy (optionally substituted with one to three halogens), —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Het^1$, $Ar^2$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$) alkyl-N($R^{13}$)($R^{14}$);

wherein $R^{11}$ and $R^{12}$ are each independently hydrogen or —($C_1$-$C_4$)alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl);

wherein $R^{13}$ and $R^{14}$ are each independently hydrogen or —($C_1$-$C_4$)alkyl (optionally substituted with one to three halogens), or $R^{13}$ and $R^{14}$ taken together with the nitrogen to which they are attached form piperidinyl, pyrrolidinyl, or piperazinyl;

provided that when L is —O— or —S—, then $R^6$ is not hydrogen;

$Ar^1$ is phenyl or naphthyl;

$Ar^2$ is $Ar^1$ optionally and independently substituted one to three times with
halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$) ($R^{16}$), —O—($C_1$-$C_4$)alkyl-N($R^{15}$)($R^{16}$), —O—($C_1$-$C_4$) alkyl-C(O)O—($C_1$-$C_4$)alkyl, —O—($C_1$-$C_4$ alkyl)-piperidinyl, imidazolyl, pyridinyl, or —($C_1$-$C_4$)alkyl-imidazolyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently
imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl, indolyl, isoindolyl, indolinyl, benzofuranyl, benzothiophenyl, quinolinyl, isoquinolinyl, quinoxalinyl, quinazolinyl, or phthalazinyl;

$Het^2$ is $Het^1$ optionally and independently substituted one to three times with
halogen, hydroxy, —($C_1$-$C_6$)alkoxy (optionally substituted with one to three halogens), —C(O)OH, —$NH_2$, cyano, —$CF_3$, —($C_1$-$C_4$)alkyl (optionally substituted with one to three halogens), —($C_1$-$C_4$)alkyl-C(O)OH, —O($C_1$-$C_4$)alkyl-C(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$) ($R^{18}$), imidazolyl, pyridinyl, or —($C_1$-$C_4$)alkyl-imidazolyl;

wherein $R^{17}$ and $R^{18}$ are each independently hydrogen or —($C_1$-$C_4$)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —($C_1$-$C_4$)alkyl (optionally substituted with one to three halogens); and $R^{20}$ is hydroxy, —($C_1$-$C_4$)alkyl (optionally substituted with one to three halogens), —$CH_2OH$, or phenyl.

The present invention provides compounds of formula I that are useful as potent and selective inhibition of 11-beta hydroxysteroid dehydrogenase 1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

Due to their inhibition of 11-beta hydroxysteroid dehydrogenase 1, the present compounds are useful in the treatment of a wide range of conditions and disorders in which inhibition of 11-beta hydroxysteroid dehydrogenase 1 is beneficial. These disorders and conditions are defined herein as "diabetic disorders" and "metabolic syndrome disorders". One of skill in the art is able to identify "diabetic disorders" and "metabolic syndrome disorders" by the involvement of 11-beta hydroxysteroid dehydrogenase 1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrythmia, premature death, anti-apoptosis, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

Thus the present invention also provides a method of treatment of a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) osteoporosis, as well as other conditions and disorders where insulin resistance is a component, in a patient in need of such treatment, comprising administering to said patient a a therapeutically effective amount of a compound of formula (I) or a pharmaceutically acceptable salt thereof.

DETAILED DESCRIPTION OF THE INVENTION

General terms used in the description of compounds herein described bear their usual meanings.

As used herein, the term "$C_1$-$C_4$ alkyl" refers to straight-chain or branched-chain saturated aliphatic groups of 1 to 4 carbon atoms including methyl, ethyl, n-propyl, isopropyl, n-butyl, isobutyl, sec-butyl, t-butyl, and the like.

Similarly, the term "$C_1$-$C_6$ alkoxy" represents a $C_1$-$C_6$ alkyl group attached through an oxygen molecule and include moieties such as, for example, methoxy, ethoxy, n-propoxy, isopropoxy, and the like.

The term "$C_1$-$C_4$ alkylene" refers to straight-chain or branched-chain saturated divalent aliphatic groups including moieties such as methylene, ethylene, n-propylene, gemdimethyl methylene, and the like.

The term "($C_2$-$C_6$)alkynyl" means a hydrocarbon chain of two to six carbon atoms of either a straight or branched configuration and having at least one carbon-carbon triple bond, which may occur at any point along the chain. Example of alkynyl is acetylene.

The term "($C_3$-$C_8$)cycloalkyl" refers to a saturated or partially saturated carbocycle ring of from 3 to 8 carbon atoms, typically 3 to 7 carbon atoms. Examples of ($C_3$-$C_8$)cycloalkyl include but are not limited to cyclopropyl, cyclobutyl, cyclopentyl, cyclohexyl, cycloheptyl, and the like.

The term "halogen" refers to fluoro, chloro, bromo, and iodo.

"$HET^1$" and "$HET^2$" may be attached at any point which affords a stable structure.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

As used herein, the term "patient" refers to a warm-blooded animal or mammal that has or is at risk of developing a disease selected from (1) through (20) described below. It is understood that guinea pigs, dogs, cats, rats, mice, hamsters, and primates, including humans, are examples of patients within the scope of the meaning of the term "patient". Preferred patients include humans. The term "patient" includes and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater-than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ◂■ " refers to a bond that protrudes forward out of the plane of the page.

The designation " ⋯▪▪▪ " refers to a bond that protrudes backward out of the plane of the page.

The designation " ∼∼∼ " refers to a bond wherein the stereochemistry is not defined.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In a preferred embodiment the present invention provides a compound structurally represented by formula (I), or a pharmaceutically acceptable salt thereof, wherein $G^1$ is methylene or ethylene; L is methylene; $R^1$ is hydrogen, or —$CH_3$; $R^{1a}$ is hydrogen;

$R^3$ is —H, or —$CH_3$, $R^2$ is

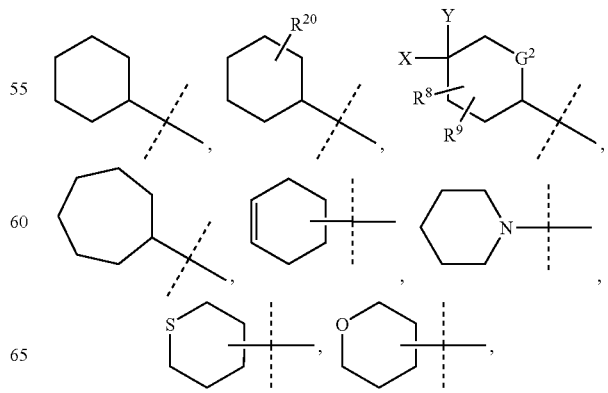

-continued

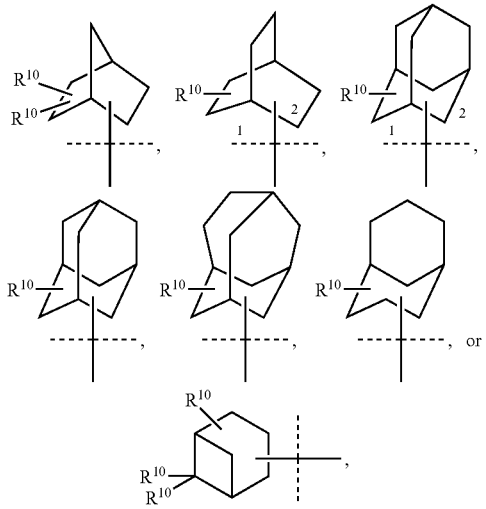

wherein the dashed line represents the point of attachment to the $R^2$ positon in formula I; wherein X is hydrogen, hydroxy, —O—$CH_3$, —$CH_2$OH, or —O—C(O)-phenyl-$NO_2$; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, or —($C_1$-$C_4$)alkyl; $R^9$ is independently hydrogen, hydroxy, —($C_1$-$C_4$)alkyl, or phenyl; $R^{10}$ is independently at each occurrence hydrogen, hydroxy, or —($C_1$-$C_4$)alkyl; and $G^2$ is methylene, ethylene, or 1-propylene;

$R^3$ is hydrogen, hydroxyl (provided that $R^3$ cannot be hydroxy when L is —S— or —CH(OH)—), or —($C_1$-$C_4$)alkyl (optionally substituted with one to three halogens);

$R^4$ and $R^5$ are each independently
hydrogen, hydroxy, —C(O)OH, —($C_1$-$C_4$)alkyl (optionally substituted with one to three halogens), —($C_1$-$C_6$) alkoxy (optionally substituted with one to three halogens), halogen, cyano, —$CF_3$, —$OCF_3$, —($C_1$-$C_4$) alkyl-C(O)OH, —($C_1$-$C_4$)alkyl-C(O)O($C_1$-$C_4$)alkyl, or —($C_1$-$C_4$)alkyl-OH;

$R^{5a}$ and $R^{5b}$ are independently hydrogen or halogen, $R^6$ is
hydrogen, hydroxy, —($C_1$-$C_4$)alkyl (optionally substituted with one to three halogens), —($C_1$-$C_6$)alkoxy (optionally substituted with one to three halogens), —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Het^1$, $Ar^2$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$) alkyl-N($R^{13}$)($R^{14}$);

wherein $R^{11}$ and $R^{12}$ are each independently hydrogen or $C_1$-$C_4$ alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl (optionally substituted with one to three halogens), or $R^{13}$ and $R^{14}$ taken together with the nitrogen to which they are attached form piperidinyl, pyrrolidinyl, or piperazinyl;

$Ar^1$ is phenyl;

$Ar^2$ is $Ar^1$ optionally and independently substituted one to three times with
halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$) ($R^{16}$), —O—($C_1$-$C_4$)alkyl-N($R^{15}$)($R^{16}$), —O—($C_1$-$C_4$) alkyl-C(O)O—($C_1$-$C_4$)alkyl, —O—($C_1$-$C_4$)alkyl-piperidinyl, imidazolyl, pyridinyl, or —($C_1$-$C_4$)alkyl-imidazolyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently
imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl, indolyl, isoindolyl, indolinyl, benzofuranyl, benzothiophenyl, quinolinyl, isoquinolinyl, quinoxalinyl, quinazolinyl, or phthalazinyl;

$Het^2$ is $Het^1$ optionally and independently substituted one to three times with
halogen, hydroxy, —($C_1$-$C_6$)alkoxy (optionally substituted with one to three halogens), —C(O)OH, —$NH_2$, cyano, —$CF_3$, —($C_1$-$C_4$)alkyl (optionally substituted with one to three halogens), —($C_1$-$C_4$)alkyl-C(O)OH, —O($C_1$-$C_4$)alkyl-C(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$) ($R^{18}$), imidazolyl, pyridinyl, or —($C_1$-$C_4$)alkyl-imidazolyl;

wherein $R^{17}$ and $R^{18}$ are each independently hydrogen or —($C_1$-$C_4$)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —($C_1$-$C_4$)alkyl (optionally substituted with one to three halogens); and $R^{20}$ is hydroxy, —($C_1$-$C_4$)alkyl (optionally substituted with one to three halogens), —$CH_2$OH, or phenyl.

In another preferred embodiment the present invention provides a compound structurally represented by formula (I), or a pharmaceutically acceptable salt thereof, wherein $G^1$ is methylene; L is methylene; $R^1$ is hydrogen; $R^{1a}$ is hydrogen; $R^3$ is —H;

$R^2$ is

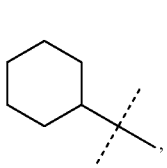 , 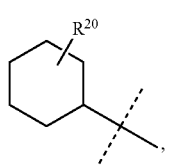 ,

-continued

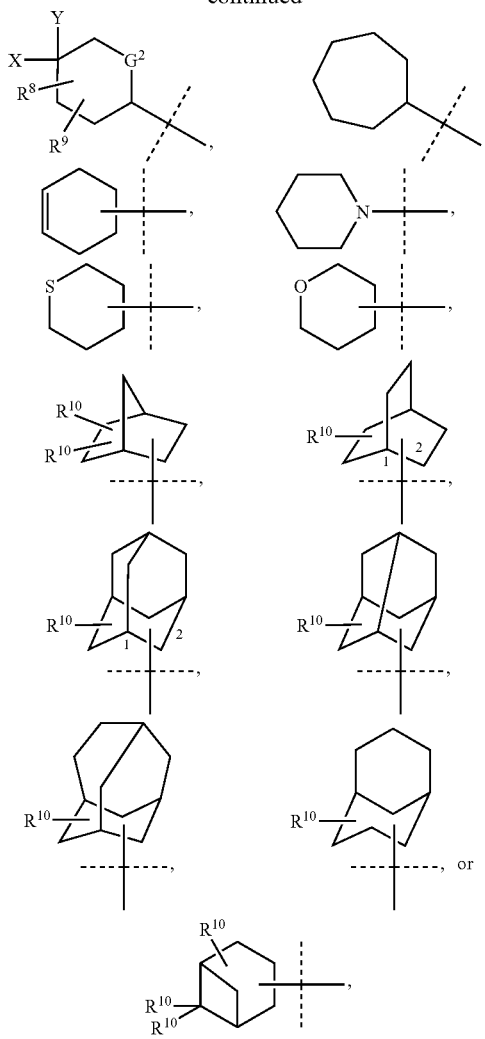

wherein the dashed line represents the point of attachment to the $R^2$ positon in formula I; wherein X is hydrogen, hydroxy, —O—$CH_3$, —$CH_2$OH, or —O—C(O)-phenyl-$NO_2$; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, or —($C_1$-$C_4$)alkyl; $R^9$ is independently hydrogen, hydroxy, —($C_1$-$C_4$)alkyl, or phenyl; $R^{10}$ is independently at each occurrence hydrogen, hydroxy, or —($C_1$-$C_4$)alkyl; and $G^2$ is methylene, ethylene, or 1-propylene;

$R^4$ and $R^5$ are each independently
hydrogen, hydroxy, —C(O)OH, —($C_1$-$C_4$)alkyl (optionally substituted with one to three halogens), —($C_1$-$C_6$) alkoxy (optionally substituted with one to three halogens), halogen, cyano, —$CF_3$, —$OCF_3$, —($C_1$-$C_4$) alkyl-C(O)OH, —($C_1$-$C_4$)alkyl-C(O)O($C_1$-$C_4$)alkyl, or —($C_1$-$C_4$)alkyl-OH;

$R^{5a}$ and $R^{5b}$ are independently hydrogen or halogen, $R^6$ is
hydrogen, hydroxy, —($C_1$-$C_4$)alkyl (optionally substituted with one to three halogens), —($C_1$-$C_6$)alkoxy (optionally substituted with one to three halogens), —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Het^1$, $Ar^2$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$) alkyl-N($R^{13}$)($R^{14}$);
wherein $R^{11}$ and $R^{12}$ are each independently hydrogen or —($C_1$-$C_4$)alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and
wherein $R^{13}$ and $R^{14}$ are each independently hydrogen or —($C_1$-$C_4$)alkyl (optionally substituted with one to three halogens), or $R^{13}$ and $R^{14}$ taken together with the nitrogen to which they are attached form piperidinyl, pyrrolidinyl, or piperazinyl;

$Ar^1$ is phenyl;

$Ar^2$ is $Ar^1$ optionally and independently substituted one to three times with
halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$), —O—($C_1$-$C_4$) alkyl-C(O)O—($C_1$-$C_4$)alkyl, —O—($C_1$-$C_4$ alkyl)-piperidinyl, imidazolyl, pyridinyl, or —($C_1$-$C_4$)alkyl-imidazolyl;
wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently
imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl, indolyl, isoindolyl, indolinyl, benzofuranyl, benzothiophenyl, quinolinyl, isoquinolinyl, quinoxalinyl, quinazolinyl, or phthalazinyl;

$Het^2$ is $Het^1$ optionally and independently substituted one to three times with
halogen, hydroxy, —($C_1$-$C_6$)alkoxy (optionally substituted with one to three halogens), —C(O)OH, —$NH_2$, cyano, —$CF_3$, —($C_1$-$C_4$)alkyl (optionally substituted with one to three halogens), —($C_1$-$C_4$)alkyl-C(O)OH, —O($C_1$-$C_4$)alkyl-C(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$)($R^{18}$), imidazolyl, pyridinyl, or —($C_1$-$C_4$)alkyl-imidazolyl;
wherein $R^{17}$ and $R^{18}$ are each independently hydrogen or —($C_1$-$C_4$)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —($C_1$-$C_4$)alkyl (optionally substituted with one to three halogens); and $R^{20}$ is hydroxy, —($C_1$-$C_4$)alkyl (optionally substituted with one to three halogens), —$CH_2$OH, or phenyl.

In another preferred embodiment the present invention provides a compound structurally represented by formula (I), or a pharmaceutically acceptable salt thereof, wherein $G^1$ is methylene; L is methylene; $R^1$ is hydrogen; $R^{1a}$ is hydrogen; $R^3$ is —H;
$R^2$ is

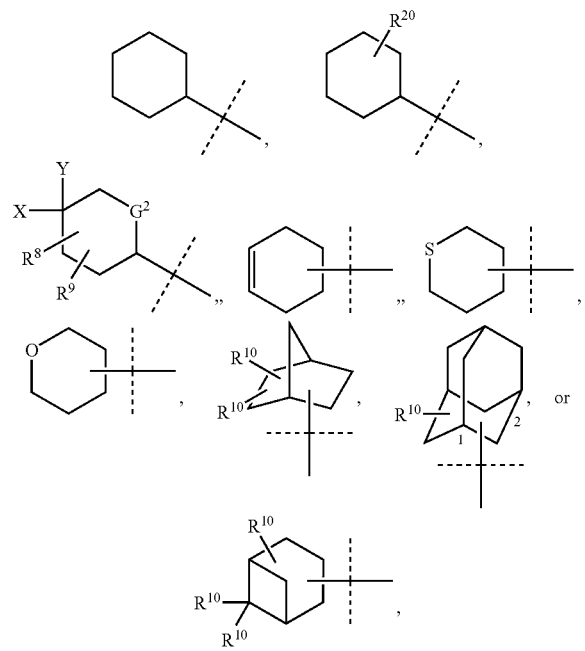

wherein the dashed line represents the point of attachment to the $R^2$ positon in formula I;

wherein X is hydrogen, hydroxy, —O—$CH_3$, or —$CH_2OH$; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, —($C_1$-$C_4$)alkyl; $R^9$ is independently hydrogen, hydroxy, or —($C_1$-$C_4$)alkyl; $R^{10}$ is independently at each occurrence hydrogen, hydroxy, or —($C_1$-$C_4$)alkyl; and $G^2$ is methylene, ethylene, or 1-propylene;

$R^4$ and $R^5$ are each independently
hydrogen, hydroxy, —C(O)OH, —($C_1$-$C_4$)alkyl (optionally substituted with one to three halogens), —($C_1$-$C_6$)alkoxy (optionally substituted with one to three halogens), halogen, cyano, —$CF_3$, —$OCF_3$, —($C_1$-$C_4$)alkyl-C(O)OH, —($C_1$-$C_4$)alkyl-C(O)O($C_1$-$C_4$)alkyl, or —($C_1$-$C_4$)alkyl-OH;

$R^{5a}$ and $R^{5b}$ are hydrogen,
$R^6$ is
hydrogen, hydroxy, —($C_1$-$C_4$)alkyl (optionally substituted with one to three halogens), —($C_1$-$C_6$)alkoxy (optionally substituted with one to three halogens), —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Het^1$, $Ar^2$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkylC(O)N($R^{11}$)($R^{12}$), or —($C_1$-$C_4$)alkyl-N($R^{13}$)($R^{14}$);

wherein $R^{11}$ and $R^{12}$ are each independently hydrogen or —($C_1$-$C_4$)alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl (optionally substituted with one to three halogens), or $R^{13}$ and $R^{14}$ taken together with the nitrogen to which they are attached form piperidinyl, pyrrolidinyl, or piperazinyl;

$Ar^1$ is phenyl;
$Ar^2$ is $Ar^1$ optionally and independently substituted one or two times with
halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$), —O—($C_1$-$C_4$)alkyl-C(O)O—($C_1$-$C_4$)alkyl, —O—($C_1$-$C_4$)alkyl-piperidinyl, imidazolyl, pyridinyl, or —($C_1$-$C_4$)alkyl-imidazolyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently
imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

$Het^2$ is $Het^1$ optionally and independently substituted one or two times with halogen, hydroxy, —($C_1$-$C_6$)alkoxy (optionally substituted with one to three halogens), —C(O)OH, —$NH_2$, cyano, —$CF_3$, —($C_1$-$C_4$)alkyl (optionally substituted with one to three halogens), —($C_1$-$C_4$)alkyl-C(O)OH, —O($C_1$-$C_4$ alkyl)C(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$)($R^{18}$), imidazolyl, pyridinyl, or —($C_1$-$C_4$)alkyl-imidazolyl;

wherein $R^{17}$ and $R^{18}$ are each independently hydrogen or —($C_1$-$C_4$)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —($C_1$-$C_4$)alkyl (optionally substituted with one to three halogens); and $R^{20}$ is hydroxy, —($C_1$-$C_4$)alkyl (optionally substituted with one to three halogens), or —$CH_2OH$.

In another preferred embodiment the present invention provides a compound structurally represented by formula (Ia),

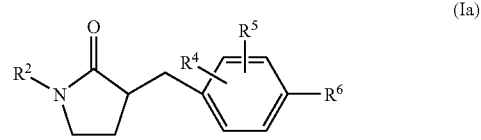

(Ia)

or a pharmaceutically acceptable salt thereof, wherein R² is

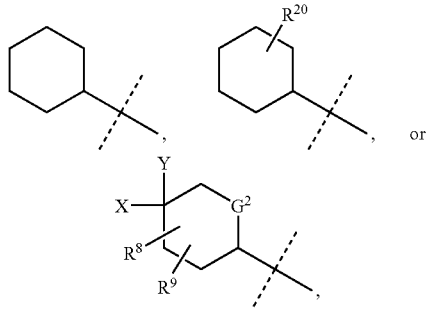

wherein the dashed line represents the point of attachment to the R² positon in formula I; wherein X is hydrogen, hydroxy, —O—CH₃, or —CH₂OH; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, or —(C₁-C₄)alkyl; $R^9$ is independently hydrogen, hydroxy, or —(C₁-C₄)alkyl; $R^{10}$ is independently at each occurrence hydrogen, hydroxy, or —(C₁-C₄)alkyl; and G² is methylene;

$R^4$ and $R^5$ are each independently hydrogen, halogen, or hydroxy;

$R^{5a}$ and $R^{5b}$ are hydrogen, $R^6$ is hydroxy, —(C₁-C₄)alkyl (optionally substituted with one to three halogens), —(C₁-C₆)alkoxy (optionally substituted with one to three halogens), —O—(C₂-C₆)alkynyl, halogen, cyano, —NH₂, —CF₃, —SCF₃, —C(O)O (C₁-C₄)alkyl, —(C₃-C₈)cycloalkyl, —O—SO₂—(C₁-C₄)alkyl, —O—SO₂—CF₃, —O-phenyl, —O—(C₁-C₄)alkyl-phenyl, —O-phenyl-C(O)O—(C₁-C₄)alkyl, —O—(C₁-C₄)alkyl-phenyl-C(O)O—(C₁-C₄)alkyl, —NH-phenyl, —CH₂-phenyl, —O—(C₁-C₄)alkyl-pyridinyl, $Ar^1$, $Het^1$, $Ar^2$, $Het^2$, —C(O)(C₁-C₄)alkyl, —C(O)—$Ar^2$, —C(O)-$Het^2$, —NHSO₂—(C₁-C₄)alkyl, —NHSO₂-phenyl($R^{19}$)($R^{19}$), —(C₁-C₄)alkylC(O)N ($R^{11}$)($R^{12}$), or —(C₁-C₄)alkyl-N($R^{13}$)($R^{14}$);

wherein $R^{11}$ and $R^{12}$ are each independently hydrogen or —(C₁-C₄)alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —(C₁-C₄)alkyl); and wherein $R^{13}$ and $R^{14}$ are each independently hydrogen or —(C₁-C₄)alkyl (optionally substituted with one to three halogens), or $R^{13}$ and $R^{14}$ taken together with the nitrogen to which they are attached form piperidinyl, pyrrolidinyl, or piperazinyl;

$Ar^1$ is phenyl;

$Ar^2$ is $Ar^1$ optionally and independently substituted one or two times with halogen, hydroxy, —C(O)OH, —(C₁-C₆)alkoxy, cyano, —CF₃, —(C₁-C₄)alkyl, —(C₁-C₄)alkyl-C(O)OH, —O(C₁-C₄)alkyl-C(O)OH, —(C₁-C₄)alkyl-N($R^{15}$) ($R^{16}$), —O—(C₁-C₄)alkyl-N($R^{15}$)($R^{16}$), —O—(C₁-C₄) alkyl-C(O)O—(C₁-C₄)alkyl;

wherein $R^{15}$ and $R^{16}$ are each independently hydrogen or —(C₁-C₄)alkyl, or $R^{15}$ and $R^{16}$ taken together with the nitrogen to which they are attached form piperidinyl, pyrrolidinyl, morpholinyl, or imidazolyl;

$Het^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

$Het^2$ is $Het^1$ optionally and independently substituted one or two times with halogen, hydroxy, —(C₁-C₆)alkoxy (optionally substituted with one to three halogens), —C(O)OH, —NH₂, cyano, —CF₃, —(C₁-C₄)alkyl (optionally substituted with one to three halogens), —(C₁-C₄)alkyl-C(O)OH, —O(C₁-C₄)alkylC(O)OH, —C(O)O—(C₁-C₄)alkyl, —(C₁-C₄)alkyl-N($R^{17}$)($R^{18}$), —O(C₁-C₄)alkyl-N($R^{17}$) ($R^{18}$);

wherein $R^{17}$ and $R^{18}$ are each independently hydrogen or —(C₁-C₄)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —(C₁-C₄)alkyl (optionally substituted with one to three halogens); and $R^{20}$ is hydroxy, —(C₁-C₄)alkyl (optionally substituted with one to three halogens), or —CH₂OH.

The following listings set out several groups of preferred compounds. Embodiments of the present invention include compounds of Formula I, or the the narrower embodiments described above, or a pharmaceutically acceptable salt thereof, wherein the variables therein indicated are further specified by the following preferences.

$G^1$ is preferably ethylene. $G^1$ is preferably methylene. Preferably $G^1$ is methylene and L is C₁-C₄ alkylene. Preferably $G^1$ is methylene and L is methylene. Preferably $G^1$ is methylene and L is —S—, and wherein when L is —S— then $R^6$ is not hydrogen. Preferably $G^1$ is methylene and L is —CH(OH)—, or —O— and wherein when L is —O— then $R^6$ is not hydrogen. Preferably $G^1$ is ethylene and L is C₁-C₄ alkylene. Preferably $G^1$ is ethylene and L is methylene. Preferably $G^1$ is ethylene and L is —S—. Preferably $G^1$ is ethylene and L is —CH(OH)—, or —O—.

Preferably $R^1$ is at the 4 or 5 position. Preferably $R^1$ is hydrogen, —(C₁-C₄)alkyl, or —CH₂O—(C₁-C₄)alkyl. Preferably $R^1$ is hydrogen or —CH₃. Preferably $R^1$ is hydrogen.

Preferably $R^3$ is hydrogen or —(C₁-C₄)alkyl. Preferably $R^3$ is —H or —CH₃.

Preferably $R^3$ is —H.

Preferably $R^2$ is

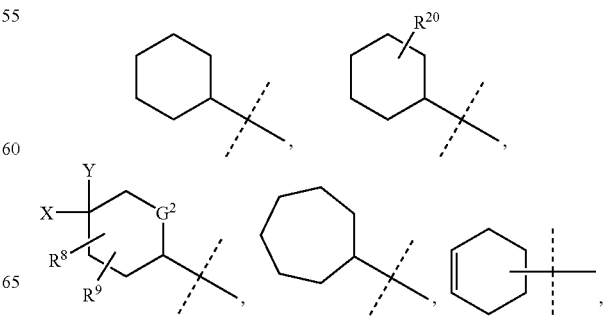

-continued

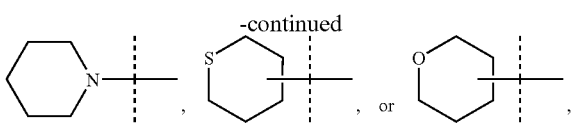

wherein the dashed line represents the point of attachment to the $R^2$ positon in formula I; wherein X is hydrogen, hydroxy, —O—$CH_3$, or —$CH_2OH$; wherein Y is hydrogen or methyl, provided that at least one of X and Y is not hydrogen; and wherein optionally X and Y together with the carbon to which they are attached form carbonyl; and wherein $R^8$ is independently hydrogen, hydroxy, or —($C_1$-$C_4$)alkyl; and wherein $R^9$ is independently hydrogen, hydroxy, —($C_1$-$C_4$)alkyl, or phenyl.

Preferably $R^2$ is

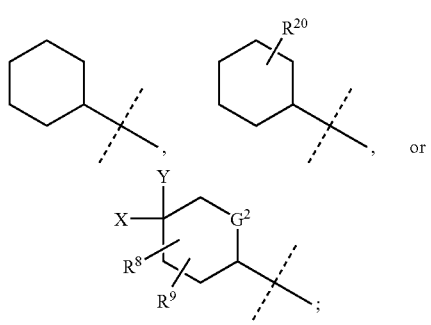

wherein the dashed line represents the point of attachment to the $R^2$ positon in formula I; wherein X is —OH —$CH_3$, —$CH_2OH$, or —$OCH_3$; Y is hydrogen or methyl; wherein optionally X and Y together with the carbon to which they are attached form carbonyl; $R^8$ is hydrogen; $R^9$ is independently hydrogen or —$CH_3$; $R^{10}$ is independently at each occurrence hydrogen, hydroxy, or —($C_1$-$C_4$)alkyl; $G^2$ is methylene; and wherein $R^{20}$ is hydroxyl, —$CH_2OH$ or —$CH_3$.

Preferably $R^2$ is

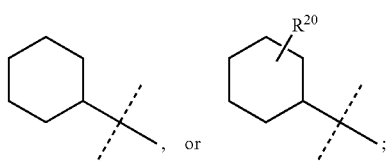

wherein the dashed line represents the point of attachment to the $R^2$ positon in formula I; and wherein $R^{20}$ is hydroxyl, —$CH_2OH$ or —$CH_3$.

Preferably $R^2$ is

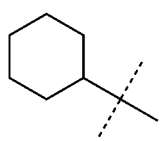

wherein the dashed line represents the point of attachment to the $R^2$ positon in formula I.

Preferably $R^2$ is

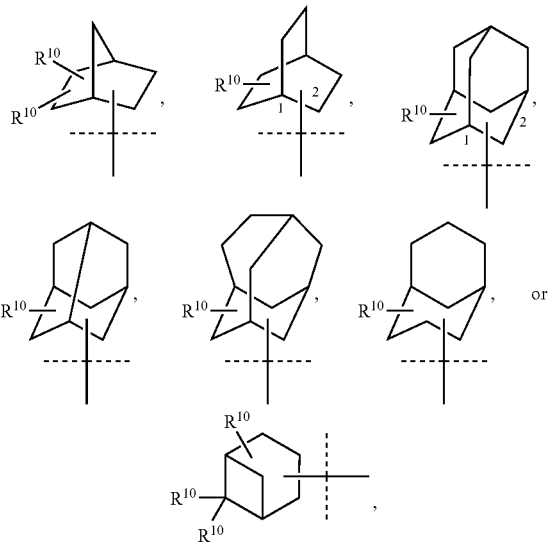

wherein the dashed line represents the point of attachment to the $R^2$ positon in formula I; $R^{10}$ is independently at each occurrence hydrogen, hydroxy, or —($C_1$-$C_4$)alkyl.

Preferably $R^2$ is

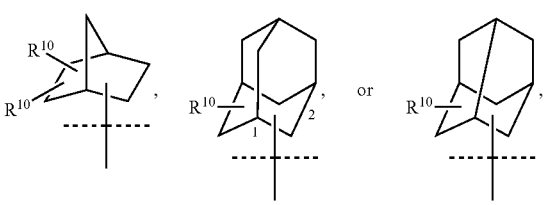

wherein the dashed line represents the point of attachment to the $R^2$ positon in formula I; and wherein $R^{10}$ is independently at each occurrence hydrogen, hydroxy, or —$CH_3$.

Preferably $R^3$ is hydrogen or —$CH_3$. Preferably $R^3$ is hydrogen.

Preferably $R^4$ and $R^5$ are each independently hydrogen, halogen, hydroxy, —$CH_3$, —$OCH_3$, cyano, —$CF_3$, or —$OCF_3$. Preferably $R^4$ and $R^5$ are each independently hydrogen, or halogen. Preferably $R^4$ and $R^5$ are hydrogen. Preferably $R^{5a}$ and $R^{5b}$ are hydrogen.

Preferably $R^6$ is attached at the 4 position.

Preferably $R^6$ is hydroxy, —($C_1$-$C_4$)alkyl, —($C_1$-$C_6$)alkoxy, —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Ar^2$, $Het^1$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$)alkyl-N($R^{13}$)($R^{14}$);

wherein $R^{11}$ and $R^{12}$ are each independently hydrogen or —($C_1$-$C_4$)alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl, or $R^{13}$ and $R^{14}$ taken together with the nitrogen to which they are attached form piperidinyl, pyrrolidinyl, or piperazinyl;

Preferably $Ar^1$ is phenyl;

Preferably $Ar^2$ is $Ar^1$ optionally and independently substituted one or times with halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$)($R^{16}$), —O—($C_1$-$C_4$)alkyl-N($R^{14}$)($R^{16}$), —O—($C_1$-$C_4$) alkyl-C(O)O—($C_1$-$C_4$)alkyl, —O—($C_1$-$C_4$ alkyl)-piperidinyl, imidazolyl, pyridinyl, or —($C_1$-$C_4$)alkyl-imidazolyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

Preferably $Het^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

Preferably $Het^2$ is $Het^1$ optionally and independently substituted once with halogen, hydroxy, —($C_1$-$C_6$)alkoxy, —C(O)OH, —$NH_2$, cyano, —$CF_3$, —($C_1$-$C_4$)alkyl, —($C_1$-$C_4$)alkyl-C(O)OH, —O($C_1$-$C_4$ alkyl)C(O)OH, —C(O)O—($C_1$-$C_4$) alkyl, —($C_1$-$C_4$)alkyl-N($R^{17}$)($R^{18}$), —O($C_1$-$C_4$)alkyl-N($R^{17}$)($R^{18}$);

wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl.

Preferably $R^6$ is hydroxy, —($C_1$-$C_4$)alkyl, —($C_1$-$C_6$)alkoxy, —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Ar^2$, —C(O)($C_1$-$C_4$) alkyl, —C(O)—$Ar^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$)alkyl-N($R^{13}$)($R^{14}$);

wherein $R^{11}$ and $R^{12}$ are each independently hydrogen or $C_1$-$C_4$ alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl, or $R^{13}$ and $R^{14}$ taken together with the nitrogen to which they are attached form piperidinyl, pyrrolidinyl, or piperazinyl;

Preferably $Ar^1$ is phenyl;

Preferably $Ar^2$ is $Ar^1$ optionally and independently substituted one or times with halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15$})($R^{16}$), —O—($C_1$-$C_4$)alkyl-N($R^{15}$)($R^{16}$), —O—($C_1$-$C_4$) alkyl-C(O)O—($C_1$-$C_4$)alkyl, —O—($C_1$-$C_4$)alkyl-piperidinyl, imidazolyl, pyridinyl, or —($C_1$-$C_4$)alkyl-imidazolyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl.

Preferably $R^6$ is hydroxy, —($C_1$-$C_4$)alkyl, —($C_1$-$C_6$)alkoxy, —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —C(O)($C_1$-$C_4$)alkyl, —$NHSO_2$—($C_1$-$C_4$)alkyl, —($C_1$-$C_4$)alkylC(O)N($R^{11}$)($R^{12}$), or —($C_1$-$C_4$)alkyl-N($R^{13}$)($R^{14}$);

wherein $R^{11}$ and $R^{12}$ are each independently hydrogen or $C_1$-$C_4$ alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl, or $R^{13}$ and $R^{14}$ taken together with the nitrogen to which they are attached form piperidinyl, pyrrolidinyl, or piperazinyl;

Preferably $R^6$ is attached at the 4 position and is hydroxy, —($C_1$-$C_4$)alkyl, —($C_1$-$C_6$)alkoxy, —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$ alkyl)-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Ar^2$, $Het^1$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl($R^{19}$)($R^{19}$), —($C_1$-$C_4$)alkyl-C(O)N($R^{11}$)($R^{12}$), or —($C_1$-$C_4$)alkyl-N($R^{13}$)($R^{14}$);

wherein $R^{11}$ and $R^{12}$ are each independently hydrogen or $C_1$-$C_4$ alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl, or $R^{13}$ and $R^{14}$ taken together with the nitrogen to which they are attached form piperidinyl, pyrrolidinyl, or piperazinyl;

$Ar^1$ is phenyl;

$Ar^2$ is $Ar^1$ optionally and independently substituted one or times with halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$), —O—($C_1$-$C_4$)alkyl-C(O)O—($C_1$-$C_4$)alkyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

Het² is Het¹ optionally and independently substituted once with halogen, hydroxy, —($C_1$-$C_6$)alkoxy, —C(O)OH, —$NH_2$, cyano, —$CF_3$, —($C_1$-$C_4$)alkyl, —($C_1$-$C_4$)alkyl-C(O)OH, —O($C_1$-$C_4$ alkyl)C(O)OH, —C(O)O—($C_1$-$C_4$)alkyl, —($C_1$-$C_4$)alkyl-N($R^{17}$)($R^{18}$), —O($C_1$-$C_4$) alkyl-N($R^{17}$)($R^{18}$);

wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl.

Preferably $R^{19}$ is hydrogen, halogen, or —$CH_3$.

In another preferred embodiment the invention provides a compound structurally represented by formula I, or a pharmaceutically acceptable salt thereof, wherein; $G^1$ is methylene or ethylene; L is —$CH_2$—, —S—, —$CH_2CH_2$—, —$CH_2CH_2CH_2$, —CH(OH)—, —C($CH_3$)$_2$—, or —CH ($CH_3$)—; $R^1$ is —H, —$CH_3$, or —$CH_2OCH_3$; $R^2$ is Cyclohexyl (optionally substituted once with —OH, —$CH_2OH$, —$OCH_3$, or optionally substituted once or twice with —$CH_3$, or wherein optionally an oxygen atom combines with the carbon at the 4 position to form carbonyl), Adamantanyl (optionally substituted once with —OH), Piperidinyl, Cycloheptyl, Cyclohexenyl, tetrahydro-pyran-4-yl, tetrahydro-thiopyran-4-yl, bicyclo[2.2.1]hept-2-yl, or bicyclo[3.1.1]hept-3-yl (optionally substituted once or twice with —$CH_3$); $R^3$ is —H or —$CH_3$; $R^4$ and $R^5$ are each independently hydrogen, —F, —Cl, —Br, —I, hydroxy, or —$CH_3$; $R^{5a}$ and $R^{5b}$ are hydrogen; $R^6$ is —H, —F, —Cl, —Br, —I, —$CH_3$, —$SCF_3$, —OH, —$OCF_3$, —$CF_3$, —$OCH_3$, —CN, —C(O)OH, —$CH_2CH_2CH_2$C(O)-(4-methyl-piperazin-1-yl), benzyl, tert-butyl, nicotinonitrile, nicotinic acid, —$OCH_2$CCH, —$NH_2$, cyclohexyl, —C(O)-phenyl, —C(O)$OCH_3$, —$NHSO_2$-phenyl (wherein the phenyl is optionally substituted by —$CH_3$, —Cl), —NH-phenyl, —$OCH_2$-phenyl, —$OCH_2$-pyridinyl, phenoxy (optionally optionally substituted with —C(O)$OCH_3$), isopropoxy, —$OSO_2CF_3$, —$NSO_2CH_3$, —$NSO_2$-phenyl, phenyl (optionally substituted by one or two moieties independently selected from —F, —COOH, —OH, —$CH_3$, —$OCH_3$, —$OCH_2CH_2$-piperidinyl, —$OCH_2CH_2$N($CH_3$)$_2$, —$OCH_2CH_2CH_2$N($CH_3$)$_2$, —$OCH_2CH_2CH_2$COOH, —$OCH_2$-piperidinyl, —$OCH_2CH_2$-imidazolyl, —$OCH_2CH_2CH_2$-piperidinyl, —$OCH_2CH_2$-morpholinyl, —OC($CH_3$)$_2$COO$CH_2CH_3$, —OC($CH_3$)$_2$COOH, —$OCH_2$COO$CH_2CH_3$, —$OCH_2$COOH, —$OCH_2CH_2$COOH, or —$CH_2CH_2$COOH), pyridinyl (optionally substituted once with Cl, —CN, —C(O)OH, —$NH_2$, Br, —$CH_3$, —$OCH_3$, or —OH,), pyrazinyl, pyrimidinyl, 1,3-dihydro-benzoimidazol-2-one, pyrrolidinyl (optionally substituted once with with —OH), piperidinyl, piperazinyl (optionally substituted once with with —$CH_3$), morpholinyl, pyrazolyl (optionally substituted once —$CH_3$), —$CH_2$-pyrrolidinyl, or thiophenyl (optionally substituted once with —C(O)$OCH_3$ or —C(O)OH);

provided that when L is —O— or —S— then $R^6$ is not hydrogen.

Further, preferred embodiments of the invention are compounds represented by the following formulae, and pharmaceutically acceptable salts thereof:

3-(2,4-dichloro-benzyl)-1-(2-hydroxy-cyclohexyl)-pyrrolidin-2-one;
3-(2,4-Dichloro-benzyl)-1-(2,6,6-trimethyl-bicyclo[3.1.1] hept-3-yl)-pyrrolidin-2-one;
3-(4-Bromo-2-chloro-benzyl)-1-(4-hydroxy-cyclohexyl)-pyrrolidin-2-one;
1-(4-hydroxy-cyclohexyl)-3-(2,4,6-trichloro-benzyl)-pyrrolidin-2-one;
3-(2,6-Dichloro-benzyl)-1-(4-hydroxy-cyclohexyl)-pyrrolidin-2-one;
3-(2,6-Dichloro-4-trifluoromethyl-benzyl)-1-(4-hydroxy-cyclohexyl)-pyrrolidin-2-one;
3-(2-Chloro-6-methoxy-benzyl)-1-(4-hydroxy-cyclohexyl)-pyrrolidin-2-one;
3-(2-Chloro-6-hydroxy-benzyl)-1-(4-hydroxy-cyclohexyl)-pyrrolidin-2-one;
3-(2-Chloro-4-pyridin-3-yl-benzyl)-1-(4-hydroxy-cyclohexyl)-pyrrolidin-2-one;
3-(2-Chloro-4-pyridin-4-yl-benzyl)-1-(4-hydroxy-cyclohexyl)-pyrrolidin-2-one;
3-(3-Chloro-biphenyl-4-ylmethyl)-1-(4-hydroxy-cyclohexyl)-pyrrolidin-2-one;
3-(2,4-Dichloro-benzyl)-1-(4-hydroxy-cyclohexyl)-pyrrolidin-2-one;
4-nitro-benzoic acid 4-[3-(2,4-dichloro-benzyl)-2-oxo-pyrrolidin-1-yl]-cyclohexyl ester;
3-(2,4-Dichloro-benzyl)-1-(4-hydroxy-cyclohexyl)-pyrrolidin-2-one;
3-(2-Chloro-6-fluoro-benzyl)-1-cyclohexyl-pyrrolidin-2-one;
3-(2-Chloro-6-fluoro-benzyl)-1-(4-hydroxy-cyclohexyl)-pyrrolidin-2-one;
3-(2-Chloro-6-fluoro-benzyl)-1-(4-hydroxy-cyclohexyl)-pyrrolidin-2-one;
3-(2-Chloro-6-fluoro-benzyl)-1-(2-methyl-cyclohexyl)-pyrrolidin-2-one;
3-(2,4-Dichloro-benzyl)-1-(2-methyl-cyclohexyl)-pyrrolidin-2-one;
1-(2-Methyl-cyclohexyl)-3-(4-trifluoromethyl-benzyl)-pyrrolidin-2-one;
3-Biphenyl-4-ylmethyl-1-(2-methyl-cyclohexyl)-pyrrolidin-2-one;
3-(4-Bromo-2-chloro-benzyl)-1-(2-methyl-cyclohexyl)-pyrrolidin-2-one;
3-(2-Chloro-4-pyridin-3-yl-benzyl)-1-(2-methyl-cyclohexyl)-pyrrolidin-2-one;
3-(2-Chloro-6-fluoro-benzyl)-1-(2-methyl-cyclohexyl)-pyrrolidin-2-one;
3-(2-Chloro-6-fluoro-benzyl)-1-(4-hydroxymethyl-cyclohexyl)-pyrrolidin-2-one;
3-(2,4-Dichloro-benzyl)-1-(4-hydroxymethyl-cyclohexyl)-pyrrolidin-2-one;
3-(2-Chloro-4-pyridin-3-yl-benzyl)-1-(4-hydroxymethyl-cyclohexyl)-pyrrolidin-2-one;
3-(2-Chloro-6-fluoro-benzyl)-1-(4-hydroxymethyl-cyclohexyl)-pyrrolidin-2-one;
3-(2,4-Dichloro-benzyl)-1-(4-hydroxy-4-methyl-cyclohexyl)-pyrrolidin-2-one;
3-(2,4-Dichloro-benzyl)-1-(4-hydroxy-4-methyl-cyclohexyl)-pyrrolidin-2-one;
3-(2,4-Dichloro-benzyl)-1-(4-hydroxy-2-methyl-cyclohexyl)-pyrrolidin-2-one;
3-(2-Chloro-6-fluoro-benzyl)-1-cyclohexyl-pyrrolidin-2-one;
3-(2,4-Dichloro-benzyl)-1-(4-hydroxy-3,5-dimethyl-cyclohexyl)-pyrrolidin-2-one;
3-(4-Dichloro-benzyl)-1-(4-hydroxy-3-methyl-cyclohexyl)-pyrrolidin-2-one;
3-(2,6-Dichloro-4-hydroxybenzyl)-1-(2-methylcyclohexyl) pyrrolidin-2-one;
3-(2,6-Dichloro-4-(pyridin-4-yl)benzyl)-1-(2-methylcyclohexyl)pyrrolidin-2-one;
3-(4-Bromo-2-chlorobenzyl)-1-(4-methoxycyclohexyl)pyrrolidin-2-one;

3-(2,4-Dichlorobenzyl)-1-(4-methoxycyclohexyl)pyrrolidin-2-one;
1-(4-hydroxy-cyclohexyl)-3-(4-trifluoromethyl-benzyl)-pyrrolidin-2-one;
3-[1-(2,4-Dichloro-phenyl)-1-methyl-ethyl]-1-(4-hydroxy-cyclohexyl)-pyrrolidin-2-one;
3-(2,6-Dichloro-4-methoxy-benzyl)-1-(4-hydroxy-cyclohexyl)-pyrrolidin-2-one;
3-(4-chloro-6-fluoro-benzyl)-1-(4-hydroxy-cyclohexyl)-piperidin-2-one;
3-(2-chloro-4-pyridin-3-yl-benzyl)-1-(4-hydroxy-cyclohexyl)-piperidin-2-one;
3-(2-chloro-4-pyridin-3-yl-benzyl)-1-(4-hydroxy-cyclohexyl)-piperidine-2-one;
3-(2-chloro-4-pyridin-4-yl-benzyl)-1-(4-hydroxy-cyclohexyl)-piperidine-2-one;
3-(2,4-Dichloro-benzyl)-1-(4-hydroxy-cyclohexyl)-3-methyl-pyrrolidin-2-one;
3-(2,4-Dichloro-3-methyl-benzyl)-1-(4-hydroxy-cyclohexyl)-3-methyl-pyrrolidin-2-one;
3-(4-Benzyloxy-2,6-dichloro-benzyl)-1-(4-hydroxy-cyclohexyl)-pyrrolidin-2-one;
3-[2,6-Dichloro-4-(pyridin-3-ylmethoxy)-benzyl]-1-(4-hydroxy-cyclohexyl)-pyrrolidin-2-one;
3-(2,6-Dichloro-4-pyridin-3-yl-benzyl)-1-(4-hydroxy-cyclohexyl)-pyrrolidin-2-one;
3-(2,6-Dichloro-4-hydroxy-benzyl)-1-(4-hydroxy-cyclohexyl)-pyrrolidin-2-one;
3-(2,6-Dichloro-4-pyridin-4-yl-benzyl)-1-(4-hydroxy-cyclohexyl)-pyrrolidin-2-one;
3-[2,6-Dichloro-4-(1-methyl-1H-pyrazol-4-yl)-benzyl]-1-(4-hydroxy-cyclohexyl)-pyrrolidin-2-one;
3-(2,6-Dichloro-4-isopropoxy-benzyl)-1-(4-hydroxy-cyclohexyl)-pyrrolidin-2-one; and
3-(4-Dichloro-benzyl)-1-(4-hydroxy-3-methyl-cyclohexyl)-pyrrolidin-2-one.

The present invention relates to a compound or a pharmaceutically acceptable salt thereof represented by formula (I):

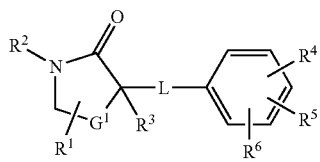
(I)

wherein
G¹ is methylene or ethylene;
L is a divalent linking group selected from $C_1$-$C_4$ alkylene, —S—, —CH(OH)—, —O—, or —NH—;
R¹ is hydrogen, hydroxy, $C_1$-$C_4$ alkyl, $C_1$-$C_4$ alkoxy, or —CH₂OR⁷ wherein R⁷ is hydrogen or $C_1$-$C_4$ alkyl;
R² is a monovalent radical having one of the following formulae

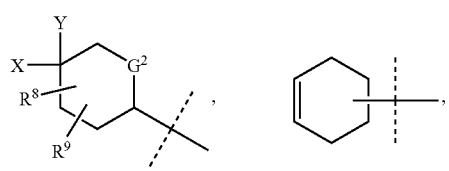

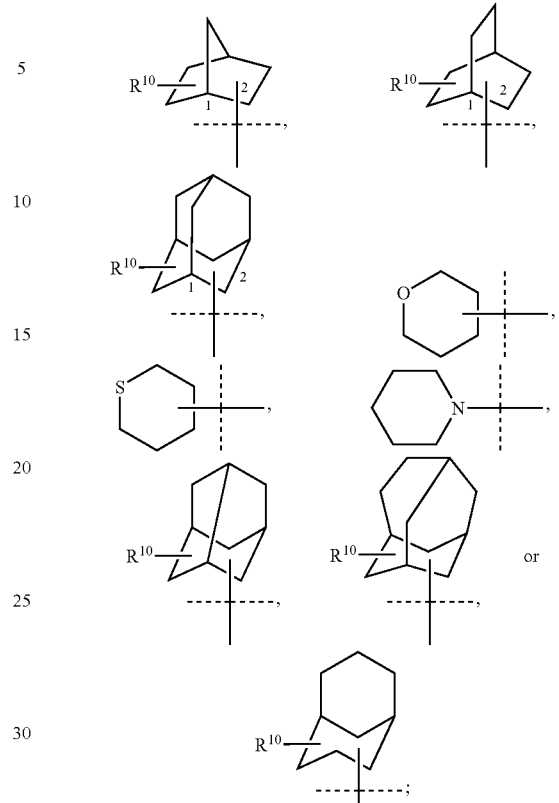

wherein X is hydrogen, hydroxy or —CH₂OH and Y is hydrogen or methyl or X and Y together form (=O) and wherein R⁸ and R⁹ are each independently hydrogen, hydroxy, $C_1$-$C_4$ alkyl or phenyl, and R¹⁰ is hydrogen, hydroxy, or $C_1$-$C_4$ alkyl and G² is methylene, ethylene, or 1-propylene;

R³ is hydrogen, hydroxy, or $C_1$-$C_4$ alkyl;

R⁴ and R⁵ are each independently hydrogen, hydroxy, $C_1$-$C_4$ alkyl, $C_1$-$C_4$ alkoxy, halo, cyano, trifluoromethyl, trifluoromethylsulfanyl, trifluoromethoxy, Ar¹, Het¹, Ar¹—($C_1$-$C_4$ alkyl), Het¹-($C_1$-$C_4$ alkyl), —($C_1$-$C_4$ alkyl)COOH, —($C_1$-$C_4$ alkyl)COO($C_1$-$C_4$ alkyl), —($C_1$-$C_4$ alkyl)OH, or —($C_1$-$C_4$ alkyl)CON(R¹¹)(R¹²); wherein R¹¹ and R¹² are each independently hydrogen or $C_1$-$C_4$ alkyl or R¹¹ and R¹² taken together with the nitrogen to which they are attached form piperidinyl or pyrrolidinyl;

R⁶ is hydrogen, hydroxy, $C_1$-$C_4$ alkyl, $C_1$-$C_4$ alkoxy, halo, cyano, trifluoromethyl, Ar², Het², Ar²—($C_1$-$C_4$ alkyl), Het²-($C_1$-$C_4$ alkyl), —CO($C_1$-$C_4$ alkyl), —CO—Ar², —CO-Het², or —($C_1$-$C_4$ alkyl)N(R¹³)(R¹⁴); wherein R¹³ and R¹⁴ are each independently hydrogen or $C_1$-$C_4$ alkyl or R¹³ and R¹⁴ taken together with the nitrogen to which they are attached form piperidinyl or pyrrolidinyl;

Ar¹ is phenyl or naphthyl;

Ar² is Ar¹ optionally substituted with from one to three moieties selected from halo, hydroxy, cyano, trifluoromethyl, $C_1$-$C_4$ alkyl, —($C_1$-$C_4$ alkyl)COOH, —O($C_1$-$C_4$ alkyl)COOH, —($C_1$-$C_4$ alkyl)N(R¹⁵)(R¹⁶), —O($C_1$-$C_4$ alkyl)N(R¹⁵)(R¹⁶), imidazolyl, pyridyl, or —($C_1$-$C_4$ alkyl)-imidazolyl; wherein R¹⁵ and R¹⁶ are each independently hydrogen or $C_1$-$C_4$ alkyl or R¹⁵ and R¹⁶ taken together with the nitrogen to which they are attached form piperidinyl or pyrrolidinyl;

Het[1] is a heterocyclic radical selected from pyridinyl, piperidinyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, quinolinyl, isoquinolinyl, quinoxalinyl, quinazolinyl, or phthalazinyl; and Het[2] is Het[1] optionally substituted with from one to three moieties selected from halo, hydroxy, cyano, trifluoromethyl, $C_1$-$C_4$ alkyl, —($C_1$-$C_4$ alkyl)COOH, —O($C_1$-$C_4$ alkyl)COOH, —($C_1$-$C_4$ alkyl)N($R^{17}$)($R^{18}$), —O($C_1$-$C_4$ alkyl)N($R^{17}$)($R^{18}$), imidazolyl, pyridyl, or —($C_1$-$C_4$ alkyl)-imidazolyl; wherein $R^{17}$ and $R^{18}$ are each independently hydrogen or $C_1$-$C_4$ alkyl or $R^{17}$ and $R^{18}$ taken together with the nitrogen to which they are attached form piperidinyl or pyrrolidinyl.

Preferred compounds of the invention include compounds or pharmaceutically acceptable salts of formula (I) wherein:

(1) $G^1$ is methylene;
(2) L is methylene;
(3) $R^1$ is hydrogen or methyl;
(4) $R^2$ is cyclohexyl, 6-hydroxycyclohexyl, or 1-adamantyl;
(5) $R^3$ is hydrogen;
(6) $R^4$ and $R^5$ are each independently hydrogen, hydroxy, $C_1$-$C_4$ alkyl, $C_1$-$C_4$ alkoxy, halo, cyano, or trifluoromethyl;
(7) $R^6$ is hydrogen, hydroxy, $C_1$-$C_4$ alkyl, $C_1$-$C_4$ alkoxy, halo, cyano, or trifluoromethyl.

Further, any combination of the above groups, e.g., (1) and (2); (3) and (5); (3), (4), (5), (6), and (7); and (1), (2), (3), (4), (5), (6), (7), are specifically contemplated.

Preferred compounds of the invention also include compounds or pharmaceutically acceptable salts of formula (II):

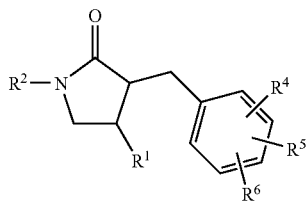

(II)

wherein $R^1$ is hydrogen or methyl;

$R^2$ is a monovalent radical having one of the following formulae

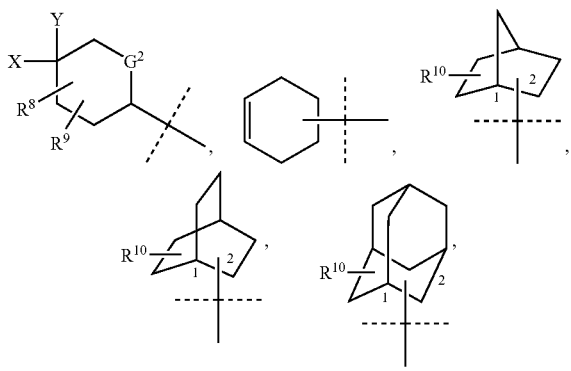

wherein X is hydrogen, hydroxy or —$CH_2OH$ and Y is hydrogen or methyl or X and Y together form (=O) and wherein $R^8$ and $R^9$ are each independently hydrogen, hydroxy, $C_1$-$C_4$ alkyl or phenyl, and $R^{10}$ is hydrogen, hydroxy, or $C_1$-$C_4$ alkyl and $G^2$ is methylene, ethylene, or 1-propylene;

$R^4$ and $R^5$ are each independently hydrogen, hydroxy, $C_1$-$C_4$ alkyl, $C_1$-$C_4$ alkoxy, halo, cyano, or trifluoromethyl; and $R^6$ is hydrogen, hydroxy, $C_1$-$C_4$ alkyl, $C_1$-$C_4$ alkoxy, halo, cyano, trifluoromethyl, phenyl optionally substituted with $C_1$-$C_4$ alkyl, hydroxy, or $C_1$-$C_4$ alkoxy; or pyridinyl.

Other preferred compounds of the invention include compounds or pharmaceutically acceptable salts of formula (II) wherein $R^1$ is hydrogen; $R^2$ is cyclohexyl; $R^4$ and $R^5$ are each independently hydrogen, hydroxy, $C_1$-$C_4$ alkyl, $C_1$-$C_4$ alkoxy, halo, cyano, or trifluoromethyl; and $R^6$ is hydrogen.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius.

"TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates [M+H] unless indicated otherwise. "MS (FD)" refers to field desorption mass spectrometry, "MS (IS)" refers to ion spray mass spectrometry, "Mass spectrum (ion spray)" refers to ion-spray ionization mode. "MS (FIA)" refers to flow injection analysis mass spectrometry, "MS (FAB)" refers to fast atom bombardment mass spectrometry, "MS (EI)" refers to electron impact mass spectrometry, "MS (ES)" refers to electron spray mass spectrometry, "MS (EI)" refers to electron impact mass spectrometry-electrospray ionization, "MS (ES+)" refers to mass spectrometry-electrospray ionization, "MS (APCi) refers to atmospheric pressure chemical ionization mass spectrometry, "UV" refers to ultraviolet spectrometry, "$^1$H NMR" refers to proton nuclear magnetic resonance spectrometry. "LC-MS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylforamide, "HCl" refers to hydrochloric acid, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$," refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCI" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$," refers to Bis(dibenzylideneacetone)palladium, "BINAP" refers to 2,2'-Bis(diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide. In a structure, "Ph" refers to phenyl, "Me" refers to methyl, "Et" refers to ethyl, "Bn" refers to benzyl, "MeOH" refers to methanol.

General Procedures

Compounds of the present invention have been formed as specifically described in the examples. Alternative synthesis methods may also be effective and known to the skilled artisan. Unless otherwise indicated, all variables, such as L, G$^1$, R$^1$ to R$^{20}$, etc., are as defined for analogous variables in the summary of the invention, and otherwise as defined herein.

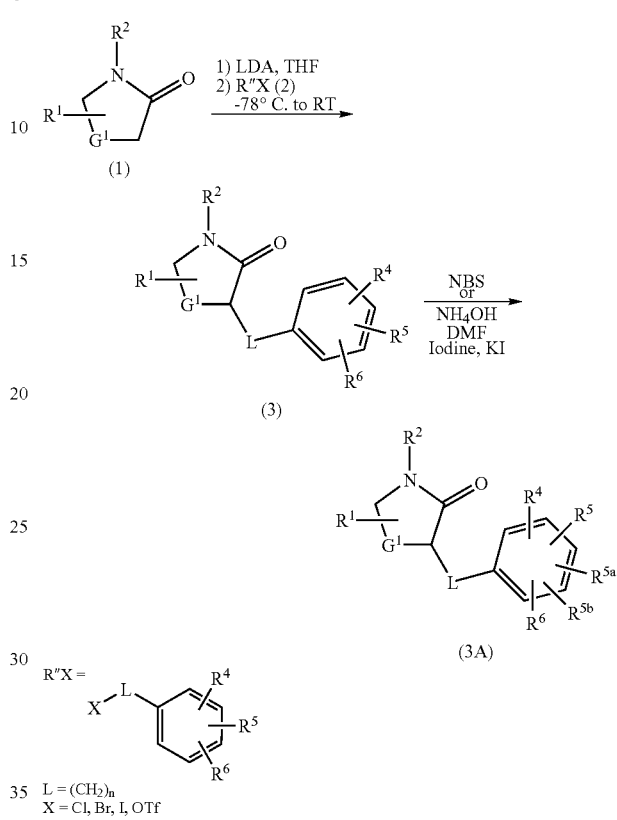

In Scheme A the lactam (1) is conjugated with an alkylating agent R"X (2) to give (3). The reaction is carried out using lithium diisopropylamide (LDA) to form the lithium anion of the lactam but other bases could be used (lithium hexamethyl disilazide, sodium hydride, phosphazenes, potassium tert-butoxide) (Conditions used are a modification of the conditions to alkylate 1-methyl-pyrrolidinone, see: Hullet, P. et al. Can. J. Chem. (1976) 54, 1098-1104; For use of phosphazenes in alkylation of lactams, see: Goumri-Magnet et al. J. Org. Chem. (1999) 64, 3741-3744). The reaction is carried out in THF but other solvents could be used (i.e.; dichloromethane, ether, toluene, etc. to facilitate solubility of the components). The reaction can be run with either an excess of the lactam and LDA or with an excess of the alkylating agent. The ease of purification of the product from the starting materials and the relative expense of the components and the preference of the chemist lead to different choices of which ratios of starting materials to use. In general the reaction affords good to moderate yields of product; especially for benzylic alkylating reagents. The reaction is initiated at temperatures of −78° C. and warmed to room temperature. Depending on the reactivity of the alkylating reagent, the time varies. Alkyl alkylating agents take longer (1-3 hours or more, while the subset of benzyl alkylating agents proceed rapidly at −78° C. (<15 minutes). The alkylating agents are but are not limited to halides; generally the iodides or bromides, but also chlorides; however one skilled in the art will recognize that tosylates, triflates, nosylates, and other alkylating agents would work. When R$^1$ is not hydrogen, the major product of the alkylation is the trans-isomer and this is the preferred method for the preparation of these compounds. Optionally, compound 3 can be brominated using NBS or iodinated using iodine using aqueous potassium iodide.

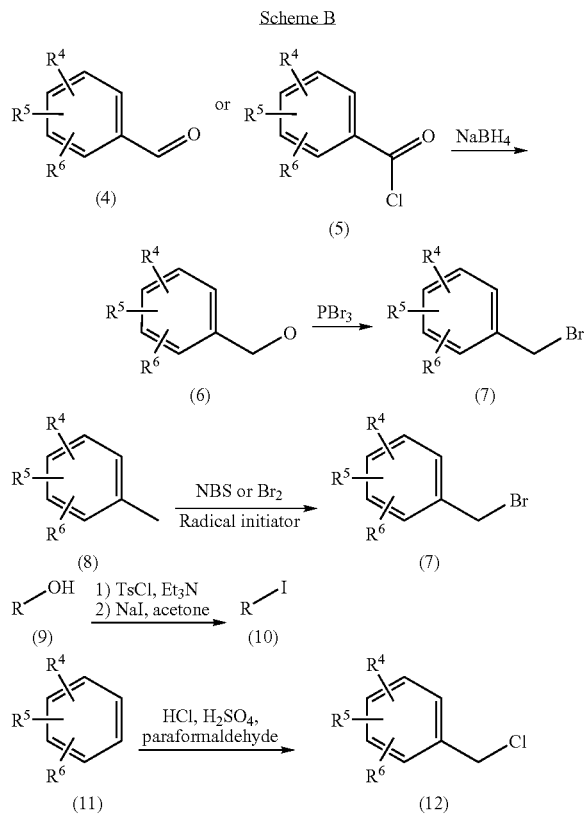

In Scheme B the benzylating agents (7) can be prepared by modifications of a variety of literature conditions a few of which are illustrated here. Substituted benzaldehydes (4) or substituted benzoyl chlorides (5), which are readily available from the corresponding benzoic acids with thionyl chloride or oxalyl chloride, are reduced readily by dropwise addition into a mixture of sodium borohydride in ethanol/THF to form the substituted benzylic alcohols (6). Conversion of the substituted benzylic alcohols (6) to the bromides (7) can generally be achieved by adding a moderate excess of phosphorous tribromide to a solution of the alcohol in a solvent (either ether or dichloromethane have been used; but others compatible with phosphorous tribromide would work). Other literature procedures can effect the conversion of (6) to (7); i.e.; treatment with HBr in AcOH with some substrates; conversion of the alcohol to a mesylate followed by Br— displacement, or treatment with CBr$_4$ and triphenylphosphine to name but three of many possibilities. The benzylic iodides and chlorides can be made by trivial modifications of the above procedures.

In cases where there is but one alkyl moiety attached to the aryl moiety as in (8), conversion of the methyl moiety to the benzyl halide (7) can be effected by treatment with a radical precursor (AIBN, benzyl peroxide, a peroxide, etc.) in a suitable solvent with a bromide radical precursor (NBS, bromine, etc.) to afford the benzyl bromide (7). Replacement of the bromide radical precursor with a chloride or iodide radical precursor can afford the corresponding benzylic halides.

In cases where R is not benzylic, the alkyl iodides are generally the best alkylating agent for the reaction in General Scheme A. A versatile method of preparing these alkylating partners is to first make the tosylate (triflate and mesylate with alternative bases than triethyl amine can also be effectively used) from an alcohol (9) and then displace the tosylate with iodide ion in acetone.

Benzylic chlorides in certain cases can be easily made from paraformaldehyde or freshly cracked formaldehyde or another formaldehyde synthetic equivalent via acid catalyzed aromatic substitution. This procedure is most efficient with electron rich aromatic or heteroaromatic rings (11) to form the newly formed —CH$_2$Cl bond at a position para or ortho to an electron donating substituent (*J. Med Chem*. (1988) 31, 72-83).

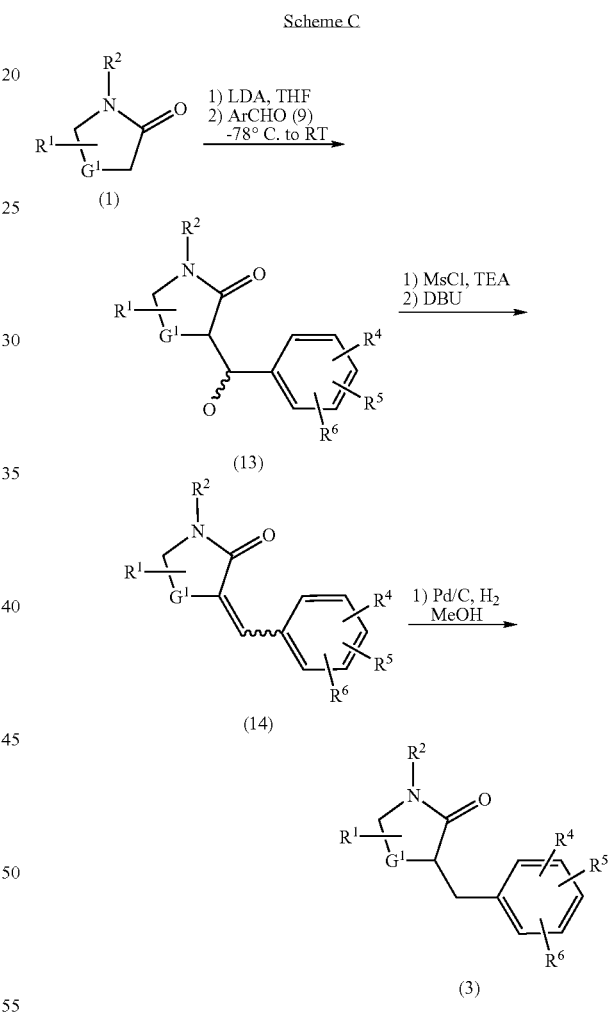

In Scheme C, an alternative to using an alkylating agent to prepare (3) is described. Substituted lactams (1) can be converted to the alcohols (13) (*J. Med. Chem.* (1991) 34, 887-900) by treatment of the lactam with LDA followed by treatment with an aldehyde. Alternatively, these alcohols could be access from carboxylic esters via a Claisen reaction to form an intermediate ketone, followed by a hydride reduction (*Liebigs, Ann. Chemie*. (1983) 165-180). Elimination of the alcohol to the α,β- unsaturated lactam (14) can be effected by formation of the mesylate with methanesulfonyl chloride and triethyl amine as base; followed by treatment with DBU (*Chem. Pharm. Bull.* (1990) 38 393-399). Other conditions to affect this transformation (i.e.; different bases to substitute for triethyl amine or DBU or different activation agents to replace DBU) could be used and should be evident to those trained in the art. Reduction of the double bond moiety of (14) by catalytic hydrogenation affords (3). Catalytic hydrogenation could potentially be replaced with 1,4-conjugate addition of hydride or alkyl metal species to form (3) or alkylated variants thereof.

When $R^1$ does not equal hydrogen, the major compound of these reduction is the cis-isomer and this is the preferred method for the preparation of these compounds.

Scheme D

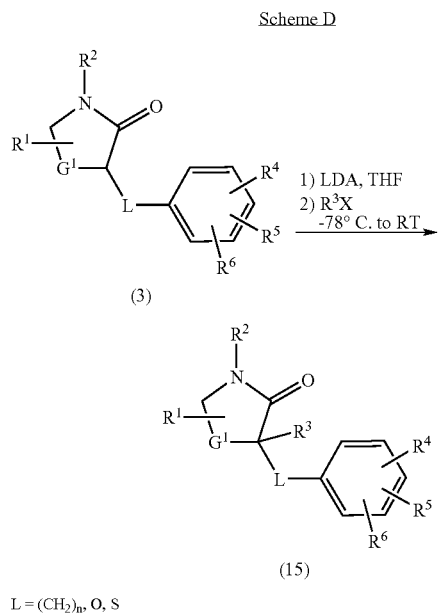

In Scheme D the lactam (3) is conjugated with an alkylating agent (2) to give (15). As in the case of Scheme A, other bases and solvents can be used. When $R^1$ does not equal H, the major product has a trans-relationship between the 3-substitutent on the lactam and $R^1$. It is evident to those trained in the art that both isomers of (15) when $L=(CH_2)_n$ can be preferentially made as the major product by judicious choice of which alkylating agent, $R^3X$ or ArLX, to introduce first.

Scheme E

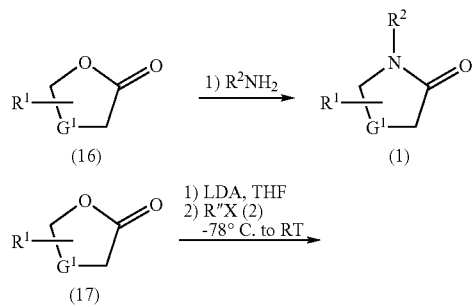

-continued

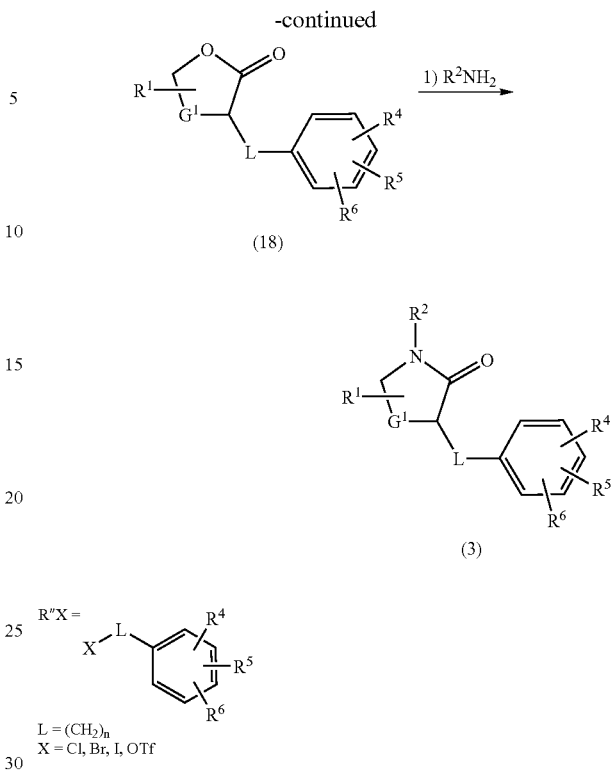

In Scheme E the butyrolactone (16) is reacted with a primary amine to form the lactam starting material (*J. Am. Chem. Soc.* (1947) 69, 715-716). A large number of primary amines can be utilized in this procedure. Benzyl amines, substituted cycloalkyl amines (substituted with alkyl, amine, alcohols, etc), and fused bi- and tri-cyclic amines (i.e., adamantyl, norborenyl, camphoryl, etc) may be used. The reaction proceeds in two steps and involves a thermal elimination of water at high temperature. No solvent is used; but a high boiling solvent could be added if perceived to be desirable. It should be noted that if $R^3$ is at the 3-position of the pyrrolidinone, then the product is the same as (3) and an alkylation is not necessary. This procedure is done as shown in the second synthetic depiction in Scheme E. Alkylation of the lactone (17) with LDA and an alkylating agent using the conditions of Scheme A affords (18) and condensation with the amine under thermal conditions without solvent forms (3) directly.

Scheme F

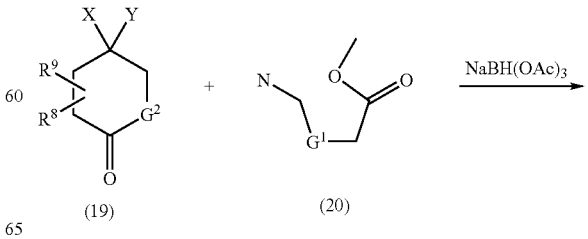

-continued

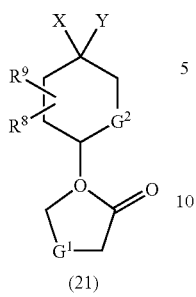
(21)

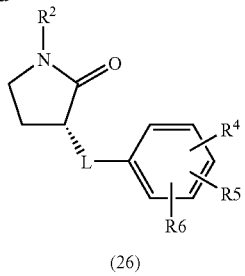
(26)

In Scheme F, cyclic ketones (19) are condensed with methyl 4-aminobutyrate hydrochloride (20) in a reductive amination with sodium triacetoxyborohydride to afford the lactams (21) (*Syn Lett*. (1994) 81-83). The reaction is done using a modification of the conditions described by Marynoff et al. The solvent is 1,2-dichloroethane and the reaction takes 1-4 days to complete depending upon the ketone. In some cases, the crude product is heated to reflux in toluene to force the ring closure and drive the reaction to completion. This cyclization can be done with 5-, 6-, and 7-member ring ketones (19); substituted and not, and with ketals (Y and Z connect to form =OCH$_2$CH$_2$O) on the ring to aid in the further preparation of advanced intermediates.

In Scheme G, a route to chiral 3-substituted lactams is shown. Acylation of the chiral auxiliary (22) with pent-4-enoyl chloride (acylation with longer unsaturated acyl chlorides would give 6-and higher member ring lactams via analogy) affords the imide (24). Alkylation of the imide (24) using the general alkylation conditions of general Scheme A affords in high diastereomeric excess the drawn diastereomer (25). It is probable that other chiral auxiliaries similar to (22) could be utilized with similar or higher diastereomeric excess. Ozonolysis of the olefin affords an aldehyde intermediate that is immediately reductively cyclized with a primary amine in conditions similar to those of Scheme F to afford the lactam (26) (*Bioorg. Med. Chem. Lett*. (2003) 2035-2040). Of course, utilization of the other enantiomer of (22) gives the other enantiomer of (26) and both enantiomers are claimed.

Scheme G

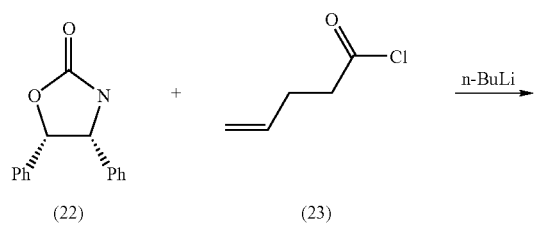

Scheme H

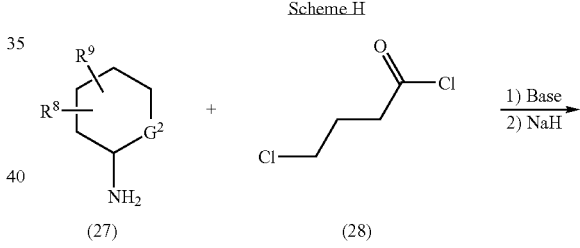

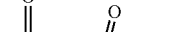

In Scheme H, substituted cyclohexyl amines are acylated with 4-chlorobutyryl chloride using triethylamine, pyridine, or another appropriate acid scavenger base. The second cyclization sometimes occurs in this acylation, but usually a stronger base such as NaH or KH is necessary to effect the second cyclization. Other strong bases such as tert-BuOK could potentially be used. This procedure is particularly effective to make lactams with a 1-alkyl substituent on the cyclic amine moiety.

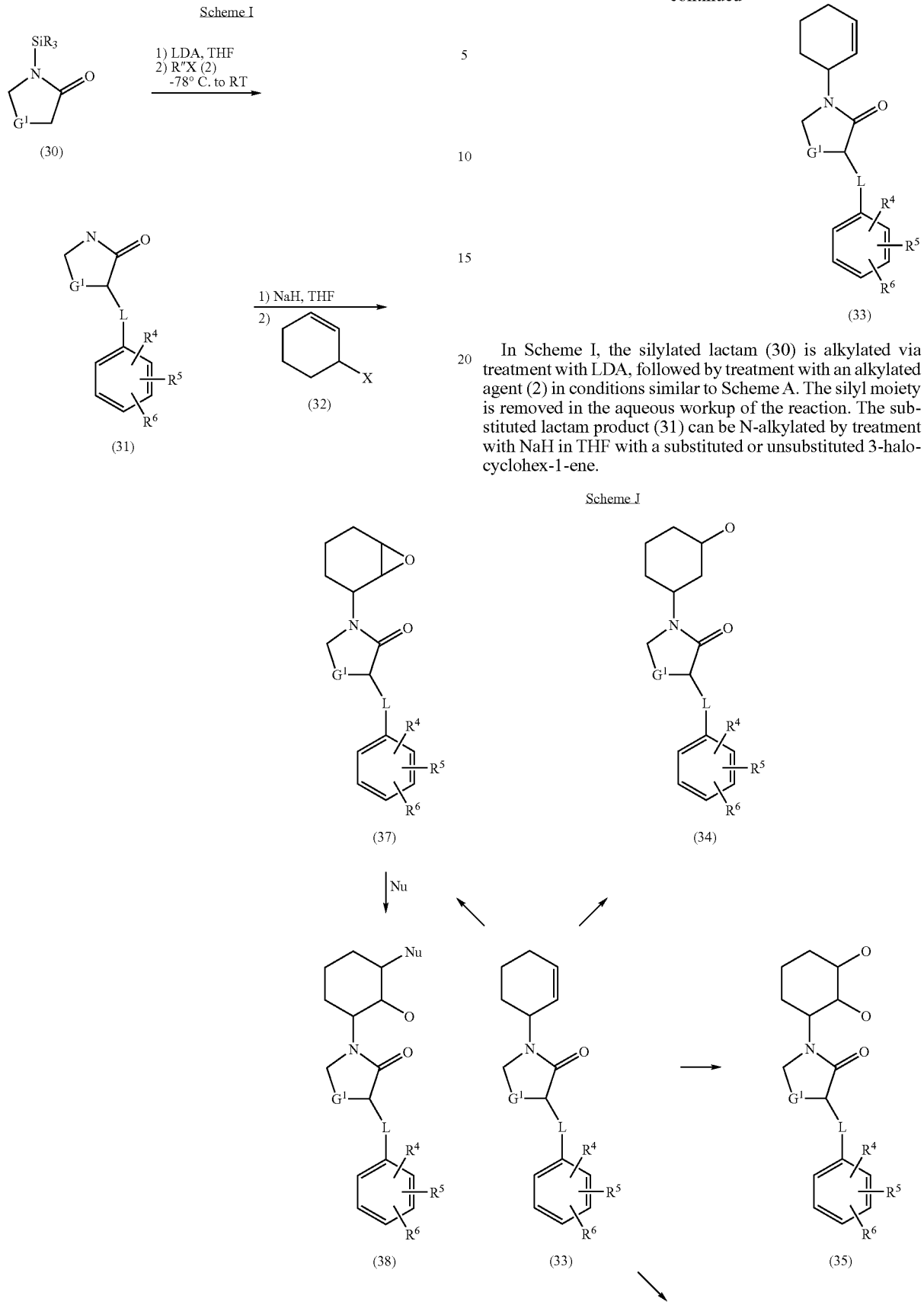
In Scheme I, the silylated lactam (30) is alkylated via treatment with LDA, followed by treatment with an alkylated agent (2) in conditions similar to Scheme A. The silyl moiety is removed in the aqueous workup of the reaction. The substituted lactam product (31) can be N-alkylated by treatment with NaH in THF with a substituted or unsubstituted 3-halo-cyclohex-1-ene.

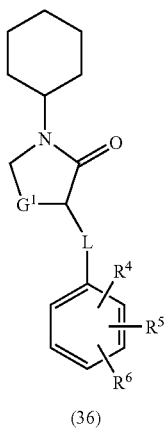

(36)

In Scheme J, the cyclohexenyl product (33) can be optionally oxidized via literature procedures to cyclohexyl alcohols (34), diols (35), reduced to the cyclohexyl moiety (36), or be oxidized to an epoxide intermediate (37). Epoxide intermediate (37) can be further functionalized with a nucleophile to form substituted alcohols (38).

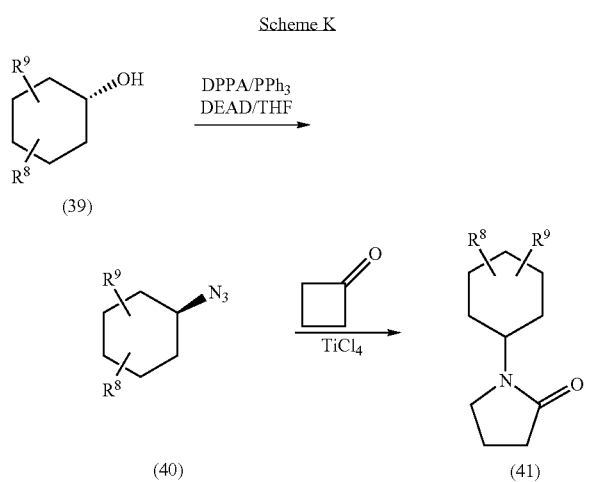

Scheme K

In Scheme K, substituted cyclohexyl alcohols (39), which are readily available either commercially or by known literature procedures can be converted to azides via treatment with diphenylphosphoryl azide (DPPA) and triphenyl azide and DEAD in THF to form the azide (40). During this reaction, the relative stereochemistry of the starting alcohol is inverted and is evident to those trained in the art. Treatment of the azide (40) with butyrylactone forms the lactam (41). During the Schmidt reaction the relative stereochemistry of the N-moiety to the substituents $R^8$ and $R^9$ is conserved as is evident to those trained in the art and is illustrated in the examples below.

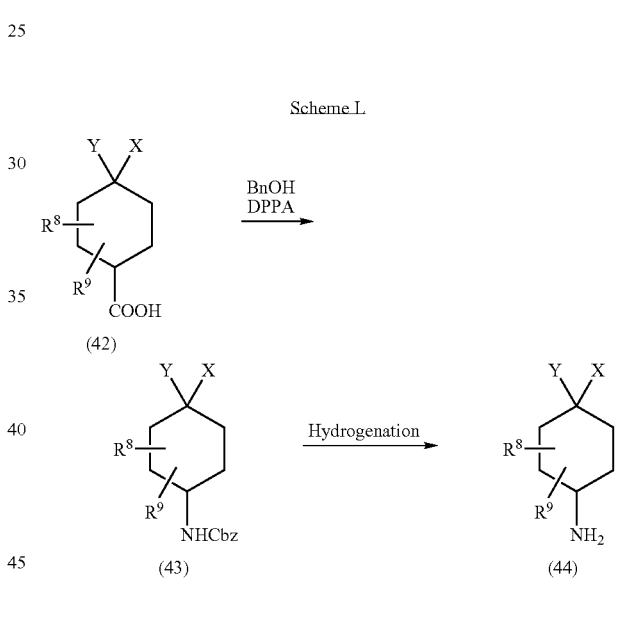

Scheme L

In Scheme L, a variety of substituted cyclohexyl amines can be easily acquired from the substituted carboxylic acids (42), which are easily prepared via known literature methods [i.e., alkylation of a parent carboxylic acid with RX (X=halide or triflate)]. In this procedure the carboxylic acid is first subjected to Curtius rearrangement in the presence of benzyl alcohol to form the CBZ carbamate (43). In this reaction the relative stereochemistry of the starting material (42) is conserved as is evident to those trained in the art. Hydrogenation of the CBZ carbamate forms the amine (44). A variety of hydrogenation conditions can be used to effect this transformation as is evident to those trained in the art (i.e.; see Green's protecting group book for numerous conditions) (Greene, Protective Groups in Organic Synthesis, John Wiley & Sons, New York, N.Y.). These amine starting materials (44) are useful starting materials for Schemes E, G, H, and M to prepare the claimed lactams.

Scheme M

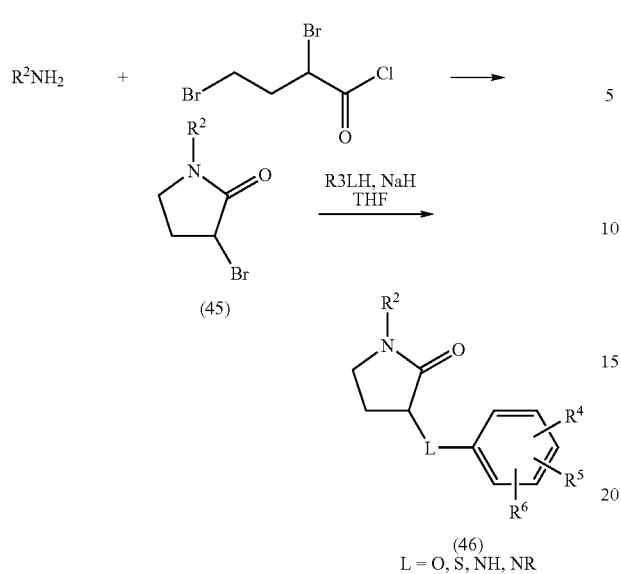

In Scheme M, amines are bis acylated and cyclized with 2,4-dibromobutryl chloride to produce the N-alkylated-3-bromopyrrolidinones (45) in good yield (*J. Med. Chem.* (1987) 30, 1995-1998). The bromide can be displaced by phenols, thiophenols, anilines, alcohols, thiols, and amines to form the lactams (46) [L=O, S, NH, NR].

Scheme N

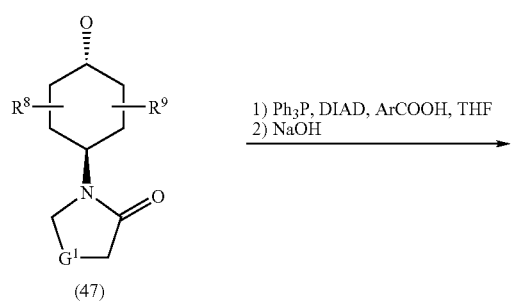

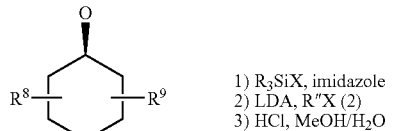

In Scheme N, a hydroxyl substituted lactam (47) stereochemistry is inverted with the Mitsunobu reaction to form its diastereomer (48) (trans to cis conversion illustrated here; but the reverse could easily be done). The alcohol substituted lactams are conveniently alkylated by first protecting the alcohol moiety with a silyl protecting group (TBS used but a variety of protecting groups from Green's Protecting Groups in Org Synthesis could be employed), and then alkylated employing the conditions of Scheme A. Deprotection of the alcohol with appropriate conditions (acid/HCl or fluoride deprotection of silyl moieties are convenient) yield the hydroxylated lactams (49).

Scheme O

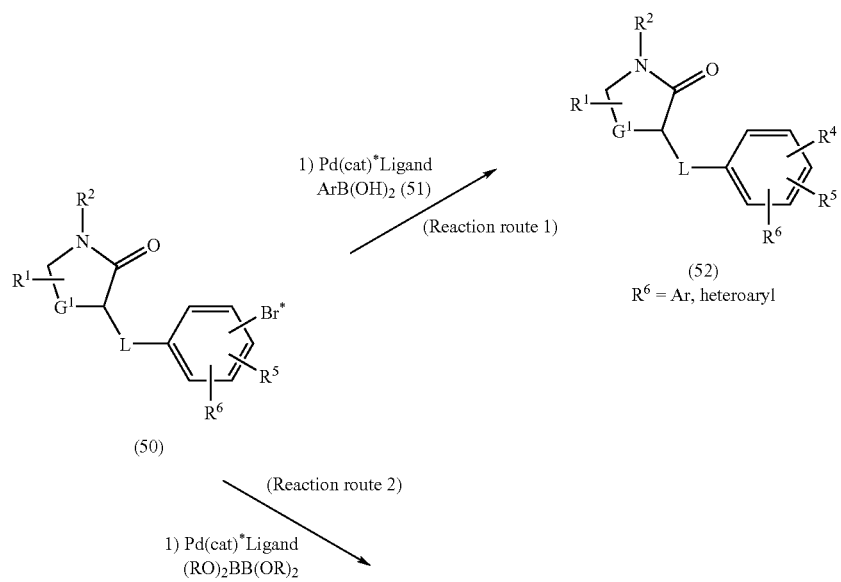

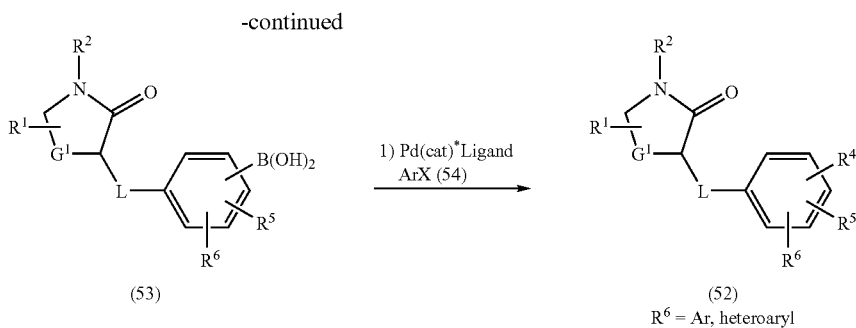

In Scheme O, aryl "Br" lactams (50) (bromine as indicated by Br* can also be I, Cl, or OTf and this same chemistry would produce the drawn compounds with the appropriate catalysts known in the literature by those trained in the art) are converted to the biaryl/aryl-heteroaryl compounds by coupling to the appropriate aryl/heteroaryl boronic acid (51) via reaction route 1 to produce the lactams (52) directly. The linker (L) can be any of the following [$CH_2$, CHR, O, S, NH, or $(CH_2)_n$]. It is also convenient to make the boronic acid convergent intermediate (53) and couple with the appropriate Pd(cat) ligand system with a variety of aryl/heteroaryl halides/triflates (54) to form the lactams in two steps as shown in reaction route 2. This route is convenient and more versatile if the boronic acids (51) are not easy to prepare or acquire from commercial sources or literature methods.

substituted arylalkyl lactams (eg., Br, I, Cl or Tf conversion to alkyl). This conversion (reaction route 1) is achieved via Pd-catalyzed insertion of $(R^6)_3B$ (54) or BBN—$R^6$ [a subclass of (54) (made from either BBN—H regioselective addition to primary alkenes, or via organometalic addition of $R^6$-Metal to BBN—OMe)]. In reaction route 2, organometallic conversion to introduce alkyl moieties containing nitrile, ester and other functionality is a Pd-catalyzed Negishi insertion of an $R^6$ zinc halide (56) to the halide/triflate (50) to produce the lactams (57). This route is the preferred method for preparation of compounds of the structure where $R^6$=$(CH_2)_n$FG (FG=COOR, CN). A similar Negishi reaction has been used to produce (57) where $R^6$=CN when $R^6$ZnX (56) is replaced with ZnCN in the reaction.

Scheme P

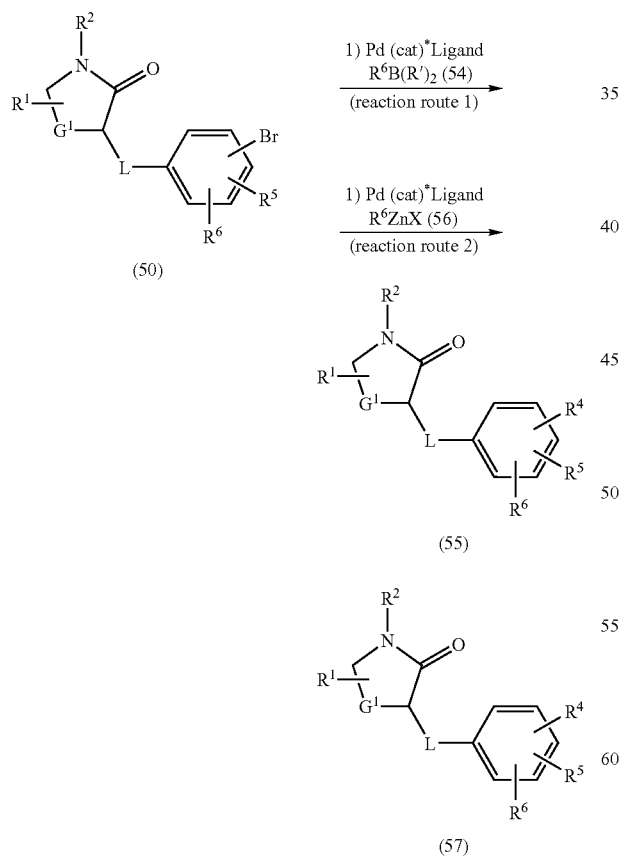

Scheme Q

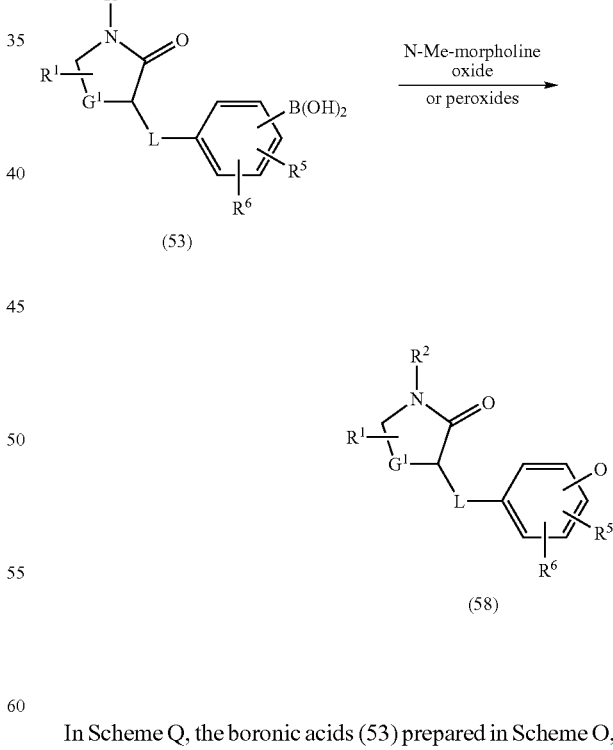

In Scheme P, the aryl bromides (Br could also be expected to be replaced with OTf, I) are conveniently converted into In Scheme Q, the boronic acids (53) prepared in Scheme O, are conveniently converted into phenols (58) via oxidation with N-methyl morpholine oxide in a suitable solvent or via treatment of the boronic acid with another oxidizing agent such as peroxides. Other oxidants known in the literature could likely also be utilized. These phenolic products (58) are useful starting materials in alkylations as in Scheme Q.

Scheme R

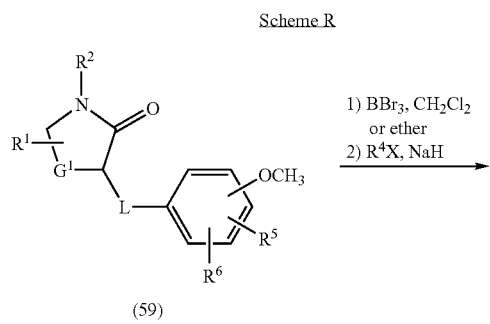

(59)

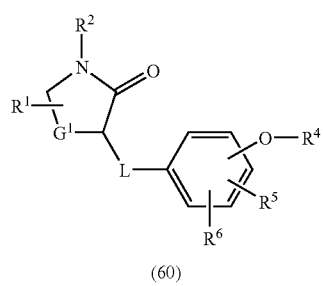

(60)

In Scheme R, the methoxy functionalized lactams prepared via one of the above schemes, can be further elaborated via demethylation of the OCH$_3$ moiety of the lactam (59) to make a phenol (58) which can be alkylated with (CH$_2$)$_n$FG (FG=functionalized group) to produce the lactam (60). This chemistry is used to introduce moieties where R=(CH$_2$)$_n$FG where FG=ester, acid, primary, secondary, and tertiary amines. It is expected that Mitsunobu reactions of the phenols (59) with alcohols could also produce the lactams (60). This should be the preferred method for more functionalized and sensitive R$^4$-substituents.

Scheme S

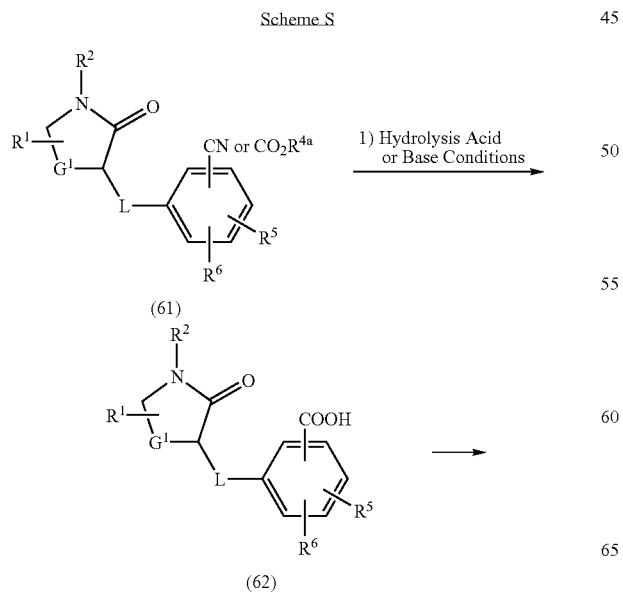

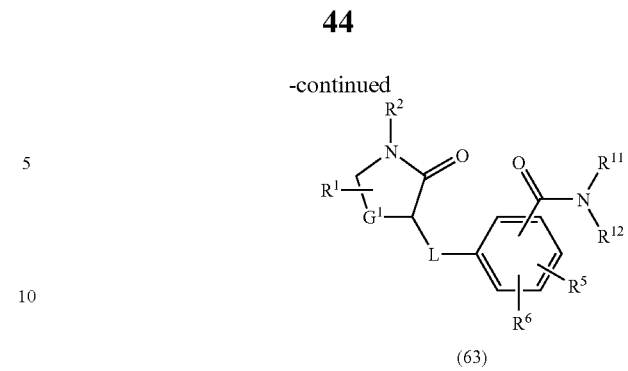

(63)

In Scheme S, the nitrites (61) prepared via Scheme P) or the esters (61) (on biaryl substituted compounds to date prepared via Scheme O) are hydrolyzed under standard basic or acidic conditions (the optimal condition varies with the sensitivity of R$^5$ and R$^6$) to afford the carboxylic acid compound (62) which is further elaborated using standard dicarbodiimide coupling methods to prepare amides (63). Other amide coupling techniques (which are numerous and known to those trained in the art) would give amides (63).

Scheme T

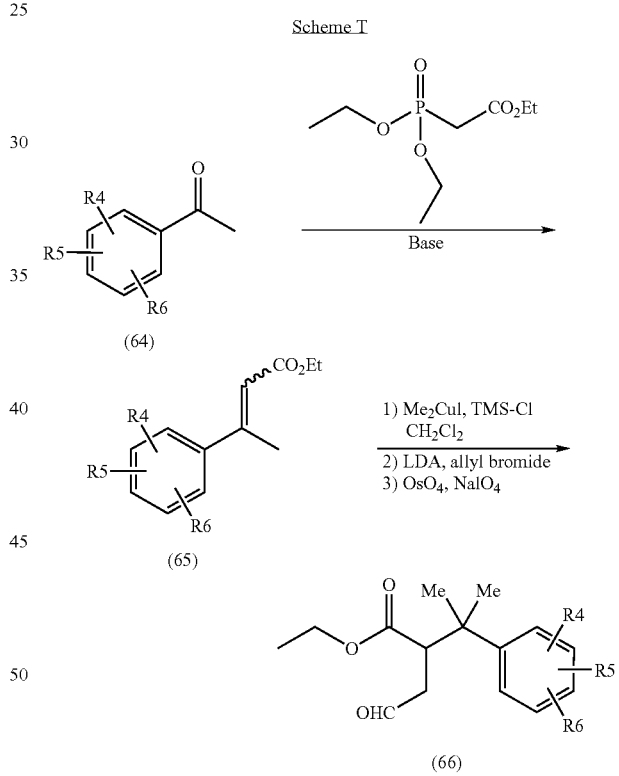

In Scheme T, substituted acetophenones (64) are condensed with phosphonate esters to yield enoates (65) which can subsequently alkylated in a 1,4-Michael addition (*Tetrahedron Lett.*, (2003), 4265), followed by a second alkylation with allyl bromide and oxidation of the olefin to yield geminal disubstitued aldehyde (66). Conversion to lactams is described in Scheme F.

PREPARATIONS AND EXAMPLES

The Examples provided herein are illustrative of the invention claimed herein and are not intended to limit the scope of the claimed invention in any way. The preparations and examples are named using AutoNom 2000 in MDL ISIS/Draw version 2.5 SPI from MDL Information Systems, Inc.

A Varian INOVA 400 MHz spectrometer is used to obtain $^1$H NMR Specta the in the solvent indicated. A Finnigan LCQ Duo instrument using a mobile phase of 50% acetonitrile, 25% methanol, and 25% 2 mM aqueous ammonium acetate is used to obtain the Electrospray mass spectra. A Varian Prostar 210 instrument equipped with a PDA detector is used to run the analytical HPLC. A 5-cm YMC ODS-AQ column with a particle size of 3 microns is used as the stationary phase and 0.1% TFA in water is used as mobile phase A and 0.05% TFA in acetonitrile is used as mobile phase B. The standard method is a gradient of 5 to 95% B over 5 minutes, unless otherwise indicated. Starting materials can be purchased commercially or prepared as described herein or prepared by procedures known in the art.

Preparation 1

3-Bromo-1-cyclohexyl-pyrrolidin-2-one

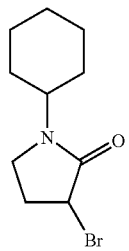

Dissolve 2,4-dibromo-butyryl chloride (17.0 g, 64.3 mmol) in chloroform (3 ml) and add to a mixture of cyclohexylamine (7.65 g, 77.2 mmol) in chloroform (20 mL) and H$_2$O (3 mL) at 0° C. Add sodium hydroxide (5.92 g, 147.9 mmol) slowly while keeping the reaction temperature below 10° C. Stir for 1 hour. Wash the organic layer with 0.5M hydrochloride and brine. Dry over sodium sulfate, filter, and concentrate. Place the residue in THF (200 mL) and cool to 0° C. Add sodium hydride (1.02 g, 42.6 mmol) and stir for two days. Add additional sodium hydride (1.02 g, 42.6 mmol) and stir for 3 days. Pour onto water and ice and extract with methylene chloride. Dry over sodium sulfate, filter, and concentrate to yield 6.36 g (34%) of the title compound: NMR (CDCl$_3$) δ 4.41 (dd, 1H), 3.94 (m, 1H), 3.48 (m, 1H), 3.33 (m, 1H), 2.51 (m, 1H), 2.30 (m, 1H), 1.82 (m, 3H), 1.70 (m, 2H), 1.38 (m, 4H), 1.11 (m, 1H).

Preparation 2

1-Cyclohexyl-4-hydroxymethyl-pyrrolidin-2-one

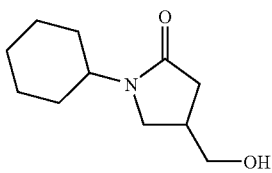

Place 2-methylene-succinic acid (12.0 g, 92.2 mmol) and cyclohexylamine (9.15 g, 92.2 mmol) and heat to 160° C. for hours. Cool to give 18.8 g (96%) of 1-cyclohexyl-5-oxo-pyrrolidine-3-carboxylic acid. Charge a flask with 1-cyclohexyl-5-oxo-pyrrolidine-3-carboxylic acid (16.2 g, 76.7 mmol), add methylene chloride (20 mL) and cool to 0° C. Slowly add borane in THF (1M, 115.1 mL, 115.1 mmol) and stir for two hours at 0° C. Quench the reaction with ice and extract with methylene chloride. Dry over sodium sulfate, filter, and concentrate. Purify by silica gel (1-5% methanol in methylene chloride) to yield 9.9 g (65%) of the title compound: Mass spectrum (apci) m/z=198.1 (M+H).

Preparation 3

1-Cyclohexyl-4-methyl-pyrrolidin-2-one

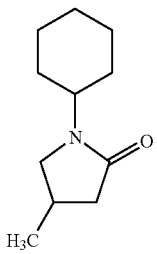

Place 1-cyclohexyl-4-hydroxymethyl-pyrrolidin-2-one (Preparation 2) (2.5 g, 12.7 mmol) and triphenylphosphene (3.7 g, 13.9 mmol) in a flask and add dry N,N-dimethyl-acetamide (20 mL). Add a solution of iodine (3.2 g, 12.7 mol) in N,N-dimethyl-acetamide (3 mL). Stir reaction for 24 hours. Quench the reaction with saturated sodium bisulfite (20 mL) and extract with methylene chloride. Dry over sodium sulfate, filter, and concentrate. Dissolve crude material in acetonitrile (100 mL) and add glacial acetic acid (15 mL) and zinc (12.4 g, 190.1 mmol), then heat to 75° C. and stir for 6 hours. Cool to room temperature, filter, and partition between water and methylene chloride. Separate layers and wash methylene chloride with saturated sodium bicarbonate. Dry over sodium sulfate, filter, and concentrate. Purify by silica gel (30-40% ethyl acetate in hexane) to yield 1.0 g (45%) of the title compound. NMR (CDCl$_3$) δ 3.94 (m, 1H), 3.45 (m, 1H), 2.88 (dd, 1H), 2.55 (dd, 1H), 2.38 (m, 1H), 2.02 (dd, 1H), 1.78 (m, 2H), 1.68 (m, 3H), 1.35 (m, 4H), 1.09 (m, 4H).

Preparation 4

1-Cyclohexyl-4-methoxymethyl-pyrrolidin-2-one

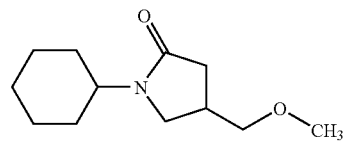

Dissolve 1-cyclohexyl-4-hydroxymethyl-pyrrolidin-2-one (preparation 2) (280 mg, 1.4 mmol) in dichloromethane (30 mL) and cool to 0° C. Add sodium hydride (57 mg, 1.4 mmol) and stir for 20 minutes. Add iodomethane (302 mg, 2.1 mmol) and stir for 24 hours. Quench reaction with water and extract with dichloromethane. Combine extracts, dry over sodium sulfate, filter, and concentrate. Purify by silica gel (1% methanol in ethyl acetate) to give 210 mg (70%) of the title compound. NMR (CDCl$_3$) δ 3.90 (m, 1H), 3.40 (m, 1H), 3.31 (m, 4H), 3.25 (m, 1H), 3.11 (m, 1H), 2.50 (m, 2H), 2.12 (m, 1H), 1.75 (m, 2H), 1.65 (m, 3H), 1.33 (m, 4H), 1.05 (m, 1H).

Preparation 5

4-Bromo-1-bromomethyl-2-chloro-benzene

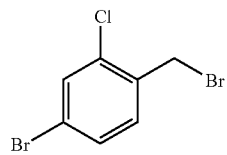

Dissolve 4-bromo-2-chloro-1-methyl-benzene (64.3 g, 312.9 mmol) in carbon tetrachloride (1 L). Add benzoyl peroxide (760 mg, 3.1 mmol) and N-bromosuccinamide (58.5 g, 329 mmol) and heat to 80° C. for 18 hours. Cool reaction to room temperature and filter. Concentrate the filtrate and purify by silica gel (hexanes) to yield 63 g (71%) of the title compound. NMR (CDCl$_3$) δ 7.57 (d, 1H), 7.39 (dd, 1H), 7.31 (d, 1H), 4.53 (s, 2H).

Preparation 6

3-(4-boronic acid-2-chloro-benzyl)-1-cyclohexyl-pyrrolidin-2-one

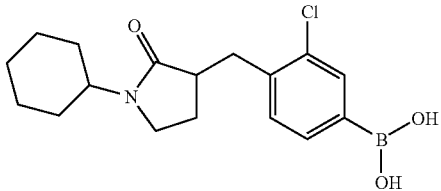

Using the procedure to synthesize Example 1 and using reagents N-cyclohexylpyrrolidinone (15 g, 89.7 mmol), LDA (2.0 M, 53.8 mL, 107.6 mmol) and 4-bromo-1-bromomethyl-2-chloro-benzene (preparation 5) (30.6 mg, 107.6 mmol) affords 22 g (66%) of 3-(4-bromo-2-chloro-benzyl)-1-cyclohexyl-pyrrolidin-2-one.

Place 3-(4-bromo-2-chloro-benzyl)-1-cyclohexyl-pyrrolidin-2-one (5.0 g, 13.5 mmol), bis(neopentyl-glycolato) diboron (3.7 g, 16.2 mmol), Pd(dppf)Cl$_2$ (1.1 g 1.4 mmol, and potassium acetate (4.0 g, 40.5 mmol) into a flask and purge with nitrogen. Add dry DMSO, heat to 80° C., and stir for 18 hours. Cool to room temperature and add ether (500 mL). Filter off any solids. Add sodium hydroxide (1M, 300 mL) and stir for 15 minutes. Extract several times with ether. Adjust the aqueous layer to a pH of 2 with 1M HCl and extract several times with ether. Combine extracts, dry over sodium sulfate, filter, and concentrate to give 4.28 g (95%) of the title compound. NMR (d$_6$-DMSO) δ 8.17 (s, 2H), 7.78 (s, 1H), 7.64 (m, 1H), 7.33 (d, 1H), 3.74 (m, 1H), 3.21 (m, 2H), 3.15 (m, 1H), 2.64 (m, 2H), 1.88 (m, 2H), 1.74 (m, 2H), 1.56 (m, 4H), 1.35 (m, 4H), 1.09 (m, 1H).

Preparation 7

3-bromo-6-chloro-2-fluoro-benzaldehyde

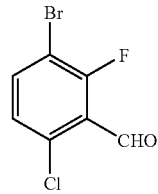

Add a 2M LDA in THF (22 mL, 44 mmol) to 1-bromo-4-chloro-2-fluorobenzene (9.2 g, 44 mmol) in THF (100 mL) at −78° C. Stir for 10 minutes. Add DMF (10 mL, 132 mmol) and warm up to room temperature. Add the reaction mixture to ice and water. Extract the mixture with ethyl acetate (100 mL). Wash the organic layer with aqueous LiCl (20 mL, 10%), dry with magnesium sulfate, filter and evaporate solvent under reduced pressure to obtain 5 g (48%) of the title compound as a white solid.

Preparation 8

(3-bromo-6-chloro-2-fluoro-phenyl)methanol

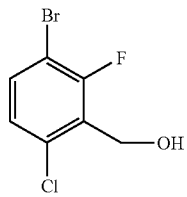

Add 1M LAH in THF (20 mL, 20 mmol) to 3-bromo-6-chloro-2-fluoro-benzaldehyde (Preparation 7) (4.9 g, 20 mmol) in THF (20 mL) at −78° C. Stir for 15 minutes and warm up to room temperature. Add reaction mixture into ice and water. Add 1M HCl (5 mL, 5 mmol) to dissolve the solid. Extract the mixture with ethyl acetate (50 mL), dry with magnesium sulfate, filter and evaporate solvent under reduced pressure to obtain 4.6 g (94%) of the title compound as a white solid.

Preparation 9

1-bromo-3-bromomethyl-4-chloro-2-fluorobenzene

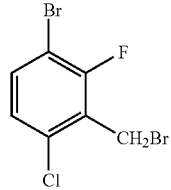

Add phosphorous tribromide (1.8 mL, 19.2 mmol) to (3-bromo-6-chloro-2-fluoro-phenyl)methanol (Preparation 8) (4.6 g, 19 mmol) in dichloromethane (50 mL) at 0° C. Stir for 20 minutes. Add the reaction mixture into ice and water. Extract with dichloromethane (100 mL), dry with magnesium sulfate, filter and evaporate solvent under reduced pressure. Purify the residue by biotage chromatography to yield the product to give 1.7 g (30%) of the title compound as a white solid. $^1$HNMR (CDCl$_3$) 7.48-7.44 (m, 1H), 7.14-7.11 (m, 1H), 4.62-4.61(m, 2H).

Preparation 10

4-Chloro-N-piperidin-1-yl-butyramide

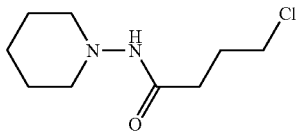

Add 4-chloro-butyryl chloride (5 mL, 43 mmol) to piperidin-1-ylamine (4.3 g, 43 mmol) in dichloromethane (100 mL) at room temp. Stir the reaction mixture at room temp for two hours. Add the reaction mixture into ice and saturated sodium bicarbonate solution. Extract the mixture with dichloromethane (100 mL). Wash the organic layer with saturated sodium bicarbonate solution (50 mL), dry with magnesium sulfate, filter and evaporate solvent under reduced pressure to obtain 5 g (57%) of the title compound as a white solid: Mass spectrum (ion spray): m/z=205.1 (M+H).

Preparation 11

1-Piperidin-1-yl-pyrrolidin-2-one

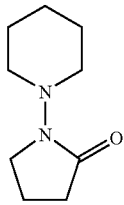

Add NaH (1 g, 25 mmol) into 4-chloro-N-piperidin-1-yl-butyramide (Preparation 10) (3.2 g, 16 mmol) in THF (100 mL) and stir for 1 hour. Add the reaction mixture into water and extract with ethyl acetate (100 mL). Wash the organic layer with brine (20 mL), dry with magnesium sulfate, filter and evaporate solvent under reduced pressure. Purify the residue by column chromatography to give the title product (2 g, 76%) as yellow oil: Mass spectrum (ion spray): m/z=169.1 (M+H).

Preparation 12

1-Bromo-3-bromomethyl-2,4-dichloro-benzene

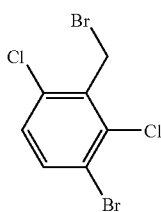

By the method in Preparation 5 and using the reagents 1-bromo-2,4-dichloro-3-methyl-benzene (74.4 g, 310 mmol), N-bromosuccinimide (58.0 g, 326 mmol) and benzoyl peroxide (750 mg) affords the title compound as an amber oil (98.5 g, 99%):

Preparation 13

3-(2,4-Dichloro-benzyl)-dihydro-furan-2-one

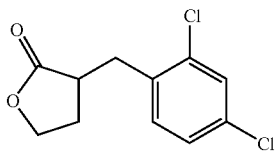

Using the procedure to synthesize Example 1 and using reagents γ-butyrolactone (1.1 g, 13 mmol), and 2,4-dichlorobenzyl iodide (5.6 g, 20 mmol) affords 2.5 g (78%) of the title compound as a tan solid. $^1$H NMR (CDCl$_3$) δ 7.36 (d, 1H), 7.17 (m, 2H), 4.30 (m, 1H), 4.10 (m, 1H), 3.32 (dd, 1H), 2.87-2.78 (m, 2H), 2.20 (m, 1H), 1.95 (m, 1H).

Preparation 14

1-(trans-4-hydroxy-cyclohexyl)-pyrrolidin-2-one

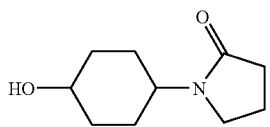

Add trans-4-aminocyclohexanol (230 g; 2.0 mol) to γ-butyrolactone (140 mL; 1.82 mol) in a 1 L round-bottom flask equipped with large magnetic stirrer, thermometer and condenser/nitrogen bubbler. Heat at 190° C. for 68 hours. Cool to ambient temperature and dissolve in water (1 L). Extract into dichloromethane (10×1.5 L). Dry the extracts over magnesium sulfate, filter and evaporate to a brown solid. Triturate with diethyl ether to afford 144.7 g (43%) of the title compound: LC-MS (M+1=184).

Preparation 15 cis-4-Nitro-benzoic acid 4-(2-oxo-pyrrolidin-1-yl)-cyclohexyl ester

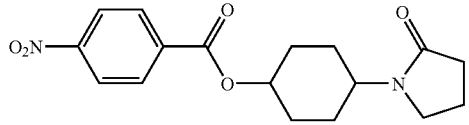

Dissolve 1-(trans-4-hydroxy-cyclohexyl)-pyrrolidin-2-one (Preparation 14) (144 g; 0.79 mol) in dry tetrahydrofuran (5 L) and cool to −5° C. under nitrogen. Add triphenylphosphine (310 g; 1.185 mol) and 4-nitrobenzoic acid (198 g; 1.185 mol). Add diisopropyl azodicarboxylate (230 mL; 1.185 mol) drop-wise and stir at room temperature overnight. Add saturated aqueous sodium hydrogencarbonate (1 L) extract into dichloromethane (2×2.5 L) in a 20 L separating funnel. Dry the combined organic layers over magnesium sulfate, filter and concentrate. Purify over silica gel (iso-hexane/ethyl acetate 50-100% then 10% methanol in ethyl acetate) to afford 163 g (62%) of the title compound.

Preparation 16 cis-1-(4-hydroxy-cyclohexyl)-pyrrolidin-2-one

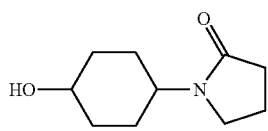

Dissolve cis-4-nitro-benzoic acid 4-(2-oxo-pyrrolidin-1-yl)-cyclohexyl ester (Preparation 15) (87.9 g; 264 mmol) in methanol (1.35 L) and water (150 mL) and add potassium carbonate (109.5 g; 800 mmol). Stir at room temperature overnight to give a white precipitate. Evaporate to dryness. Azeotrope with ethanol (×2). Stir in tetrahydrofuran (1 L) for 1 hour then filter. Evaporate the filtrate to an oil and crystallize from diethyl ether (100 mL) to afford 40 g (83%) of the title compound.

Preparation 17 cis-1-[4-(tert-butyl-dimethyl-silanyloxy)-cyclohexyl]-pyrrolidin-2-one

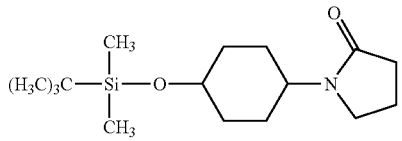

Dissolve cis-1-(4-hydroxy-cyclohexyl)-pyrrolidin-2-one (Preparation 16) (40 g; 220 mmol) in dry dichloromethane (1 L). Add imidazole (22.5 g; 330 mmol) followed by tert-butyldimethylsilyl chloride (50 g; 330 mmol). Stir under nitrogen at room temperature overnight. Wash with water (250 mL) and saturated aqueous sodium hydrogencarbonate (250 mL). Dry over magnesium sulfate, filter and evaporate to an oil. Pass through a silica gel pad with iso-hexane/ethyl acetate (0-50%) to afford 51 g (79%) the title compound as a clear, pale-yellow oil: LC-MS (M+1=298.5).

Preparation 18

2-Bromomethyl-1,3-dichloro-5-trifluoromethyl-benzene

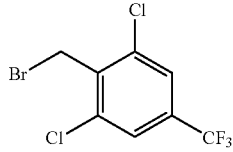

Dissolve (2,6-dichloro-4-trifluoromethyl-phenyl)-methanol (7.5 g, 31 mmol) is THF (40 mL) and cool to 0° C. Add PBr$_3$ (5.0 g, 18 mmol) under nitrogen and stir at 0° C. for 30 minutes. Pour into saturated aqueous sodium bicarbonate and extract with methylene chloride. Dry over sodium sulfate, filter and concentrate. Purify over silica gel (hexanes) to obtain 9.0 g (96%) of the title compound.

Preparation 19

3-(2,4-Dichloro-benzyl)-pyrrolidin-2-one

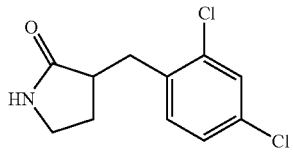

Charge a flask with 1-trimethylsilanyl-pyrrolidin-2-one (5.0 g, 32 mmol), dissolve in THF (150 mL) and cool to −78° C. under nitrogen. Add LDA (2M, 19 mL, 38 mmol) and stir at −78° C. for 10 minutes. Add 2,4-dichloro-1-chloromethyl-benzene (8.1 g, 41 mmol) and warm to room temperature. Pour into water after 2 hours and extract with methylene chloride. Dry over sodium sulfate, filter and concentrate. Purify the residue over silica gel (1:1 hexanes:ethylacetate to 100% ethyl acetate) to afford 5.2 g (67%) of the title compound as a white solid. $^1$H NMR (CDCl$_3$) δ 7.38 (d, 1H), 7.23 (d, 1H), 7.18 (dd, 1H), 6.01 (bs, 1H), 3.31 (m, 3H), 2.75 (m, 2H), 2.13 (m, 1H), 1.84 (m, 1H).

Preparation 20

(4R,5S)-(cis)-3-Pent-4-enoyl-4,5-diphenyl-oxazolidin-2-one

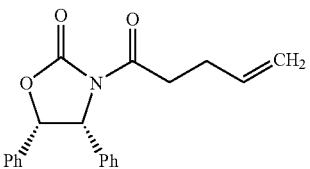

Dissolve (4R,5S)-(+)-cis-4,5-diphenyl-2-oxazolidin-one (2.06 g, 8.62 mmol) in THF (100 mL) and cool to −78° C. Add n-BuLi (5.66 mL, 9.05 mmol, 1.6 M in hexane) and stir for 30 minutes. Then add pent-4-enoyl chloride (1.53 g, 12.93 mmol) and continue stir the solution for one hour. Add water (100 mL) and extract the aqueous layer with ethyl acetate (3×200 mL). Combine the organic layers and dry with Na$_2$SO$_4$, filter, concentrate and purify by flash column chromatography (silica gel, 20-40% of EtOAc-hexane) to give 1.42 g (51%) of the title compound as a white solid.

Preparation 21

(4R,5S)-(cis)-3-[2-(S)-(2-Chloro-6-fluoro-benzyl)-pent-4-enoyl]-4,5-diphenyl-oxazolidin-2-one

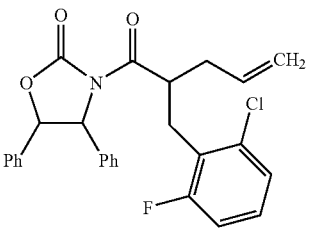

Using the procedure to synthesize Example 1, alkylation of (4R,5S)-(cis)-3-pent-4-enoyl-4,5-diphenyl-oxazolidin-2-one (Preparation 20) (1.48 g, 6.61 mmol) with 2-bromomethyl-1-chloro-3-fluoro-benzene affords 1.28 g (62%) of the title compound as a white solid.

Preparation 22

(4R,5S)-(cis)-3-(2-(R)-Chloro-6-fluoro-benzyl)-4-oxo-4-(2-oxo-4,5-diphenyl-oxazolidin-3-yl)-butyraldehyde

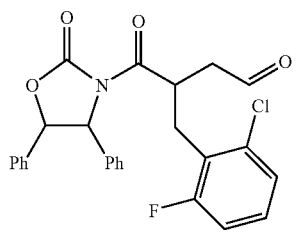

Dissolve (4R,5S)-(cis)-3-[2-(S)-(2-chloro-6-fluoro-benzyl)-pent-4-enoyl]-4,5-diphenyl-oxazolidin-2-one (Preparation 21) (1.28 g, 2.75 mmol) in dichloromethane (100 mL) and cool to 0° C. Bubble ozone into the solution with stirring until the solution becomes blue. Continue to stir the solution for one hour, then bubble nitrogen through the mixture until the blue color disappears. Add $Me_2S$ (0.85 g, 13.75 mmol) and stir the solution for 6 hours. Remove the solvent under reduced pressure and purify the residue with column chromatography (silica gel, 20-40% of EtOAc-Hexane) to give 0.45 g (35%) of the title compound as a colorless oil. $^1H$ NMR ($CDCl_3$) δ 9.70 (s, 1H), 7.15-7.20 (m, 2H), 7.04-7.13 (m, 6H), 6.91-7.00 (m, 3H), 6.80-6.84 (m, 2H), 6.00 (d, 1H), 5.70 (d, 1H), 4.68-4.78 (m, 1H), 3.23-3.25 (m, 1H), 3.09-3.16 (m, 1H), 2.91-2.97 (m, 1H, 2.61 (dd, 1H).

Preparation 23

3-Pent-4-enoyl-oxazolidin-2-one

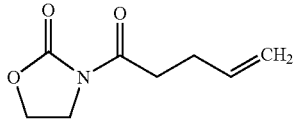

Using the method of preparation 20 and reagents oxazolidin-2-one (10.22 g, 117.3 mmol) and pent-4-enoyl chloride affords 10.62 g (53%) of the title compound as a colorless oil.

Preparation 24

3-[2-(2-Chloro-6-fluoro-benzyl)-pent-4-enoyl]-oxazolidin-2-one

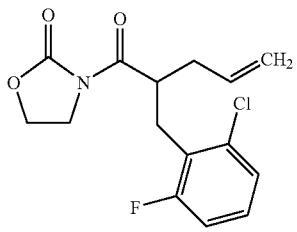

Using the procedure to synthesize Example 1, alkylation of 3-pent-4-enoyl-oxazolidin-2-one (Preparation 23) (5.0 g, 30.0 mmol) with 2-bromomethyl-1-chloro-3-fluoro-benzene affords 6.81 g (74%) of the title compound as a white solid.

Preparation 25

3-(2-Chloro-6-fluoro-benzyl)-4-oxo-4-(2-oxo-oxazolidin-3-yl)-butyraldehyde

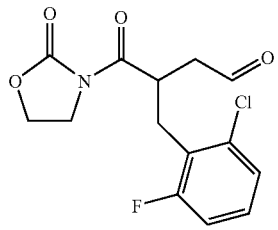

Using the method of preparation 22 and using the reagents 3-[2-(2-chloro-6-fluoro-benzyl)-pent-4-enoyl]-oxazolidin-2-one (Preparation 24) (6.81 g, 21.9 mmol) yields 4.04 g (59%) of the title compound as a colorless oil. $^1H$ NMR ($CDCl_3$) δ 9.66 (s, 1H), 7.15-7.24 (m, 2H), 6.94-7.01 (m, 1H), 4.59-4.67 (m, 1H), 4.29-4.45 (m, 2H), 3.93-4.07 (m, 2H), 3.06-3.19 (m, 3H), 2.71 (dd, 1H).

Preparation 26

Cis-4-Nitro-benzoic acid 4-[3-(2-chloro-6-fluoro-benzyl)-2-oxo-pyrrolidin-1-yl]-cyclohexyl ester

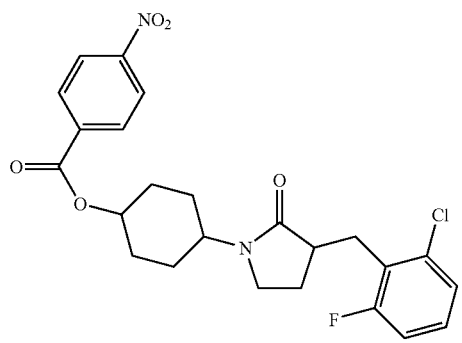

Using the method of Example 16 and using reagents 3-(2-chloro-6-fluoro-benzyl)-1-(trans-4-hydroxy-cyclohexyl)-pyrrolidin-2-one (Example 168) (0.50 g, 1.50 mmol) yields 0.73 g (100%) of the title compound as a white solid: Mass spectrum (ion spray): m/z=475.3, 477.2 (M+1).

Preparation 27

(1-Phenyl-cyclohexyl)-carbamic acid benzyl ester

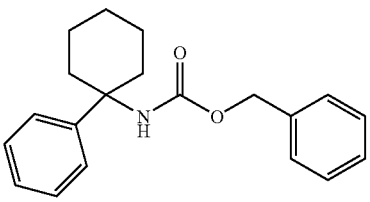

Dissolve 1-phenyl-cyclohexanecarboxylic acid (5.0 g, 24.48 mmol) in benzene (200 mL). Add triethylamine (2.45 g, 24.48 mmol), diphenylphosphoryl azide (6.74 g, 24.48 mmol), and benzyl alcohol (3.97 g, 36.72 mmol) under nitrogen. Stir and heat the reaction mixture to 80° C. Continue to heat the reaction at 80° C. for 8 hours, then cool to room temperature. Add water (250 mL), and extract the aqueous layer with ethyl acetate (3×300 mL). Combine the organic layers and dry with Na$_2$SO$_4$, filter, concentrate and purify by flash column chromatography (silica gel, 5-25% of EtOAc/Hexane) to give 2.87 g (38%) of the title compound as a colorless oil.

Preparation 28

1-Phenyl-cyclohexylamine

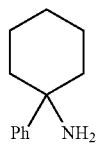

Dissolve (1-phenyl-cyclohexyl)-carbamic acid benzyl ester (Preparation 27) (2.87 g, 9.26 mmol) in MeOH (100 mL). Exchange air with nitrogen for three times and then add Pd—C (0.5 g, 10%). Exchange the nitrogen with H$_2$ for three times. Stir the reaction mixture under H$_2$ for over night then remove the Pd—C by filtration. Remove the solvent under reduced pressure to give 1.468 g (90%) of the crude title compound as a colorless oil.

Preparation 29

4-Chloro-N-(1-phenyl-cyclohexyl)-butyramide

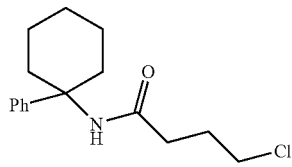

Dissolve 1-phenyl-cyclohexylamine (Preparation 28) (0.41 g, 2.32 mmol) in dichloromethane (50 mL) and cool to 0° C. Add pyridine (1.18 g, 11.61 mmol) and 4-chloro-butyryl chloride (0.65 g, 4.64 mmol). Stir the reaction mixture for one hour under nitrogen. Add water (50 mL), and extract the aqueous layer with ethyl acetate (3×100 mL). Combine the organic layers and dry with Na$_2$SO$_4$, filter, concentrate and purify by flash column chromatography (silica gel, 10-50% of EtOAc/Hexane) to give 0.58 g (89%) of the title compound as a colorless oil.

Preparation 30

1-(1-Phenyl-cyclohexyl)-pyrrolidin-2-one

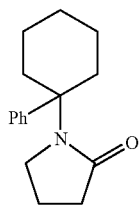

Dissolve 4-chloro-N-(1-phenyl-cyclohexyl)-butyramide (Preparation 29) (0.15 g, 0.53 mmol) in THF (20 mL) and add NaH (0.21 g, 5.29 mmol. 65% wt). Stir and heat the reaction mixture to 70° C. under nitrogen. Continue to heat the reaction at 70° C. for over night then cool it to room temperature. Add water (20 mL), and extract the aqueous layer with dichloromethane (3×50 mL). Combine the organic layers and dry with Na$_2$SO$_4$, filter, concentrate and purify by flash column chromatography (silica gel, 10-40% of EtOAc/Hexane) to give 0.16 g (89%) of the title compound as a colorless oil: Mass spectrum (ion spray): m/z=243.9 (M$^+$).

Preparation 31

Cis-1-azido-2-methyl-cyclohexane

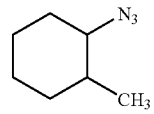

Dissolve trans-2-methyl-cyclohexanol (5.0 g, 44.0 mmol) in anhydrous THF (500 mL) and cool to −20° C. Add triphenylphosphine (57.43 g, 218.9 mmol), diethyl azodicarboxylate (38.13 g, 218.9 mmol), and diphenylphosphoryl azide (60.25 g, 218.9 mmol) respectively under nitrogen. Stir the reaction mixture for 6 hours at the same temperature then warm it to room temperature and stir overnight Add water (500 mL), and extract the aqueous layer with EtOAc (3×500 mL). Combine the organic layers and dry with Na$_2$SO$_4$, filter, concentrate and purify by flash column chromatography (silica gel, 0-25% of EtOAc/Hexane) to give 3.98 g (65%) of the title compound as a colorless oil: $^1$H NMR (CDCl$_3$) δ 3.08-3.16 (m, 1H), 1.90-1.98 (m, 1H), 1.56-1.78 (m, 3H), 1.16-1.35 (m, 4H), 1.01 (d, 3H), 0.93-1.03 (m, 1H).

Preparation 32

1-(Cis-2-methyl-cyclohexyl)-pyrrolidin-2-one

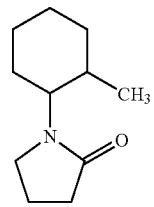

Dissolve cis-1-azido-2-methyl-cyclohexane (Preparation 31) (3.68 g, 26.41 mmol) and cyclobutanone (1.85 g, 26.41 mmol) in dichloromethane (200 mL). Cool the solution to 0° C. and add titanium chloride (15.03 g, 79.23 mmol) under nitrogen. Stir the reaction for 24 hours at room temperature. Add water (200 mL), and extract the aqueous layer with dichloromethane (3×200 mL). Combine the organic layers and dry with Na$_2$SO$_4$, filter, concentrate and purify by flash column chromatography (silica gel, 20-50% of EtOAc/Hexane) to give 1.74 g (36%) of the title compound as a colorless oil.

Preparation 33

Trans-1-azido-2-methyl-cyclohexane

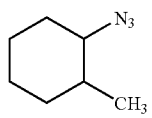

Using the method of Preparation 31 and reagent cis-2-methyl-cyclohexanol (5.0 g, 44.0 mmol) gives 4.68 g (77%) of the title compound as a white solid:.

Preparation 34

1-(Trans-2-methyl-cyclohexyl)-pyrrolidin-2-one

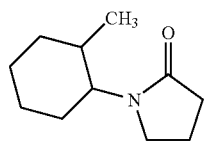

Using the method of Preparation 32 and reagent trans-1-azido-2-methyl-cyclohexane (Preparation 33) (4.68 g, 33.59 mmol) yields 0.78 g (12%) of the title compound as a colorless oil.

Preparation 35

1-(Cis-4-hydroxymethyl-cyclohexyl)-pyrrolidin-2-one

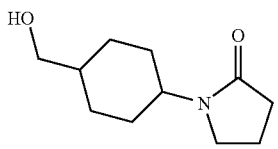

Using the method of Example 167, 4-oxo-4-(2-oxo-oxazolidin-3-yl)-butyraldehyde (Dominique Urban, Troels Skrydstrup, and Jean-Marie Beau, *J. Org. Chem.*, 1998, 63(8), 2507-2516) (4.2 g, 24.54 mmol) and (cis-4-amino-cyclohexyl)-methanol (Thomas P. Johnston, etc. *J. Med. Chem.*, 1977, 20(2), 279-290) (3.17 g, 24.54 mmol) yield 4.87 g (100%) of the title compound as a colorless oil.

Preparation 36

1-[cis-4-(tert-butyl-dimethyl-silanyloxymethyl)-cyclohexyl]-pyrrolidin-2-one

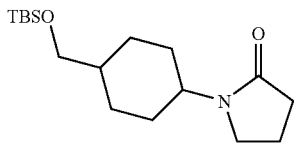

Dissolve 1-(cis-4-hydroxymethyl-cyclohexyl)-pyrrolidin-2-one (Preparation 35) (0.89 g, 4.53 mmol) in anhydrous THF (50 mL) and cool to 0° C. Add triethylamine (2.29 g, 22.65 mmol) and TBSCl (1.02 g, 6.79 mmol) under nitrogen. Stir the reaction overnight at room temperature. Then add water (50 mL) and extract the aqueous layer with dichloromethane (3×100 mL). Combine the organic layers and dry with $Na_2SO_4$, filter, concentrate and purify by flash column chromatography (silica gel, 10-40% EtOAc-Hexane) to give 1.24 g (88%) of the title compound as a colorless oil.

Preparation 37

1-[Cis-4-(tert-butyl-dimethyl-silayloxymethyl)-cyclohexyl]-3-(2,4-dichloro-benzyl)-pyrrolidin-2-one

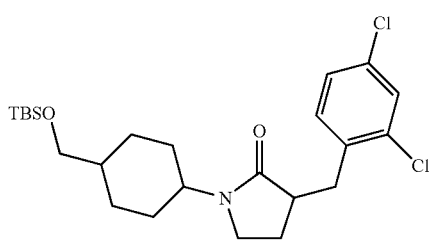

Using the procedure to synthesize Example 1 and using reagent 1-[cis-4-(tert-butyl-dimethyl-silanyloxymethyl)-cyclohexyl]-pyrrolidin-2-one (Preparation 36) (0.16 g, 0.51 mmol) yields 0.12 g (49%) of the title compound as a white solid. $^1$H NMR (CDCl$_3$) δ 7.32 (d, 1H), 7.18 (d, 1H), 7.12 (dd, 1H), 3.86-3.96 (m, 1H), 3.53 (d, 2H), 3.16-3.32 (m, 3H), 2.66-2.76 (m, 2H), 1.92-2.02 (m, 1H), 1.38-1.70 (m, 10H), 0.85 (s, 9H), 0.02 (s, 6H).

Preparation 38

3-(4-Bromo-2-chloro-benzyl)-1-[cis-4-(tert-butyl-dimethyl-silanyloxymethyl)-cyclohexyl]-pyrrolidin-2-one

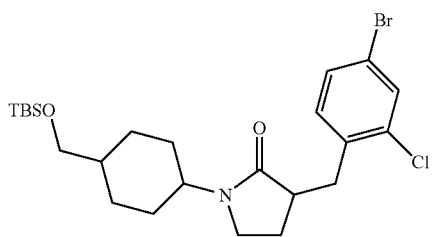

Using the procedure to synthesize Example 1 and using reagent 1-[cis-4-(tert-butyl-dimethyl-silanyloxymethyl)-cyclohexyl]-pyrrolidin-2-one (Preparation 36) (0.40 g, 1.28 mmol) affords 0.55 (83%) of the title compound as a white solid. $^1$H NMR (CDCl$_3$) δ 7.47 (d, 1H), 7.27 (dd, 1H), 7.18 (d, 1H), 3.85-3.96 (m, 1H), 3.54 (d, 2H), 3.12-3.30 (m, 3H), 2.68-2.76 (m, 2H), 1.92-2.01 (m, 1H), 1.69-1.79 (m, 3H), 1.38-1.66 (m, 7H), 0.85 (s, 9H), 0.04 (s, 6H).

Preparation 39

3-[2-(2,4-Dichloro-benzyl)-pent-4-enoyl]-oxazolidin-2-one

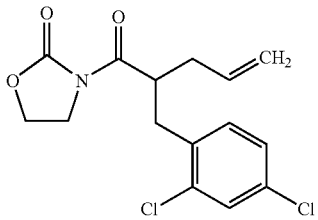

Using the procedure to synthesize Example 1 and using reagent 3-pent-4-enoyl-oxazolidin-2-one (10.0 g, 59.11 mmol) affords 8.93 g (46%) of the title compound as a colorless oil.

Preparation 40

3-(2,4-Dichloro-benzyl)-4-oxo-4-(2-oxo-oxazolidin-3-yl)-butyraldehyde

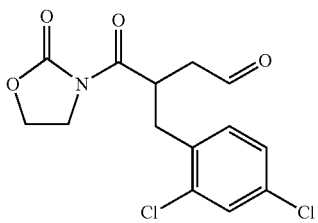

Using the method of Preparation 22 and reagent 3-[2-(2,4-dichloro-benzyl)-pent-4-enoyl]-oxazolidin-2-one (Preparation 39) (8.93 g, 27.22 mmol) affords 3.15 g (35%) of the title compound as a colorless oil. $^1$H NMR (CDCl$_3$) δ 9.67 (s, 1H), 7.38 (d, 1H), 7.34 (d, 1H), 7.20 (dd, 1H), 4.36-4.47 (m, 3H), 3.94-4.13 (m, 2H), 3.09-3.16 (m, 1H), 2.97-3.02 (m, 2H), 2.54 (dd, 1H).

Preparation 41

Trans-4-amino-1-methyl-cyclohexanol

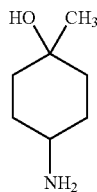

Dissolve trans-4-dibenzylamino-1-methyl-cyclohexanol (1.0 g, 3.23 mmol) in MeOH (50 mL). Exchange air with nitrogen for three times and then add Pd—C (0.4 g, 10%). Exchange the nitrogen with H$_2$ for three times. Stir the reaction mixture under 50 psi of H$_2$ overnight then remove the Pd—C by filtration. Remove the solvent under reduced pressure to give 0.42 g (100%) of the crude title compound as a colorless oil.

Preparation 42

Cis-7-methyl-1,4-dioxa-spiro[4.5]decane-8-carboxylic acid

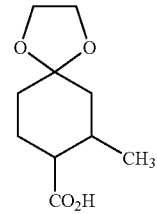

Dissolve 7-methyl-1,4-dioxa-spiro[4.5]decane-8-carboxylic acid ethyl ester (R. R. Crenshaw, etc., *J. Med. Chem.*, 1973, 16(7), 813-823) (14.09 g, 61.7 mmol) in MeOH (300 mL) and add 2M KOH (60 mL, 120 mmol, 2M in H$_2$O). Stir the reaction for overnight at room temperature, then add 1N HCl until pH=3. Remove MeOH under reduced pressure and add water (200 mL). Extract the aqueous layer with ethyl acetate (3×400 mL). Combine the organic layers and dry with Na$_2$SO$_4$, filter and concentrate to give 11.74 g (95%) of the crude title compound as a white solid

Preparation 43

(Cis-7-methyl-1,4-dioxa-spiro[4.5]dec-8-yl)-carbamic acid benzyl ester

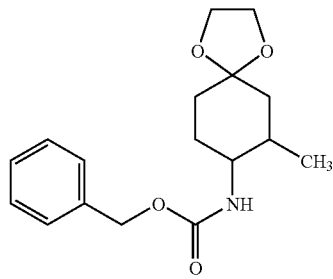

Using the method in Preparation 27 and reagent cis-7-methyl-1,4-dioxa-spiro[4.5]decane-8-carboxylic acid (Preparation 42) (11.74 g, 58.65 mmol) yields 8.26 g (46%) of the title compound as a colorless oil.

Preparation 44

Cis-7-methyl-1,4-dioxa-spiro[4.5]dec-8-ylamine

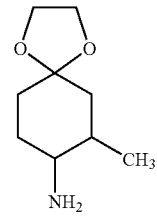

Using the method in Preparation 28 and reagent (cis-7-methyl-1,4-dioxa-spiro[4.5]dec-8-yl)-carbamic acid benzyl ester (Preparation 43) (4.33 g, 14.17 mmol) affords 2.30 g (95%) of the title compound as a colorless oil.

Preparation 45

1-(cis-7-Methyl-1,4-dioxa-spiro[4.5]dec-8-yl)-pyrrolidin-2-one

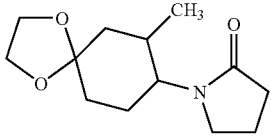

Using the method in Example 167 and reagents cis-7-methyl-1,4-dioxa-spiro[4.5]dec-8-ylamine (Preparation 44) (2.3 g, 13.4 mmol) and 4-oxo-4-(2-oxo-oxazolidin-3-yl)-butyraldehyde (2.3 g, 13.43 mmol) yields 2.49 g (77%) of the title compound as a white solid. $^1$H NMR (CDCl$_3$) δ 4.05-4.12 (m, 1H), 3.81-3.93 (m, 4H), 3.44 (t, 2H), 2.23-2.35 (m, 3H), 1.51-1.98 (m, 8H), 0.94 (d, 3H).

Preparation 46

2,6-Dichloro-3-methoxy-benzaldehyde

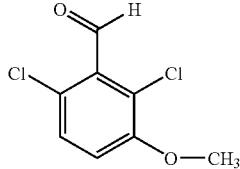

Dissolve 2,4-dichloro-phenol (30 g, 184 mmol) and cool to 0° C. Add imidazole (28 g, 405 mmol) followed by t-butyldimethylsilyl chloride (31 g, 202 mmol). Warm reaction mixture to room temperature, and stir for 20 minutes. Pour reaction mixture into water and extract with ether. Separate layers and wash organics with water, 2× brine, dry over sodium sulfate, filter and concentrate to yield 48.4 g (95%) of tert-butyl-(2,4-dichloro-phenoxy)-dimethyl-silane.

Dissolve tert-Butyl-(2,4-dichloro-phenoxy)-dimethyl-silane (48.4 g, 175 mmol) in tetrahydrofuran (575ml) and cool to −78° C. Add sec-butyl lithium (1.4M, 131 ml, 183 mmol) slowly at −78° C. and stir at −78° C. for 30 minutes. Add N,N-dimethylformamide and stir at −78° C. for 1.5 hours. Pour reaction mixture into acetic acid in water (1:12, 830 ml) and stir warming to room temperature. Extract with ether, wash with water, brine dry over sodium sulfate, filter and concentrate to yield a mixture of the title compound and TBS protected analog. Slur in hexanes and filter to yield 15 g (45%) of 2,6-dichloro-3-hydroxy-benzaldehyde.

Dissolve 2,6-dichloro-3-hydroxy-benzaldehyde (10.7 g, 56 mmol) in N,N-dimethylformamide (80 ml), add potassium carbonate (15 g, 112 mmol), cesium carbonate(18.3 g, 56 mmol), iodomethane (7 ml, 112 mmol) and stir over night at room temperature. Filter reaction mixture into water washing solids with DMF, extract filtrate with ethyl acetate wash with water, brine, dry over sodium sulfate, filter and concentrate to yield 10 g (87%) of 2,6-dichloro-3-methoxy-benzaldehyde.

Preparation 47

(2,6-Dichloro-3-methoxy-phenyl)-methanol

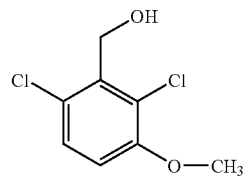

Dissolve 2,6-dichloro-3-methoxy-benzaldehyde (10 g, 48.8 mmol) in ethanol (330 ml) add sodiumborohydride (1.8 g, 48.8 mmol) and stir at room temperature over night. Partition reaction mixture between water and ethyl acetate separate layers wash organic with brine, dry over sodium sulfate, filter and concentrate to yield 9.43 g (93%) of (2,6-Dichloro-3-methoxy-phenyl)-methanol.

Preparation 48

2-Bromomethyl-1,3-dichloro-4-methoxy-benzene

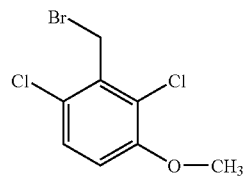

Dissolve (2,6-dichloro-3-methoxy-phenyl)-methanol (9.43 g, 45.5 mmol) in methylene chloride (180 ml) cool to 0° and add phosphorus tribromide (1.0M, 23 ml, 23 mmol) dropwise. Stir for 10 minutes at 0°, dilute with methylene chloride, quench with saturated aqueous sodium bicarbonate, separate layers, wash organic with water, brine dry over sodium sulfate, filter and concentrate to yield 7 g (57%) of the title compound: NMR (CDCl$_3$) δ 7.28 (d, 1H), 6.85 (d, 1H), 4.77 (s, 2H), 3.90 (s, 3H).

Preparation 49

5-[3-chloro-4-(1-cyclohexyl-2-oxo-pyrrolidin-3-ylmethyl)-phenyl]-pyridine-2-carbaldehyde

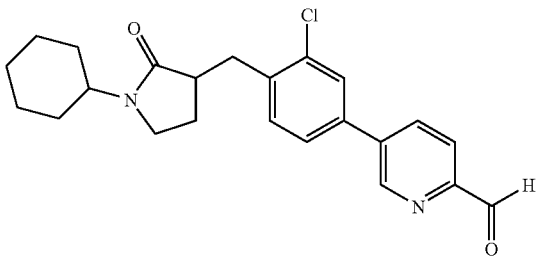

Using the procedure to synthesize Example 81 and using reagents 3-(4-boronic acid-2-chloro-benzyl)-1-cyclohexyl-pyrrolidin-2-one (Preparation 6) (500 mg, 1.5 mmol), 5-bromopicolinaldehyde (277 mg, 1.5 mmol), and palladium tetrakis (172 mg, 0.15 mmol) affords 262 mg (44%) of the title compound. $^1$H NMR (CDCl$_3$) δ 10.14 (s, 1H), 9.12 (d, 1H), 8.24 (dd, 1H), 8.13 (d, 1H), 7.88 (d, 2H), 7.45 (d, 1H), 3.96 (m, 1H), 3.44 (m, 1H), 3.22 (m, 2H), 2.87 (m, 2H), 2.05 (m, 1H), 1.79 (m, 2H), 1.70 (m, 4H), 1.37 (m, 4H), 1.10 (m, 1H).

Preparation 50

2-bromo-4-(bromomethyl)-1,3-dichlorobenzene

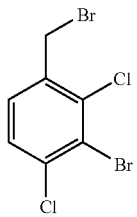

Place 2-bromo-1,3-dichloro-4-methylbenzene (50 g, 208 mmol) in carbon tetrachloride (400 mL). Add benzoyl peroxide (5 g, 20.8 mmol) and NBS (38.9 g, 219 mmol) and heat to 80° C. and stir for 16 hours. Cool reaction and filter. Dissolve in hexanes and wash with sodium bisulfate and then with sodium bicarbonate. Purify by distillation. Collect product at 135° C. under reduced pressure to give 43.5 g (65%) of 2-bromo-4-(bromomethyl)-1,3-dichlorobenzene.

Preparation 51

3-(2-Chloro-4-(pyridin-3-yl)benzyl)-1-(exo-bicyclo[2.2.1]hept-5-en-2-yl)pyrrolidin-2-one

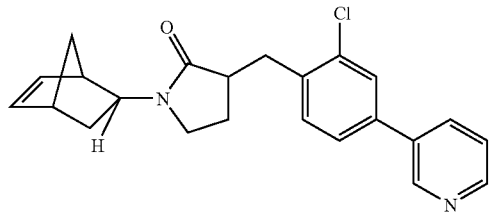

Using the procedure to synthesize Preparation 14 and using reagents γ-butyrolactone (1.1 g, 13 mmol) and exo-bicyclo[2.2.1]hept-5-en-2-amine (1.0 g, 9.2 mmol) affords 770 mg (47%) of 1-(exo-bicyclo[2.2.1]hept-5-en-2-yl)pyrrolidin-2-one. Using the procedure to synthesize Example 1 and using reagents 1-(exo-bicyclo[2.2.1]hept-5-en-2-yl)pyrrolidin-2-one (770 mg, 4.3 mmol), LDA (2.0 M, 2.6 mL, 5.2 mmol) and 4-bromo-1-bromomethyl-2-chloro-benzene (preparation 5) (1.5 g, 5.2 mmol) affords 1.1 g (67%) of 3-(4-Bromo-2-chlorobenzyl)-1-(exo-bicyclo[2.2.1]hept-5-en-2-yl)pyrrolidin-2-one as a clear and colorless oil. Mass spectrum (apci) m/z=382.2 (M+H). Using the procedure to synthesize Example 81 and using reagents 3-(4-bromo-2-chlorobenzyl)-1-(exo-bicyclo[2.2.1]hept-5-en-2-yl)pyrrolidin-2-one (1.1 g, 2.9 mmol) and 3-pyridylboronic acid (1.1 g, 8.7 mmol) affords 800 mg (73%) of the title compound:

Mass spectrum (apci) m/z=379.2 (M+H).

Preparation 52

1-Cyclohexyl-3-(3,5-dichloro-4'-hydroxy-biphenyl-4-ylmethyl)-pyrrolidin-2-one

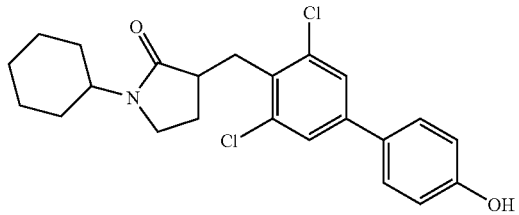

Using the procedure to synthesize Example 81 and using reagents 3,5-dichloro-4-((1-cyclohexyl-2-oxopyrrolidin-3-yl)methyl)phenyl trifluoromethanesulfonate (Example 240) (750 mg, 1.58 mmol) and 4-hydroxyphenylboronic acid (650 mg, 4.7 mmol) affords 600 mg (91%) of the title compound: Mass spectrum (apci) m/z=418.2 (M+H—HCl).

Preparation 53

1-Cyclohexyl-3-(3,5-dichloro-2',6'-difluoro-4'-hydroxy-biphenyl-4-ylmethyl)-pyrrolidin-2-one

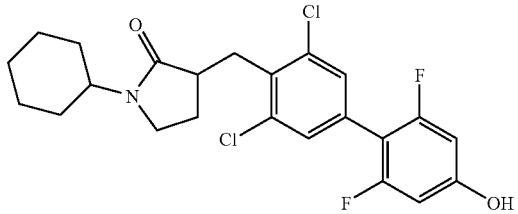

Using the procedure to synthesize Example 81 and using reagents 3,5-dichloro-4-((1-cyclohexyl-2-oxopyrrolidin-3-yl)methyl)phenyl trifluoromethanesulfonate (Example 240) (500 mg, 1.0 mmol) and 2,6-difluoro-4-methoxyphenylboronic acid (590 mg, 3.2 mmol) affords 494 mg (100%) of 1-Cyclohexyl-3-(3,5-dichloro-2',6'-difluoro-4'-methoxy-biphenyl-4-ylmethyl)-pyrrolidin-2-one. Charge a flask with 1-cyclohexyl-3-(3,5-dichloro-2',6'-difluoro-4'-methoxy-biphenyl-4-ylmethyl)-pyrrolidin-2-one (500 mg, 1.1 mmol), dissolve in dry methylene chloride (10 mL) and cool to 0° C. under nitrogen. Add BBr₃ (0.25 mL, 2.7 mmol) and stir at 0° C. for 1.5 hours. Pour into saturated aqueous sodium bicarbonate and extract with methylene chloride. Dry over sodium sulfate, filter and concentrate in vacuo to yield 470 mg (97%) of the title compound.

Preparation 54

1-Adamantan-2-yl-3-(3-chloro-4'-hydroxy-biphenyl-4-ylmethyl)-pyrrolidin-2-one

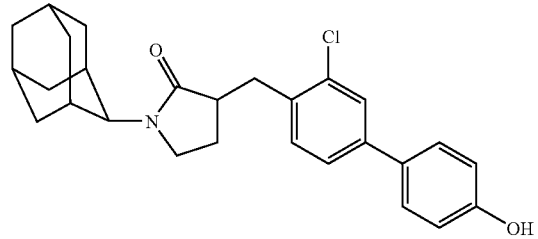

Using the procedure to synthesize Example 81 and using reagents 1-adamantan-2-yl-3-(4-bromo-2-chloro-benzyl)-pyrrolidin-2-one (Example 76) (1.0 g, 2.4 mmol) and 4-hydroxyphenylboronic acid (980 mg, 7.1 mmol) affords 740 mg (72%) of the title compound: Mass spectrum (apci) m/z=436.2 (M+H).

Preparation 55

3-(2,4-Dichloro-benzyl)-1-[cis-3,5-dimethyl-cis-4-(tetrahydro-pyran-2-yloxy)-cyclohexyl]-pyrrolidin-2-one

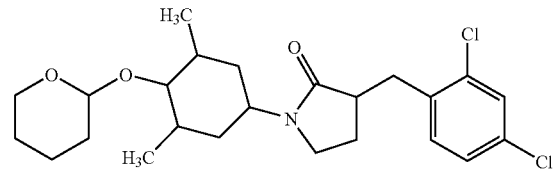

Dissolve cis-3,5-dimethyl-cis-4-(tetrahydro-pyran-2-yloxy)-cyclohexanol (3.07 g, 8.96 mmol) (*Tetrahedron Lett.*, 1989, 30(9), 1029-1032) in THF (150 mL) and cool the solution to −20° C. Add PPh₃ (11.75 g, 44.8 mmol), 4-nitrobenzoic acid (7.49 g, 44.8 mmol), and diethyl azodicarboxylate (7.8 g, 44.8 mmol). Stir the reaction mixture for 6 hours at the same temperature, and then warm the reaction to room temperature. Continue to stir the reaction overnight. Add water (150 mL), and extract the aqueous layer with dichloromethane (3×200 mL). Combine the organic layers and dry with $Na_2SO_4$, filter, concentrate and purify by flash column chromatography (silica gel, 10-30% of EtOAc/Hexane) to give 2.13 g of the impure compound.

Dissolve the impure product (2.13 g, 5.65 mmol) in MeOH (100 mL). Add 2 M $K_2CO_3$ (20 mL). Stir the reaction mixture overnight at room temperature. Add water (100 mL), and extract the aqueous layer with EtOAc (3×300 mL). Combine the organic layers and dry with $Na_2SO_4$, filter, concentrate and purify by flash column chromatography (silica gel, 30-50% of EtOAc/Hexane) to give trans-3,5-Dimethyl-trans-4-(tetrahydro-pyran-2-yloxy)-cyclohexanol.

Dissolve trans-3,5-Dimethyl-trans-4-(tetrahydro-pyran-2-yloxy)-cyclohexanol (1.05 g, 4.59 mmol) in THF (80 mL) and cool the solution to −20° C. Add $PPh_3$ (6.02 g, 22.95 mmol), diphenylphosphoryl azide (6.32 g, 22.95 mmol), and diethyl azodicarboxylate (4.0 g, 22.95 mmol). Stir the reaction mixture for 6 hours at the same temperature, and then warm the reaction to room temperature. Continue to stir the reaction overnight. Add water (100 mL), and extract the aqueous layer with dichloromethane (3×200 mL). Combine the organic layers and dry with $Na_2SO_4$, filter, concentrate and purify by flash column chromatography (silica gel, 10-30% of EtOAc/Hexane) to give 2-(cis-4-Azido-cis-2,6-dimethyl-cyclohexyloxy)-tetrahydro-pyran.

Dissolve 2-(cis-4-azido-cis-2,6-dimethyl-cyclohexyloxy)-tetrahydro-pyran (0.63 g, 2.47 mmol) in MeOH (150 mL). Add Pd—C (0.29 g, 5%) under $N_2$. Stir the reaction mixture overnight under $H_2$. Filter to remove Pd—C, and then concentrate to give cis-3,5-Dimethyl-cis-4-(tetrahydro-pyran-2-yloxy)-cyclohexylamine.

Dissolve 3-(2,4-dichloro-benzyl)-4-oxo-4-(2-oxo-oxazolidin-3-yl)-butyraldehyde (0.18 g, 0.53 mmol) in 1,2-dichloroethane (20 mL). Add cis-3,5-Dimethyl-cis-4-(tetrahydro-pyran-2-yloxy)-cyclohexylamine (0.18 g, 0.80 mmol) and sodium acetoxyborohydride (0.22 g, 1.06 mmol). Stir the mixture at room temperature for 48 hours under nitrogen. Add water (20 mL), and extract the aqueous layer with dichloromethane (3×50 mL). Combine the organic layers and dry with $Na_2SO_4$, filter, concentrate and purify by flash column chromatography (silica gel, 20-50% of EtOAc/Hexane) to give the title compound as a white solid (0.15 g, 61%). $^1$H NMR (CDCl$_3$) δ 7.36 (d, 1H), 7.22 (d, 1H), 7.16 (dd, 1H), 4.46 (m, 1H), 3.94-4.10 (m, 2H), 3.45 (m, 2H), 3.16-3.34 (m, 3H), 2.78 (m, 2H), 2.01 (m, 1H), 1.41-1.83 (m, 11H), 1.25-1.34 (m, 2H), 1.02 (dd, 3H), 0.94 (dd, 3H).

Preparation 56 cis-4-Amino-cis-2-methyl-cyclohexanol

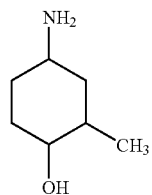

Dissolve 7-methyl-1,4-dioxa-spiro[4.5]decan-8-one (11.45 g, 67.28 mmol) in THF (300 mL) and cool the solution to 0° C. under $N_2$. Add super-hydride (74.0 mL, 74.0 mmol, 1 M in THF) and stir the reaction mixture overnight. Add water (200 mL), and extract the aqueous layer with dichloromethane (3×300 mL). Combine the organic layers and dry with $Na_2SO_4$, filter, concentrate and purify by flash column chromatography (silica gel, 30-50% of EtOAc/Hexane) to give cis-7-Methyl-1,4-dioxa-spiro[4.5]decan-8-ol.

Dissolve cis-7-methyl-1,4-dioxa-spiro[4.5]decan-8-ol (3.82 g, 22.25 mmol) in THF (200 mL) and cool the solution to 0° C. under $N_2$. Add NaH (0.89 g, 22.25 mmol, 60% wt) and stir the reaction mixture for one hour. Add BnBr (3.81 g, 22.25 mmol) and continue to stir the reaction mixture overnight. Add water (200 mL), and extract the aqueous layer with dichloromethane (3×300 mL). Combine the organic layers and dry with $Na_2SO_4$, filter, concentrate and purify by flash column chromatography (silica gel, 10-30% of EtOAc/Hexane) to give cis-8-benzyloxy-cis-7-methyl-1,4-dioxa-spiro[4.5]decane as an oil (5.80 g, 99%).

Dissolve cis-8-benzyloxy-cis-7-methyl-1,4-dioxa-spiro[4.5]decane (5.8 g, 22.1 mmol) in MeOH (200 mL) and add $TsOH.H_2O$ (3.81 g, 22.1 mmol) under $N_2$. Stir the reaction mixture overnight. Add water (200 mL), and extract the aqueous layer with dichloromethane (4×400 mL). Combine the organic layers and dry with $Na_2SO_4$, filter, concentrate and purify by flash column chromatography (silica gel, 10-30% of EtOAc/Hexane) to give cis-4-benzyloxy-cis-3-methyl-cyclohexanone as a white solid (4.0 g, 83%).

Dissolve cis-4-benzyloxy-cis-3-methyl-cyclohexanone (3.77 g, 17.26 mmol) in MeOH (150 mL) and cool the solution to 0° C. under $N_2$. Add $NaBH_4$ (0.72 g, 19.0 mmol) and stir the reaction mixture for two hours. Add water (100 mL), and extract the aqueous layer with dichloromethane (3×400 mL). Combine the organic layers and dry with $Na_2SO_4$, filter, concentrate and purify by flash column chromatography (silica gel, 30-50% of EtOAc/Hexane) to give cis-4-benzyloxy-cis-3-methyl-cyclohexanol as a white solid (3.8 g, 99%).

Dissolve cis-4-Benzyloxy-cis-3-methyl-cyclohexanol (3.8 g, 17.2 mmol) in THF (300 mL) and cool the solution to −20° C. Add $PPh_3$ (22.61 g, 86.2 mmol), 4-nitro-benzoic acid (14.41 g, 86.2 mmol), and diethyl azodicarboxylate (15.01 g, 86.2 mmol). Stir the reaction mixture for 6 hours at the same temperature, and then warm the reaction to room temperature. Continue to stir the reaction overnight. Add water (300 mL), and extract the aqueous layer with dichloromethane (3×500 mL). Combine the organic layers and dry with $Na_2SO_4$, filter, concentrate and purify by flash column chromatography (silica gel, 10-30% of EtOAc/Hexane) to 4-nitro-benzoic acid trans-4-benzyloxy-trans-3-methyl-cyclohexyl ester as a white solid (3.52 g, 55%).

Dissolve 4-nitro-benzoic acid trans-4-benzyloxy-trans-3-methyl-cyclohexyl ester (3.52 g, 9.54 mmol) in MeOH (50 mL). Add 2 N KOH (20 mL). Stir the reaction mixture overnight at room temperature. Add water (50 mL), and extract the aqueous layer with EtOAc (3×100 mL). Combine the organic layers and dry with $Na_2SO_4$, filter, concentrate and purify by flash column chromatography (silica gel, 30-50% of EtOAc/Hexane) to give trans-4-Benzyloxy-trans-3-methyl-cyclohexanol as a colorless oil (1.86 g, 88%).

Dissolve trans-4-benzyloxy-trans-3-methyl-cyclohexanol (1.86 g, 8.43 mmol) in THF (200 mL) and cool the solution to −20° C. Add $PPh_3$ (11.5 g, 42.12 mmol), diphenylphosphoryl azide (11.59 g, 42.12 mmol), and diethyl azodicarboxylate (7.34 g, 42.12 mmol). Stir the reaction mixture for 6 hours at the same temperature, and then warm the reaction to room temperature. Continue to stir the reaction overnight. Add water (200 mL), and extract the aqueous layer with dichloromethane (3×300 mL). Combine the organic layers and dry with $Na_2SO_4$, filter, concentrate and purify by flash column chromatography (silica gel, 10-30% of EtOAc/Hexane) to give (cis-4-azido-cis-2-methyl-cyclohexyloxymethyl)-benzene as a colorless oil (1.42 g, 68.5%).

Dissolve (cis-4-azido-cis-2-methyl-cyclohexyloxymethyl)-benzene (1.42 g, 5.77 mmol) in MeOH (150 mL). Add Pd—C (0.27 g, 10%) under $N_2$. Set up the reaction on Parr shaker and hydrogenate at 60 psi under $H_2$ overnight. Filter to remove Pd—C, and then concentrate to give the crude cis-4-benzyloxy-cis-3-methyl-cyclohexylamine as a colorless oil (1.01 g, 80%).

Dissolve cis-4-benzyloxy-cis-3-methyl-cyclohexylamine (0.43 g, 1.94 mmol) in MeOH (50 mL). Add 1N HCl (5 mL) and Pd—C (0.23 g, 10%) under $N_2$. Set up the reaction on Parr shaker and hydrogenate at 60 psi under $H_2$ overnight. Filter to remove Pd—C, and then concentrate to remove all of the solvent to give crude product (0.25 g, 99%) as colorless oil. $^1H$ NMR ($CD_3OD$) δ 3.73 (m, 1H), 3.13 (m, 1H), 1.93 (m, 1H), 1.42-1.96 (m, 6H), 1.01 (d, 3H).

Preparation 57

4-(3-(2,4-Dichlorobenzyl)-2-oxopyrrolidin-1-yl)-4-methylcyclohexyl 4-nitrobenzoate

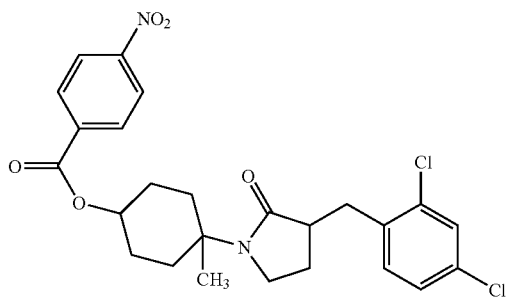

Dissolve 8-methyl-1,4-dioxa-spiro[4.5]decane-8-carboxylic acid (Chem. Pharm. Bull., 1984, 32(6), 2267-2278) (10.9 g, 54.4 mmol) in benzene (500 mL). Add triethylamine (6.61 g, 65.32 mmol), diphenylphosphoryl azide (16.48 g, 59.88 mmol), and benzyl alcohol (8.83 g, 81.66 mmol) under nitrogen. Stir and heat the reaction mixture to 80° C. Continue to heat the reaction at 80° C. for 8 hours, then cool to room temperature. Add water (500 mL), and extract the aqueous layer with ethyl acetate (3×500 mL). Combine the organic layers and dry with $Na_2SO_4$, filter, concentrate and purify by flash column chromatography (silica gel, 5-25% of EtOAc/Hexane) to give 13.45 g (81%) of (8-Methyl-1,4-dioxa-spiro[4.5]dec-8-yl)-carbamic acid benzyl ester as a colorless oil.

Dissolve (8-methyl-1,4-dioxa-spiro[4.5]dec-8-yl)-carbamic acid benzyl ester (13.12 g, 43.0 mmol) in MeOH (400 mL). Exchange air with nitrogen for three times and then add Pd—C (1.0 g, 10%). Exchange the nitrogen with $H_2$ for three times. Stir the reaction mixture under $H_2$ for over night then remove the Pd—C by filtration. Remove the solvent under reduced pressure to give 7.36 g (100%) of the crude 8-Methyl-1,4-dioxa-spiro[4.5]dec-8-ylamine as a colorless oil.

Dissolve 4-oxo-4-(2-oxo-oxazolidin-3-yl)-butyraldehyde (7.35 g, 42.96 mmol) in DCE (400 mL). Add 8-methyl-1,4-dioxa-spiro[4.5]dec-8-ylamine (7.36 g, 42.96 mmol), and acetic acid (2.58 g, 42.96 mmol) at room temperature under nitrogen. Stir the solution for one hour and then add sodium triacetoxyborohydride (18.21 g, 85.92 mmol). Stir the reaction mixture for over night and then add water (400 mL). Extract the aqueous layer with dichloromethane (3×400 mL). Combine the organic layers and dry with $Na_2SO_4$, filter, concentrate and purify by flash column chromatography (silica gel, 20-50% of EtOAc-Hexane) to give 0.92 g (9.0%) of 1-(8-Methyl-1,4-dioxa-spiro[4.5]dec-8-yl)-pyrrolidin-2-one as a colorless oil.

Using the procedure to synthesize Example 1 and using reagent 1-(8-methyl-1,4-dioxa-spiro[4.5]dec-8-yl)-pyrrolidin-2-one (0.92 g, 3.86 mmol) yields 1.33 g (87%) of 3-(2,4-Dichloro-benzyl)-1-(8-methyl-1,4-dioxa-spiro[4.5]dec-8-yl)-pyrrolidin-2-one as a white solid.

Dissolve 3-(2,4-dichloro-benzyl)-1-(8-methyl-1,4-dioxa-spiro[4.5]dec-8-yl)-pyrrolidin-2-one (1.33 g, 3.35 mmol) in acetone (100 mL) and add TsOH (0.58 g, 3.35 mmol). Stir the reaction at room temperature for 24 hours until the starting material has been gone. Add saturated $NaHCO_3$ (100 mL) and extract the aqueous layer with ethyl acetate (3×200 mL). Combine the organic layers and dry with $Na_2SO_4$, filter and concentrate to give 1.08 g (91%) of 3-(2,4-Dichlorobenzyl)-1-(1-methyl-4-oxocyclohexyl)pyrrolidin-2-one as a white solid.

Dissolve 3-(2,4-dichlorobenzyl)-1-(1-methyl-4-oxocyclohexyl)pyrrolidin-2-one (0.50 g, 1.41 mmol) in THF (20 mL) and cool to −78° C. under nitrogen. Add L-selectride (1.55 mL, 1.55 mmol, 1.0 M in THF) and stir the reaction at the same temperature for five hours. Warm the reaction to room temperature and add water (20 mL). Extract the aqueous layer with ethyl acetate (3×50 mL). Combine the organic layers and dry with $Na_2SO_4$, filter, and concentrate to give 0.50 g (99%) of the crude 3-(2,4-Dichlorobenzyl)-1-(4-hydroxy-1-methylcyclohexyl)pyrrolidin-2-one as colorless oil.

Dissolve 3-(2,4-dichlorobenzyl)-1-(4-hydroxy-1-methylcyclohexyl)pyrrolidin-2-one (0.50 g, 0.51 mmol) in DCM (100 mL) and cool the solution to 0° C. under $N_2$. Add $Et_3N$ (0.71 g, 7.06 mmol) and 4-nitrobenzoyl chloride (0.52 g, 2.82 mmol) and stir the reaction overnight at room temperature. Add water (100 mL) and extract the aqueous with EtOAc (3×100 mL). Combine the organic layers and dry with $Na_2SO_4$, filter, concentrate and purify by flash column chromatography (silica gel, 20-60% of EtOAc/Hexane) to give 0.38 g (54%) of the title compound as a white solid. $^1H$ NMR ($CDCl_3$) δ 8.25 (m, 2H), 8.16 (m, 2H), 7.38 (d, 1H), 7.20 (d, 1H), 7.16 (dd, 1H), 5.18 (m, 1H), 3.25 (m, 3H), 2.65 (m, 2H), 2.42 (m, 1H), 2.19 (m, 1H), 1.95 (m, 1H), 1.80 (m, 6H), 1.62 (m, 1H), 1.28 (s, 3H).

Preparation 58

3,5-Dichloro-4-((1-(cis-2-methylcyclohexyl)-2-oxopyrrolidin-3-yl)methyl)phenyl trifluoromethanesulfonate

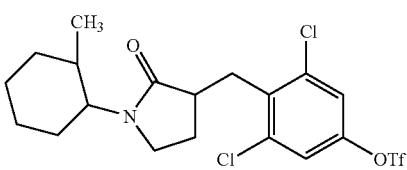

Dissolve 3-(2,6-dichloro-4-hydroxybenzyl)-1-(cis-2-methylcyclohexyl)pyrrolidin-2-one (1.0 g, 2.81 mmol) in DCM (100 mL) and cool to 0° C. under $N_2$. Add DMAP (0.069 g, 0.56 mmol), Et₃N (2.84 g, 28.01 mmol), and Tf₂O (0.83 g, 2.95 mmol) at the same temperature. Stir the reaction for six hour and then add water (100 mL). Extract the aqueous layer with dichloromethane (3×100 mL). Combine the organic layers and dry with Na₂SO₄, filter, concentrate and purify by flash column chromatography (silica gel, 20-50% of EtOAc-Hexane) to give 1.2 g (88%) of the title compound as a colorless oil. ¹H NMR (CDCl₃) δ 7.28 (s, 2H), 4.02 (m, 1H), 3.46 (m, 2H), 3.38 (m, 1H), 3.02 (m, 1H), 2.91 (m, 1H), 2.35 (m, 1H), 2.02 (m, 1H), 1.31-1.87 (m, 9H), 0.92 (d, 3H).

Preparation 59

1-(1-Methylcyclohexyl)pyrrolidin-2-one

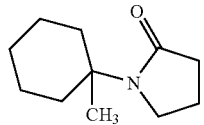

Dissolve 1-methylcyclohexanamine (0.78 g, 6.89 mmol) in anhydrous THF (100 mL) and cool to 0° C. Add Et₃N (3.49 g, 34.45 mmol) and 4-chlorobutanoyl chloride (1.94 g, 13.78 mmol) with stirring under N₂. Stir the reaction mixture for 2 hours at room temperature and add water (100 mL). Extract the aqueous with EtOAc (3×200 mL) and then combine the organic layers and dry with Na₂SO₄, filter, concentrate and purify by flash column chromatography (silica gel, 30-80% of EtOAc-Hexane) to give 1.35 g (90%) of 4-chloro-N-(1-methylcyclohexyl)butanamide as a colorless oil.

Dissolve 4-chloro-N-(1-methylcyclohexyl)butanamide (1.35 g, 6.20 mmol) in anhydrous THF (100 mL) and add NaH (1.24 g, 31.00 mmol, 60% wt in oil). Heat and stir the reaction mixture at 60° C. overnight then cool it to room temperature. Add water (50 mL) carefully and extract the aqueous with EtOAc (3×200 mL). Combine the organic layers and dry with Na₂SO₄, filter, concentrate and purify by flash column chromatography (silica gel, 20-70% of EtOAc-Hexane) to give 0.64 g (57%) of the title compound as a colorless oil. ¹H NMR (CDCl₃) δ 3.41 (t, 2H), 2.34 (t, 2H), 2.26 (m, 2H), 1.92 (m, 2H), 1.32-1.56 (m, 8H), 1.26 (s, 3H).

Preparation 60

1-cyclohexylpiperidin-2-one

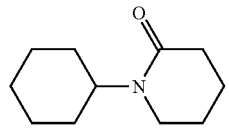

Add 1,1'-carbonylimidazole (12 g, 76 mmol) into a solution of 5-chloropentanoic acid (9.4 g, 69 mmol) in THF (200 nL) and stir at room temp for 10 minutes. Add cyclohexylamine (7.9 ml, 69 mmol) and stir for 12 hours. Dilute the reaction mixture with ethyl acetate and wash the organic layer with 2M HCl. Dry the organic layer with sodium sulfate, filter and concentrated to 5-chloro-N-cyclohexylpentanamide (15 g, 100%) as a white solid.

Add NaH (550 g, 14 mmol) into a solution of 5-chloro-N-cyclohexylpentanamide (3 g, 14 mmol) in acetonitrile (100 mL). Stir the reaction at room temperature for 12 hours. Add NaH (1 g, 28 mmol) and continue to stir for 2 days. Pour the reaction into ice and water. Wash the reaction with brine, dry with sodium sulfate, filter and concentrate. Purify the residue by column chromatography to afford the title compound (1.5 g, 60%) as a white solid. ¹H NMR (CDCl₃): 4.44-4.54 (m, 1H), 3.14 (m, 2H), 2.36-2.42 (m, 2H), 1.70-1.84 (m, 6H), 1.60-1.70 (m, 4H), 1.32-1.48 (m, 4H), 1.00-1.12 (m, 1H).

Preparation 61

3-(2,4-Dichloro-phenyl)-3-methyl-2-(2-oxo-ethyl)-butyric acid ethyl ester

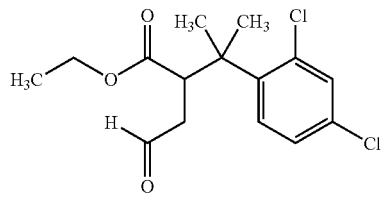

Step 1. Dissolve 1.0 equivalent of (Diethoxy-phosphoryl)-acetic acid ethyl ester in THF, cool to 0° C. and treat with 2.3 equivalents of LiHMDS. Allow reaction to stir for 1 hour, and treat resulting anion with 2.2 equivalents of 1-(2,4-Dichloro-phenyl)-ethanone. Warm reaction to room temperature and stir for 72 h, quench with sodium bicarbonate (sat), dilute with diethyl ether, wash with brine, dry over sodium sulfate, filter and evaporate to a thick oil. Chromatography (silica, 2% EtOAc in hexanes) yields the first eluting olefin isomer 3-(2, 4-Dichloro-phenyl)-but-2-enoic acid ethyl ester in 36% yield.

Step 2. To a cooled (0° C.) suspension of CuI (2.0 eq) in diethyl ether, add MeLi (4.0 eq) and stir for 1 hour. The diethyl ether is removed under reduced pressure and replaced with methylene chloride followed by cooling to −78° C. Add TMS—Cl (2.0 eq) followed by 1-(2,4-Dichloro-phenyl)-ethanone (obtained in Step 1) and warm to room temperature. Quench reaction with a 1:1 mixture of NH₄Cl (sat)/NH₄OH (28%), separate, wash organics with brine, dry over sodium sulfate, filter and evaporate. Chromatography (silica, 2% EtOAc in hexanes) provides 47% of 3-(2,4-Dichloro-phenyl)-3-methyl-butyric acid ethyl ester.

Step 3. Cool a THF solution of 1.0 equivalent of 3-(2,4-Dichloro-phenyl)-3-methyl-butyric acid ethyl ester, obtained above, to −78° C., treat with LDA (2.0 eq), followed by allyl bromide (1.1 eq), warm to room temperature and stir 17 h. Quench reaction with NH₄Cl, dilute with diethyl ether, wash organics with 0.1 N HCl, brine, dry over sodium sulfate, filter and evaporate. Chromatography, (silica, hexanes/EtOAc, 98:2) provides 2-[1-(2,4-dichloro-phenyl)-1-methyl-ethyl]-pent-4-enoic acid ethyl ester in 52% yield.

Step 4. Treat a stirred solution of 2-[1-(2,4-dichloro-phenyl)-1-methyl-ethyl]-pent-4-enoic acid ethyl ester, obtained above, in THF/water (3:1) with OsO₄ (0.1 eq) at room temperature. In 15 minutes, add NaIO₄ (3.0 eq) in portions, and stir an additional 45 minutes. Dilute reaction mixture with diethyl ether/water, back-extract aqueous layer with ether, combine organics, dry over sodium sulfate, filter and evaporate to yield 3-(2,4-Dichloro-phenyl)-3-methyl-2-(2-oxo-ethyl)-butyric acid ethyl ester. This material is used without purification.

Preparation 62

2-Bromomethyl-1,3-dichloro-5-methoxy-benzene

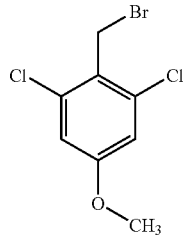

Using the procedure to synthesize Preparation 48 and using reagent 3,5-Dichlorophenol affords the title compound: NMR (CDCl$_3$) δ 6.88 (s, 2H), 4.73 (s, 2H), 3.79 (s, 3H).

Preparation 63

1-Cyclohexyl-piperidin-2-one

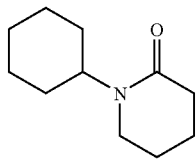

Dissolve cyclohexylamine (8.86 mL, 77.5 mmol) in dichloromethane (700 mL), cool to 0° C. and add 5-chloro-pentanoyl chloride (10 mL, 77.5 mmol). After 6 h, wash the mixture with 1N HCl and saturated aqueous sodium bicarbonate and brine, dry the organic layer over sodium sulfate and evaporate to a white solid to obtain 5-chloro-pentanoic acid cyclohexylamide: MS (EI) m/z=217 (M+).

Take up the 5-chloro-pentanoic acid cyclohexylamide in THF (700 mL), add sodium hydride (31 g, 60% dispersion on mineral oil, 775 mmol) and heat at 70° C. 19 h. Cool the mixture, filter through a fritted funnel, wash the filtrate with brine, dry the organic layer over sodium sulfate and evaporate. Purify the residue by column chromatography on silica gel (eluting 50% to 100% ethyl acetate) to obtain 1-cyclohexyl-piperidin-2-one as a beige solid (8.8 g, 63%). MS (EI) m/z=181 (M+).

Preparation 64

Trans-1-[4-(tert-butyl-dimethyl-silaniloxy)-cyclohexyl]-piperidin-2-one

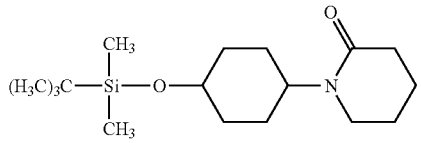

Combine trans-cyclohexylamine hydrochloride (14.0 g, 92.3 mmol), sodium carbonate (19.6 g, 0.185 mol), DCM (50 mL), water (50 mL) and stir for 5 minutes at room temperature. Add benzoyl chloroformate (15.6 mL, 111 mmol) dropwise to the reaction mixture and stir at room temperature for 2 hours. Separate the organic layer, wash with water (3×50 mL) and dry over anhydrous Na$_2$SO$_4$. Evaporate the solvent to obtain trans-(4-hydroxy-cyclohexyl)-carbamic acid benzyl ester as a white solid (22.7 g, 99%).

Combine trans-(4-hydroxy-cyclohexyl)-carbamic acid benzyl ester (16.0 g, 0.064 mol), immidazol (13.9 g, 0.10 mol), and anhydrous THF (300 mL), add tert-butyldimethylsilyl chloride (14.5 g, 0.10 mol) and stir at room temperature for 18 hours. Wash the reaction mixture with water (250 mL), saturated aqueous NaHCO$_3$ (250 mL) and dry the organic layer over anhydrous Na$_2$SO$_4$. Remove the solvent and purify the residue by chromatography over silica gel (eluting with 0 to 30% EtOAc in hexane) to obtain trans-[4-(tert-butyl-dimethyl-silanyloxy)-cyclohexyl]-carbamic acid benzyl ester as clear oil (23.0 g, 98%).

Combine trans-[4-(tert-butyl-dimethyl-silanyloxy)-cyclohexyl]-carbamic acid benzyl ester (23.0 g, 0.06 mol), palladium, 10% wt. on activated carbon (0.5 g), in EtOAc (100 mL) and charge the flask with hydrogen (50 psi). After 3 hours, filter the reaction mixture through a pad of Celite® and evaporate the solvent to obtain trans-4-(tert-butyl-dimethyl-silanyloxy)-cyclohexylamine as a dark oil (14.4 g, 99%): MS (EI) m/z=229 (M+).

Combine 5-chlorovaleric acid (19.7 g, 0.16 mol), thionyl chloride (20 mL) and reflux for 3 hours. Remove unreacted thionyl chloride by evaporation with toluene (3×10 mL) to obtain 5-chloro-pentanoyl chloride as a clear oil (24.1 g, 97%). Combine trans-4-(tert-butyl-dimethyl-silanyloxy)-cyclohexylamine (17.7 g, 0.08 mol), and anhydrous pyridine (10.9 mL, 0.23 mol) in anhydrous DCM (100 mL) and cool to 0° C. Add 5-chloro-pentanoyl chloride (14.2 g, 0.09 mol) dropwise to the reaction mixture and stir at room temperature for 1 hour. Partition the reaction mixture between brine and EtOAc. Dry the organic layer over Na$_2$SO$_4$, evaporate the solvent and purify the residue by chromatography over silica gel (eluting with 0 to 30% EtOAc in hexane) to obtain trans-5-chloro-pentanoic acid-[4-tert-butyl-dimethyl-silanyloxy)-cyclohexyl]-amide the desired intermediate as a colorless oil (22.7 g, 85%): MS (ES+) m/z=349 (M+H)$^+$.

Dissolve trans-5-chloro-pentanoic acid-[4-(tert-butyl-dimethyl-silanyloxy)-cyclohexyl]-amide (22.7 g, 65.1 mmol) in anhydrous THF (500 mL), add sodium hydride (60% dispersion in mineral oil, 13.0 g, 0.32 mol) by portions and heat the reaction mixture at 70° C. for 18 hours. Cool the reaction mixture to room temperature, quench with water (200 mL) and extract with DCM (3×100 mL). Dry the organic layer over anhydrous Na$_2$SO$_4$, remove the solvent and purify the residue by chromatography over silica gel (eluting with 0 to 50% EtOAc in hexane) to obtain trans-1-(4-[tert-butyl-dimethyl-silanyloxy)-cyclohexyl]-piperidin-2-one as a white solid (15.0 g, 74%): MS (ES+) m/z=312 (M+H)$^+$.

Preparation 65

Trans-3-(4-bromo-2-chloro-benzyl)-1-[4-(tert-butyl-dimethyl-silanyloxy)-cyclohexyl]-piperidin-2-one

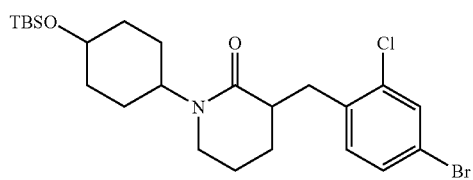

Dissolve trans-1-(4-[tert-butyl-dimethyl-silanyloxy)-cyclohexyl]-piperedin-2-one (Preparation 64) (0.3 g, 0.96 mmol) in anhydrous THF (6 mL) under nitrogen, cool to −78° C. and add LDA (2M solution in THF, 0.72 mL, 1.44 mmol) dropwise. Stir the reaction mixture for 5 minutes and add 4-bromo-1-bromomethyl-2-chloro-benzene (0.4 g, 1.44 mmol) in anhydrous THF (2 mL) dropwise. Stir the reaction mixture at −78° C. for 3 hours, slowly warm to room temperature, quench with saturated aqueous NH$_4$Cl (5 mL) and extract with DCM (3×5 mL). Dry the organic layer over Na$_2$SO$_4$, remove the solvent and purify the residue by chromatography over silica gel (eluting with 0 to 30% EtOAc in hexane) to obtain the title compound as a white solid (255 mg, 52%).

Preparation 66

1-Cyclohex-3-enyl-pyrrolidin-2-one

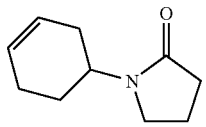

Using trans-1-(4-hydroxy-cyclohexyl)-pyrrolidin-2-one (6.0 g, 0.03 mol Preparation 14)) and DAST (8.6 mL, 0.06 mol) and purification by chromatography on silica gel, obtain the title compound as a clear oil (1.29 g, 26%). MS (EI) m/z=165 (M+).

Preparation 67

3-(2,4-Dichloro-benzyl)-1-(cis-4-t-butyldimethylsilyloxy-cyclohexyl)-pyrrolidin-2-one

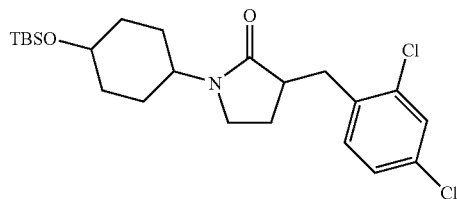

Dissolve 3-(2,4-dichloro-benzyl)-1-(cis-4-hydroxy-cyclohexyl)-pyrrolidin-2-one (0.5 g, 1.46 mmol) in dichloromethane (15 mL), cool to 0° C., and add triethylamine (0.26 mL, 1.90 mmol) and t-butyldimethylsilyl trifluoromethanesulfonate (0.40 mL, 1.75 mmol). After 16 h, wash the mixture with 1 N HCl, saturated aqueous $NaHCO_3$ and brine, dry over $Na_2SO_4$ and evaporate the solvent. Purify the residue by column chromatography on silica gel (eluting 0% to 40% ethyl acetate in hexanes) to give the desired intermediate (0.54 g, 81%).

Preparation 68

3-(2,4-Dichloro-benzyl)-1-(cis-4-t-butyldimethylsilyloxy-cyclohexyl)-3-methyl-pyrrolidin-2-one and 3-(2,4-dichloro-3-methyl-benzyl)-1-(cis-4-t-butyldimethylsilyloxy-cyclohexyl)-3-methyl-pyrrolidin-2-one

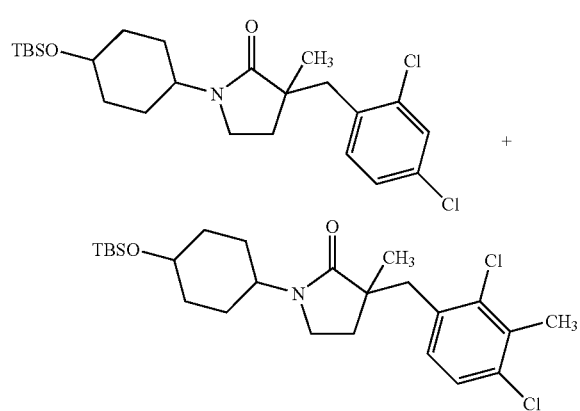

Dissolve 3-(2,4-dichloro-benzyl)-1-(cis-4-t-butyldimethylsilyloxy-cyclohexyl)-pyrrolidin-2-one (0.54 g, 1.19 mmol) in THF (12 mL) and cool to −78° C. Add lithium diisopropylamide mono(tetrahydrofuran) (1.59 mL of 1.5 M solution in cyclohexane, 2.38 mmol) and stir 10 min. Add iodomethane (0.22 mL, 3.57 mmol) and stir 3 h. Wash the mixture with brine, dry the organic layer over $Na_2SO_4$ and evaporate. Purify the residue by column chromatography on silica gel (eluting 0% to 40% ethyl acetate in hexanes) to give a mixture of the desired intermediates (approx. 1:1 mixture, 0.42 g, 75%).

Preparation 69

Cis-1-[4-(tert-Butyl-dimethyl-silanyloxy)-cyclohexyl]-pyrrolidin-2-one

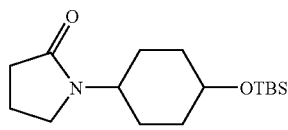

Combine trans-4-aminocyclohexanol (230 g; 2.0 mol) and γ-butyrolactone (140 ml; 1.82 mol) in a 1 L round-bottom flask equipped with large magnetic stirrer, thermometer and condenser/nitrogen bubbler and heat at 190° C. for 68 h. Cool to ambient temperature and dissolve the resulting solid in water (1 L). Extract into dichloromethane (10×1.5 L). Dry the extracts over magnesium sulfate, filter and evaporate to a brown solid. Triturate with diethyl ether to recover 144.7 g (43%) of product.

Dissolve trans-1-(4-hydroxy-cyclohexyl)-pyrrolidin-2-one (144 g; 0.79mol) in dry tetrahydrofuran (5 L) and cool to −5° C. under nitrogen. Add triphenylphosphine (310 g; 1.185 mol) and 4-nitrobenzoic acid (198 g; 1.185 mol). Treat this mixture with diisopropyl azodicarboxylate (230 ml; 1.185 mol) dropwise and stir the reaction at room temperature overnight. Dilute with saturated aqueous sodium hydrogen carbonate solution (1 L) and extract into dichloromethane (2×2.5 L). Dry the combined organic layers over magnesium sulfate and concentrate under vacuum. Purify by chromatography (iso-hexane/ethyl acetate 50-100% then 10% methanol in ethyl acetate) or by trituration with toluene or diethyl ether to afford 163 g (62%) of the product.

Dissolve 4-nitro-benzoic acid 4-(2-oxo-pyrrolidin-1-yl)-cyclohexyl ester (87.9 g; 264 mmol) in methanol (1.35 L) and water (150 ml) and add potassium carbonate (109.5 g; 800 mmol). Stirr at room temperature overnight to give a white precipitate then evaporate to dryness by co-evaporating with ethanol (×2). Stir in tetrahydrofuran (1 L) for 1 h then filter, washing with tetrahydrofuran. Evaporate the filtrate to an oil and crystallize from diethyl ether (100 ml) to give 40 g (83%) of product.

Dissolve 1-(4-hydroxy-cyclohexyl)-pyrrolidin-2-one (40 g; 220 mmol) in dry dichloromethane (1 L). Add imidazole (22.5 g; 330 mmol) then tert-butyldimethylsilyl chloride (50 g; 330 mmol). Stir under nitrogen at room temperature overnight to get a cloudy reaction mixture. Transfer to a separating funnel and wash with water (250 ml) and saturated aqueous sodium hydrogencarbonate solution (250 ml). Dry over magnesium sulfate, filter and evaporate to an oil. Pass through a silica gel pad with iso-hexane/ethyl acetate (0-50%) to give the 51 g (79%) of product as a clear, pale-yellow oil.

Preparation 70

5-benzyloxy-2-bromomethyl-1,3-dichloro-benzene

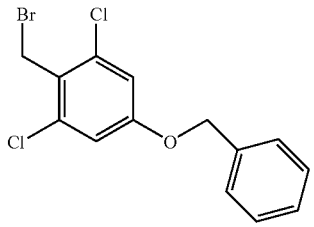

Dissolve 250 g (1.31 mol) 2,6-dichloro-4-hydroxy-benzaldehyde in 2 L DMF and add 361.76 g (2.62 mol) $K_2CO_3$. Add 268.74 g (1.57 mol) benzyl bromide and stir at room temperature for 1 hour. Filter off solids and pour into 12 L of $H_2O$. Filter off-white solids wash several times with $H_2O$, air dry and take up in EtOAc. Dry over $MgSO_4$, filter and reduce volume to approximately 1 liter. Allow to sit overnight, filter off the crystals, wash with minimal amount of hexane and vacuum dry. Tritrate filtrate with hexane to yield a second crop of white crystals to recover 245 g 4-benzyloxy-2,6-dichloro-benzaldehyde (67%) of the white needles.

Suspend 2,6-dichloro-4-hydroxy-benzaldehyde in 3 L EtOH and cool in an ice bath at 0° C. Add 32.97 g (871.45 mmol) $NaBH_4$ caplets portionwise. Remove the ice bath and stir for 2 hours. Carefully add the reaction mixture to 8 L sat'd. $NH_4Cl$ solution and stir until fully quenched. Extract with $CH_2Cl_2$ (2×2 L) and dry the combined organic extracts over $Na_2SO_4$. Filter and concentrate under vacuum to yield 247 g (100%) of (4-benzyloxy-2,6-dichloro-phenyl)methanol as a white solid.

Dissolve (4-benzyloxy-2,6-dichloro-phenyl)-methanol in 2.5 L THF and cool to 0° C. under $N_2$. Add 94.45 g $PBr_3$ dropwise and stir at 0° C. for 30 minutes. Pour the reaction mixture into sat'd. $NaHCO_3$ and extract with EtOAc (2×). Dry over $Na_2SO_4$, filter and concentrate under vacuum to yield 269 g (89%) of the title compound as a white solid. MS (electrospray), 345.1, 347.1 (ES−).

Preparation 71

3-(4-Benzyloxy-2,6-dichloro-benzyl)-1-[cis-4-(tert-butyl-dimethyl-silanyloxy)-cyclohexyl]-pyrrolidin-2-one

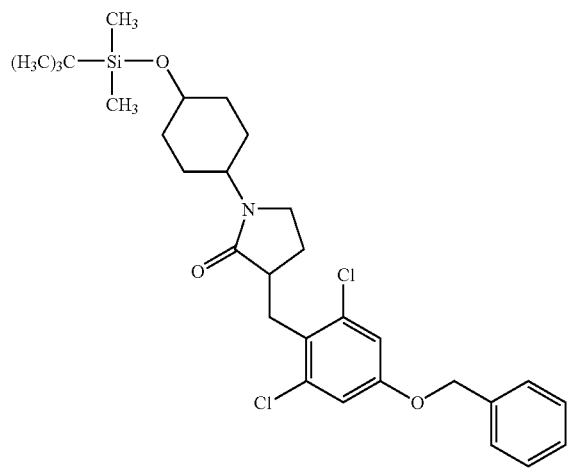

Dissolve 2 g (6.7 mmol) cis-1-[4-(tert-butyl-dimethyl-silanyloxy)-cyclohexyl]-pyrrolidin-2-one (Preparation 69) in 40 mL of dry THF and cool to −78° C. Add 4 mL 2M LDA dropwise and continue stirring at −78° C. for 30 minutes. Allow the mixture to warm to −40° C. for 0.5 hour then re-cool to −78° C. Add a solution of 2.3 g (6.6 mmol) of the 5-benzyloxy-2-bromomethyl-1,3-dichloro-benzene (Preparation 70) in 20 mL dry THF dropwise, remove the cooling bath and stir the reaction at ambient temperature for 72 hours. Dilute the mixture with 100 mL saturated aqueous $NaHCO_3$ and 50 mL EtOAc. Separate the layers, dry the organic layer with $MgSO_4$ and concentrate under vacuum to an oil. Purify by chromatography using 80/20 Hex/EtOAc to recover 2.3 g (59%) of the title compound as an oil.

Preparation 72

1-[cis-4-(tert-Butyl-dimethyl-silanyloxy)-cyclohexyl]-3-(2,6-dichloro-4-hydroxy-benzyl)-pyrrolidin-2-one

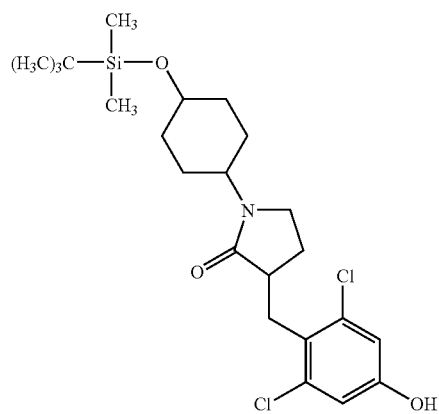

Combine 2 g (3.6 mmol) of 3-(4-benzyloxy-2,6-dichloro-benzyl)-1-[cis-4-(tert-butyl-dimethyl-silanyloxy)-cyclohexyl]-pyrrolidin-2-one (Preparation 71) with 150 mg $Pd(OH)_2$ and 25 mL THF. Hydrogenate with a balloon of $H_2$ for 3 hours. Filter the reaction through Celite®, concentrate under vacuum and purify by chromatography using $CHCl_3$/MeOH 98/2 to recover 1.54 g (88%) of the title compound as an oil.

Preparation 73

4-(4-{1-[cis-4-(tert-Butyl-dimethyl-silanyloxy)-cyclohexyl]-2-oxo-pyrrolidin-3-ylmethyl}-3,5-dichloro-phenoxy)-benzoic acid methyl ester

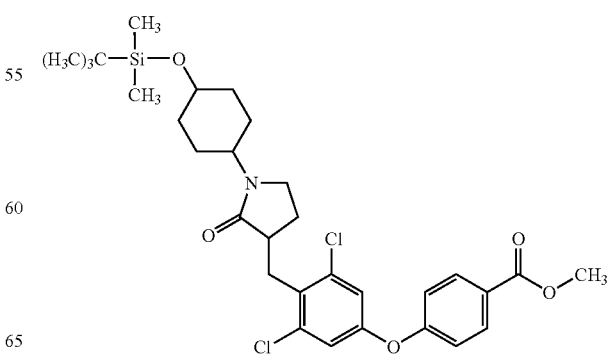

Combine 0.5 g (1 mmol) of 1-[cis-4-(tert-butyl-dimethyl-silanyloxy)-cyclohexyl]-3-(2,6-dichloro-4-hydroxy-benzyl)-pyrrolidin-2-one (Preparation 72) 0.7 g (2 mmol) Cs₂CO₃ and 0.49 g (3 mmol) p-fluoromethylbenzoate in 10 mL dry DMF and heat at 100° C. for 4 hours. Dilute the mixture with 25 mL H₂O and 50 mL EtOAc. Separate the layers and extract the aqueous with 50 mL EtOAc. Combine the organic layers, wash with brine, dry over MgSO₄ and concentrate under vacuum. Purify via chromatography using 30% EtOAc in hexanes to recover 0.47 g of an oil.

Preparation 74

Trifluoro-methanesulfonic acid 4-{1-[cis-4-(tert-butyl-dimethyl-silanyloxy)-cyclohexyl]-2-oxo-pyrrolidin-3-yl methyl}-3,5-dichloro-phenyl ester

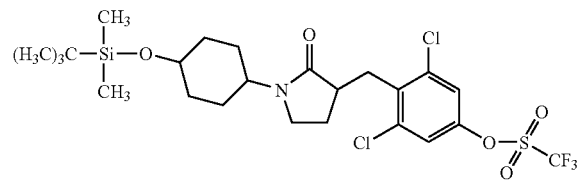

Using the method of Example 240 and using 1-[cis-4-(tert-butyl-dimethyl-silanyloxy)-cyclohexyl]-3-(2,6-dichloro-4-hydroxy-benzyl)-pyrrolidin-2-one (Preparation 72) (0.204 g, 0.432 mmol), pyridine (5 mL), trifluoromethanesulfonic anhydride (0.146 g, 0.518 mmol) and 1 hour at room temperature gives the title compound. Purify the crude mixture over silica gel (5% ethyl acetate in hexane, KMnO₄ stain) to yield 0.204 g (78%) of the title compound as a clear oil: mass spectrum (m/z): 606(M+1).

Preparation 75

1-[cis-4-(tert-Butyl-dimethyl-silanyloxy)-cyclohexyl]-3-(2,6-dichloro-4-pyridin-3-yl-benzyl)-pyrrolidin-2-one

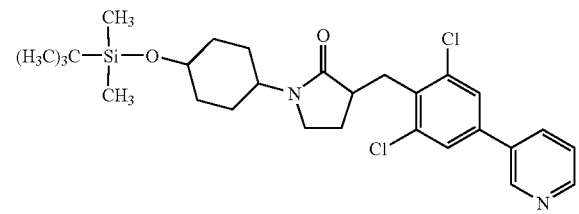

Using the method of Example 81 and trifluoro-methanesulfonic acid 4-{1-[cis-4-(tert-butyl-dimethyl-silanyloxy)-cyclohexyl]-2-oxo-pyrrolidin-3-yl methyl}-3,5-dichlorophenyl ester (Preparation 74) (0.204 g, 0.337 mmol), 3-pyridineboronic acid (0.124 g, 1.01 mmol), tetrakis(triphenylphosphine)palladium (0.039 g, 0.0337 mmol), dimethoxyethane (5 mL) and sodium carbonate (2M, 0.9 mL) gives the title compound. Purify the crude material over silica gel (3/1 hexane in ethyl acetate to ethyl acetate) to yield 0.027 g (15%) of the title compound: mass spectrum (m/z): 535(M+1).

Preparation 76

1-[cis-4-(tert-Butyl-dimethyl-silanyloxy)-cyclohexyl]-3-(2,6-dichloro-4-pyridin-4-yl-benzyl)-pyrrolidin-2-one

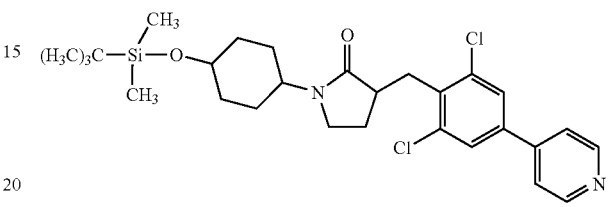

Using the method of Example 81 and trifluoro-methanesulfonic acid 4-{1-[cis-4-(tert-butyl-dimethyl-silanyloxy)-cyclohexyl]-2-oxo-pyrrolidin-3-yl methyl}-3,5-dichlorophenyl ester (Preparation 74) (0.398 g, 0.658 mmol), 4-pyridine boronic acid (0.242, 1.97 mmol) tetrakis(triphenylphosphine)palladium (0.076 g, 0.0658 mmol), dimethoxyethane (5 mL) and sodium carbonate (2M, 1.8 mL) gives the title compound. Purify the crude material over silica gel (3/1 hexane in ethyl acetate to ethyl acetate) to yield 0.189 g (54%) of the title compound: mass spectrum (m/z): 535(M+1).

Preparation 77

1-[cis-4-(tert-Butyl-dimethyl-silanyloxy)-cyclohexyl]-3-[2,6-dichloro-4-(1-methyl-1H-pyrazol-4-yl)-benzyl]-pyrrolidin-2-one

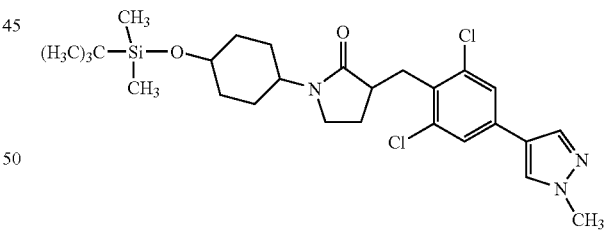

Using the method of Example 81 and trifluoro-methanesulfonic acid 4-{1-[cis-4-(tert-butyl-dimethyl-silanyloxy)-cyclohexyl]-2-oxo-pyrrolidin-3-yl methyl}-3,5-dichlorophenyl ester (Preparation 74) (0.400 g, 0.658 mmol), 1-methyl-4-(4,4,5,5-tetramethyl-1,3,2-dioxaborolan-2-yl)-1H-pyrazole (0.411, 1.97 mmol), tetrakis(triphenylphosphine)palladium (0.076 g, 0.0658 mmol), dimethoxyethane (5 mL) and sodium carbonate (2M, 1.8 mL) gives the title compound. Purify the crude material over silica gel (3/1 hexane in ethyl acetate to ethyl acetate) to yield 0.301 g (85%) of the title compound: mass spectrum (m/z): 538(M+1).

Preparation 78

1-[cis-4-(tert-Butyl-dimethyl-silanyloxy)-cyclohexyl]-3-(2,6-dichloro-4-isopropoxy-benzyl)-pyrrolidin-2-one

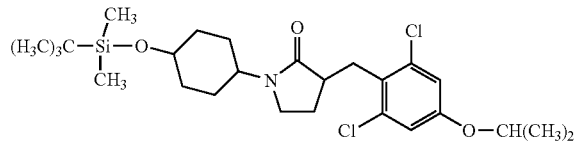

Add 1-[cis-4-(tert-butyl-dimethyl-silanyloxy)-cyclohexyl]-3-(2,6-dichloro-4-hydroxy-benzyl)-pyrrolidin-2-one (Preparation 72) (0.543 g, 1.15 mmol), 2-bromopropane (0.212 g, 1.72 mmol), and potassium carbonate (0.365 g, 2.64 mmol) together with acetone (10 mL) and reflux overnight. Concentrate the reaction mixture under reduced pressure to give a residue. Purify the residue over silica gel, (98:2 dichloromethane in methanol) to give 0.080 g (14%) of the title compound: mass spectrum m/z: 516(M+1).

Preparation 79

4-[4-chloro-3-(1-cyclohexyl-2-oxo-pyrrolidin-3-ylmethyl)-2-fluoro-phenyl]-butyric acid ethyl ester

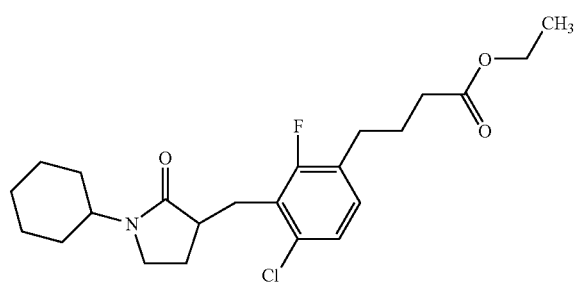

Dissolve 3-(3-bromo-6-chloro-2-fluoro-benzyl)-1-cyclohexyl-pyrrolidin-2-one (Example 30) (1 g, 2.6 mmol) and Pd(dppf)Cl$_2$ (80 mg, 0.1 mol) in THF (degassed, 40 mL) and add 4-ethoxy-4-oxo-butylzinc bromide (15 mL, 7.7 mmol, 0.5 M THF solution). Reflux the reaction for 3 hours. Add the reaction mixture into ice and water. Extract the mixture with ethyl acetate (100 mL). Wash the organic layer with brine (50 mL), dry with magnesium sulfate, filter and evaporate solvent under reduced pressure. Purify the residue by column chromatography using 10% EA/H to 30% EA/H to obtain the title compound (1 g, 92%) as yellow oil: Mass spectrum (ion spray): m/z=424.1 (M+H).

Preparation 80

4-[4-chloro-3-(1-cyclohexyl-2-oxo-pyrrolidin-3-ylmethyl)-2-fluoro-phenyl]-butyric acid

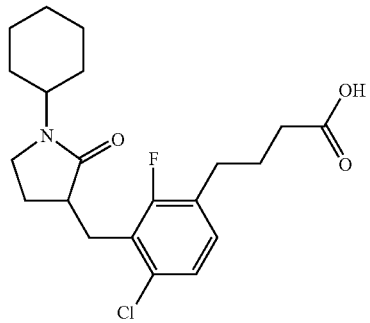

Add 5 N NaOH solution (3 mL, 3 mmol) into 4-[4-chloro-3-(1-cyclohexyl-2-oxo-pyrrolidin-3-ylmethyl)-2-fluoro-phenyl]-butyric acid ethyl ester (Preparation 79) (0.58 g, 1.4 mmol) in methanol (5 mL) at room temperature and stir for 30 minutes. Evaporate MeOH under reduced pressure and neutralize the residue by 1N HCl. Extract the mixture with ethyl acetate (10 mL) and separate the organic layer. Dry the organic layer with magnesium sulfate, filter and evaporate solvent under reduced pressure. Purify the residue by column chromatography to obtain the title product as white solid (300 mg, 55%): Mass spectrum (ion spray): m/z=396.0 (M+H).

Preparation 81

3'-Chloro-4'-(1-cyclohexyl-2-oxo-pyrrolidin-3-ylmethyl)-biphenyl-2-carboxylic acid ethyl ester

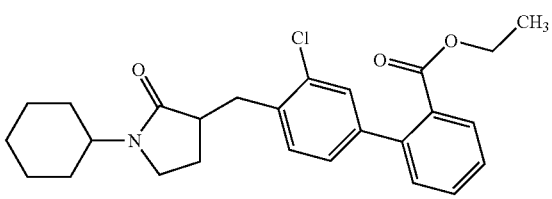

Using the procedure to synthesize Example 81 and using reagents 3-(4-bromo-2-chloro-benzyl)-1-cyclohexyl-pyrrolidin-2-one (500 mg, 1.35 mmol) and ethyl-2-(4,4,5,5-tetramethyl-1,3,2-dioxaborolan-2-yl)benzoate (560 mg, 2.0 mmol) affords 287 mg (48%) of the title compound: Mass spectrum (apci) m/z=440.2 (M+H).

Preparation 82

3'-Chloro-4'-(1-cyclohexyl-2-oxo-pyrrolidin-3-ylmethyl)-biphenyl-3-carboxylic acid tert-butyl ester

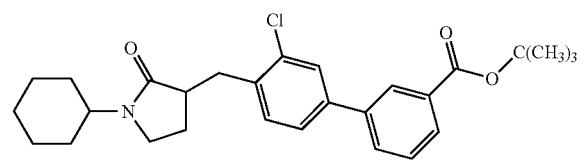

Using the procedure to synthesize Example 81 and using reagents 3-(4-bromo-2-chloro-benzyl)-1-cyclohexyl-pyrrolidin-2-one (500 mg, 1.35 mmol) and 3-(tert-butoxycarbonyl)phenylboronic acid (900 mg, 4.0 mmol) affords 506 mg (80%) of the title compound: Mass spectrum (apci) m/z=468.2 (M+H).

Preparation 83

3'-Chloro-4'-(1-cyclohexyl-2-oxo-pyrrolidin-3-ylmethyl)-biphenyl-4-carboxylic acid tert-butyl ester

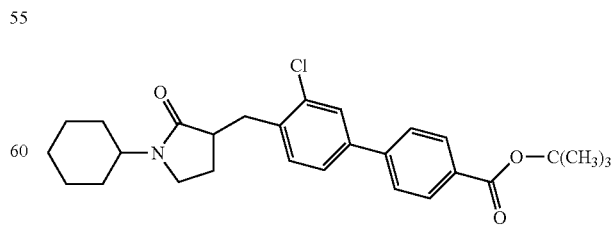

Using the procedure to synthesize Example 81 and using reagents 3-(4-bromo-2-chloro-benzyl)-1-cyclohexyl-pyrrolidin-2-one (500 mg, 1.35 mmol) and 4-(tert-butoxycarbonyl)

phenylboronic acid (900 mg, 4.0 mmol) affords 495 mg (78%) of the title compound: Mass spectrum (apci) m/z=468.2 (M+H).

Preparation 84

3-(2,4-Dichloro-benzyl)-1-(cis-2-methyl-4-oxo-cyclohexyl)-pyrrolidin-2-one

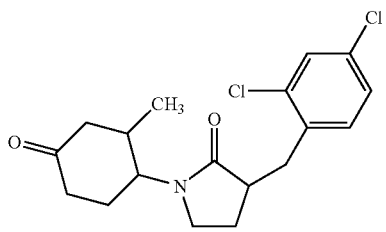

Using the procedure to synthesize Example 1 and using reagent 1-(cis-7-methyl-1,4-dioxa-spiro[4.5]dec-8-yl)-pyrrolidin-2-one (Preparation 45) (2.49 g, 10.4 mmol), LDA (1.5M, 8.3 mL, 12.5 mmol) and 1-(bromomethyl)-2,4-dichlorobenzene (4.07 g, 20.8 mmol) yields 2.34 g (56%) of 3-(2,4-dichloro-benzyl)-1-(cis-7-methyl-1,4-dioxa-spiro[4.5]dec-8-yl)-pyrrolidin-2-one as a white solid.

Dissolve 3-(2,4-dichloro-benzyl)-1-(cis-7-methyl-1,4-dioxa-spiro[4.5]dec-8-yl)-pyrrolidin-2-one (2.34 g, 5.87 mmol) in acetone (100 mL) and add TsOH (1.01 g, 5.87 mmol). Stir the reaction at room temperature for 24 hours until the starting material has been gone. Add saturated NaHCO$_3$ (100 mL) and extract the aqueous layer with ethyl acetate (3×200 mL). Combine the organic layers and dry with Na$_2$SO$_4$, filter and concentrate to give 1.95 g (94%) of the crude title compound as a white solid: Mass spectrum (ion spray): m/z=354.2, 356.1 (M+1).

Preparation 85

(S)-3-(2-Chloro-6-fluoro-benzyl)-4-oxo-4-((4S,5R)-2-oxo-4,5-diphenyl-oxazolidin-3-butyraldehyde

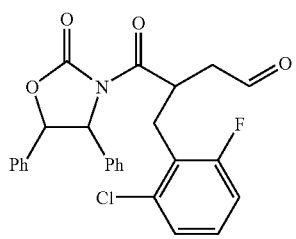

Charge a 250 mL, single-neck, round-bottomed flask with (4S,5R)-4,5-diphenyloxazolidin-2-one (5.0 g, 21.0 mmol) and THF (300 mL). Stir the mixture at −78° C. and add dropwise BuLi (13.7 mL, 21.9 mmol). Stir the reaction mixture for 0.5 hours and then add pent-4-enoyl chloride (3.71 g, 31.3 mmol). Stir the reaction mixture one hour until TLC shows that the starting material has been consumed. Add water (100 mL) and extract the aqueous with CH$_2$Cl$_2$ (3×250 mL). Combine the organic layers and dry over Na$_2$SO$_4$. Concentrate and purify by chromatography (Silica gel) to afford (4S,5R)-3-Pent-4-enoyl-4,5-diphenyloxazolidin-2-one (4.49 g, 67%).

Dissolve (4S,5R)-3-pent-4-enoyl-4,5-diphenyloxazolidin-2-one (1.0 g, 3.1 mmol) in THF (50 mL) and cool the mixture to −78° C. under N$_2$ with stirring. Add dropwise LDA (2.7 mL, 4.0 mmol, 1.5 M in THF) and stir the mixture for 0.5 hours. Then add 2-(bromomethyl)-1-chloro-3-fluorobenzene (1.39 g, 6.22 mmol). Continue to stir the reaction mixture for one hour until TLC shows that the starting material has been consumed. Add water (50 mL) and extract the aqueous with CH$_2$Cl$_2$ (3×250 mL). Combine the organic layers and dry over Na$_2$SO$_4$. Concentrate and purify by chromatography (Silica gel) to afford (4S,5R)-3-((R)-2-(2-Chloro-6-fluorobenzyl)pent-4-enoyl)-4,5-diphenyloxazolidin-2-one (1.44 g, 75.5%).

Dissolve (4S,5R)-3-((R)-2-(2-chloro-6-fluorobenzyl)pent-4-enoyl)-4,5-diphenyloxazolidin-2-one (1.05 g, 2.27 mmol) in CH$_2$Cl$_2$ (200 mL). Cool the solution to −78° C. Bubble O$_2$ into the solution until the solution turns blue. Then bubble N$_2$ for 5 minutes and add Me$_2$S (0.706 g, 11.3 mmol). Stir the mixture for one hour and then remove the solvent. Purify the residue by chromatography (Silica gel) to afford (S)-3-(2-Chloro-6-fluorobenzyl)-4-oxo-4-((4S,5R)-2-oxo-4,5-diphenyloxazolidin-3-yl)butanal (0.384 g, 36%). $^1$H NMR (CDCl$_3$) δ 7.18 (m, 2H), 7.12 (m, 6H), 6.98 (m, 3H), 6.82 (m, 2H), 6.00 (d, 1H), 5.69 (d, 1H), 4.72 (m, 1H), 3.28 (m, 1H), 3.14 (m, 1H), 2.92 (m, 1H), 2.61 (m, 1H).

Preparation 86

5-bromo-thiophene-2-carboxylic acid methyl ester

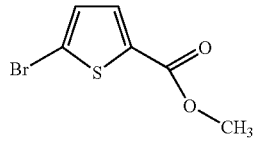

To a solution of 5-bromo-thiophene-2-carboxylic acid (1.04 g, 5.0 mmol) in 15 mL of methanol, add concentrated sulfuric acid (0.5 ml, 10 mmol). After heating to reflux for an hour, cool the reaction to room temp, and dilute with EtOAc/H$_2$O=50/50. Then, neutralize with 1.0 N NaOH to pH=7, extract the aqueous solution with ethyl acetate (30 ml×3), and dry the combined organic layers over sodium sulfate. Purify the crude material via flash chromatograpgy on sila gel to give the title compound 0.62 g. GC/MS (m/z) 222 (M+1), 191 (M—OMe+1).

Preparation 87

Toluene-4-sulfonic acid 1-cyclohexyl-4,4-dimethyl-2-oxo-pyrrolidin-3-yl ester

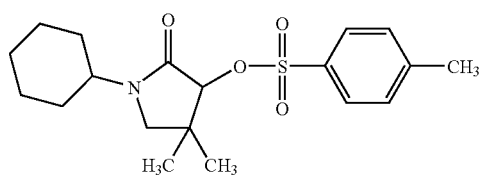

Place 2-hydroxy-3,3-dimethyl-cyclopentanone (1.044 g, 7.86 mmol), cyclohexylamine (1.91 ml, 16.51 mmol) and toluenesulfonic acid monohydrate (0.152 g, 0.1 mmol) in EtOH (4 mL) in a microwave reactor. Stir for 1 hour at 150° C. Quench with 1N HCl and extract with ethyl acetate. Wash the extract with NaHCO₃, brine. Dry over magnesium sulfate, filter, and concentrate to afford N-cyclohexyl-2,4-dihydroxy-3,3-dimethyl-butyramide.

Place N-cyclohexyl-2,4-dihydroxy-3,3-dimethyl-butyramide (2.178 g, 9.51 mmol), triethylamine (2.7 ml, 19.31 mmol) and toluenesulfonyl chloride (3.70 g, 19.21 mmol) in CH₂Cl₂ (50 mL) at 0° C. Stir for 30 minutes at 0° C. Quench with hexane and warm to room temperature. Filter white precipitate. Strip the solvent and dissolve the residue in 40 ml of dry THF under the nitrogen atmosphere. Add sodium hydride (3.4 g, 85 mmol) and stir at room temperature for 12 hours. Quench the reaction with methanol/water mixture. Extract with ethyl acetate. Wash the extract with brine and dry over magnesium sulfate. Purification by flash chromatography affords 1.25 g (36%) of the title compound: Mass spectrum (apci) m/z=366 (M+H).

Example 1

3-Benzyl-1-cyclohexyl-pyrrolidin-2-one

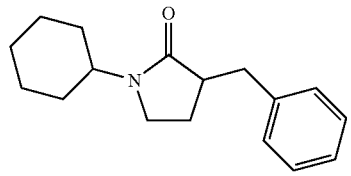

Place 1-cyclohexyl-pyrrolidin-2-one (400 mg, 2.4 mmol) in THF (30 mL) and cool to −78° C. Slowly add LDA (2.0 M, 2.4 mL, 4.8 mmol) and stir for 15 minutes. Add benzyl bromide (1.23 g, 7.2 mmol) and stir for 3 hours. Quench with ammonium chloride and extract with dichloromethane. Dry over sodium sulfate, filter, and concentrate. Purify by silica gel (20-50% ethyl acetate in hexanes) to afford 432 mg (70%) of the title compound: Mass spectrum (apci) m/z=258.2 (M+H).

Example 2

1-Cyclohexyl-3-(2,4-dichloro-phenylsulfanyl)-pyrrolidin-2-one

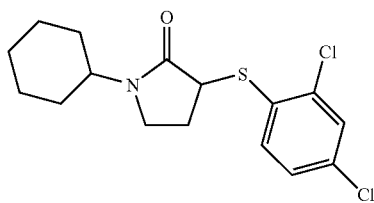

Place 2,4-dichloro-benzenethiol (728 mg, 4.1 mmol) in tetrahydrofuran (10 mL) and cool to 0° C. Slowly add sodium hydride (98 mg, 4.1 mmol) and stir for 30 minutes. To this solution, add a solution of 3-bromo-1-cyclohexyl-pyrrolidin-2-one (Preparation 1) in tetrahydrofuran (2 mL) and stir at room temperature for 30 minutes. Pour reaction mixture onto ice and extract with methylene chloride. Dry over sodium sulfate, filter, and concentrate. Purify by silica gel (20-30% ethyl acetate in hexane) to yield 641 mg (92%) of the title compound: Mass spectrum (apci) m/z=344.1 (M+H).

Example 3

3-{6-Chloro-2-fluoro-3-[4-(4-methyl-piperazin-1-yl)-4-oxo-butyl]-benzyl}-1-cyclohexyl-pyrrolidin-2-one

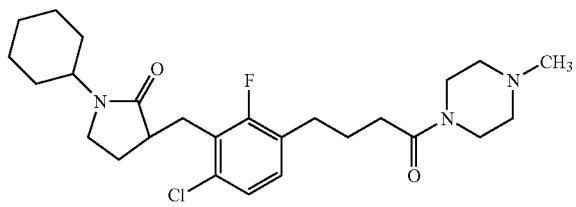

Add 4-[4-chloro-3-(1-cyclohexyl-2-oxo-pyrrolidin-3-yl-methyl)-2-fluoro-phenyl]-butyric acid (Preparation 80) (200 mg, 0.22 mmol), EDAC (63 mg, 0.33 mmol), HOBT (45, mg, 0.33 mmol), triethylamine (0.1 mL, 0.7 mmol) and 1-methylpiperazine (0.1 mL, 0.9 mmol) in THF (5 mL). Heat the mixture at 80° C. for 3 hours. Evaporate solvent and purify the residue by column chromatography to give the title product as white solid: Mass spectrum (ion spray): m/z=478.3 (M+H).

Example 4

1-Cyclohexyl-3-(2-hydroxy-benzyl)-pyrrolidin-2-one

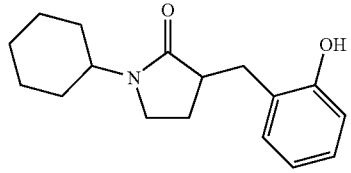

Add boron tribromide (0.21 mL, 2.2 mmol) to a solution of 1-cyclohexyl-3-(2-methoxy-benzyl)-pyrrolidin-2-one (210 mg, 0.73 mmol) in dichloromethane (5 mL). Stir 20 minutes. Pour mixture onto a mixture of ice and saturated sodium bicarbonate. Stir 5 minutes. Wash the organic layer with water, brine, dry, concentrate, and purify the residue on a Biotage cartridge, eluting with 4:1 hexanes:ethyl acetate to afford the title compound (115 mg): MS (APCI-pos mode) m/z (rel intensity) 274 (100).

Example 5

3-(2-Chloro-6-hydroxy-benzyl)-1-(cis-4-hydroxy-cyclohexyl)-pyrrolidin-2-one

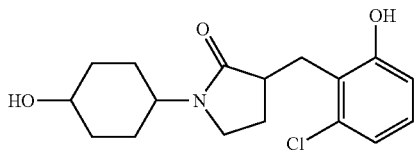

Dissolve 3-(2-chloro-6-methoxy-benzyl)-1-(cis-4-hydroxy-cyclohexyl)-pyrrolidin-2-one (Example 57) (150 mg, 0.44 mmol) in DMF (5 mL) and purge with nitrogen. Add sodium ethane thiol (110 mg, 1.3 mmol) and heat to 120° C. for 4 hours. Cool to room temperature and pour into ammonium chloride and extract with methylene chloride, dry over sodium sulfate, filter and concentrate. Purify over silica gel (20% hexanes in ethyl acetate) to yield 90 mg (63%) of the title compound as a pale yellow solid: Mass spectrum (apci) m/z=324.1 (M+H).

Example 6

3'-Chloro-4'-(1-cyclohexyl-2-oxo-pyrrolidin-3-ylmethyl)-biphenyl-2-carboxylic acid

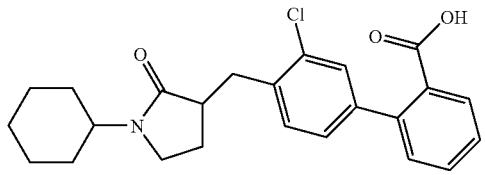

Dissolve 3'-chloro-4'-(1-cyclohexyl-2-oxo-pyrrolidin-3-ylmethyl)-biphenyl-2-carboxylic acid ethyl ester (Preparation 81) (287 mg, 0.65 mmol) in ethanol (10 mL) and add KOH (370 mg, 6.5 mmol). Stir at room temperature for 3 days. Pour into water and extract with ether. Acidify the aqueous layer to pH 1. Extract with ether. Dry over sodium sulfate, filter and concentrate to yield 220 mg (82%) of the title compound as a pale yellow solid: Mass spectrum (apci) m/z=410.3 (M−H).

Example 7

3'-Chloro-4'-(1-cyclohexyl-2-oxo-pyrrolidin-3-ylmethyl)-biphenyl-3-carboxylic acid

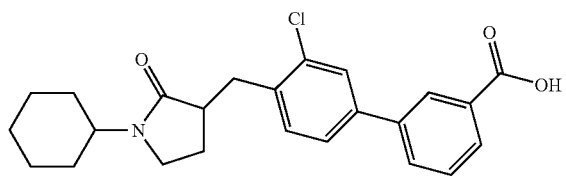

Dissolve 3'-chloro-4'-(1-cyclohexyl-2-oxo-pyrrolidin-3-ylmethyl)-biphenyl-3-carboxylic acid tert-butyl ester (Preparation 82) (506 mg, 1.08 mmol) in methylene chloride (5 mL). Add trifluoroacetic acid (5 mL) and stir at room temperature for 1 hour. Concentrate and redissolve in methylene chloride. Pour into 1N NaOH. Extract with ether. Acidify aqueous phase to pH 1. Extract with ether. Dry over sodium sulfate, filter and concentrate to yield 420 mg (94%) of the title compound as a white solid. Mass spectrum (apci) m/z=410.3

Example 8

3'-Chloro-4'-(1-cyclohexyl-2-oxo-pyrrolidin-3-ylmethyl)-biphenyl-4-carboxylic acid sodium salt

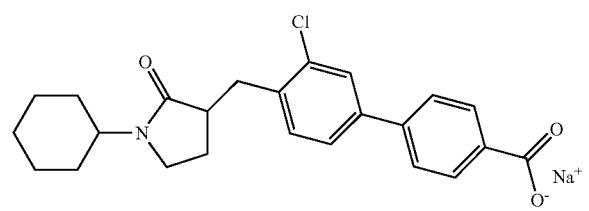

Dissolve 3'-chloro-4'-(1-cyclohexyl-2-oxo-pyrrolidin-3-ylmethyl)-biphenyl-4-carboxylic acid tert-butyl ester (Preparation 83) (495 mg, 1.06 mmol) in methylene chloride (5 mL). Add trifluoroacetic acid (5 mL) and stir at room temperature for 1 hour. Concentrate and redissolve in methylene chloride.

Pour into 1N NaOH and filter to yield 380 mg (87%) of the title compound as a white solid. Mass spectrum (apci) m/z=410.2 (M−H).

Example 9

3-(2-Benzyl-6-chloro-benzyl)-1-cyclohexyl-pyrrolidin-2-one

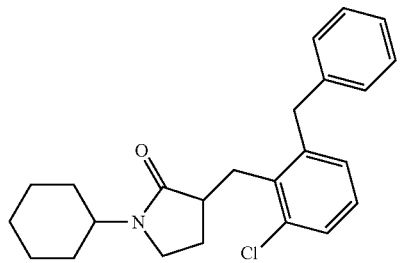

Charge a flask with 3-(2-bromo-6-chloro-benzyl)-1-cyclohexyl-pyrrolidin-2-one (Example 56) (250 mg, 0.67 mmol), Pd(dppf)Cl$_2$ (54 mg, 0.067 mmol) and Cs$_2$CO$_3$ (660 mg, 2.0 mmol) and purge with nitrogen. Add DMF (6 mL) and water (0.6 mL) and stir. Add Bn-9-BBN (0.5 M, 4.0 mL, 2.0 mmol) and heat to 60° C. for 1 hour. Pour into saturated aqueous bicarbonate and extract with methylene chloride. Dry over sodium sulfate, filter and concentrate. Purify over silica gel (10% ethyl acetate in hexanes) to yield 155 mg (60%) of the title compound as a clear colorless oil. Mass spectrum (apci) m/z=382.3 (M+H).

Example 10

3-(4-Benzyl-2-chloro-benzyl)-1-cyclohexyl-pyrrolidin-2-one

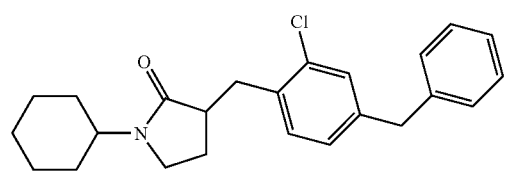

Using the method of Example 9 and using 3-(4-bromo-2-chloro-benzyl)-1-cyclohexyl-pyrrolidin-2-one (Example 55) (250 mg, 0.67 mmol) affords 154 mg (60%) of the title compound as a clear colorless oil. Mass spectrum (apci) m/z=382.3 (M+H).

Example 11

3-(2-Chloro-6-hydroxy-benzyl)-1-cyclohexyl-pyrrolidin-2-one

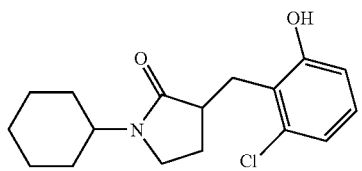

Charge a flask with 3-(2-bromo-6-chloro-benzyl)-1-cyclohexyl-pyrrolidin-2-one (Example 56) (210 mg, 0.57 mmol), bis(neopentyl glycolato)diboron (150 mg, 0.68 mmol), KOAc (200 mg, 2.0 mmol) and Pd(dppf)Cl$_2$ (23 mg, 0.03 mmol) and purge with nitrogen. Add DMSO (5 mL) and plunge into an 80° C. oil bath and stir under nitrogen for 24 hours. Cool to room temperature and pour into water. Extract with ether. Dry over sodium sulfate, filter and concentrate. Dissolve residue in 1N NaOH (10 mL) and stir at room temperature overnight. Extract water with ether and acidify the aqueous layer with HCl. Extract with ether, dry over sodium sulfate, filter and concentrate. Dissolve residue in THF (5 mL) and add N-methyl morpholine N-oxide (200 mg, 1.7 mmol) and heat to reflux for 6 hours. Cool to room temperature and pour into saturated aqueous sodium bisulfite. Extract with methylene chloride. Dry over sodium sulfate, filter and concentrate. Purify over silica gel (3:1 to 1:1 hexanes:ethyl acetate). Triturate the recovered material with 2:1 hexanes:ethyl acetate to afford 47 mg (27%) of the title compound as a white solid. Mass spectrum (apci) m/z=308.1 (M+H).

Example 12

1-Cyclohex-2-enyl-3-(2,4-dichloro-benzyl)-pyrrolidin-2-one

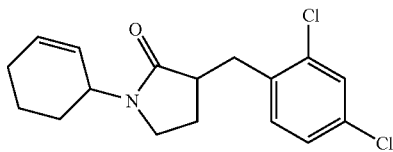

Charge a flask with 3-(2,4-dichloro-benzyl)-pyrrolidin-2-one (Preparation 19) (100 mg, 0.41 mmol), dissolve in THF (4 mL) and cool to 0° C. under nitrogen. Add NaH (15 mg, 0.61 mmol) and stir at 0° C. for 20 minutes. Add 3-bromo-cyclohexene (198 mg, 1.23 mmol) and stir at room temperature overnight. Pour into saturated aqueous sodium bicarbonate and extract with methylene chloride. Dry over sodium sulfate, filter and concentrate. Purify residue over silica gel (5:1 hexanes:ethyl acetate) to afford 68 mg (51%) of the title compound as a white solid. Mass spectrum (apci) m/z=324.1 (M+H).

Example 13

3-Benzyl-1-cyclohexyl-5-methyl-pyrrolidin-2-one

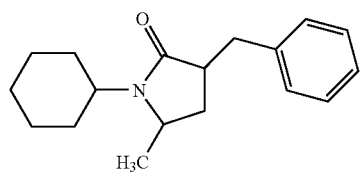

Charge a flask with 1-cyclohexyl-5-methyl-pyrrolidin-2-one (U.S. Pat. No. 6,743,819, 500 mg, 2.8 mmol), dissolve in THF (30 mL) and cool to −78° C. under nitrogen. Add LDA (2M, 1.7 mL, 3.3 mmol) and stir at −78° C. for 10 minutes. Add 2-chlorobenzaldehyde (500 mg, 3.6 mmol) and warm to room temperature. Pour into saturated aqueous ammonium chloride and extract with methylene chloride. Dry over sodium sulfate, filter and concentrate. Dissolve the residue in THF (30 mL) and add triethylamine (360 mg, 3.6 mmol) and methanesulfonyl chloride (380 mg, 3.3 mmol). Stir at room temperature for 2 hours and filter. Add DBU (440 mg, 3.6 mmol) to the filtrate and stir overnight. Pour the reaction into water and extract with methylene chloride. Dry over sodium sulfate, filter and concentrate. Purify residue over silica gel (5:1 hexanes:ethyl acetate). Dissolve the residue in methanol (10 mL) and add 10% palladium on carbon (40 mg) and stir under a balloon of hydrogen for 3 days. Filter through celite® and concentrate. Purify over silica gel (9:1 hexanes:ethyl acetate) to afford two separable isomers.

Example 13a

Isomer 1—Mass spectrum (apci) m/z=272.2 (M+H). HPLC (50 to 95) R$_t$ (Purity at 220 mn)=1.92 min (100%).

Example 13b

Isomer 2—Mass spectrum (apci) m/z=272.2 (M+H). HPLC (50 to 95) R$_t$ (Purity at 220 mn)=1.88 min (100%).

Example 14

3-(2,4-Dichloro-benzyl)-1-(4-oxo-cyclohexyl)-pyrrolidin-2-one

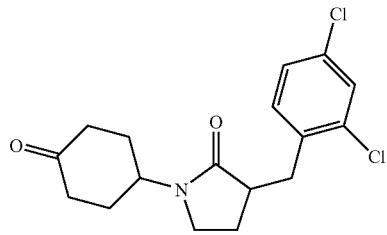

Dissolve 3-(2,4-dichloro-benzyl)-1-(4-hydroxy-cyclohexyl)-pyrrolidin-2-one (14.56 g, 37.90 mmol) in acetone (400 mL) with stirring at room temperature. Add p-toluene sulfonic acid (6.53 g, 37.90 mmol) and stir the reaction at room temperature for 48 hours. Then add water and extract the aqueous layer with ethyl acetate (3×400 mL). Combine the organic layers and dry with Na$_2$SO$_4$. Filter and concentrate to give 12.95 g (100%) of the crude title compound as a white solid: Mass spectrum (ion spray): m/z=340.1, 342.0 (M+1).

Example 15

3-(2,4-Dichloro-benzyl)-1-(trans-4-hydroxy-cyclohexyl)-pyrrolidin-2-one

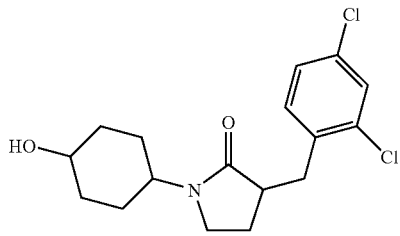

Dissolve 3-(2,4-dichloro-benzyl)-1-(4-oxo-cyclohexyl)-pyrrolidin-2-one (Example 14) (6.19 g, 18.19 mmol) in MeOH (200 mL) and cool to 0° C. under nitrogen. Add sodium borohydride (1.38 g, 36.39 mmol) and stir the solution at 0° C. for 4 hours. Add water (200 mL) and extract the aqueous layer with ethyl acetate (3×300 mL). Combine the organic layers and dry with Na$_2$SO$_4$, filter, concentrate and purify by flash column chromatography (silica gel, 50-80% EtOAc-Hexane) to give 5.49 g (88%) of the title product as a white solid. ¹H NMR (CDCl₃) δ 7.37 (d, 1H), 7.22 (d, 1H), 7.17 (dd, 1H), 3.91-4.00 (m, 1H), 3.52-3.62 (m, 1H), 3.27-3.36 (m, 1H), 3.12-3.21 (m, 2H), 2.73-2.82 (m, 2H), 1.98-2.07 (m, 3H), 1.56-1.77 (m, 4H), 1.38-1.54 (m, 4H).

Example 16

Cis-4-nitro-benzoic acid 4-[3-(2,4-dichloro-benzyl)-2-oxo-pyrrolidin-1-yl]-cyclohexyl ester

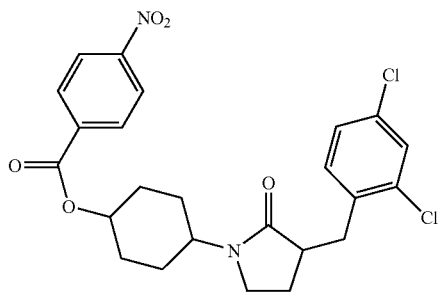

Dissolve 3-(2,4-dichloro-benzyl)-1-(trans-4-hydroxy-cyclohexyl)-pyrrolidin-2-one (Example 15) (3.32 g, 9.70 mmol) in anhydrous THF (200 mL) and cool to −20 °C. Add triphenyl phosphine (12.71 g, 48.48 mmol), diethyl azodicarboxylate (8.44 g, 48.48 mmol), and 4-nitro-benzoic acid (8.10 g, 48.48 mmol). Stir the reaction mixture for 6 hours at the same temperature, then warm the reaction to room temperature and continue to stir the reaction overnight. Add water (200 mL) and extract the aqueous layer with ethyl acetate (3×200 mL). Combine the organic layers and dry with Na₂SO₄, filter, concentrate and purify by flash column chromatography (silica gel, 30-60% of EtOAc-Hexane) to give 1.76 g (100%) of the title compound as a white solid: ¹H NMR (CDCl₃) δ 8.28-8.32 (m, 2H), 8.17-8.24 (m, 2H), 7.38 (d, 1H), 7.23 (d, 1H), 7.18 (dd, 1H), 5.28-5.32 (m, 1H), 4.05-4.15 (m, 1H), 3.25-3.40 (m, 3H), 2.74-2.83 (m, 2H), 2.10-2.23 (m, 1H), 2.02-2.10 (m, 1H), 1.60-1.92 (m, 8H).

Example 17

3-(2,4-Dichloro-benzyl)-1-(cis-4-hydroxy-cyclohexyl)-pyrrolidin-2-one

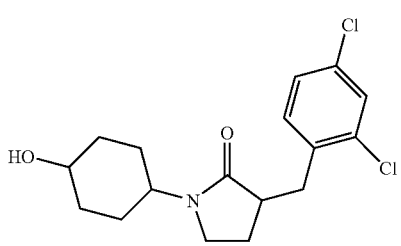

Dissolve cis-4-nitro-benzoic acid 4-[3-(2,4-dichloro-benzyl)-2-oxo-pyrrolidin-1-yl]-cyclohexyl ester (Example 16) (3.58 g, 7.29 mmol) in MeOH (200 mL). Add 2M K₂CO₃ (50 nL) and stir the reaction mixture overnight. Add water (200 mL) and extract the aqueous layer with ethyl acetate (3×300 mL). Combine the organic layers and dry with Na₂SO₄, filter, concentrate and purify by flash column chromatography (silica gel, 50-100% of EtOAc-Hexane) to give 1.54 g (62%) of the title compound as a white solid. Mass spectrum (ion spray): m/z=342.0, 344.0 (M+1).

Example 18

3-(2-Chloro-6-fluoro-benzyl)-1-(cis-4-hydroxy-cyclohexyl)-pyrrolidin-2-one

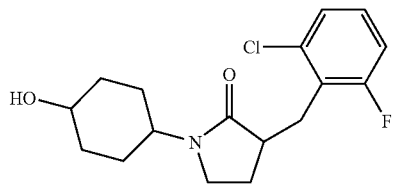

Using the method of Example 17, cis-4-nitro-benzoic acid 4-[3-(2-chloro-6-fluoro-benzyl)-2-oxo-pyrrolidin-1-yl]-cyclohexyl ester (0.73 g, 1.54 mmol) gives 0.31 g (61%) of the title compound as a white solid. Mass spectrum (ion spray): m/z=326.0, 328.0 (M+1).

Example 19

3-(2,4-Dichloro-benzyl)-1-(cis-4-hydroxymethyl-cyclohexyl)-pyrrolidin-2-one

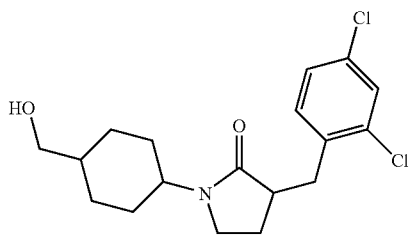

Dissolve 1-[cis-4-(tert-butyl-dimethyl-silanyloxymethyl)-cyclohexyl]-3-(2,4-dichloro-benzyl)-pyrrolidin-2-one (Preparation 37) (0.12 g, 0.25 mmol) in THF (50 mL) and add TBAF (0.50 mL, 1.0 M in THF) at room temperature under nitrogen. Stir the solution overnight. Then add water (50 mL) and extract the aqueous layer with dichloromethane (3×100 mL). Combine the organic layers and dry with Na₂SO₄, filter, concentrate and purify by flash column chromatography (silica gel, 50-80% EtOAc-Hexane) to give 0.085 g (95%) of the title compound as a white solid: Mass spectrum (ion spray): m/z=356.2, 358.2 (M+1).

Example 20

3-(2,4-Dichloro-benzyl)-1-(cis-4-hydroxy-4-methyl-cyclohexyl)-pyrrolidin-2-one

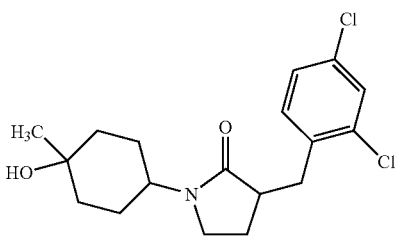

Dissolve 3-(2,4-dichloro-benzyl)-1-(4-oxo-cyclohexyl)-pyrrolidin-2-one (Example 14) (0.20 g, 0.59 mmol) in anhydrous THF (20 mL) and cool to −78° C. Add MeTi(Oi-Pr)₃ (0.17 g, 0.71 mmol) under nitrogen and stir the reaction mixture for 8 hours at the same temperature. Warm the reaction to room temperature and add water (20 mL). Extract the aqueous layer with dichloromethane (3×50 mL). Combine the organic layers and dry with Na₂SO₄, filter, concentrate and purify by flash column chromatography (silica gel, 20-60% of EtOAc-Hexane) to give 0.16 g (75%) of the title compound as a white solid: Mass spectrum (ion spray): m/z=338.2, 340.1 (M-18).

Example 21

3-(2,4-Dichloro-benzyl)-1-(cis-4-hydroxy-cis-2-methyl-cyclohexyl)-pyrrolidin-2-one

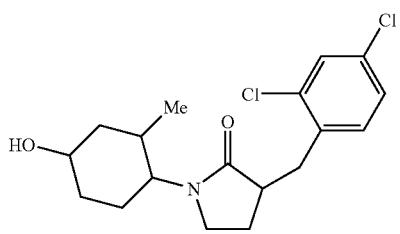

Dissolve 3-(2,4-dichloro-benzyl)-1-(cis-2-methyl-4-oxo-cyclohexyl)-pyrrolidin-2-one (Preparation 84) (1.0 g, 2.82 mmol) in anhydrous THF (50 mL) and cool to −78° C. under nitrogen. Add L-selectride (2.82 mL, 2.82 mmol, 1.0 M in THF) and stir the reaction at the same temperature for five hours. Warm the reaction to room temperature and add water (50 mL). Extract the aqueous layer with ethyl acetate (3×100 mL). Combine the organic layers and dry with Na₂SO₄, filter, concentrate and purify by flash column chromatography (silica gel, 10-70% of EtOAc/Hexane) to give 0.57 g (57%) of the title compound (as the major product) as a white solid: Mass spectrum (ion spray): m/z=356.0, 358.0 (M+1).

Example 22

(S)-3-(2-Chloro-6-fluoro-benzyl)-1-cyclohexyl-pyrrolidin-2-one

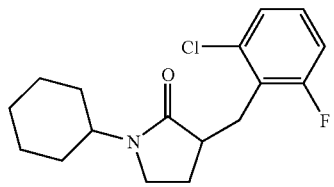

Dissolve (S)-3-(2-Chloro-6-fluoro-benzyl)-4-oxo-4-((4S,5R)-2-oxo-4,5-diphenyl-oxazolidin-3-yl)-butyraldehyde (Preparation 85) (0.384 g, 0.825 mmol) in THF (20 mL). Add cyclohexanamine (0.098 g, 0.99 mmol) and AcOH (0.049 g, 0.82 mmol). Stir the mixture for one hour and then add NaBH(OAc)₃ (0.262 g, 1.24 mmol). Stir the reaction mixture for 24 hours until LC-MS shows the starting material has been gone. Add water (20 mL) and extract the aqueous with CH₂Cl₂ (3×50 mL). Combine the organic layers and dry over Na₂SO₄. Concentrate and purify by chromatography (Silica gel) to afford (S)-3-(2-Chloro-6-fluorobenzyl)-1-cyclohexylpyrrolidin-2-one (0.172 g, 67%). MS (APCI-pos mode) m,/z (rel intensity) 310 (100), 312 (35).

Example 23

3-(2,4-Dichlorobenzyl)-1-(trans-4-methoxycyclohexyl)pyrrolidin-2-one

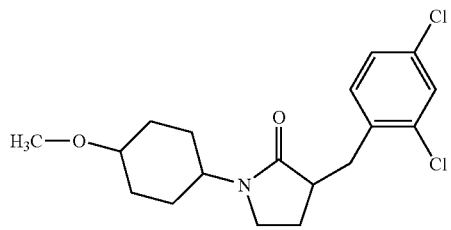

Using the procedure to synthesize Example 28 and using reagent 3-(2,4-dichlorobenzyl)-1-(trans-4-hydroxycyclohexyl) pyrrolidin-2-one (Example 15) (0.2 g, 0.58 mmol) yields 0.19 g (90%) of the title compound as colorless oil: MS (APCI-pos mode) f/z (rel intensity) 356.1 (100), 358.1 (50).

TABLE 1

The following compounds are prepared essentially as described in Example 1 except using the reagents in the "Reagents used" column.

| Example | Structure and name | Reagents used | Mass spec |
| --- | --- | --- | --- |
| 24 | 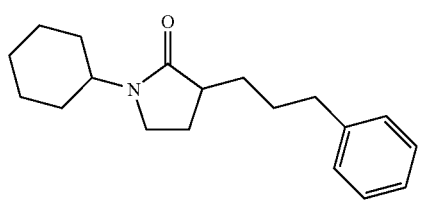<br>1-Cyclohexyl-3-(3-phenyl-propyl)-pyrrolidin-2-one | 1-cyclohexyl-pyrrolidin-2-one (300 mg, 1.8 mmol), LDA (2.0 M, 1.8 mL, 3.6 mmol), and 3-bromo-1-propyl-benzene (1.07 g, 5.4 mmol) | (apci) m/z = 286.2 (M + H) |

TABLE 1-continued

The following compounds are prepared essentially as described in Example 1 except using the reagents in the "Reagents used" column.

| Example | Structure and name | Reagents used | Mass spec |
|---------|-------------------|---------------|-----------|
| 25 | 3-Benzyl-1-cyclohexyl-3-methyl-pyrrolidin-2-one | 3-benzyl-1-cyclohexyl-pyrrolidin-2-one (345 mg, 1.3 mmol), LDA (2.0 M, 1.3 mL, 2.7 mmol), and iodomethane (507 mg, 4.0 mmol) | (apci) m/z = 272.2 (M + H) |
| 26 | 1-Adamantan-1-yl-3-(2,4-dichloro-benzyl)-pyrrolidin-2-one | 1-adamantan-1-yl-pyrrolidin-2-one (400 mg, 1.8 mmol), LDA (2.0 M, 1.8 mL, 3.6 mmol), and 2,4-dichloro-1-chloromethyl-benzene (1.07 g, 5.5 mmol) | (apci) m/z = 286.2 (M + H) |
| 27 | 1-Cyclohexyl-3-(2,4-dichloro-benzyl)-3-methyl-pyrrolidin-2-one | 1-cyclohexyl-3-(2,4-dichloro-benzyl)-pyrrolidin-2-one (300 mg, 0.92 mmol), LDA (2.0 M, 0.9 mL, 1.8 mmol) and iodomethane (392 mg, 2.8 mmol) | (apci) m/z = 340.2 (M + H) |
| 28 | 3-(2-Chloro-6-fluoro-benzyl)-1-cyclohexyl-4-methyl-pyrrolidin-2-one | 1-cyclohexyl-4-methyl-pyrrolidin-2-one (preparation 3) (350 mg, 1.9 mmol), LDA (2.0 M, 1.3 mL, 2.5 mmol) and 2-bromomethyl-1-chloro-3-fluoro-benzene (518 mg, 2.3 mmol) | (apci) m/z = 324.2 (M + H) |
| 29 | 1-Cyclohexyl-4-methoxymethyl-3-(4-trifluoromethyl-benzyl)-pyrrolidin-2-one | 1-cyclohexyl-4-methoxymethyl-pyrrolidin-2-one (preparation 4) (210 mg, 1.0 mmol), LDA (2.0 M, 0.6 mL, 1.2 mmol), and 1-bromomethyl-4-trifluoromethyl-benzene (356 mg, 1.5 mmol) | (APCI-pos mode) m/z (rel intensity) 370 (100) |

TABLE 1-continued

The following compounds are prepared essentially as described in Example 1 except using the reagents in the "Reagents used" column.

| Example | Structure and name | Reagents used | Mass spec |
|---|---|---|---|
| 30 | 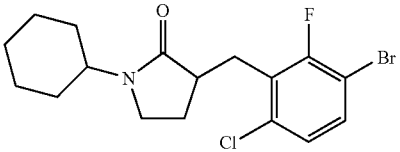<br>3-(3-bromo-6-chloro-2-fluoro-benzyl)-1-cyclohexyl-pyrrolidin-2-one | 1-cyclohexylpyrrolidin-2-one (12 g, 72 mmol) and 1-bromo-3-bromomethyl-4-chloro-2-fluorobenzene (preparation 9) (19 g, 63 mmol) | (ion spray): m/z = 390.0 (M + H) |
| 31 | 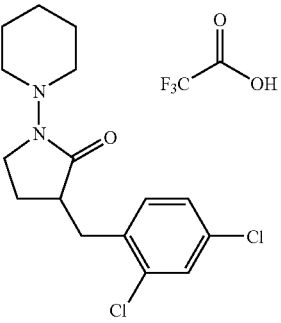<br>3-(2,4-Dichloro-benzyl)-1-piperidin-1-yl-pyrrolidin-2-one trifluoroacetate | 1-piperidin-1-yl-pyrrolidin-2-one (1.1 g, 6.5 mmol) and 2,4-dichloro-1-chloromethylbenzene (3 g, 13 mmol) | (ion spray): m/z = 327.2 (M + H − TFA |
| 32 | 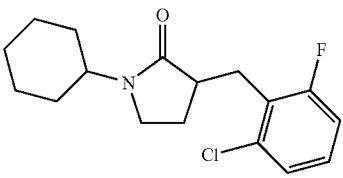<br>3-(2-Chloro-6-fluoro-benzyl)-1-cyclohexyl-pyrrolidin-2-one | 1-cyclohexyl pyrrolidinone (500 mg, 2.99 mmol) and 2-chloro-6-fluorobenzyl bromide (2.00 g, 8.97 mmol) | (APCI-pos mode) m/z (rel intensity) 310 (100), 312 (36) |
| 33 | 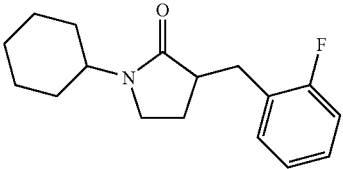<br>1-Cyclohexyl-3-(2-fluoro-benzyl)-pyrrolidin-2-one | 1-bromomethyl-2-fluorobenzene (1.70 g) and 1-cyclohexyl pyrrolidinone (0.50 g, 3.0 mmol) | (APCI-pos mode) m/z (rel intensity) 276 (100) |
| 34 | 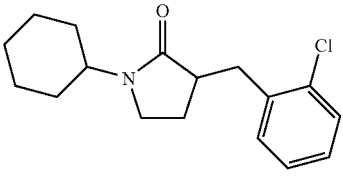<br>1-Cyclohexyl-3-(2-chloro-benzyl)-pyrrolidin-2-one | 1-bromomethyl-2-chlorobenzene (1.23 g) and 1-cyclohexyl pyrrolidinone (0.50 g, 3.0 mmol) | (APCI-pos mode) m/z (rel intensity) 292 (100), 294 (36) |

TABLE 1-continued

The following compounds are prepared essentially as described in Example 1 except using the reagents in the "Reagents used" column.

| Example | Structure and name | Reagents used | Mass spec |
|---|---|---|---|
| 35 | 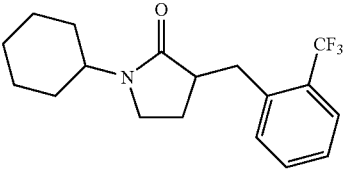<br>1-Cyclohexyl-3-(2-trifluoromethyl-benzyl)-pyrrolidin-2-one | 1-bromomethyl-2-trifluoromethylbenzene (1.43 g) and 1-cyclohexyl pyrrolidinone (0.50 g, 3.0 mmol) | MS (APCI-pos mode) m/z (rel intensity) 326 (100) |
| 36 | 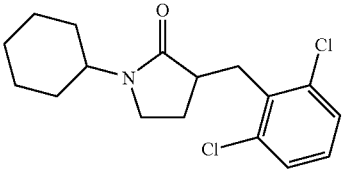<br>1-Cyclohexyl-3-(2,6-dichloro-benzyl)-pyrrolidin-2-one | 1-bromomethyl-2,6-dichlorobenzene (1.0 g) and 1-cyclohexyl pyrrolidinone (0.50 g, 3.0 mmol) | (APCI-pos mode) m/z (rel intensity) 326 (100), 328 (64) |
| 37 | 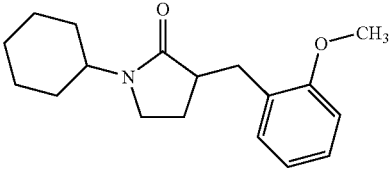<br>1-Cyclohexyl-3-(2-methoxy-benzyl)-pyrrolidin-2-one | 1-chloromethyl-2-methoxybenzene (936 mg) and 1-cyclohexyl pyrrolidinone (0.50 g, 3.0 mmol) | (APCI-pos mode) m/z (rel intensity) 288 (100) |
| 38 | 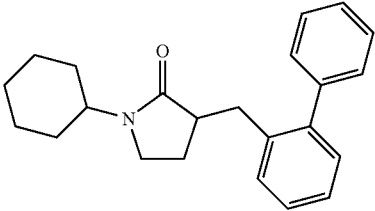<br>3-Biphenyl-2-ylmethyl-1-cyclohexyl-pyrrolidin-2-one | 2-bromomethyl-biphenyl (1.48 g) and 1-cyclohexyl pyrrolidinone (0.50 g, 3.0 mmol) | (APCI-pos mode) m/z (rel intensity) 334 (100) |
| 39 | 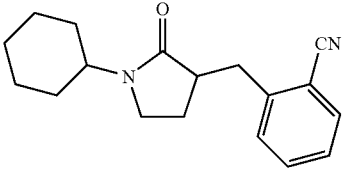<br>2-(1-Cyclohexyl-2-oxo-pyrrolidin-3-ylmethyl)-benzonitrile | 2-bromomethyl-benzonitrile (1.0 g) and 1-cyclohexyl pyrrolidinone (0.50 g, 3.0 mmol) | (APCI-pos mode) m/z (rel intensity) 283 (100) |

TABLE 1-continued

The following compounds are prepared essentially as described in Example 1 except using the reagents in the "Reagents used" column.

| Example | Structure and name | Reagents used | Mass spec |
|---|---|---|---|
| 40 | 3-(4-tert-Butyl-benzyl)-1-cyclohexyl-pyrrolidin-2-one | 1-bromomethyl-4-tert-butyl-benzene (1.36 g) and 1-cyclohexyl pyrrolidinone (0.50 g, 3.0 mmol) | MS (APCI-pos mode) m/z (rel intensity) 314 (100) |
| 41 | 1-Cyclohexyl-3-(2-methyl-benzyl)-pyrrolidin-2-one | 1-bromomethyl-2-methyl-benzene (1.11 g) and 1-cyclohexyl pyrrolidinone (0.50 g, 3.0 mmol) | (APCI-pos mode) m/z (rel intensity) 272 (100) |
| 42 | 1-Cyclohexyl-3-(4-methoxy-benzyl)-pyrrolidin-2-one | 1-bromomethyl-4-methoxy-benzene (1.0 g) and 1-cyclohexyl pyrrolidinone (0.50 g, 3.0 mmol) | (APCI-pos mode) m/z (rel intensity) 288 (100) |
| 43 | 1-Cyclohexyl-3-(2,6-difluoro-benzyl)-pyrrolidin-2-one | 2-bromomethyl-1,3-difluoro-benzene (1.0 g) and 1-cyclohexyl pyrrolidinone (0.50 g, 3.0 mmol) | (APCI-pos mode) m/z (rel intensity) 294 (100) |
| 44 | 3-Biphenyl-4-ylmethyl-1-cyclohexyl-pyrrolidin-2-one | 4-bromomethyl-biphenyl (1 g) and 1-cyclohexyl pyrrolidinone (0.50 g, 3.0 mmol) | (APCI-pos mode) m/z (rel intensity) 334 (100) |

TABLE 1-continued

The following compounds are prepared essentially as described in Example 1 except using the reagents in the "Reagents used" column.

| Example | Structure and name | Reagents used | Mass spec |
|---|---|---|---|
| 45 | 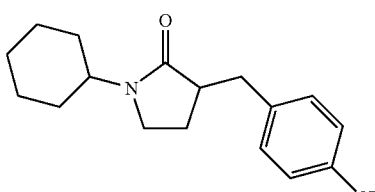<br>1-Cyclohexyl-3-(4-trifluoromethyl-benzyl)-pyrrolidin-2-one | 1-bromomethyl-4-trifluoromethyl-benzene (1 g) and 1-cyclohexyl pyrrolidinone (0.50 g, 3.0 mmol) | (APCI-pos mode) m/z (rel intensity) 326 (100) |
| 46 | 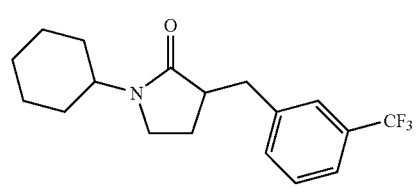<br>1-Cyclohexyl-3-(3-trifluoromethyl-benzyl)-pyrrolidin-2-one | 1-bromomethyl-3-trifluoromethyl-benzene (1.43 g) and 1-cyclohexyl pyrrolidinone (0.50 g, 3.0 mmol) | (APCI-pos mode) m/z (rel intensity) 326 (100) |
| 47 | 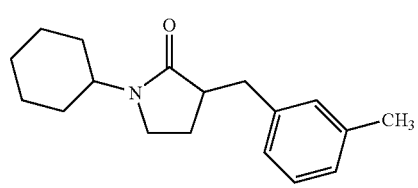<br>1-Cyclohexyl-3-(3-methyl-benzyl)-pyrrolidin-2-one | 1-bromomethyl-3-methyl-benzene (1.11 g) and 1-cyclohexyl pyrrolidinone (0.50 g, 3.0 mmol) | (APCI-pos mode) m/z (rel intensity) 272 (100) |
| 48 | 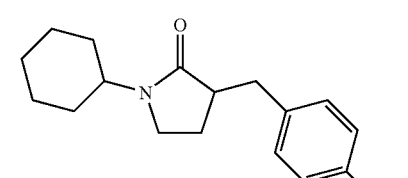<br>1-Cyclohexyl-3-(4-methyl-benzyl)-pyrrolidin-2-one | 1-bromomethyl-4-methyl-benzene (1.0 g) and 1-cyclohexyl pyrrolidinone (0.50 g, 3.0 mmol) | (APCI-pos mode) m/z (rel intensity) 272 (100) |
| 49 | 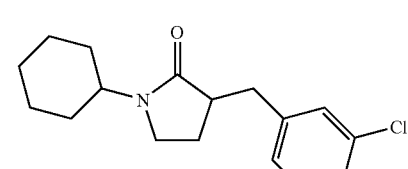<br>1-Cyclohexyl-3-(3-chloro-benzyl)-pyrrolidin-2-one | 1-bromomethyl-3-chloro-benzene (1.23 g) and 1-cyclohexyl pyrrolidinone (0.50 g, 3.0 mmol) | (APCI-pos mode) m/z (rel intensity) 292 (100), 294 (33) |

TABLE 1-continued

The following compounds are prepared essentially as described in Example 1 except using the reagents in the "Reagents used" column.

| Example | Structure and name | Reagents used | Mass spec |
|---|---|---|---|
| 50 | 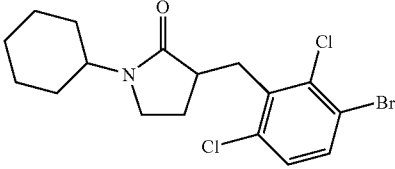<br>3-(3-Bromo-2,6-dichloro-benzyl)-1-cyclohexyl-pyrrolidin-2-one | 1-cyclohexyl pyrrolidinone (15.0 g, 89.7 mmol) and 1-bromo-3-bromomethyl-2,4-dichloro-benzene (34.3 g, 108 mmol) | (APCI-pos mode) m/z (rel intensity) 404 (62), 406 (100), 408 (40) |
| 51 | 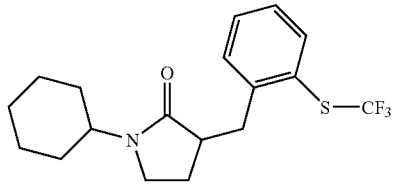<br>1-Cyclohexyl-3-(2-trifluoromethylsulfanyl-benzyl)-pyrrolidin-2-one | 1-cylcohexyl pyrrolidinone (1.73 g, 10.3 mmol) and 1-bromomethyl-2-trifluoromethylsulfanyl-benzene (1.87 g, 6.90 mmol) | (APCI-pos mode) m/z (rel intensity) 358 (100) |
| 52 | 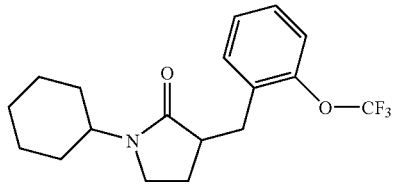<br>1-Cyclohexyl-3-(2-trifluoromethoxy-benzyl)-pyrrolidin-2-one | 1-cyclohexyl pyrrolidinone (573 mg, 3.37 mmol) and 1-bromomethyl-2-trifluoromethoxy-benzene (573 mg, 2.25 mmol) | (APCI-pos mode) m/z (rel intensity) 342 (100) |
| 53 | 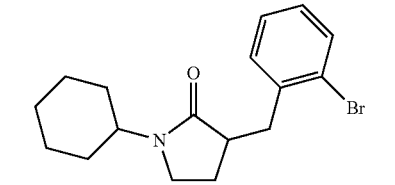<br>3-(2-Bromo-benzyl)-1-cyclohexyl-pyrrolidin-2-one | 1-cyclohexyl pyrrolidinone (7.03 g, 42 mmol) and 1-bromomethyl-2-bromo-benzene (7.00 g, 28 mmol) | (APCI-pos mode) m/z (rel intensity) 336 (100), 338 (100) |
| 54 | 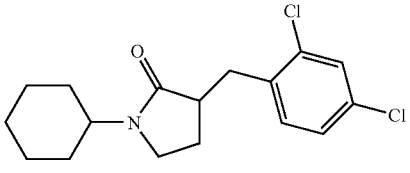<br>1-Cyclohexyl-3-(2,4-dichloro-benzyl)-pyrrolidin-2-one | 1-cyclohexyl-pyrrolidin-2-one (5.0 g, 30 mmol) and 2,4-dichlorobenzylchloride (4.0 g, 37 mmol) | (apci) m/z = 326.2 (M + H) |

TABLE 1-continued

The following compounds are prepared essentially as described in Example 1 except using the reagents in the "Reagents used" column.

| Example | Structure and name | Reagents used | Mass spec |
|---|---|---|---|
| 55 | 3-(4-Bromo-2-chloro-benzyl)-1-cyclohexyl-pyrrolidin-2-one | 1-cyclohexyl-pyrrolidin-2-one (10.5 g, 62.8 mmol) and 4-bromo-1-bromomethyl-2-chloro-benzene (21.4 g, 75.3 mmol) | (apci) m/z = 372.1 (M + H) |
| 56 | 3-(2-Bromo-6-chloro-benzyl)-1-cyclohexyl-pyrrolidin-2-one | 1-cyclohexyl-pyrrolidin-2-one (5.0 g, 30 mmol) and 2-bromo-6-chlorobenzyl bromide (13 g, 45 mmol) | (apci) m/z = 372.0 (M + H) |
| 57 | 3-(2-Chloro-6-methoxy-benzyl)-1-(cis-4-hydroxy-cyclohexyl)-pyrrolidin-2-one | cis-1-[4-(tert-butyl-dimethyl-silanyloxy)-cyclohexyl]-pyrrolidin-2-one (preparation 17) (330 mg, 1.1 mmol) and 2-bromomethyl-1-chloro-3-methoxy-benzene, 390 mg, 1.7 mmol) | (apci) m/z = 338.1 (M + H) |
| 58 | 3-(2-Chloro-6-fluoro-benzyl)-1-(1-phenyl-cyclohexyl)-pyrrolidin-2-one | 1-(1-phenyl-cyclohexyl)-pyrrolidin-2-one (0.16 g, 0.47 mmol) and 2-bromomethyl-1-chloro-3-fluoro-benzene | (ion spray): m/z = 386.0, 387.9 (M + 1) |
| 59 | 3-(2-Chloro-6-fluoro-benzyl)-1-(cis-2-methyl-cyclohexyl)-pyrrolidin-2-one | 1-(cis-2-methyl-cyclohexyl)-pyrrolidin-2-one (Preparation 32) (0.48 g, 2.65 mmol) and 2-bromomethyl-1-chloro-3-fluoro-benzene | (ion spray): m/z = 324.1, 326.1 (M + 1) |

TABLE 1-continued

The following compounds are prepared essentially as described in Example 1 except using the reagents in the "Reagents used" column.

| Example | Structure and name | Reagents used | Mass spec |
|---|---|---|---|
| 60 | 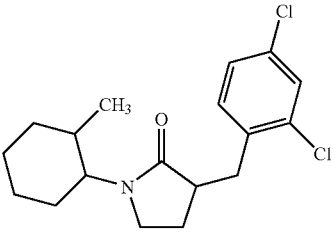<br>3-(2,4-Dichloro-benzyl)-1-(cis-2-methyl-cyclohexyl)-pyrrolidin-2-one | 1-(cis-2-methyl-cylcohexyl)-pyrrolidin-2-one (Preparation 32) (0.10 g, 0.55 mmol) and 1-bromomethyl-2,4-dichloro-benzene (216 mg, 1.10 mmol) | (ion spray): m/z = 340.2, 342.1 (M + 1) |
| 61 | 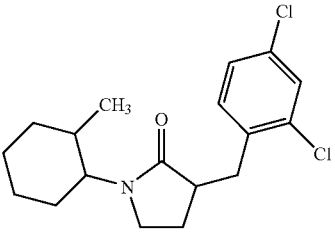<br>1-(cis-2-Methyl-cyclohexyl)-3-(4-trifluoromethyl-benzyl)-pyrrolidin-2-one | 1-(cis-2-methyl-cyclohexyl)-pyrrolidin-2-one (Preparation 32) (0.082 g, 0.45 mmol), LDA (1.5 M, 0.32 mL, 0.47 mmol), and 1-(bromomethyl)-4-(trifluoromethyl)benzene (162 mg, 0.68 mmol) | (ion spray): m/z = 340.2 (M + 1) |
| 62 | 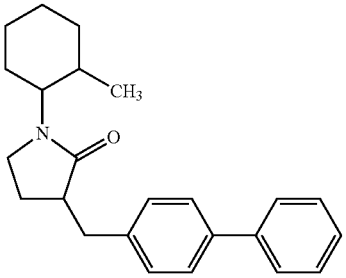<br>3-Biphenyl-4-ylmethyl-1-(cis-2-methyl-cyclohexyl)-pyrrolidin-2-one, Isomer A | 1-(cis-2-methyl-cyclohexyl)-pyrrolidin-2-one (Preparation 32) (0.10 g) and 4-bromomethyl-biphenyl (0.24 g, 0.86 mmol) | (ion spray): m/z = 348.2 (M + 1) |
| 63 | 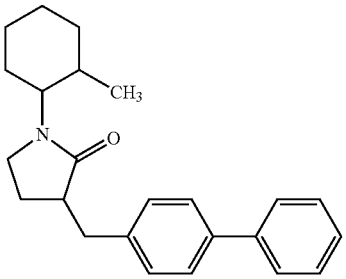<br>3-Biphenyl-4-ylmethyl-1-(cis-2-methyl-cyclohexyl)-pyrrolidin-2-one, Isomer B | 1-(cis-2-methyl-cyclohexyl)-pyrrolidin-2-one (Preparation 32) (0.10 g, 0.57 mmol) and 4-bromomethyl-biphenyl (0.24 g, 0.86 mmol) | (ion spray): m/z = 348.2 (M + 1) |

TABLE 1-continued

The following compounds are prepared essentially as described in Example 1 except using the reagents in the "Reagents used" column.

| Example | Structure and name | Reagents used | Mass spec |
|---|---|---|---|
| 64 | 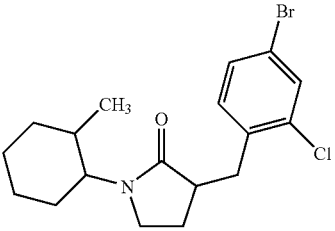<br>3-(4-Bromo-2-chloro-benzyl)-1-(cis-2-methyl-cyclohexyl)-pyrrolidin-2-one | 1-(cis-2-methyl-cyclohexyl)-pyrrolidin-2-one (Preparation 32) (0.25 g, 1.4 mmol), LDA (1.5 M, 1.0 mL, 1.5 mmol) and 4-bromo-1-(bromomethyl)-2-chlorobenzene (0.43 g, 1.5 mmol) | $^1$H NMR (CDCl$_3$) δ 7.56 (d, 1 H), 7.35 (dd, 1 H), 7.18 (d, 1 H), 4.05 (dt, 1 H), 3.36-3.40 (m, 3 H), 2.76-2.84 (m, 2 H), 2.28-2.39 (m, 1 H), 2.00-2.08 (m, 1 H), 1.62-1.84 (m, 4 H), 1.32-1.57 (m, 5 H), 0.92 (d, 3 H) |
| 65 | 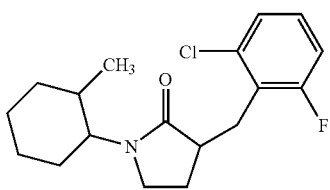<br>3-(2-Chloro-6-fluoro-benzyl)-1-(trans-2-methyl-cyclohexyl)-pyrrolidin-2-one | 1-(trans-2-methyl-cyclohexyl)-pyrrolidin-2-one (Preparation 34) (0.78 g, 4.83 mmol) and 2-bromomethyl-1-chloro-3-fluoro-benzene | (ion spray): m/z = 324.1, 326.2 (M + 1) |
| 66 | 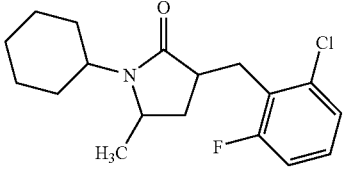<br>3-(2-Chloro-6-fluoro-benzyl)-1-cyclohexyl-5-methyl-pyrrolidin-2-one | 1-cyloexyl-5-methyl-pyrrolidin-2-one (US6743819, 500 mg, 3 mmol) and 2-Bromomethyl-1-chloro-3-fluoro-benzene (1 g, 6 mmol) | (APCI-pos mode) m/z (rel intensity) 324 (100) |
| 67 | 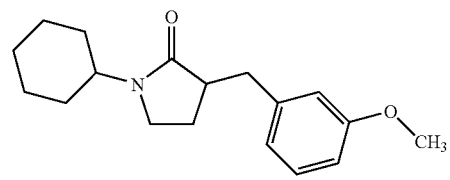<br>1-Cyclohexyl-3-(3-methoxy-benzyl)-pyrrolidin-2-one | 1-cyclohexyl-pyrrolidin-2-one (500 mg, 2.9 mmol), LDA (2.0 M, 3 mL, 6 mmol), and 1-chloromethyl-3-methoxy-benzene (940 mg, 6 mmol) | (apci) m/z = 288 (M + H) |
| 68 | 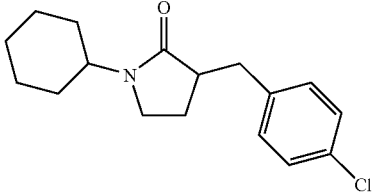<br>3-(4-Chloro-benzyl)-1-cyclohexyl-pyrrolidin-2-one | 1-cyclohexyl-pyrrolidin-2-one (500 mg, 2.9 mmol), LDA (2.0 M, 3 mL, 6 mmol), and 1-bromomethyl-4-chloro-benzene (640 mg, 6 mmol) | (apci) m/z = 292 (M + H) |

TABLE 1-continued

The following compounds are prepared essentially as described in Example 1 except using the reagents in the "Reagents used" column.

| Example | Structure and name | Reagents used | Mass spec |
|---|---|---|---|
| 69 | 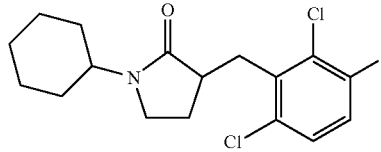<br>1-Cyclohexyl-3-(2,6-dichloro-3-methoxy-benzyl)-pyrrolidin-2-one | 1-cyclohexyl-pyrrolidin-2-one (5.2 g, 31 mmol), LDA (2.0 M, 16 mL, 31 mmol), and 2-bromomethyl-1,3-dichloro-4-methoxy-benzene (7 g, 26 mmol) | (apci) m/z = 356 (M + H) |
| 70 | 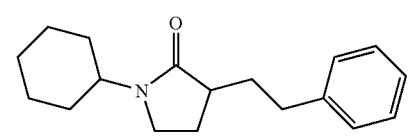<br>1-Cyclohexyl-3-phenethylpyrrolidin-2-one | 1-cyclohexyl pyrrolidinone (300 mg, 1.79 mmol) and 1-(2-bromoethyl)benzene (1.00 g, 3.38 mmol) | (apci) m/z = 272.2 (M + H) |
| 71 | 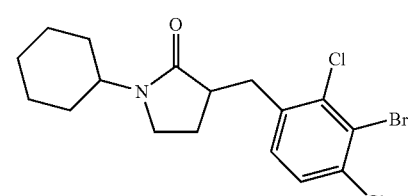<br>3-(3-Bromo-2,4-dichlorobenzyl)-1-cyclohexylpyrrolidin-2-one | 1-cyclohexyl pyrrolidinone (53.9 g, 322 mmol), LDA (2.0 M, 166.5 mL, 333 mmol), and 2-bromo-4-(bromomethyl)-1,3-dichlorobenzene (68.5 g, 214.9 mmol) | (apci) m/z = 406.1 (M + H) |
| 72 | 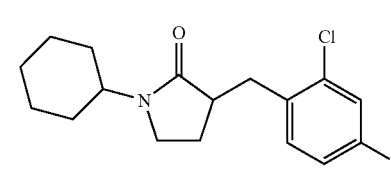<br>3-(2-Chloro-4-fluorobenzyl)-1-cyclohexylpyrrolidin-2-one | 1-cyclohexyl pyrrolidinone (2.0 g, 12.0 mmol), LDA (2.0 M, 12.0 mL, 24.0 mmol) and 1-(bromomethyl)-2-chloro-4-fluorobenzene (4.0 g, 18 mmol) | (apci) m/z = 310.2 (M + H) |
| 73 | 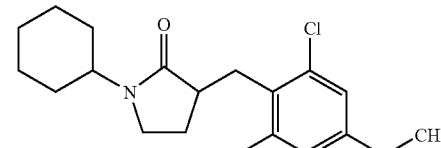<br>3-(2,6-Dichloro-4-methoxybenzyl)-1-cyclohexylpyrrolidin-2-one | 1-cyclohexylpyrrolidin-2-one (37.2 g, 222 mmol) and 2-(bromomethyl)-1,3-dichloro-5-methoxybenzene [J. Org. Chem. (1985), 50(3), 408-10] (40.0 g, 148 mmol) | (apci) m/z = 356.2 (M + H) |
| 74 | 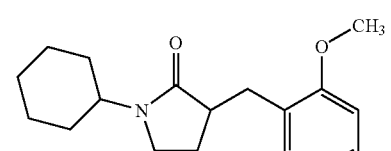<br>3-(2,4-dichloro-6-methoxybenzyl)-1-cyclohexylpyrrolidin-2-one | 1-cyclohexyl-pyrrolidin-2-one (16.0 g, 95.8 mmol), LDA (47.9 mL, 95.6 mmol) and 1,5-Dichloro-2-(chloromethyl)-3-methoxybenzene (J. Med. Chem. (1988) 31, 72-83) (14.4 g, 63.2 mmol) | (apci) m/z = 356.2 (M + H) |

TABLE 1-continued

The following compounds are prepared essentially as described in Example 1 except using the reagents in the "Reagents used" column.

| Example | Structure and name | Reagents used | Mass spec |
|---|---|---|---|
| 75 | 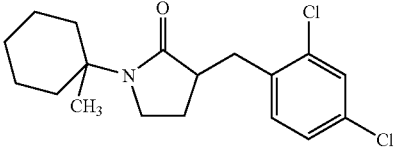<br>3-(2,4-Dichlorobenzyl)-1-(1-methylcyclohexyl)pyrrolidin-2-one | 1-(1-methylcyclohexyl)pyrrolidin-2-one (0.10 g, 0.55 mmol) and 2,4-dichloro-1-(chloromethyl)benzene (0.22 g, 1.10 mmol) | (APCI-pos mode) m/z (rel intensity) 340.0 (100), 342.0 (50) |
| 76 | 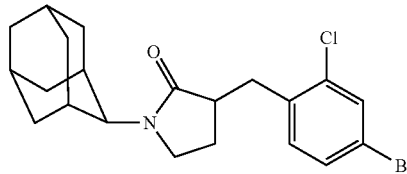<br>1-Adamantan-2-yl-3-(4-bromo-2-chloro-benzyl)-pyrrolidin-2-one | 1-adamantan-2-yl-pyrrolidin-2-one [Khimiko-Farmatsevticheskii Zhurnal (1982), 16(10), 1197] (2.7 g, 12 mmol), LDA (2.0 M, 8.0 mL, 16 mmol) and 4-bromo-1-bromomethyl-2-chloro-benzene (preparation 5) (3.5 g, 12 mmol) | (apci) m/z = 424.1 (M + H) |

Example 55 can also be made using N-cyclohexylpyrrolidinone (15 g, 89.7 mmol), LDA (2.0 M, 53.8 mL, 107.6 mmol) and 4-bromo-1-bromomethyl-2-chloro-benzene (30.6 mg, 107.6 mmol).

Examples 77, 78 and 79

1-Cyclohexyl-3-[(2,4-dichloro-phenyl)-hydroxymethyl]-pyrrolidin-2-one

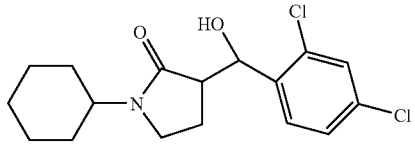

Using the procedure to synthesize Example 1 and using reagents 1-cyclohexyl-pyrrolidin-2-one (500 mg, 3.0 mmol), LDA (2.0 M, 1.8 mL, 3.6 mmol) and 2,4-dichlorobenzaldehyde (630 mg, 3.6 mmol) affords 530 mg (53%) of the title compound as a white solid. Separate the diastereomers over silica gel (30% ethyl acetate in hexanes) Isomer 1 (Example 78): (25%) Mass spectrum (apci) m/z=342.0 (M+H). HPLC (5 to 95) $R_t$ (Purity at 220 mn)=3.77 min (98%). Isomer 2 (Example 79): (28%) Mass spectrum (apci) m/z=342.0 (M+H). HPLC (5 to 95) $R_t$ (Purity at 220 nm)=3.52 min (100%).

Example 80

3-(2,6-Dichloro-4-hydroxybenzyl)-1-(cis-2-methylcyclohexyl) pyrrolidin-2-one

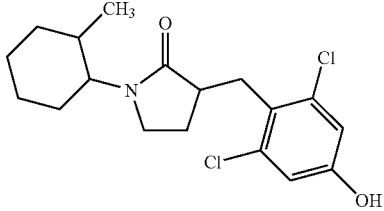

Using the procedure to synthesize Example 1 and using reagents 1-(cis-2-methyl-cyclohexyl)-pyrrolidin-2-one (Preparation 32) (1.0 g, 5.52 mmol) and 2-(bromomethyl)-1,3-dichloro-5-methoxybenzene (1.24 g, 5.52 mmol) gives 1.29 g (63%) 3-(2,6-Dichloro-4-methoxybenzyl)-1-(cis-2-methylcyclohexyl)pyrrolidin-2-one as a white solid.

Dissolve 3-(2,6-dichloro-4-methoxybenzyl)-1-(cis-2-methylcyclohexyl) pyrrolidin-2-one (1.29 g, 3.47 mmol) in DCM (100 mL) and cool to 0° C. Stir the solution under $N_2$ and add $BBr_3$ (2.61 g, 10.42 mmol). Continue to stir the reaction mixture for 2 hours and add water (100 mL). Extract the aqueous layer with dichloromethane (3×200 mL). Combine the organic layers and dry with $Na_2SO_4$, filter, concentrate and purify by flash column chromatography (silica gel, 40-100% of EtOAc-Hexane) to give 1.06 g (85%) of the title compound as a white solid: MS (APCI-pos mode) m/z (rel intensity) 356.1 (100), 358.1 (60).

Example 81

3-[2-Chloro-4-(2-chloro-pyridin-3-yl)-benzyl]-1-cyclohexyl-pyrrolidin-2-one

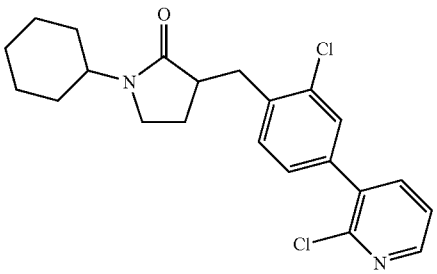

Place 3-(4-boronic acid-2-chloro-benzyl)-1-cyclohexyl-pyrrolidin-2-one (Preparation 6) (140 mg, 0.4 mmol), 2-chloro-3-iodo-pyridine (200 mg, 0.8 mmol) and palladium tetrakis (45 mg, 0.04 mmol) in a flask and purge with nitro gen. Add dimethoxyethane (DME) (3 mL) and sodium carbonate (2M, 0.3 mL) and heat to 75° C. for 24 hours. Cool and filter through celite. Wash with saturated sodium bicarbonate and extract with dichloromethane (DCM). Combine extracts, dry over sodium sulfate, filter, and concentrate. Purify by silica gel (20-70% ethyl acetate in hexane) to afford 30 mg (18%) of the title compound: Mass spectrum (apci) m/z=403.2 (M+H).

TABLE 2

The following compounds are prepared essentially as described in Example 10 except using the reagents in the "Reagents used" column.

| Example | Structure and name | Reagents used | Mass spec |
|---|---|---|---|
| 82 | <br>5-[3-Chloro-4-(1-cyclohexyl-2-oxo-pyrrolidin-3-ylmethyl)-phenyl]-pyridine-2-carbonitrile | 3-(4-boronic acid-2-chloro-benzyl)-1-cyclohexyl-pyrrolidin-2-one (Preparation 6) (140 mg, 0.4 mmol), 5-bromo-pyridine-2-carbonitrile (153 mg, 0.8 mmol), and palladium tetrakis (48 mg, 0.04 mmol) | (apci)<br>m/z = 403.2<br>(M + H) |
| 83 | 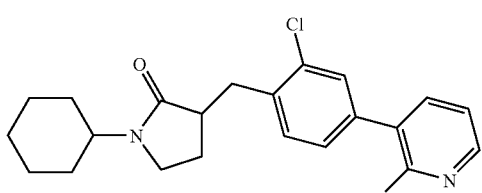<br>3-[3-Chloro-4-(1-cyclohexyl-2-oxo-pyrrolidin-3-ylmethyl)-phenyl]-pyridine-2-carbonitrile | 3-(4-boronic acid-2-chloro-benzyl)-1-cyclohexyl-pyrrolidin-2-one (Preparation 6) (150 mg, 0.4 mmol), 3-bromo-pyridine-2-carbonitrile (164 mg, 0.9 mmol), and palladium tetrakis (52 mg, 0.04 mmol) | (apci)<br>m/z = 394.2<br>(M + H) |
| 84 | 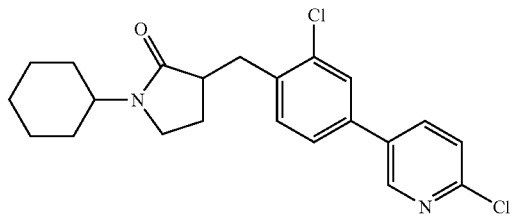<br>3-[2-Chloro-4-(6-chloro-pyridin-3-yl)-benzyl]-1-cyclohexyl-pyrrolidin-2-one | 3-(4-boronic acid-2-chloro-benzyl)-1-cyclohexyl-pyrrolidin-2-one (Preparation 6) (175 mg, 0.5 mmol), 2-chloro-5-iodo-pyridine (250 mg, 1.0 mmol), and palladium tetrakis (60 mg, 0.05 mmol) | (apci)<br>m/z = 403.2<br>(M + H) |
| 85 | 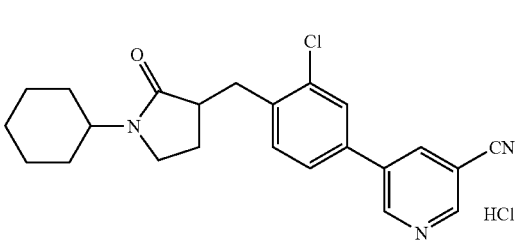<br>5-[3-Chloro-4-(1-cyclohexyl-2-oxo-pyrrolidin-3-ylmethyl)-phenyl]-nicotinonitrile hydrochloride salt | 3-(4-boronic acid-2-chloro-benzyl)-1-cyclohexyl-pyrrolidin-2-one (Preparation 6) (175 mg, 0.5 mmol), 2-chloro-5-iodo-pyridine (250 mg, 1.0 mmol), and palladium tetrakis (60 mg, 0.05 mmol) yields the freebase of the title compound. Dissolve in dichloromethane and add HCl in ether (2 M, 0.2 mL) and concentrate | (apci)<br>m/z = 394.2<br>(M + H) |

TABLE 2-continued

The following compounds are prepared essentially as described in Example 10 except using the reagents in the "Reagents used" column.

| Example | Structure and name | Reagents used | Mass spec |
|---|---|---|---|
| 86 | 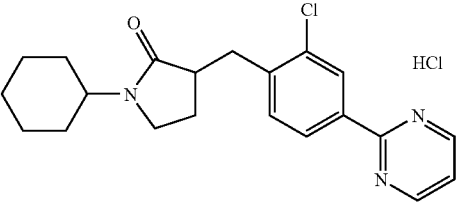<br>3-(2-Chloro-4-pyrimidin-2-yl-benzyl)-1-cyclohexyl-pyrrolidin-2-one hydrochloride salt | 3-(4-boronic acid-2-chloro-benzyl)-1-cyclohexyl-pyrrolidin-2-one (Preparation 6) (200 mg, 0.6 mmol), 2-bromo-pyrimidine (189 mg, 1.2 mmol), and palladium tetrakis (70 mg, 0.06 mmol) yields the freebase of the title compound. Dissolve in dichloromethane and add HCl in ether (2 M, 0.2 mL) and concentrate | (apci) m/z = 370.2 (M + H) |
| 87 | 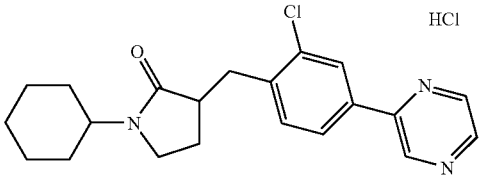<br>3-(2-Chloro-4-pyrazin-2-yl-benzyl)-1-cyclohexyl-pyrrolidin-2-one | 3-(4-boronic acid-2-chloro-benzyl)-1-cyclohexyl-pyrrolidin-2-one (Preparation 6) (200 mg, 0.6 mmol), 2-iodo-pyrazine (245 mg, 1.2 mmol), and palladium tetrakis (69 mg, 0.06 mmol) yields the freebase of the title compound. Dissolve in dichloromethane and add HCl in ether (2 M, 0.2 mL) and concentrate | spectrum (apci) m/z = 370.2 (M + H) |
| 88 | 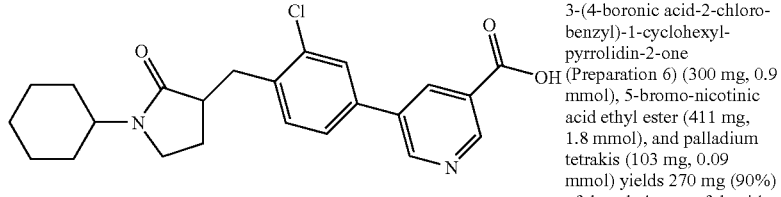<br>5-[3-Chloro-4-(1-cyclohexyl-2-oxo-pyrrolidin-3-ylmethyl)-phenyl]-nicotinic acid | 3-(4-boronic acid-2-chloro-benzyl)-1-cyclohexyl-pyrrolidin-2-one (Preparation 6) (300 mg, 0.9 mmol), 5-bromo-nicotinic acid ethyl ester (411 mg, 1.8 mmol), and palladium tetrakis (103 mg, 0.09 mmol) yields 270 mg (90%) of the ethyl ester of the title compound. Dissolve in ethanol (30 mL) and water (1 mL) and add potassium hydroxide (103 mg, 1.8 mmol) and stir for three hours. Strip off solvent and add water. Adjust to a pH of 2 with 1 M HCl. Filter precipitate | (apci) m/z = 413.3 (M + H) |
| 89 | 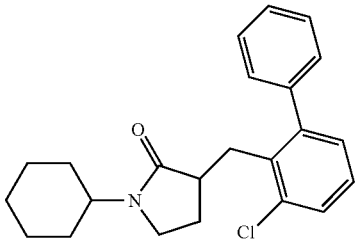<br>3-(3-Chloro-biphenyl-2-ylmethyl)-1-cyclohexyl-pyrrolidin-2-one | reagents 3-(2-bromo-6-chloro-benzyl)-1-cyclohexyl-pyrrolidin-2-one (Example 56) (210 mg, 0.57 mmol) and phenylboronic acid (210 mg, 1.7 mmol) | (apci) m/z = 368.2 (M + H) |

TABLE 2-continued

The following compounds are prepared essentially as described in Example 10 except using the reagents in the "Reagents used" column.

| Example | Structure and name | Reagents used | Mass spec |
|---|---|---|---|
| 90 | 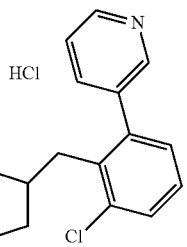<br>3-(2-Chloro-6-pyridin-3-yl-benzyl)-1-cyclohexyl-pyrrolidin-2-one hydrochloride salt | 3-(2-bromo-6-chloro-benzyl)-1-cyclohexyl-pyrrolidin-2-one (Example 56) (250 mg, 0.67 mmol) and 3-pyridylboronic acid (250 mg, 2.0 mmol) | (apci) m/z = 369.2 (M + H) Example 90a (Isomer 1) Example 90b (Isomer 2) |
| 91 | 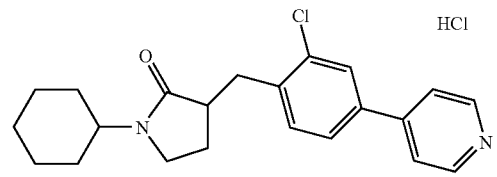<br>3-(2-Chloro-4-pyridin-4-yl-benzyl)-1-cyclohexyl-pyrrolidin-2-one hydrochloride salt | 3-(4-bromo-2-chloro-benzyl)-1-cyclohexyl-pyrrolidin-2-one (Example 55) (2.0 g, 5.4 mmol) and 4-pyridylboronic acid (2.0 g, 16 mmol) | (apci) m/z = 369.4 (M + H) |
| 92 | 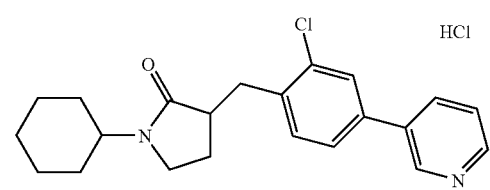<br>3-(2-Chloro-4-pyridin-3-yl-benzyl)-1-cyclohexyl-pyrrolidin-2-one hydrochloride salt | 3-(4-bromo-2-chloro-benzyl)-1-cyclohexyl-pyrrolidin-2-one (Example 55) (2.0 g, 5.4 mmol) and 3-pyridylboronic acid (2.0 g, 16 mmol) | (apci) m/z = 369.3 (M + H) Example 92a (Isomer 1) Example 92b (Isomer 2) |
| 93 | 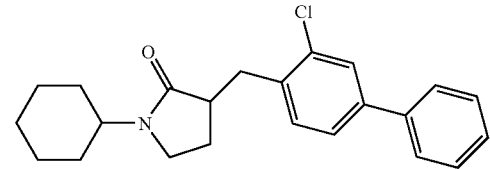<br>3-(3-Chloro-biphenyl-4-ylmethyl)-1-cyclohexyl-pyrrolidin-2-one | 3-(4-bromo-2-chloro-benzyl)-1-cyclohexyl-pyrrolidin-2-one (Example 55) (150 mg, 0.41 mmol) and phenylboronic acid (150 mg, 1.2 mmol) | (apci) m/z = 368.2 (M + H) |
| 94 | 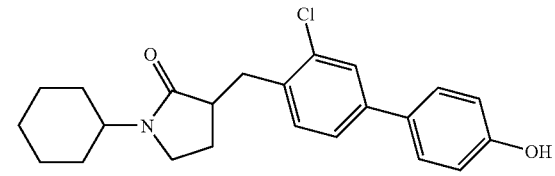<br>3-(3-Chloro-4'-hydroxy-biphenyl-4-ylmethyl)-1-cyclohexyl-pyrrolidin-2-one | 3-(4-bromo-2-chloro-benzyl)-1-cyclohexyl-pyrrolidin-2-one (Example 55) (500 mg, 1.35 mmol) and 4-hydroxyphenylboronic acid (560 mg, 4.0 mmol) | (apci) m/z = 384.2 (M + H) |

TABLE 2-continued

The following compounds are prepared essentially as described in Example 10 except using the reagents in the "Reagents used" column.

| Example | Structure and name | Reagents used | Mass spec |
|---|---|---|---|
| 95 | 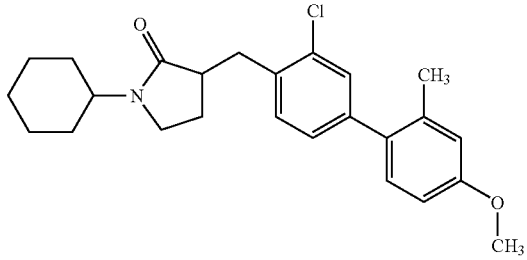<br>3-(3-Chloro-4'-methoxy-2'-methyl-biphenyl-4-ylmethyl)-1-cyclohexyl-pyrrolidin-2-one | 3-(4-bromo-2-chloro-benzyl)-1-cyclohexyl-pyrrolidin-2-one (Example 55) (1.0 g, 2.7 mmol) and 2-methyl-4-methoxyphenylboronic acid (900 mg, 5.4 mmol) | (apci) m/z = 412.3 (M + H) |
| 96 | 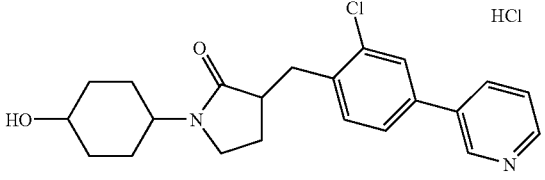<br>3-(2-Chloro-4-pyridin-3-yl-benzyl)-1-(cis-4-hydroxy-cyclohexyl)-pyrrolidin-2-one hydrochloride salt | 3-(4-bromo-2-chloro-benzyl)-1-(cis-4-hydroxy-cyclohexyl)-pyrrolidin-2-one (Example 134) (200 mg, 0.52 mmol) and 3-pyridylboronic acid (190 mg, 1.6 mmol) | (apci) m/z = 367.3 (M + H − H$_2$O) |
| 97 | <br>3-(2-Chloro-4-pyridin-4-yl-benzyl)-1-(cis-4-hydroxy-cyclohexyl)-pyrrolidin-2-one hydrochloride salt | 3-(4-bromo-2-chloro-benzyl)-1-(cis-4-hydroxy-cyclohexyl)-pyrrolidin-2-one (Example 134) (200 mg, 0.52 mmol) and 4-pyridylboronic acid (190 mg, 1.6 mmol) | (apci) m/z = 385.3 (M + H) |
| 98 | 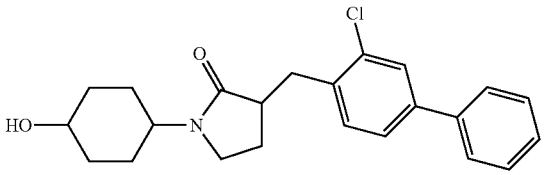<br>3-(3-Chloro-biphenyl-4-ylmethyl)-1-(cis-4-hydroxy-cyclohexyl)-pyrrolidin-2-one | 3-(4-bromo-2-chloro-benzyl)-1-(cis-4-hydroxy-cyclohexyl)-pyrrolidin-2-one (Example 134) (150 mg, 0.39 mmol) and phenylboronic acid (140 mg, 1.2 mmol) | (apci) m/z = 384.1 (M + H) |

TABLE 2-continued

The following compounds are prepared essentially as described in Example 10 except using the reagents in the "Reagents used" column.

| Example | Structure and name | Reagents used | Mass spec |
|---|---|---|---|
| 99 | 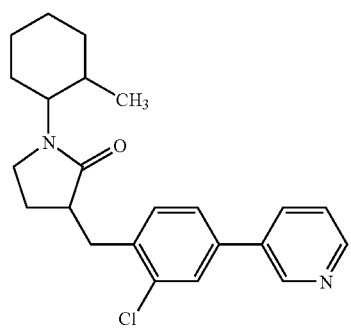<br>3-(2-Chloro-4-pyridin-3-yl-benzyl)-1-(cis-2-methyl-cyclohexyl)-pyrrolidin-2-one | 3-(4-bromo-2-chloro-benzyl)-1-(cis-2-methyl-cyclohexyl)-pyrrolidin-2-one (Example 64) (0.12 g, 0.31 mmol) and 3-pyridylboronic acid (191 mg) | (ion spray): m/z = 383.3, 385.3 (M + 1) |
| 100 | 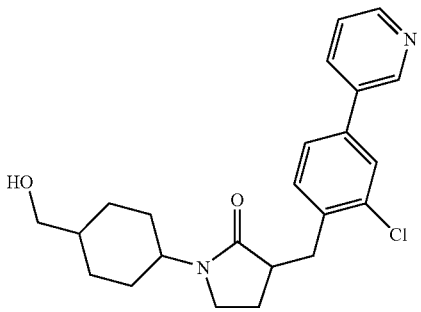<br>3-(2-Chloro-4-pyridin-3-yl-benzyl)-1-(cis-4-hydroxymethyl-cyclohexyl)-pyrrolidin-2-one | 3-(4-bromo-2-chloro-benzyl)-1-[cis-4-(tert-butyl-dimethyl-silanyloxymethyl)-cyclohexyl]-pyrrolidin-2-one (Preparation 38) (0.42 g, 0.82 mmol) 3-pyridylboronic acid (503 mg) | (ion spray): m/z = 399.3, 401.3 (M + 1) |
| 101 | 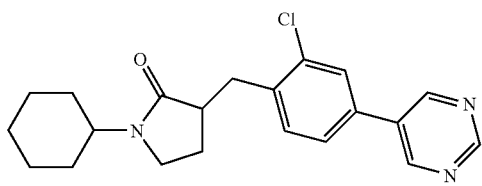<br>3-(2-Chloro-4-pyrimidin-5-yl-benzyl)-1-cyclohexyl-pyrrolidin-2-one | reagents 3-(4-boronic acid-2-chloro-benzyl)-1-cyclohexyl-pyrrolidin-2-one (Preparation 6) (200 mg, 0.6 mmol), 5-bromo-pyrimidine (189 mg, 1.2 mmol), and palladium tetrakis (69 mg, 0.06 mmol) | (apci) m/z = 370.3 (M + H) |
| 102 | 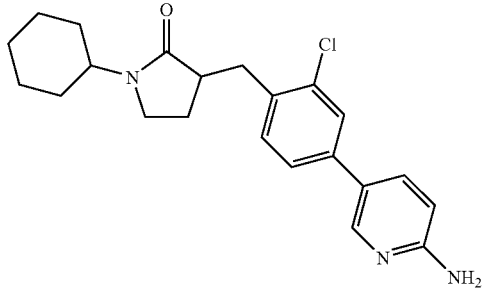<br>3-(4-(6-Aminopyridin-3-yl)-2-chlorobenzyl)-1-cyclohexylpyrrolidin-2-one | 3-(4-boronic acid-2-chloro-benzyl)-1-cyclohexyl-pyrrolidin-2-one (Preparation 6) (200 mg, 0.6 mmol), 5-iodopyridin-2-amine (262 mg, 1.2 mmol), and palladium tetrakis (69 mg, 0.06 mmol) | (apci) m/z = 384.4 (M + H) |

TABLE 2-continued

The following compounds are prepared essentially as described in Example 10 except using the reagents in the "Reagents used" column.

| Example | Structure and name | Reagents used | Mass spec |
|---|---|---|---|
| 103 | 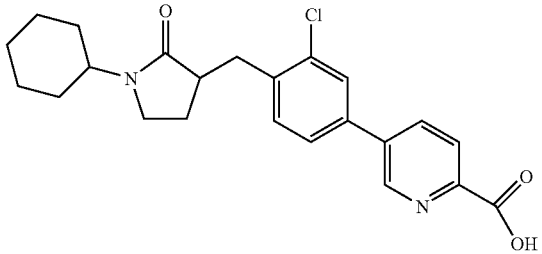<br>5-[3-Chloro-4-(1-cyclohexyl-2-oxo-pyrrolidin-3-ylmethyl)-phenyl]-pyridine-2-carboxylic acid | 3-(4-boronic acid-2-chloro-benzyl)-1-cyclohexyl-pyrrolidin-2-one (Preparation 6) (300 mg, 0.9 mmol), methyl 5-bromopicolinate (386 mg, 1.8 mmol), and palladium tetrakis (103 mg, 0.09 mmol) affords the methyl ester (194 mg), then dissolve in ethanol (50 ml) and water (1 mL) and add potassium hydroxide and stir for 3 hours. Remove solvent and add water. Bring to a pH of 2 with 1 M HCl. Filter to give crude title compound. Dissolve crude product in 1 M NaOH and wash with ether. Aqueous layer was then brought to a pH of 2 with 1 M HCl. Filter and purify by reverse phase chromatography | (apci) m/z = 413.2 (M + H) |
| 104 | 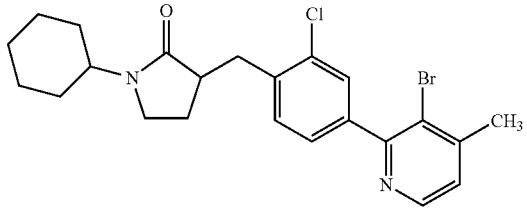<br>3-(4-(3-Bromo-4-methylpyridin-2-yl)-2-chlorobenzyl)-1-cyclohexylpyrrolidin-2-one | 3-(4-boronic acid-2-chloro-benzyl)-1-cyclohexyl-pyrrolidin-2-one (Preparation 6) (308 mg, 1.5 mmol), 3-bromo-2-chloro-4-methylpyridine (250 mg, 0.7 mmol), and palladium tetrakis (86 mg, 0.07 mmol) | m (apci) m/z = 463.2 (M + H) |
| 105 | 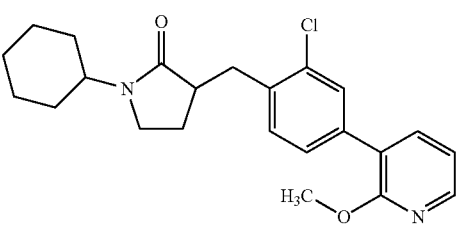<br>3-(2-Chloro-4-(2-methoxypyridin-3-yl)benzyl)-1-cyclohexyl)pyrrolidin-2-one | reagents 3-(4-boronic acid-2-chloro-benzyl)-1-cyclohexyl-pyrrolidin-2-one (Preparation 6) (350 mg, 1.04 mmol), 3-bromo-2-methoxypyridine (392 mg, 2.09 mmol), and palladium tetrakis (121 mg, 0.10 mmol) | (apci) m/z = 399.3 (M + H) |
| 106 | 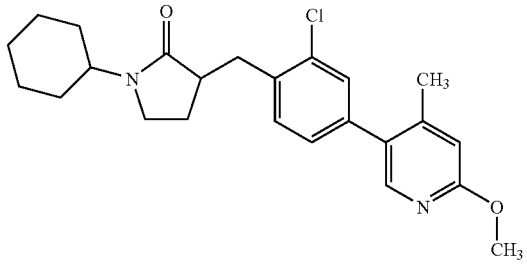<br>3-(2-Chloro-4-(6-methoxy-4-methylpyridin-3-yl)benzyl)-1-cyclohexylpyrrolidin-2-one | 3-(4-boronic acid-2-chloro-benzyl)-1-cyclohexyl-pyrrolidin-2-one (Preparation 6) (250 mg, 0.7 mmol), 5-bromo-2-methoxy-4-methylpyridine (301 mg, 1.5 mmol), and palladium tetrakis (86 mg, 0.07 mmol) | (apci) m/z = 413.4 (M + H) |

TABLE 2-continued

The following compounds are prepared essentially as described in Example 10 except using the reagents in the "Reagents used" column.

| Example | Structure and name | Reagents used | Mass spec |
|---|---|---|---|
| 107 | 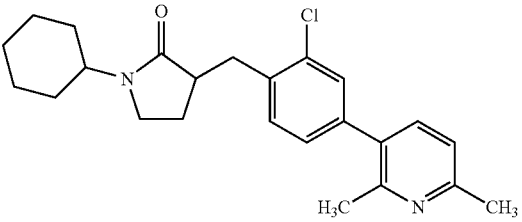<br>3-(2-Chloro-4-(2,6-dimethylpyridin-3-yl)benzyl)-1-cyclohexylpyrrolidin-2-one | 3-(4-boronic acid-2-chloro-benzyl)-1-cyclohexyl-pyrrolidin-2-one (Preparation 6) (250 mg, 0.7 mmol), 3-bromo-2,6-dimethylpyridine (277 mg, 1.5 mmol), and palladium tetrakis (86 mg, 0.07 mmol) | (apci)<br>m/z = 397.4<br>(M + H) |
| 108 | 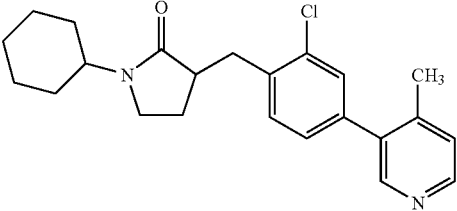<br>3-(2-Chloro-4-(4-methylpyridin-3-yl)benzyl)-1-cylcohexylpyrrolidin-2-one | 3-(4-boronic acid-2-chloro-benzyl)-1-cyclohexyl-pyrrolidin-2-one (Preparation 6) (250 mg, 0.7 mmol), 3-bromo-4-methylpyridine (256 mg, 1.5 mmol), and palladium tetrakis (86 mg, 0.07 mmol) | (apci)<br>m/z = 383.4<br>(M + H) |
| 109 | 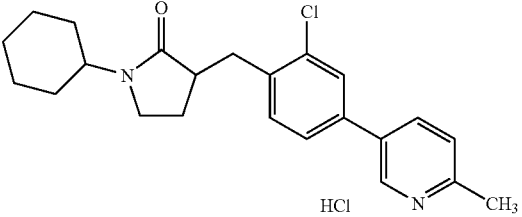<br>3-(2-Chloro-4-(6-methylpyridin-3-yl)benzyl)-1-cyclohexylpyrrolidin-2-one hydrochloride | 3-(4-boronic acid-2-chloro-benzyl)-1-cyclohexyl-pyrrolidin-2-one (Preparation 6) (510 mg, 1.5 mmol), 5-bromo-2-methylpyridine (523 mg, 3.0 mmol), and palladium tetrakis (176 mg, 0.15 mmol) | (apci)<br>m/z = 383.4<br>(M + H) |
| 110 | 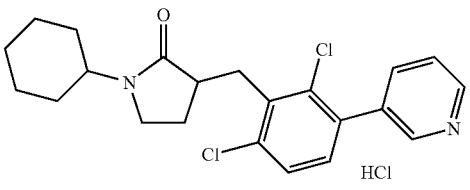<br>3-(2,6-Dichloro-3-(pyridin-3-yl)benzyl)-1-cyclohexylpyrrolidin-2-one hydrochloride | 3-(3-bromo-2,6-dichlorobenzyl)-1-cyclohexylpyrrolidin-2-one (Example 50) (350 mg, 0.9 mmol), pyridin-3-ylboronic acid (212 mg, 1.7 mmol), and palladium tetrakis (100 mg, 0.9 mmol) affords the freebase of the title compound. Dissolve in dichloromethane and add HCl in ether (2 M, 0.5 mL) and concentrate | (apci)<br>m/z = 403.2<br>(M + H) |

TABLE 2-continued

The following compounds are prepared essentially as described in Example 10 except using the reagents in the "Reagents used" column.

| Example | Structure and name | Reagents used | Mass spec |
|---|---|---|---|
| 111 | 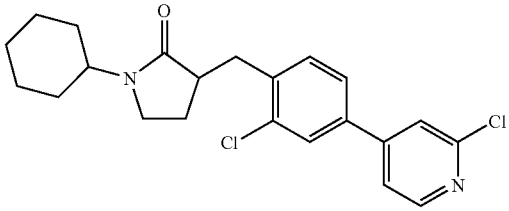<br>3-(2-Chloro-4-(2-chloropyridin-4-yl)benzyl)-1-cyclohexylpyrrolidin-2-one | 3-(4-boronic acid-2-chlorobenzyl)-1-cyclohexyl-pyrrolidin-2-one (Preparation 6) (300 mg, 0.9 mmol), 4-bromo-2-chloropyridine (344 mg, 1.8 mmol), and palladium tetrakis (103 mg, 0.09 mmol) | (apci)<br>m/z = 403.2<br>(M + H) |
| 112 | 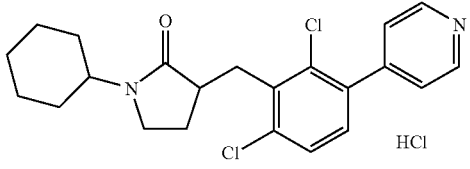<br>3-(2,6-Dichloro-3-(pyridin-4-yl)benzyl)-1-cyclohexylpyrrolidin-2-one hydrochloride | 3-(3-bromo-2,6-dichlorobenzyl)-1-cyclohexylpyrrolidin-2-one (Example 50) (350 mg, 0.9 mmol), pyridin-4-ylboronic acid (212 mg, 1.7 mmol), and palladium tetrakis (100 mg, 0.09 mmol) affords the freebase of the title compound. Dissolve in dichloromethane and add HCl in ether (2 M, 1.0 mL) and concentrate | (apci)<br>m/z = 403.2<br>(M + H) |
| 113 | 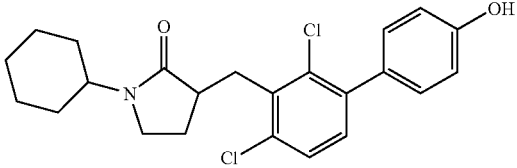<br>1-Cyclohexyl-3-(2,4-dichloro-4'-hydroxy-biphenyl-3-ylmethyl)-pyrrolidin-2-one | 3-(3-bromo-2,6-dichlorobenzyl)-1-cyclohexylpyrrolidin-2-one (Example 50) (1.50 g, 3.79 mmol), 4-hydroxyphenylboronic acid (1.02 g, 7.4 mmol), and palladium tetrakis (428 mg, 0.37 mmol) | (apci)<br>m/z = 418.2<br>(M + H) |
| 114 | 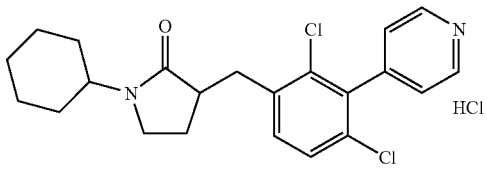<br>3-(2,4-Dichloro-3-(pyridin-4-yl)benzyl)-1-cyclohexylpyrrolidin-2-one hydrochloride | 3-(3-bromo-2,4-dichlorobenzyl)-1-cyclohexylpyrrolidin-2-one (Example 71) (350 mg, 0.9 mmol), pyridin-4-ylboronic acid (160 mg, 1.3 mmol), and palladium tetrakis (100 mg, 0.09 mmol) affords the freebase of the title compound. Dissolve in dichloromethane and add HCl in ether (2 M, 1.0 mL) and concentrate | (apci)<br>m/z = 403.3<br>(M + H) |
| 115 | 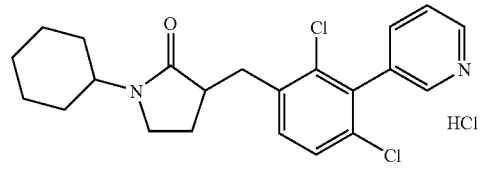<br>3-(2,4-Dichloro-3-(pyridin-3-yl)benzyl)-1-cyclohexylpyrrolidin-2-one hydrochloride | 3-(3-bromo-2,4-dichlorobenzyl)-1-cyclohexylpyrrolidin-2-one (350 mg, 0.9 mmol), pyridin-3-ylboronic acid (160 mg, 1.3 mmol), and palladium tetrakis (100 mg, 0.09 mmol) affords the freebase of the title compound. Dissolve in dichloromethane and add HCl in ether (2 M, 1.0 mL) and concentrate | (apci)<br>m/z = 403.3<br>(M + H) |

TABLE 2-continued

The following compounds are prepared essentially as described in Example 10 except using the reagents in the "Reagents used" column.

| Example | Structure and name | Reagents used | Mass spec |
|---|---|---|---|
| 116 | 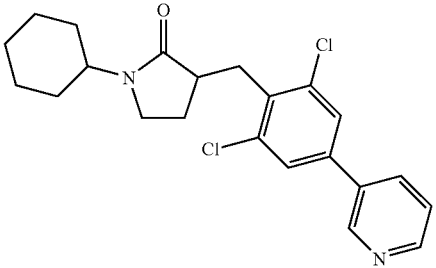<br>3-(2,6-dichloro-4-(pyridin-3-yl)benzyl)-1-cyclohexylpyrrolidin-2-one hydrochloride salt | 3,5-dichloro-4-((1-cyclohexyl-2-oxopyrrolidin-3-yl)methyl)phenyl trifluoromethanesulfonate (Example 240) (1.0 g, 2.1 mmol) and 3-pyridylboronic acid (0.78 g, 6.3 mmol) | (apci) m/z = 403.3 (M + H − HCl) |
| 117 | 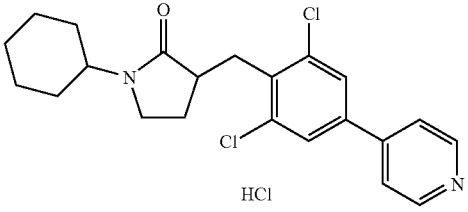<br>3-(2,6-dichloro-4-(pyridin-4-yl)benzyl)-1-cyclohexylpyrrolidin-2-one hydrochloride salt | 3,5-dichloro-4-((1-cyclohexyl-2-oxopyrrolidin-3-yl)methyl)phenyl trifluoromethanesulfonate (Example 240) (2.0 g, 4.2 mmol) and 4-pyridylboronic acid (1.5 g, 12.6 mmol) | (apci) m/z = 403.3 (M + H − HCl) |
| 118 | 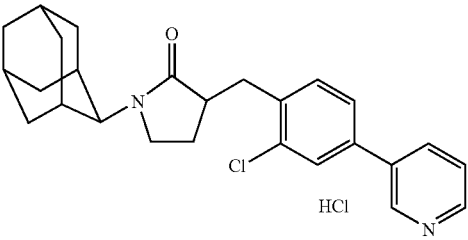<br>1-Adamantan-2-yl-3-(2-chloro-4-pyridin-3-yl-benzyl)-pyrrolidin-2-one hydrochloride salt | 1-adamantan-2-yl-3-(4-bromo-2-chloro-benzyl)-pyrrolidin-2-one (Example 76) (500 mg, 1.2 mmol) and 3-pyridylboronic acid (440 mg, 3.5 mmol) | (apci) m/z = 421.4 (M + H − HCl) |
| 119 | 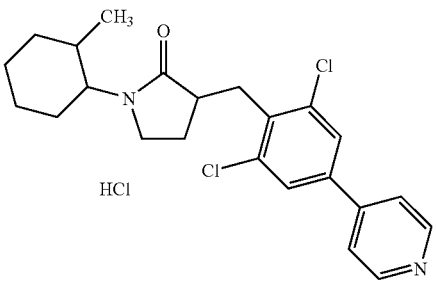<br>3-(2,6-Dichloro-4-(pyridin-4-yl)benzyl)-1-(cis-2-methylcyclohexyl)pyrrolidin-2-one hydrochloride salt | 3,5-dichloro-4-((1-(cis-2-methylcyclohexyl)-2-oxopyrrolidin-3-yl)methyl) phenyl trifluoromethanesulfonate (Preparation 58) (1.0 g, 2.05 mmol) and pyridin-4-ylboronic acid (0.76 g, 6.14 mmol) | (APCI-pos mode) m/z (rel intensity) 417.3 (100), 419.2 (50) |

TABLE 2-continued

The following compounds are prepared essentially as described in Example 10 except using the reagents in the "Reagents used" column.

| Example | Structure and name | Reagents used | Mass spec |
|---|---|---|---|
| 120 | 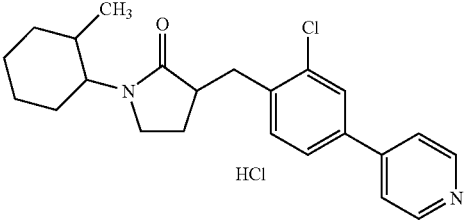<br>3-(2-Chloro-4-(pyridin-4-yl)benzyl)-1-(2-methylcyclohexyl)pyrrolidin-2-one hydrochloride | 3-(4-bromo-2-chlorobenzyl)-1-(cis-2-methylcyclohexyl)pyrrolidin-2-one (Example 64) (0.60 g, 1.56 mmol) and pyridin-4-ylboronic acid (0.19 g, 1.56 mmol) | (APCI-pos mode) m/z (rel intensity) 383.3 (100), 385.3 (30) |
| 121 | 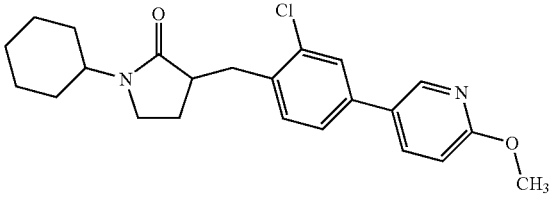<br>3-(2-Chloro-4-(6-methoxypyridin-3-yl)benzyl)-1-cyclohexyl)pyrrolidin-2-one | 3-(4-bromo-2-chlorobenzyl)-1-cyclohexylpyrrolidin-2-one (Example 55) (0.2 g, 0.54 mmol) and 6-methoxypyridin-3-ylboronic acid (0.41 g, 2.7 mmol) | (APCI-pos mode) m/z (rel intensity) 399.3 (100), 401.3 (30) |
| 122 | 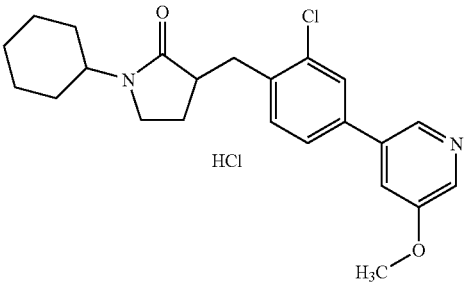<br>3-(2-Chloro-4-(5-methoxypyridin-3-yl)benzyl)-1-cyclohexylpyrrolidin-2-one hydrochloride | 3-(4-bromo-2-chlorobenzyl)-1-cyclohexylpyrrolidin-2-one (Example 55) (0.36 g, 0.96 mmol) and 5-methoxypyridin-3-ylboronic acid (0.15 g, 0.96 mmol) | (APCI-pos mode) m/z (rel intensity) 399.3 (100), 401.4 (30) |
| 123 | 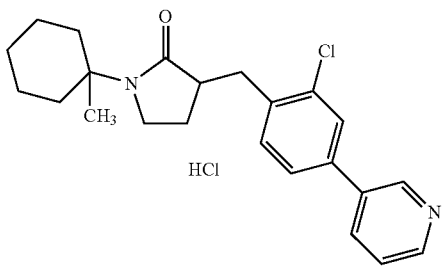<br>3-(2-Chloro-4-(pyridin-3-yl)benzyl)-1-(1-methylcyclohexyl)pyrrolidin-2-one hydrochloride | 3-(4-bromo-2-chlorobenzyl)-1-(1-methylcyclohexyl)pyrrolidin-2-one (0.14 g, 0.35 mmol) and pyridin-3-ylboronic acid (0.22 g, 1.75 mmol) | (APCI-pos mode) m/z (rel intensity) 383.3 (100), 385.3 (30) |

Example 124
1-Cycloheptyl-3-(2,4-dichloro-benzyl)-pyrrolidin-2-one

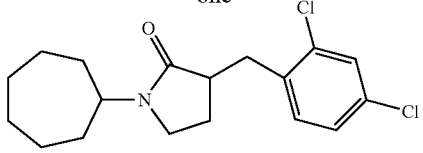

Charge vial with 3-(2,4-dichloro-benzyl)-dihydro-furan-2-one (300 mg, 1.2 mmol) and cycloheptylamine (139 mg, 1.2 mmol) and heat to 140° C. for 3 hours. Then heat to 195° C. overnight. Cool to room temperature and purify over silica gel which affords 135 mg (32%) of the title compound: Mass spectrum (apci) m/z=340.2 (M+H).

TABLE 3

The following compounds are prepared essentially as described in Example 124 except using the reagents in the "Reagents used" column.

| Example | Structure and name | Reagents used | Mass spec |
|---|---|---|---|
| 125 | 1-Adamantan-2-yl-3-(2,4-dichloro-benzyl)-pyrrolidin-2-one | 3-(2,4-dichloro-benzyl)-dihydro-furan-2-one (300 mg, 1.2 mmol) and 2-adamantylamine (277 mg, 1.8 mmol) | (apci) m/z = 378.2 (M + H) |
| 126 | 3-(2,4-Dichloro-benzyl)-1-(3-hydroxy-adamantan-1-yl)-pyrrolidin-2-one | 3-(2,4-dichloro-benzyl)-dihydro-furan-2-one (300 mg, 1.2 mmol) and 3-amino-adamantan-1-ol (310 mg, 1.8 mmol) | (apci) m/z = 394.1 (M + H) |
| 127 | 3-(2,4-Dichloro-benzyl)-1-(tetrahydro-pyran-4-yl)-pyrrolidin-2-one | 3-(2,4-dichloro-benzyl)-dihydro-furan-2-one (300 mg, 1.2 mmol) and tetrahydro-pyran-4-ylamine (250 mg, 2.4 mmol) | (apci) m/z = 328.1 (M + H) |
| 128 | 3-(2,4-Dichloro-benzyl)-1-(tetrahydro-thiopyran-4-yl)-pyrrolidin-2-one | 3-(2,4-dichloro-benzyl)-dihydro-furan-2-one (500 mg, 2.0 mmol) and tetrahydro-thiopyran-4-ylamine (360 mg, 3.0 mmol) | (apci) m/z = 344.1 (M + H). |

TABLE 3-continued

The following compounds are prepared essentially as described in Example 124 except using the reagents in the "Reagents used" column.

| Example | Structure and name | Reagents used | Mass spec |
|---|---|---|---|
| 129 | 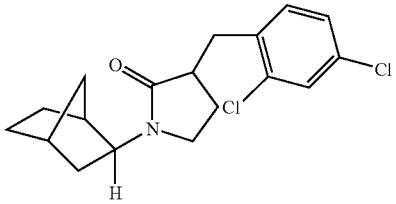<br>Exo-1-bicyclo[2.2.1]hept-2-yl-3-(2,4-dichloro-benzyl)-pyrrolidin-2-one | 3-(2,4-dichloro-benzyl)-dihydro-furan-2-one (300 mg, 1.2 mmol) and exo-2-aminonorbornane (200 mg, 1.8 mmol) | (apci) m/z = 338.1 (M + H). |
| 130 | 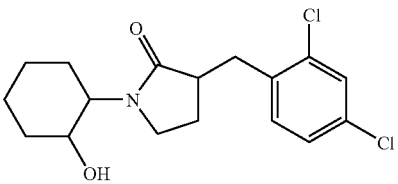<br>Trans-3-(2,4-dichloro-benzyl)-1-(cis-2-hydroxy-cyclohexyl)-pyrrolidin-2-one | 3-(2,4-dichloro-benzyl)-dihydro-furan-2-one (300 mg, 1.2 mmol) and cis-2-amino-cyclohexanol (140 mg, 1.2 mmol) | (apci) m/z = 342.1 (M + H). |
| 131 | 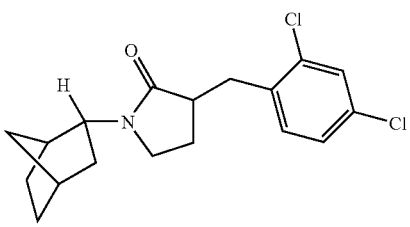<br>Endo-1-bicyclo[2.2.1]hept-2-yl-3-(2,4-dichloro-benzyl)-pyrrolidin-2-one | 3-(2,4-dichloro-benzyl)-dihydro-furan-2-one (300 mg, 1.2 mmol) and 2-aminonorbornane (270 mg, 2.4 mmol) The diastereomers separate via normal flash chromatography | Example 131a (Isomer 1): (apci) m/z = 338.2 (M + H). HPLC (50 to 95) $R_t$ (Purity at 220 nm) = 2.59 min (100%). Example 131b (Isomer 2): (apci) m/z = 338.2 (M + H). HPLC (50 to 95) $R_t$ (Purity at 220 nm) = 2.57 min (100%). |
| 132 | 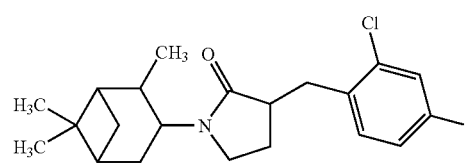<br>3-(2,4-Dichloro-benzyl)-1-((1R,2R,3R,5S)-2,6,6-trimethyl-bicyclo[3.1.1]hept-3-yl)-pyrrolidin-2-one | 3-(2,4-dichloro-benzyl)-dihydro-furan-2-one (500 mg, 2.0 mmol) and (1S,2S,3S,5R)-(+)-isopinocampheylamine (410 mg, 2.7 mmol) Diastereomers are separated using silica gel. | Example 132a (Isomer 1): (apci) m/z = 380.2 (M + H). HPLC (50 to 95) $R_t$ (Purity at 220 nm) = 3.97 min (100%). Example 132b (Isomer 2): (apci) m/z = 380.2 (M + H). HPLC (50 to 95) $R_t$ (Purity at 220 nm) = 3.97 min (100%). |

TABLE 3-continued

The following compounds are prepared essentially as described in Example 124 except using the reagents in the "Reagents used" column.

| Example | Structure and name | Reagents used | Mass spec |
|---|---|---|---|
| 133 | 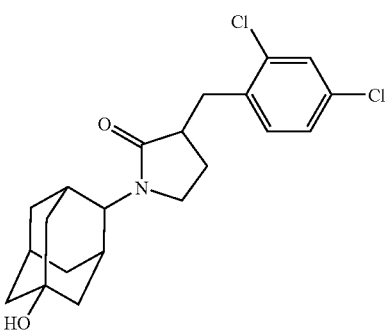<br>3-(2,4-Dichloro-benzyl)-1-(5-hydroxy-adamantan-2-yl)-pyrrolidin-2-one | 3-(2,4-dichloro-benzyl)-dihydro-furan-2-one (430 mg, 1.8 mmol) and 4-amino-adamantan-1-ol (600 mg, 3.9 mmol) | (apci) m/z = 394.1 (M + H). |

Example 134

3-(4-Bromo-2-chloro-benzyl)-1-(cis-4-hydroxy-cyclohexyl)-pyrrolidin-2-one

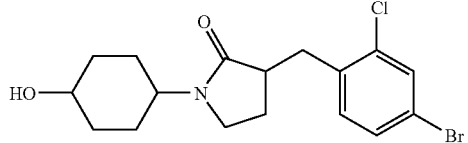

Charge a flask with cis-1-[4-(tert-butyl-dimethyl-silanyloxy)-cyclohexyl]-pyrrolidin-2-one (Preparation 17) (1.0 g, 3.4 mmol), dissolve with THF (0.2 M) and cool to −78° C. Add LDA (1.1 to 1.5 eq) and stir at −78° C. for 5 minutes. Add 4-bromo-1-bromomethyl-2-chloro-benzene (1.4 g, 5.0 mmol) and warm to room temperature overnight. Dilute with methanol (0.2 M) and add concentrated HCl (10 eq.) and stir at room temperature. Pour into water after reaction complete by HPLC and extract with methylene chloride, dry over sodium sulfate, filter and concentrate in vacuo. Purify the residue over silica gel (20% hexane in ethyl acetate) to afford 911 mg (70%) of the title compound: Mass spectrum (apci) m/z=387.9 (M+H).

TABLE 4

The following compounds are prepared essentially as described in Example 134 except using the reagents in the "Reagents used" column.

| Example | Structure and name | Reagents used | Mass spec |
|---|---|---|---|
| 135 | 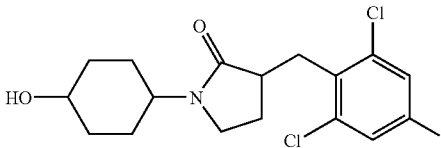<br>1-(cis-4-hydroxy-cyclohexyl)-3-(2,4,6-trichloro-benzyl)-pyrrolidin-2-one | cis-1-[4-(tert-butyl-dimethyl-silanyloxy)-cyclohexyl]-pyrrolidin-2-one (Preparation 17) (150 mg, 0.50 mmol) and 2,4,6-trichlorobenzyl chloride (350 mg, 1.0 mmol) | (apci) m/z = 376.0 (M + H). |
| 136 | 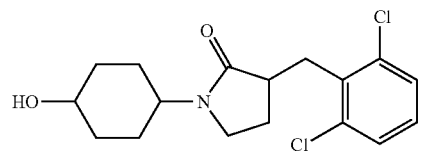<br>3-(2,6-Dichloro-benzyl)-1-(cis-4-hydroxy-cyclohexyl)-pyrrolidin-2-one | Cis-1-[4-(tert-butyl-dimethyl-silanyloxy)-cyclohexyl]-pyrrolidin-2-one (Preparation 17) (150 mg, 0.50 mmol) and 2,6-dichlorobenzyl bromide (180 mg, 0.75 mmol) | (apci) m/z = 342.1 (M + H). |

TABLE 4-continued

The following compounds are prepared essentially as described in Example 134 except using the reagents in the "Reagents used" column.

| Example | Structure and name | Reagents used | Mass spec |
|---|---|---|---|
| 137 | 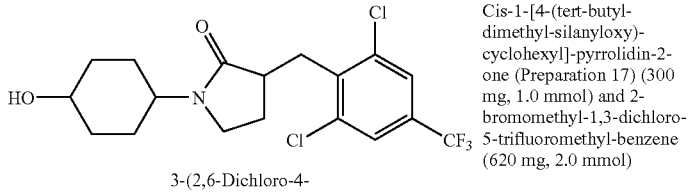<br>3-(2,6-Dichloro-4-trifluoromethyl-benzyl)-1-(cis-4-hydroxy-cyclohexyl)-pyrrolidin-2-one | Cis-1-[4-(tert-butyl-dimethyl-silanyloxy)-cyclohexyl]-pyrrolidin-2-one (Preparation 17) (300 mg, 1.0 mmol) and 2-bromomethyl-1,3-dichloro-5-trifluoromethyl-benzene (620 mg, 2.0 mmol) | (apci)<br>m/z = 410.0<br>(M + H). |

Example 138

3-[3-Chloro-2'-(4-methyl-piperazine-1-carbonyl)-biphenyl-4-ylmethyl]-1-cyclohexyl-pyrrolidin-2-one hydrochloride salt

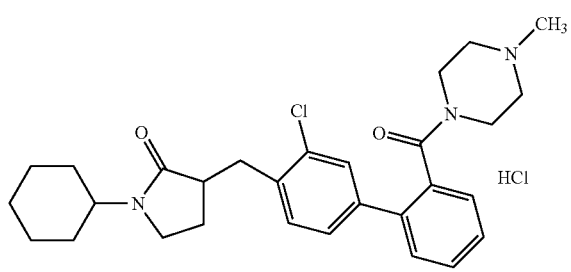

Charge a vial with 3'-chloro-4'-(1-cyclohexyl-2-oxo-pyrrolidin-3-ylmethyl)-biphenyl-2-carboxylic acid (example 6) (70 mg, 0.17 mmol), EDCl (65 mg, 0.34 mmol) and HOBt (23 mg, 0.17 mmol). Dissolve in DMF (0.1 M) and add triethylamine (95 µL, 0.68 mmol) and N-methyl piperazine (34 mg, 0.34 mmol). Stir at room temperature overnight. Pour into water and extract with ether. Dry over sodium sulfate, filter and concentrate. Purify over silica gel. Dissolve the residue in methylene chloride and acidify with 4N HCl in dioxane. Concentrate in vacuo which affords 57 mg (63%) of the title compound: Mass spectrum (apci) m/z=494.3 (M+H-HCl).

Example 139

3-[3-Chloro-3'-(4-methyl-piperazine-1-carbonyl)-biphenyl-4-ylmethyl]-1-cyclohexyl-pyrrolidin-2-one hydrochloride salt

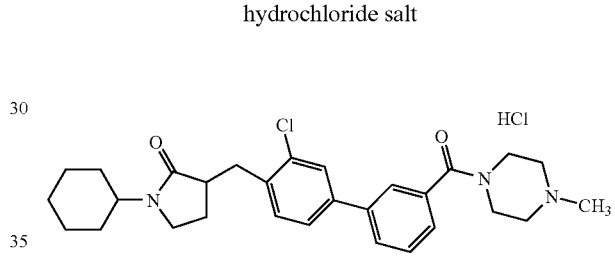

Charge a vial with 3'-chloro-4'-(1-cyclohexyl-2-oxo-pyrrolidin-3-ylmethyl)-biphenyl-3-carboxylic acid (Example 7) (70 mg, 0.17 mmol), EDCl (2.0 eq.) and HOBt (1.0 eq.). Dissolve in DMF (0.1 M) and add triethylamine (4.0 eq.) and N-methyl piperazine (34 mg, 0.34 mmol) (2.0 eq). Stir at room temperature overnight. Pour into water and extract with ether. Dry over sodium sulfate, filter and concentrate. Purify over silica gel. Dissolve the residue in methylene chloride and acidify with 4N HCl in dioxane. Concentrate in vacuo. Mass spec (apci) m/z=494.3 (M+H-HCl).

TABLE 5

The following compounds are prepared essentially as described in Example 139 except using the reagents in the "Reagents used" column.

| Example | Structure and name | Reagents used | Mass spec |
|---|---|---|---|
| 140 | 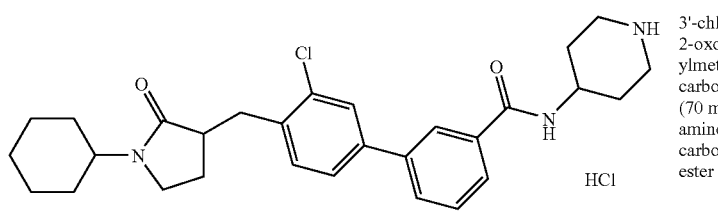<br>3'-Chloro-4'-(1-cyclohexyl-2-oxo-pyrrolidin-3-ylmethyl)-biphenyl-3-carboxylic acid piperidin-4-ylamide hydrochloride salt | 3'-chloro-4'-(1-cyclohexyl-2-oxo-pyrrolidin-3-ylmethyl)-biphenyl-3-carboxylic acid (Example 7) (70 mg, 0.17 mmol) and 4-amino-piperidine-1-carboxylic acid tert-butyl ester (68 mg, 0.34 mmol) | (apci)<br>m/z = 494.3<br>(M + H − HCl). |

TABLE 5-continued

The following compounds are prepared essentially as described in Example 139 except using the reagents in the "Reagents used" column.

| Example | Structure and name | Reagents used | Mass spec |
|---|---|---|---|
| 141 | 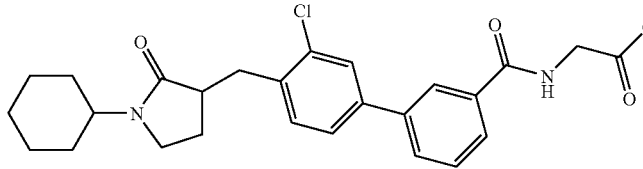<br>{[3'-Chloro-4'-(1-cyclohexyl-2-oxo-pyrrolidin-3-ylmethyl)-biphenyl-3-carbonyl]-amino}-acetic acid | 3'-chloro-4'-(1-cyclohexyl-2-oxo-pyrrolidin-3-ylmethyl)-biphenyl-3-carboxylic acid (Example 7) (70 mg, 0.17 mmol) and glycine tert-butyl ester (45 mg, 0.34 mmol) | (apci) m/z = 467.2 (M − H). |
| 142 | 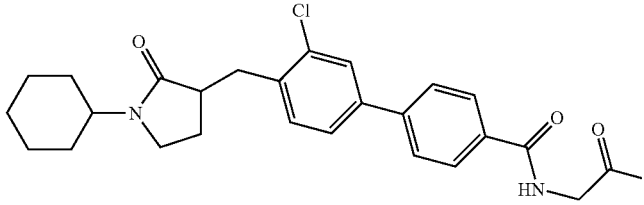<br>{[3'-Chloro-4'-(1-cyclohexyl-2-oxo-pyrrolidin-3-ylmethyl)-biphenyl-4-carbonyl]-amino}-acetic acid | 3'-chloro-4'-(1-cyclohexyl-2-oxo-pyrrolidin-3-ylmethyl)-biphenyl-4-carboxylic acid (Example 8) (70 mg, 0.17 mmol) and glycine tert-butyl ester (45 mg, 0.34 mmol) | (apci) m/z = 467.2 (M − H). |
| 143 | 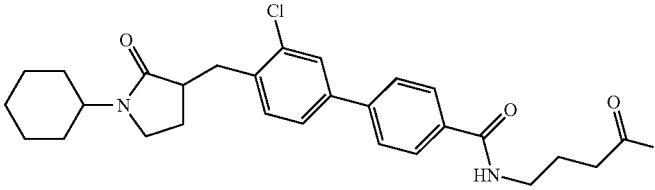<br>4-{[3'-Chloro-4'-(1-cyclohexyl-2-oxo-pyrrolidin-3-ylmethyl)-biphenyl-4-carbonyl]-amino}-butyric acid | 3'-chloro-4'-(1-cyclohexyl-2-oxo-pyrrolidin-3-ylmethyl)-biphenyl-4-carboxylic acid (Example 8) (70 mg, 0.17 mmol) and 4-amino-butyric acid tert-butyl ester hydrochloride salt (67 mg, 0.34 mmol) | (apci) m/z = 495.3 (M − H). |
| 144 | 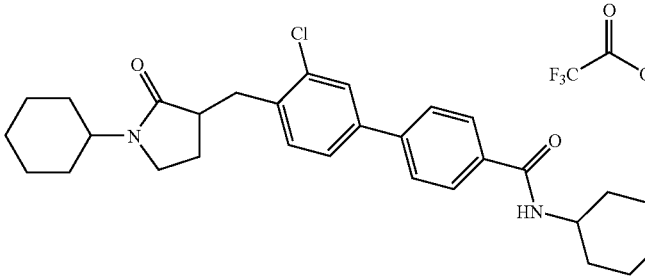<br>3'-Chloro-4'-(1-cyclohexyl-2-oxo-pyrrolidin-3-ylmethyl)-biphenyl-4-carboxylic acid piperidin-4-ylamide trifluoroacetate salt | 3'-chloro-4'-(1-cyclohexyl-2-oxo-pyrrolidin-3-ylmethyl)-biphenyl-4-carboxylic acid (Example 8) (70 mg, 0.17 mmol) and 4-amino-piperidine-1-carboxylic acid tert-butyl ester (68 mg, 0.34 mmol) | (apci) m/z = 494.3 (M + H − TFA). |
| 145 | 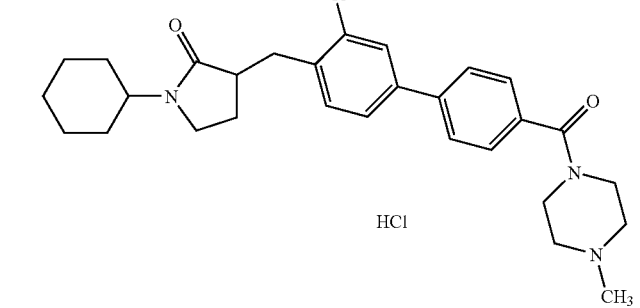<br>3-[3-Chloro-4'-(4-methyl-piperazine-1-carbonyl)-biphenyl-4-ylmethyl]-1-cyclohexyl-pyrrolidin-2-one hydrochloride salt | 3'-chloro-4'-(1-cyclohexyl-2-oxo-pyrrolidin-3-ylmethyl)-biphenyl-4-carboxylic acid (Example 8) (70 mg, 0.17 mmol) and N-methyl piperazine (34 mg, 0.34 mmol) | (apci) m/z = 494.2 (M + H − HCl). |

Example 146

3-[3-Chloro-4'-(2-piperidin-1-yl-ethoxy)-biphenyl-4-ylmethyl]-1-cyclohexyl-pyrrolidin-2-one hydrochloride salt

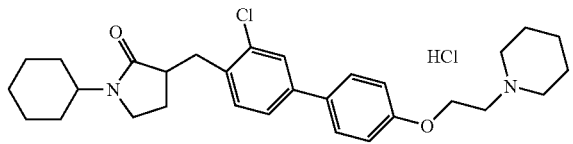

Charge a vial with 3-(3-chloro-4'-hydroxy-biphenyl-4-ylmethyl)-1-cyclohexyl-pyrrolidin-2-one (70 mg, 0.18 mmol) and dissolve in acetone (0.3 M). Add $K_2CO_3$ (250 mg, 1.8 mmol) and $Cs_2CO_3$ (59 mg, 0.18 mmol) and stir at room temperature for 5 minutes. Add 1-(2-chloro-ethyl)-piperidine hydrochloride (77 mg, 0.42 mmol) and heat to 50° C. overnight. Cool to room temperature, filter, concentrate and purify over silica gel. Dissolve the residue in methylene chloride (0.1 M) and add 2 M HCl in ether (0.18 mL, 0.36 mmol) and concentrate in vacuo to afford 94 mg (97%) of the title compound: Mass spectrum (apci) m/z=495.4 (M+H).

TABLE 6

The following compounds are prepared essentially as described in Example 146 except using the reagents in the "Reagents used" column.

| Example | Structure and name | Reagents used | Mass spec |
|---|---|---|---|
| 147 | 3-[3-Chloro-4'-(2-dimethylamino-ethoxy)-biphenyl-4-ylmethyl]-1-cyclohexyl-pyrrolidin-2-one hydrochloride salt | 3-(3-chloro-4'-hydroxy-biphenyl-4-ylmethyl)-1-cyclohexyl-pyrrolidin-2-one (Example 94) (70 mg, 0.18 mmol) and (2-chloro-ethyl)-dimethyl-amine hydrochloride (60 mg, 0.42 mmol) affords 75 mg (84%) of the title compound after HCl salt formation | (apci) m/z = 455.3 (M + H) |
| 148 | 3-[3-Chloro-4'-(3-dimethylamino-propoxy)-biphenyl-4-ylmethyl]-1-cyclohexyl-pyrrolidin-2-one hydrochloride salt | 3-(3-chloro-4'-hydroxy-biphenyl-4-ylmethyl)-1-cyclohexyl-pyrrolidin-2-one (Example 94) (40 mg, 0.10 mmol) and (3-chloro-propyl)-dimethyl-amine hydrochloride (43 mg, 0.26 mmol) affords 40 mg (76%) of the title compound after HCl salt formation | (apci) m/z = 469.4 (M + H) |
| 149 | 4-[3'-Chloro-4'-(1-cyclohexyl-2-oxo-pyrrolidin-3-ylmethyl)-biphenyl-4-yloxy]-butyric acid | 3-(3-chloro-4'-hydroxy-biphenyl-4-ylmethyl)-1-cyclohexyl-pyrrolidin-2-one (Example 94) (70 mg, 0.18 mmol) and 4-bromo-butyric acid methyl ester (86 mg, 0.47 mmol) affords 88 mg (99%) of 4-[3'-chloro-4'-(1-cyclohexyl-2-oxo-pyrrolidin-3-ylmethyl)-biphenyl-4-yloxy]-butyric acid methyl ester. Dissolve 4-[3'-chloro-4'-(1-cyclohexyl-2-oxo-pyrrolidin-3-ylmethyl)-biphenyl-4-yloxy]-butyric acid methyl ester (88 mg, 180 mmol) in methanol (5 mL) and add KOH (100 mg, 1.8 mmol) and heat to 50 deg overnight. Pour into 1N HCl and extract with methylene chloride. Dry over sodium sulfate, filter and concentrate | (apci) m/z = 470.4 (M + H). |

TABLE 6-continued

The following compounds are prepared essentially as described in Example 146 except using the reagents in the "Reagents used" column.

| Example | Structure and name | Reagents used | Mass spec |
|---|---|---|---|
| 150 | 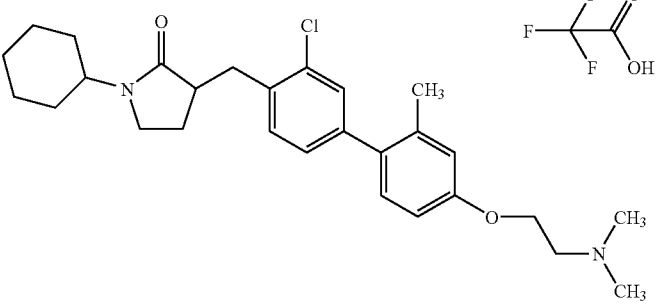<br>3-[3-Chloro-4'-(2-dimethylamino-ethoxy)-2'-methyl-biphenyl-4-ylmethyl]-1-cyclohexyl-pyrrolidin-2-one trifluoroacetate salt | 3-(3-chloro-4'-hydroxy-2'-methyl-biphenyl-4-ylmethyl)-1-cyclohexyl-pyrrolidin-2-one (Example 180) (100 mg, 0.25 mmol) and (2-chloro-ethyl)-dimethyl-amine hydrochloride (83 mg, 0.58 mmol) | (apci) m/z = 469.4 (M + H − TFA). |
| 151 | 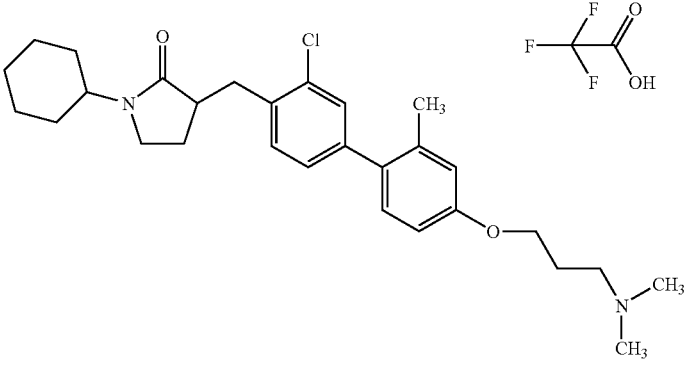<br>3-[3-Chloro-4'-(3-dimethylamino-propoxy)-2'-methyl-biphenyl-4-ylmethyl]-1-cyclohexyl-pyrrolidin-2-one trifluoroacetate salt | 3-(3-chloro-4'-hydroxy-2'-methyl-biphenyl-4-ylmethyl)-1-cyclohexyl-pyrrolidin-2-one (Example 180) (100 mg, 0.25 mmol) and (2-chloro-propyl)-dimethyl-amine hydrochloride (91 mg, 0.58 mmol) | (apci) m/z = 483.4 (M + H − TFA). |
| 152 | 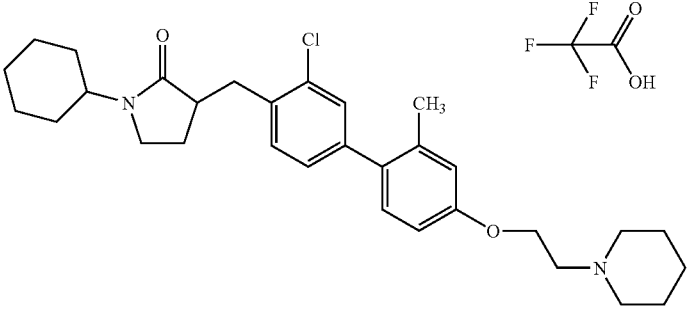<br>3-[3-Chloro-2'-methyl-4'-(2-piperidin-1-yl-ethoxy)-biphenyl-4-ylmethyl]-1-cyclohexyl-pyrrolidin-2-one trifluoroacetate salt | 3-(3-chloro-4'-hydroxy-2'-methyl-biphenyl-4-ylmethyl)-1-cyclohexyl-pyrrolidin-2-one (Example 180) (100 mg, 0.25 mmol) and 1-(2-chloro-ethyl)-piperidine hydrochloride (110 mg, 0.58 mmol) | (apci) m/z = 509.5 (M + H − TFA). |

TABLE 6-continued

The following compounds are prepared essentially as described in Example 146 except using the reagents in the "Reagents used" column.

| Example | Structure and name | Reagents used | Mass spec |
|---|---|---|---|
| 153 | 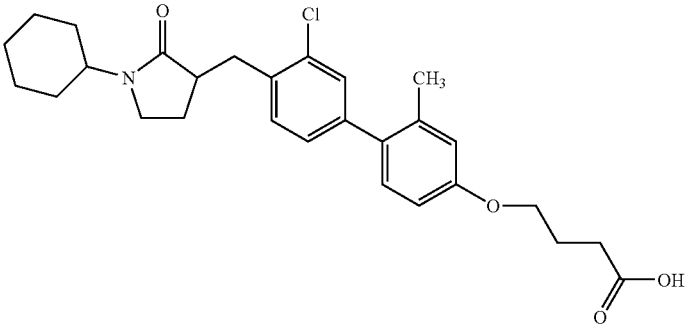<br>4-[3'-Chloro-4'-(1-cyclohexyl-2-oxo-pyrrolidin-3-ylmethyl)-2-methyl-biphenyl-4-yloxy]-butyric acid | 3-(3-chloro-4'-hydroxy-2'-methyl-biphenyl-4-ylmethyl)-1-cyclohexyl-pyrrolidin-2-one (Example 180) (100 mg, 0.25 mmol) and 4-bromo-butyric acid methyl ester (100 mg, 0.58 mmol) affords 107 mg (85%) of 2-methyl-4-[3'-chloro-4'-(1-cyclohexyl-2-oxo-pyrrolidin-3-ylmethyl)-biphenyl-4-yloxy]-butyric acid methyl ester. Dissolve 2-methyl-4-[3'-chloro-4'-(1-cyclohexyl-2-oxo-pyrrolidin-3-ylmethyl)-biphenyl-4-yloxy]-butyric acid methyl ester (107 mg, 220 mmol) in ethanol (15 mL) and add KOH (120 mg, 2.1 mmol) and heat to 50 deg for 2 hours. Pour into 1N HCl and extract with methylene chloride. Dry over sodium sulfate, filter and concentrate | (apci) m/z = 484.3 (M + H). |
| 154 | 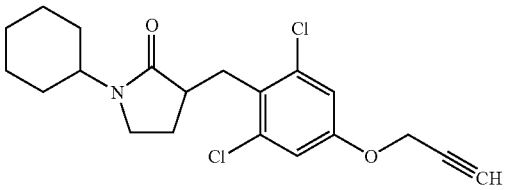<br>3-(2,6-Dichloro-4-(prop-2-ynyloxy)benzyl)-1-cyclohexylpyrrolidin-2-one | 1-cyclohexyl-3-(3,5-dichloro-4'-hydroxy-biphenyl-4-ylmethyl)-pyrrolidin-2-one (Preparation 52) (500 mg, 0.72 mmol) and propargyl bromide (230 mg, 1.9 mmol) | (apci) m/z = 380.2 (M + H). |
| 155 | 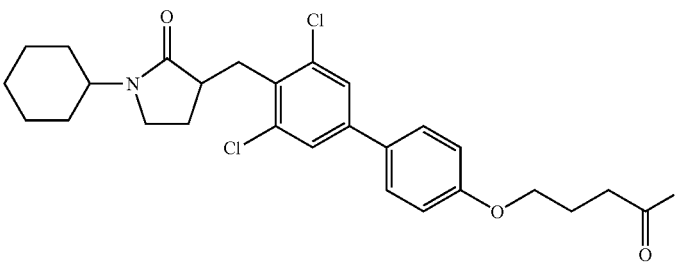<br>4-[3',5'-Dichloro-4'-(1-cyclohexyl-2-oxo-pyrrolidin-3-ylmethyl)-biphenyl-4-yloxy]-butyric acid | 1-cyclohexyl-3-(3,5-dichloro-4'-hydroxy-biphenyl-4-ylmethyl)-pyrrolidin-2-one (Preparation 52) (300 mg, 0.72 mmol) and 4-bromo-butyric acid methyl ester (390 mg, 2.2 mmol) affords 371 mg (99%) of 4-[3',5'-dichloro-4'-(1-cyclohexyl-2-oxo-pyrrolidin-3-ylmethyl)-biphenyl-4-yloxy]-butyric acid methyl ester. 4-[3',5'-dichloro-4'-(1-cyclohexyl-2-oxo-pyrrolidin-3-ylmethyl)-biphenyl-4-yloxy]-butyric acid methyl ester (370 mg, 0.71 mmol) in ethanol (7 mL) and add KOH (400 mg, 7.1 mmol) and heat to 40 deg for 6 hours. Pour into 1N HCl and extract with methylene chloride. Dry over sodium sulfate, filter and concentrate | (apci) m/z = 504.2 (M + H) |

TABLE 6-continued

The following compounds are prepared essentially as described in Example 146 except using the reagents in the "Reagents used" column.

| Example | Structure and name | Reagents used | Mass spec |
|---|---|---|---|
| 156 | 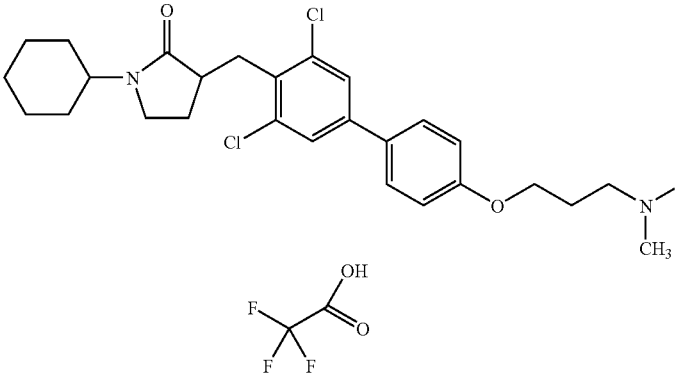<br>1-Cyclohexyl-3-[3,5-dichloro-4'-(3-dimethylamino-propoxy)-biphenyl-4-ylmethyl]-pyrrolidin-2-one trifluoroacetate salt | 1-cyclohexyl-3-(3,5-dichloro-4'-hydroxy-biphenyl-4-ylmethyl)-pyrrolidin-2-one (Preparation 52) (300 mg, 0.72 mmol) and (2-chloro-propyl)-dimethyl-amine hydrochloride (340 mg, 2.2 mmol) | (apci) m/z = 503.3 (M + H − TFA1) |
| 157 | 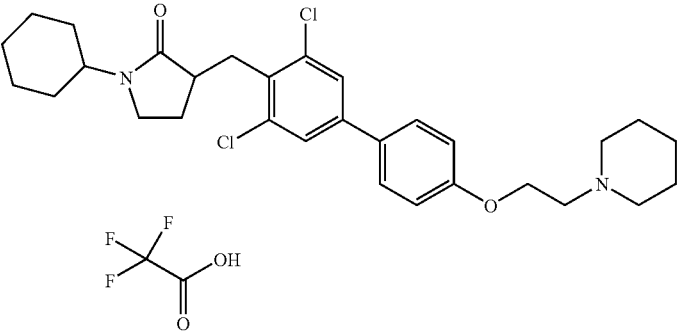<br>1-Cyclohexyl-3-[3,5-dichloro-4'-(2-piperidin-1-yl-ethoxy)-biphenyl-4-ylmethyl]-pyrrolidin-2-one trifluoroacetate salt | 1-cyclohexyl-3-(3,5-dichloro-4'-hydroxy-biphenyl-4-ylmethyl)-pyrrolidin-2-one (Preparation 52) (200 mg, 0.48 mmol) and 1-(2-chloro-ethyl)-piperidine hydrochloride (200 mg, 1.1 mmol) | (apci) m/z = 529.4 (M + H − TFA). |
| 158 | 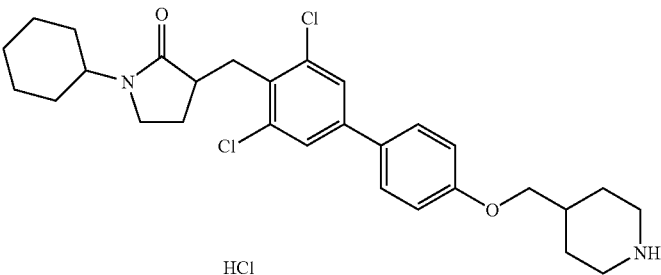<br>1-Cyclohexyl-3-[3,5-dichloro-4'-(piperidin-4-ylmethoxy)-biphenyl-4-ylmethyl]-pyrrolidin-2-one hydrochloride salt | 1-cyclohexyl-3-(3,5-dichloro-4'-hydroxy-biphenyl-4-ylmethyl)-pyrrolidin-2-one (Preparation 52) (200 mg, 0.48 mmol) and tert-butyl 4-(bromomethyl)piperidine-1-carboxylate (270 mg, 0.96 mmol) affords a crude product after silica gel purification. Dissolve in methylene chloride (2 mL) and 4M HCl in dioxane (2 mL) and stir overnight. Remove the solvent in vacuo | (apci) m/z = 529.4 (M + H − TFA). |

TABLE 6-continued

The following compounds are prepared essentially as described in Example 146 except using the reagents in the "Reagents used" column.

| Example | Structure and name | Reagents used | Mass spec |
|---------|-------------------|---------------|-----------|
| 159 | 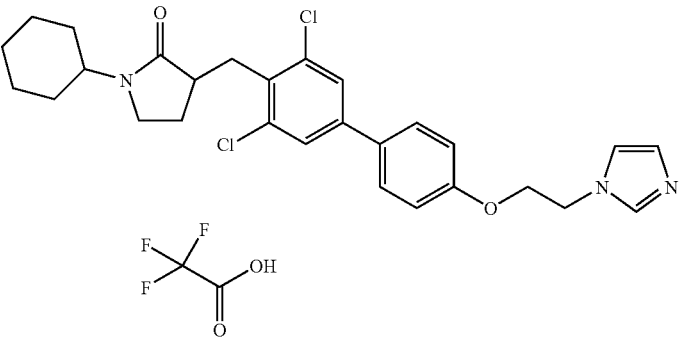<br>1-Cyclohexyl-3-[3,5-dichloro-4'-(2-imidazol-1-yl-ethoxy)-biphenyl-4-ylmethyl]-pyrrolidin-2-one trifluoroacetate salt | 1-cyclohexyl-3-(3,5-dichloro-4'-hydroxy-biphenyl-4-ylmethyl)-pyrrolidin-2-one (Preparation 52) (200 mg, 0.48 mmol) and 1-(2-chloroethyl)-1H-imidazole hydrochloride salt (160 mg, 0.96 mmol) | (apci) m/z = 512.3 (M + H − TFA) |
| 160 | 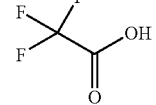<br>1-Cyclohexyl-3-[3,5-dichloro-4'-(3-piperidin-1-yl-propoxy)-biphenyl-4-ylmethyl]-pyrrolidin-2-one trifluoroacetate salt | 1-cyclohexyl-3-(3,5-dichloro-4'-hydroxy-biphenyl-4-ylmethyl)-pyrrolidin-2-one (Preparation 52) (200 mg, 0.48 mmol) and 1-(3-chloropropyl)piperidine hydrochloride salt (220 mg, 1.1 mmol) | (apci) m/z = 529.4 (M + H − TFA). |
| 161 | 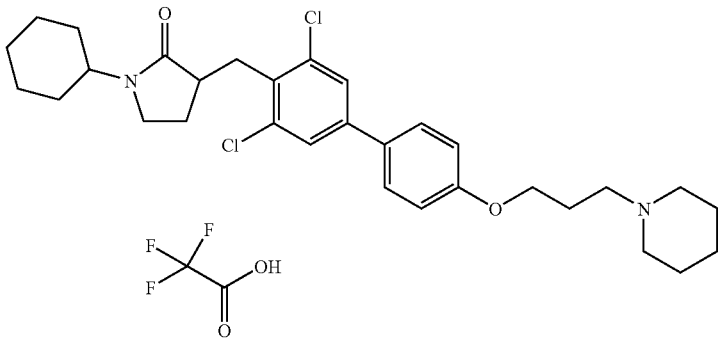<br>1-Cyclohexyl-3-[3,5-dichloro-4'-(2-morpholin-4-yl-ethoxy)-biphenyl-4-ylmethyl]-pyrrolidin-2-one hydrochloride salt | 1-cyclohexyl-3-(3,5-dichloro-4'-hydroxy-biphenyl-4-ylmethyl)-pyrrolidin-2-one (Preparation 52) (400 mg, 0.96 mmol) and 4-(2-chloroethyl)morpholine hydrochloride salt (270 mg, 1.4 mmol) | (apci) m/z = 531.3 (M + H − HCl). |
| 162 | 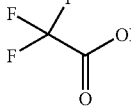<br>1-Cyclohexyl-3-[3,5-dichloro-2',6'-difluoro-4'-(2-piperidin-1-yl-ethoxy)-biphenyl-4-ylmethyl]-pyrrolidin-2-one hydrochloride salt | 1-cyclohexyl-3-(3,5-dichloro-2',6'-difluoro-4'-hydroxy-biphenyl-4-ylmethyl)-pyrrolidin-2-one (Preparation 53) (220 mg, 0.48 mmol) and 1-(2-chloro-ethyl)-piperidine hydrochloride (180 mg, 0.97 mmol) | (apci) m/z = 565.3 (M + H − HCl). |

TABLE 6-continued

The following compounds are prepared essentially as described in Example 146 except using the reagents in the "Reagents used" column.

| Example | Structure and name | Reagents used | Mass spec |
|---|---|---|---|
| 163 | 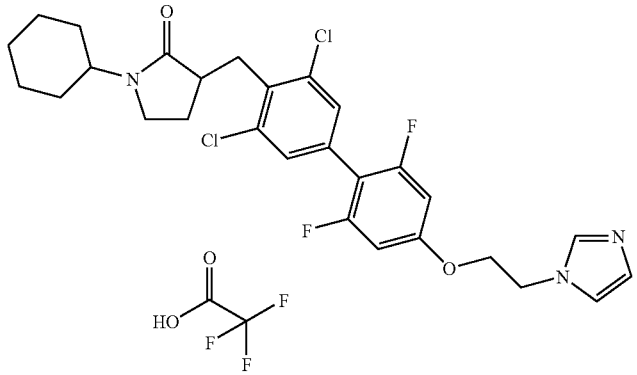<br>1-Cyclohexyl-3-[3,5-dichloro-2',6'-difluoro-4'-(2-imidazol-1-yl-ethoxy)-biphenyl-4-ylmethyl]-pyrrolidin-2-one trifluoroacetate salt | 1-cyclohexyl-3-(3,5-dichloro-2',6'-difluoro-4'-hydroxy-biphenyl-4-ylmethyl)-pyrrolidin-2-one (Preparation 53) (220 mg, 0.48 mmol) and 1-(2-chloroethyl)-1H-imidazole hydrochloride salt (160 mg, 0.97 mmol) | (apci) m/z = 548.3 (M + H − TFA). |
| 164 | 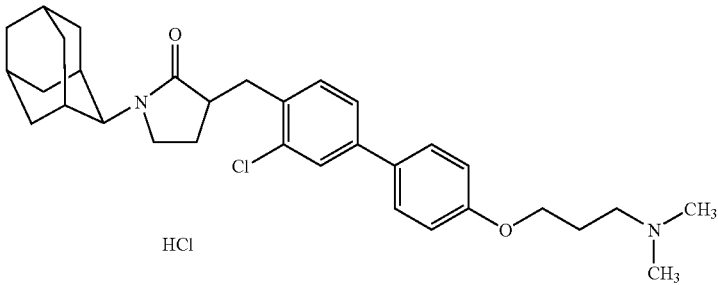<br>1-Adamantan-2-yl-3-[3-chloro-4'-(3-dimethylamino-propoxy)-biphenyl-4-ylmethyl]-pyrrolidin-2-one hydrochloride salt | 1-adamantan-2-yl-3-(3-chloro-4'-hydroxy-biphenyl-4-ylmethyl)-pyrrolidin-2-one (Preparation 54) (500 mg, 1.2 mmol) and (2-chloro-propyl)-dimethyl-amine hydrochloride (420 mg, 2.6 mmol) | (apci) m/z = 521.4 (M + H − HCl). |
| 165 | 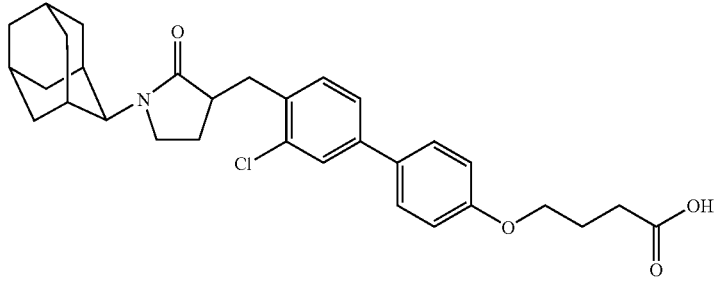<br>4-[4'-(1-Adamantan-2-yl-2-oxo-pyrrolidin-3-ylmethyl)-3'-chloro-biphenyl-4-yloxy]-butyric acid | 1-adamantan-2-yl-3-(3-chloro-4'-hydroxy-biphenyl-4-ylmethyl)-pyrrolidin-2-one (Preparation 54) (500 mg, 1.2 mmol) and 4-bromo-butyric acid methyl ester (480 mg, 2.6 mmol) affords 610 mg (99%) of 4-[4'-(1-adamantan-2-yl-2-oxo-pyrrolidin-3-ylmethyl)-3'-chloro-biphenyl-4-yloxy]-butyric acid methyl ester methyl ester. Dissolve 4-[4'-(1-adamantan-2-yl-2-oxo-pyrrolidin-3-ylmethyl)-3'-chloro-biphenyl-4-yloxy]-butyric acid methyl ester methyl ester (610 mg, 0.71 mmol) in ethanol (10 mL) and THF (10 mL) and add KOH (640 mg, 11 mmol) and stir overnight. Pour into 1N HCl and extract with methylene chloride. Dry over sodium sulfate, filter and concentrate | (apci) m/z = 522.2 (M + H). |

Example 166

3-[3-Chloro-2'-methyl-4'-(2-piperidin-1-yl-ethoxy)-biphenyl-4-ylmethyl]-1-cyclohexyl-pyrrolidin-2-one hydrochloride salt

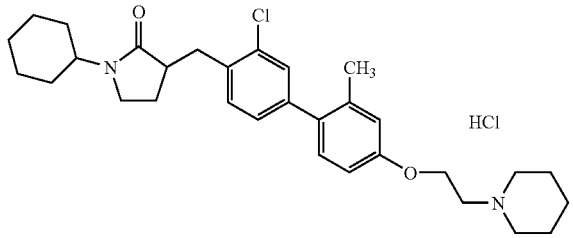

The triflate salt of Example 152 is taken-up in a suitable organic solvent such as ethyl acetate or the like, diluted with water and the pH adjusted to approximately 8-10 with a suitable base such as sodium hydroxide. The layers separated, the organics dried over sodium sulfate, filtered and evaporated. The resulting free base is dissolved in a suitable organic solvent such as methylene chloride or the like, and treated with 1.0-1.2 equivalents of HCl and the solvent removed under reduced pressure to give the hydrochloride salt.

Example 167

3-(R)-(2-Chloro-6-fluoro-benzyl)-1-cyclohexyl-pyrrolidin-2-one

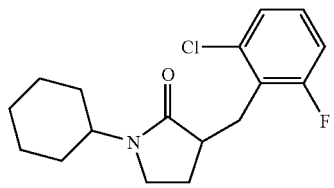

Dissolve (4R,5S)-(cis)-3-(2-(R)-chloro-6-fluoro-benzyl)-4-oxo-4-(2-oxo-4,5-diphenyl-oxazolidin-3-yl)-butyraldehyde (Preparation 22) (0.45 g, 0.97 mmol) in THF (50 mL). Add cyclohexylamine (0.19 g, 1.94 mmol), and acetic acid (0.12 g, 1.94 mmol) at room temperature under nitrogen. Stir the solution for one hour and then add sodium triacetoxyborohydride (0.82 g, 3.88 mmol). Stir the reaction mixture for over night and then add water (50 mL). Extract the aqueous layer with dichloromethane (3×100 mL). Combine the organic layers and dry with $Na_2SO_4$, filter, concentrate and purify by flash column chromatography (silica gel, 20-50% of EtOAc-Hexane) to give 0.26 g (88%) of the title compound as a colorless oil: Mass spectrum (ion spray): m/z=310.1, 312.2 (M+1). Ee value: 95% ee.

TABLE 7

The following compounds are prepared essentially as described in Example 167 except using the reagents in the "Reagents used" column.

| Example | Structure and name | Reagents used | Mass spec |
|---|---|---|---|
| 168 | 3-(2-Chloro-6-fluoro-benzyl)-1-(trans-4-hydroxy-cyclohexyl)-pyrrolidin-2-one | 3-(2-chloro-6-fluoro-benzyl)-4-oxo-4-(2-oxo-oxazolidin-3-yl)-butyraldehyde (Preparation 25) (1.0 g, 3.19 mmol) and trans-4-amino-cyclohexanol | (ion spray): m/z = 326.1, 328.0 (M + 1). |
| 169 | 3-(2-Chloro-6-fluoro-benzyl)-1-(1-methyl-cyclohexyl)-pyrrolidin-2-one | 1-methyl-cyclohexylamine (0.36 g, 3.19 mmol) and 3-(2-chloro-6-fluoro-benzyl)-4-oxo-4-(2-oxo-oxazolidin-3-yl)-butyraldehyde (0.5 g, 1.59 mmol) | (ion spray): m/z = 324.0, 326.0 (M + 1) |
| 170 | 3-(2-Chloro-6-fluoro-benzyl)-1-(cis-4-hydroxymethyl-cyclohexyl)-pyrrolidin-2-one | 3-(2-chloro-6-fluoro-benzyl)-4-oxo-4-(2-oxo-oxazolidin-3-yl)-butyraldehyde (Preparation 25) and (cis-4-amino-cyclohexyl)-methanol (Thomas P. Johnston, etc. J. Med. Chem., 1977, 20(2), 279-290) (0.75 g, 5.78 mmol) | (ion spray): m/z = 340.1, 342.0 (M + 1) |

TABLE 7-continued

The following compounds are prepared essentially as described in Example 167 except using the reagents in the "Reagents used" column.

| Example | Structure and name | Reagents used | Mass spec |
|---|---|---|---|
| 171 | 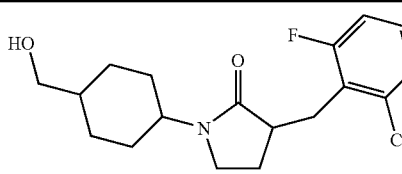  3-(2-Chloro-6-fluoro-benzyl)-1-(trans-4-hydroxymethyl-cyclohexyl)-pyrrolidin-2-one | 3-(2-chloro-6-fluoro-benzyl)-4-oxo-4-(2-oxo-oxazolidin-3-yl)-butyraldehyde (Preparation 25) (0.46 g, 1.46 mmol) and (trans-4-amino-cyclohexyl)-methanol (Thomas P. Johnston, etc. J. Med. Chem., 1977, 20(2), 279-290) (0.38 g, 2.91 mmol) | (ion spray): m/z = 340.1, 342.1 (M + 1). |
| 172 | 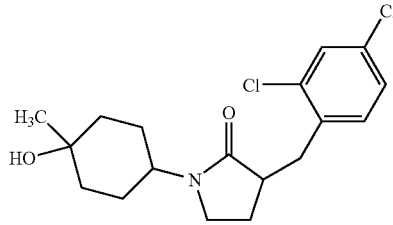  3-(2,4-Dichloro-benzyl)-1-(trans-4-hydroxy-4-methyl-cyclohexyl)-pyrrolidin-2-one | 3-(2,4-dichloro-benzyl)-4-oxo-4-(2-oxo-oxazolidin-3-yl)-butyraldehyde (Preparation 40) (0.15 g, 0.45 mmol) and trans-4-amino-1-methyl-cyclohexanol (0.059 g, 0.45 mmol) | (ion spray): m/z = 338.2, 340.2 (M – 18). |

Example 173

1-Cyclohexyl-3-(3-hydroxy-benzyl)-pyrrolidin-2-one

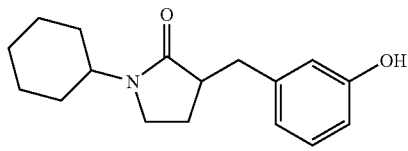

Dissolve 1-cyclohexyl-3-(3-methoxy-benzyl)-pyrrolidin-2-one (example 67) (440 mg, 1.5 mmol) in methylene chloride (50 ml) and add 2-methyl 2-butene (0.97 ml, 9.2 mmol) followed by borontribromide (0.43 ml, 4.6 mmol) and stir at room temperature for 20 minutes. Pour reaction mixture into an ice, methanol, sodium bicarbonate mixture and stir for 5 minutes. Separate layers wash organic with brine dry over sodium sulfate, filter and concentrate. Purify by silica gel (10-20% ethyl acetate in hexanes) to yield 165 mg (39%) of the title compound: Mass spectrum (apci) m/z=274 (M+H).

TABLE 8

The following compounds are prepared essentially as described in Example 173 except using reagents in the "Reagents used" column.

| Example | Structure and name | Reagents used | Mass spec |
|---|---|---|---|
| 174 | 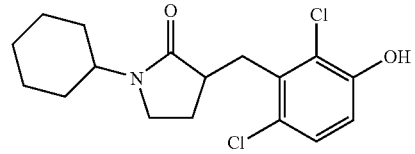  1-Cyclohexyl-3-(2,6-dichloro-3-hydroxy-benzyl)-pyrrolidin-2-one | 1-cyclohexyl-3-(2,6-dichloro-3-methoxy-benzyl)-pyrrolidin-2-one (6 g, 17 mmol) and borontribromide (8.4 g, 34 mmol) | (apci) 342 (M + H) |
| 175 | 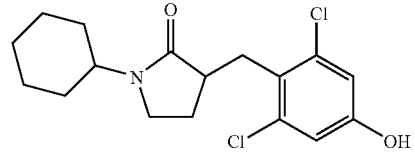  3-(2,6-Dichloro-4-hydroxybenzyl)-1-cyclohexylpyrrolidin-2-one | 3-(2,6-dichloro-4-methoxybenzyl)-1-cyclohexylpyrrolidin-2-one (8.5 g, 24 mmol) and BBr$_3$ (4.5 mL, 48 mmol) | (apci) m/z = 342.2 (M + H). |

TABLE 8-continued

The following compounds are prepared essentially as described in Example 173 except using reagents in the "Reagents used" column.

| Example | Structure and name | Reagents used | Mass spec |
|---|---|---|---|
| 176 | 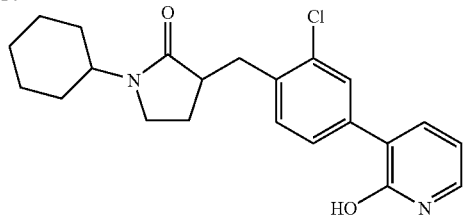<br>3-(2,4-Dichloro-6-hydroxybenzyl)-1-cyclohexylpyrrolidin-2-one | 3-(2,4-dichloro-6-methoxybenzyl)-1-cyclohexylpyrrolidin-2-one (10.5 g, 29.5 mmol) and BBr$_3$ (5.6 mL, 59 mmol) | (apci) m/z = 342.2 (M + H). |

Example 177

3-(2-Chloro-4-(2-hydroxypyridin-3-yl)benzyl)-1-cyclohexylpyrrolidin-2-one

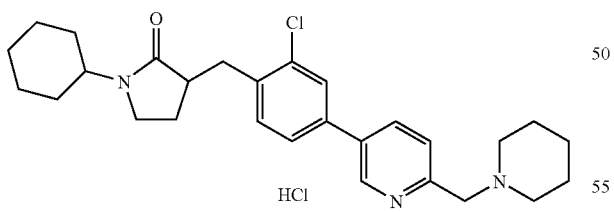

Place 3-(2-chloro-4-(2-methoxypyridin-3-yl)benzyl)-1-cyclohexylpyrrolidin-2-one (Example 105) (120 mg, 0.3 mmol) in dichloromethane (10 mL) and cool to 0° C. Add borontribromide (226 mg, 0.9 mmol) and stir of 16 hours. Add water and extract with dichloromethane. Dry over sodium sulfate, filter, and concentrate. Purify by silica gel (10% methanol in dichloromethane) to yield 65 mg (56%) of the title compound: Mass spectrum (apci) m/z=385.2 (M+H).

Example 178

3-(2-Chloro-4-(6-(piperidin-1-ylmethyl)pyridin-3-yl)benzyl)-1-cyclohexylpyrrolidin-2-one hydrochloride salt

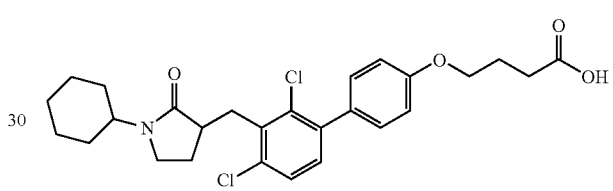

Dissolve 5-[3-chloro-4-(1-cyclohexyl-2-oxo-pyrrolidin-3-ylmrethyl)-phenyl]-pyridine-2-carbaldehyde (Preparation 49) (122 mg, 0.3 mmol) in dichloroethane (10 mL). Add piperidine (52 mg, 0.6 mmol) and triacetoxysodiumborohydride (97 mg, 0.5 mmol) stir at room temperature for two hours. Quench with water and extract with dichloromethane. Dry over sodium sulfate, filter, and concentrate. Purify by silica gel (50-70% ethylacetate in hexane) affords the free-base of the title compound. Dissolve in dichloromethane and add HCl in ether (2M, 1.0 mL) and concentrate to give title compound as a white solid. Mass spectrum (apci) m/z=466.2 (M+H).

Example 179

4-[2',4'-Dichloro-3'-(1-cyclohexyl-2-oxo-pyrrolidin-3-ylmethyl)-biphenyl-4-yloxy]-butyric acid

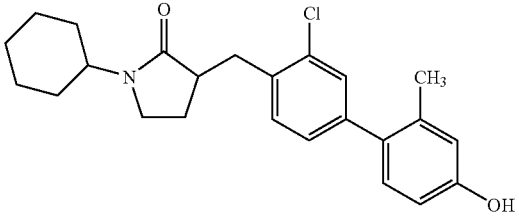

Place 1-cyclohexyl-3-(2,4-dichloro-4'-hydroxy-biphenyl-3-ylmethyl)-pyrrolidin-2-one (Example 113) (200 mg, 0.5 mmol), sodium iodide (72 mg, 0.5 mmol), and cesium carbonate (1.25 g, 3.8 mmol) in THF (10 mL). Add tert-butyl 4-bromobutanoate (213 mg, 1.0 mmol) and stir at room temperature for 3 hours. Add dichloromethane and wash with water. Dry over sodium sulfate, filter, and concentrate. Dissolve residue in dichloromethane (5 mL) and TFA (5 mL) and stir for 30 minutes. Remove solvent and dissolve product in IM NaOH. The deprotonated carboxylic acid does not go into the aqueous layer. Bring the pH ~2 with 6M HCl and extract with dichloromethane. Dry over sodium sulfate, filter, and concentrate. Purify by silica gel (dichloromethane-5% methanol in dichloromethane) affords 158 mg (66%) the title compound as a brown solid: Mass spectrum (apci) m/z=504.2 (M+H).

Example 180

3-(3-Chloro-4'-hydroxy-2'-methyl-biphenyl-4-ylmethyl)-1-cyclohexyl-pyrrolidin-2-one.

Charge a flask with 3-(3-chloro-4'-methoxy-2'-methyl-biphenyl-4-ylmethyl)-1-cyclohexyl-pyrrolidin-2-one (Example 95) (475 mg, 1.2 mmol), dissolve in dry methylene chloride (11 mL) and cool to 0° C. under nitrogen. Add BBr₃ (0.22 mL, 2.4 mmol) and stir at 0° C. for 20 minutes. Pour into saturated aqueous sodium bicarbonate and extract with methylene chloride. Dry over sodium sulfate, filter and concentrate in vacuo to yield 450 mg (98%) of the title compound. Mass spectrum (apci) m/z=398.3 (M+H).

Example 181

1-Bicyclo[2.2.1]hept-2-yl-3-(2-chloro-4-pyridin-3-yl-benzyl)-pyrrolidin-2-one hydrochloride salt

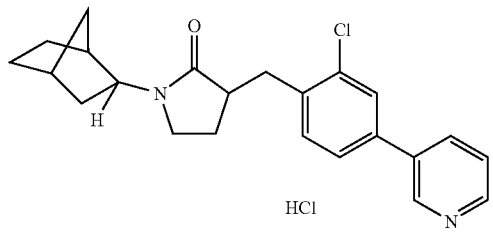

Charge a flask with 3-(2-chloro-4-(pyridin-3-yl)benzyl)-1-(exo-bicyclo[2.2.1]hept-5-en-2-yl)pyrrolidin-2-one (Preparation 51) (80 mg, 0.21 mmol) and dissolve in methanol (3 mL). Add 20% Pd(OH)₂/C (20 mg) and stir under a hydrogen atmosphere for 2 hours. Filter through Celite and concentrate. Dissolve in methylene chloride (3 mL) and add 2M HCl in ether (0.2 mL, 0.4 mmol) and concentrate in vacuo. Redissolve in methylene chloride (1 mL) and add dropwise to vigorously stirred ether (10 mL). Collect precipitate to yield 42 mg (48%) of the title compound. Mass spectrum (apci) m/z=381.4 (M+H).

Example 182

3-(2-chloro-4-(pyridin-3-yl)benzyl)-1-(exo-5,6-dihydroxybicyclo[2.2.1]heptan-exo-2-yl)pyrrolidin-2-one hydrochloride salt.

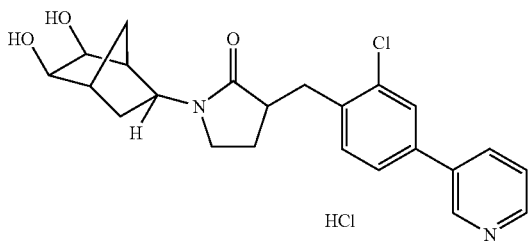

Charge a flask with 3-(2-chloro-4-(pyridin-3-yl)benzyl)-1-(exo-bicyclo[2.2.1]hept-5-en-2-yl)pyrrolidin-2-one (Preparation 51) (80 mg, 0.21 mmol) and dissolve in 4:1 Acetone/water (5 mL). Add 4-methylmorpholine N-oxide (86 mg, 0.63 mmol) followed by OsO₄ (2.5 wt % in tBuOH, 26 µL, 0.002 mmol) and stir at room temperature overnight. Pour into basic NaHSO₃ and extract twice with methylene chloride. Dry over sodium sulfate, filter and concentrate in vacuo. Purify residue over silica gel (0 to 15% methanol in ethyl acetate) to yield 65 mg (69%) of the title compound after HCl salt formation. Mass spectrum (apci) m/z=413.3 (M+H-HCl).

Example 183

3-(4-Amino-2,6-dichlorobenzyl)-1-cyclohexylpyrrolidin-2-one

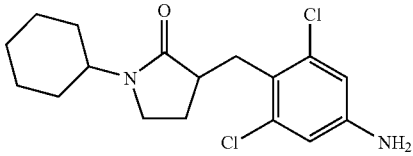

Place Pd₂(dba)₃ (710 mg, 3.16 mmol), BINAP (2.95 g, 4.74 mmol), and Cs₂CO₃ (15.0 g, 47.0 mmol) in a dry flask. Add 3,5-dichloro-4-((1-cyclohexyl-2-oxopyrrolidin-3-yl)methyl) phenyl trifluoromethanesulfonate (Example 240) (15.0 g, 32.0 mmol), benzophenone imine (8.60 g, 47.4 mmol), and 750 mL of toluene. Heat at 100° C. overnight. Cool to room temp and filter. Remove toluene under reduced pressure. Dissolve crude imine in MeOH and add sodium acetate (5.20 g, 63.0 mmol) and hydroxylamine hydrochloride (4.40 g, 63.0 mmol). Stir at room temp for 45 min. Pour into water and extract with CH₂Cl₂. Dry, filter, and concentrate. Purify the residue by Biotage eluting with a mixture of EtOAc and hexanes (30:70 to 50:50) to give the title compound (7.0 g, 65%): Mass spectrum (apci) m/z=341.2 (M+H).

Example 184

3-(3,5-dibromo-2,6-dichloro-4-hydroxybenzyl)-1-cyclohexylpyrrolidin-2-one

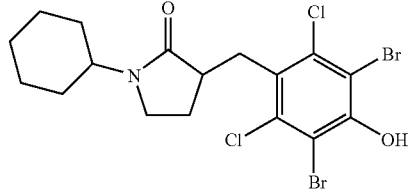

Charge a flask with 3-(2,6-dichloro-4-hydroxybenzyl)-1-cyclohexylpyrrolidin-2-one (300 mg, 0.88 mmol) and dissolve in DMF (8 mL). Add N-bromosuccinimide (156 mg, 0.88 mmol) and stir at room temperature overnight. Pour into water and extract with ether. Dry over sodium sulfate, filter and concentrate in vacuo. Purify over silica gel (50% ethyl acetate in hexanes) to afford 65 mg (13%) of the title compound. Mass spectrum (apci) m/z=500.0 (M+H).

Example 185

3-(2,4-Dichloro-benzyl)-1-(cis-4-hydroxy-cis-3,5-dimethyl-cyclohexyl)-pyrrolidin-2-one

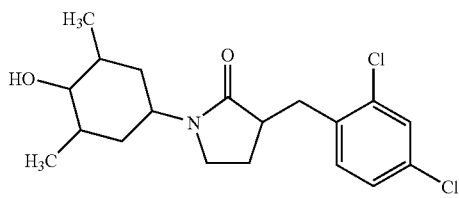

Dissolve 3-(2,4-dichloro-benzyl)-1-[cis-3,5-dimethyl-cis-4-(tetrahydro-pyran-2-yloxy)-cyclohexyl]-pyrrolidin-2-one (Preparation 55) (0.15 g, 0.33mmol) in MeOH (20 mL) and add TsOH.H$_2$O (0.056 g, 0.33 mmol) under N$_2$. Stir the reaction mixture overnight. Add water (20 mL), and extract the aqueous layer with dichloromethane (4×50 mL). Combine the organic layers and dry with Na$_2$SO$_4$, filter, concentrate and purify by flash column chromatography (silica gel, 50-80% of EtOAc/Hexane) to give of the title compound as a white solid (0.11 g, 94%): MS (APCI-pos mode) m/z (rel intensity) 370.1 (100), 372.0 (60).

Example 186

3-(2,4-Dichloro-benzyl)-1-(cis-4-hydroxy-cis-3-methyl-cyclohexyl)-pyrrolidin-2-one

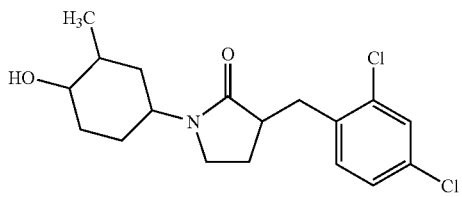

Dissolve 3-(2,4-dichloro-benzyl)-4-oxo-4-(2-oxo-oxazolidin-3-yl)-butyraldehyde (Preparation 40) (0.54 g, 1.64 mmol) in 1,2-dichloroethane (20 mL). Add cis-4-amino-cis-2-methyl-cyclohexanol (Preparation 56) (0.25 g, 1.94 mmol) and sodium acetoxyborohydride (1.04 g, 4.91 mmol). Stir the mixture at room temperature for 48 hours under nitrogen. Add water (20 mL), and extract the aqueous layer with dichloromethane (3×50 mL). Combine the organic layers and dry with Na$_2$SO$_4$, filter, concentrate and purify by flash column chromatography (silica gel, 30-80% of EtOAc/Hexane) to give the title compound as a white solid (0.20 g, 35%): MS (APCI-pos mode) mlz (rel intensity) 356.1 (100), 358.0 (50).

Example 187

3-(2,4-dichlorobenzyl)-1-(4-hydroxy-1-methylcyclohexyl)pyrrolidin-2-one

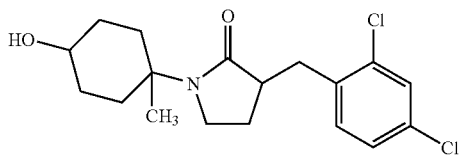

Dissolve 4-(3-(2,4-dichlorobenzyl)-2-oxopyrrolidin-1-yl)-4-methylcyclohexyl 4-nitrobenzoate (Preparation 57) (0.38 g, 0.76 mmol) in MeOH (50 mL). Add K$_2$CO$_3$ (0.21 g, 1.52 mmol) and stir the reaction overnight at room temperature. Add water (50 mL) and extract the aqueous with EtOAc (3×100 mL). Combine the organic layers and dry with Na$_2$SO$_4$, filter, concentrate and purify by flash column chromatography (silica gel, 50-80% of EtOAc/Hexane) to give 0.24 g (91%) of the title compound as a white solid. MS (APCI-pos mode) m/z (rel intensity) 356.0 (100), 358.0 (60).

Example 188

3-(4-Bromo-2-chlorobenzyl)-1-(cis-4-methoxycyclohexyl)pyrrolidin-2-one

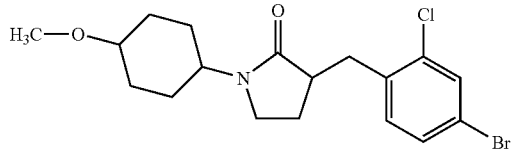

Dissolve 3-(4-bromo-2-chloro-benzyl)-1-(cis-4-hydroxy-cyclohexyl)-pyrrolidin-2-one (Example 134) (0.20 g, 0.52 mmol) in THF (10 mL) and cool to 0° C. Add NaH (0.062 g, 1.55 mmol, 60% wt.) and stir the reaction mixture for 1 hour at 0° C. Then add MeI (0.11 g, 0.78 mmol) and continue to stir the reaction mixture overnight until LC-MS shows the starting material has gone. Add water (10 mL) and extract the aqueous layer with EtOAc (3×50 mL). Combine the organic layers and dry with Na$_2$SO$_4$, filter, concentrate and purify by flash column chromatography (silica gel, 20-50% of EtOAc/Hexane) to give 0.17 g (83%) of the title compound as colorless oil: MS (APCI-pos mode) m/z (rel intensity) 400.0 (70), 402.0 (100).

Example 189

3-(2-Chloro-4-cyclohexylbenzyl)-1-cyclohexylpyrrolidin-2-one

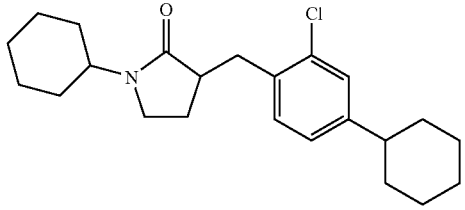

Dissolve 3-(4-bromo-2-chlorobenzyl)-1-cyclohexylpyrrolidin-2-one (Example 55) (0.20 g, 0.54 mmol) in THF/NMP (10 mL/10 mL) under N$_2$. Add Pd(dppf)Cl$_2$ (0.04 g, 0.054 mmol) and cyclohexylzinc(II) bromide (1.08 mL, 0.5 M in THF) with stiring. Heat the reaction mixture to reflux for 4 hours until LC-MS shows the starting material has gone. Cool the reaction to room temperature and add water (20 mL). Extract the aqueous with EtOAc (3×50 mL). Combine the organic layers and dry with Na$_2$SO$_4$, filter, concentrate and purify by flash column chromatography (silica gel, 10-50% of EtOAc-Hexane) to give 0.20 g (83%) of the title compound as a colorless oil: MS (APCI-pos mode) m/z (rel intensity) 374.3 (100), 376.3 (30).

Example 190

3-Chloro-4-((1-cyclohexyl-2-oxopyrrolidin-3-yl)methyl)benzonitrile

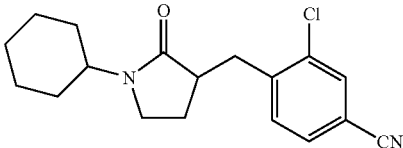

Dissolve 3-(4-bromo-2-chlorobenzyl)-1-cyclohexylpyrrolidin-2-one (Example 55) (0.50 g, 1.35 mmol) in Et$_3$N (20 mL) under $N_2$. Add $Pd(PPh_3)_4$ (0.32 g, 0.27 mmol), TMSCN (0.40 g, 4.05 mmol) with stirring. Heat the reaction mixture for 24 hours until LC-MS shows the starting material has gone. Cool the reaction to room temperature and add water (20 mL). Extract the aqueous with EtOAc (3×50 mL). Combine the organic layers and dry with $Na_2SO_4$, filter, concentrate and purify by flash column chromatography (silica gel, 30-60% of EtOAc-Hexane) to give 0.42 g (98%) of the title compound as white solid: MS (APCI-pos mode) m/z (rel intensity) 317.2 (100), 319.2 (30).

Example 191

3-(4-Benzoyl-2-chlorobenzyl)-1-cyclohexylpyrrolidin-2-one

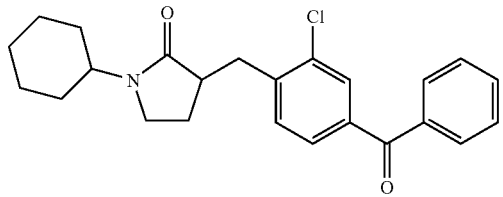

Dissolve 3-chloro-4-((1-cyclohexyl-2-oxopyrrolidin-3-yl)methyl)benzonitrile (0.20 g, 0.63 mmol) in THF (20 mL) under $N_2$ and add phenylmagnesium bromide (0.63 mL, 0.63 mmol, 1.0 M in THF). Stir the reaction mixture for 24 hours until LC-MS shows the starting material has gone. Add saturated $NH_4Cl$ (20 mL) and extract the aqueous with EtOAc (3×50 mL). Combine the organic layers and dry with $Na_2SO_4$, filter, concentrate and purify by flash column chromatography (silica gel, 20-50% of EtOAc-Hexane) to give 0.023 g (9%) of the title compound as white solid: MS (APCI-pos mode) m/z (rel intensity) 396.3 (100), 398.2 (30).

Example 192

3-(3-Amino-2,6-dichlorobenzyl)-1-cyclohexylpyrrolidin-2-one

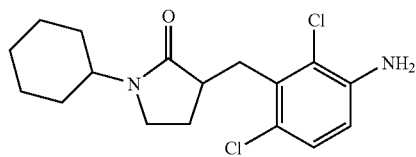

Using the procedure to synthesize Example 183 and using reagents 3-(3-Br-2,6-dichlorobenzyl)-1-cyclohexyl-pyrrolidin-2-one (Example 50) (500 mg, 1.23 mmol) and benzophenone imine (224 mg, 1.23 mmol) afforded the title compound (1.52 g, 91%): Mass spectrum (apci) m/z=341.2 (M+H).

Example 193

3-(3-Amino-4-bromo-2,6-dichlorobenzyl)-1-cyclohexylpyrrolidin-2-one

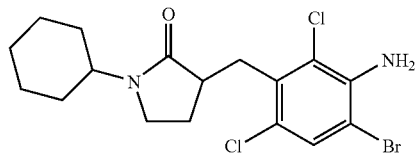

Add NBS (7.82 g, 43.9 mmol) to a solution of 3-(3-amino-2,6-dichlorobenzyl)-1-cyclohexyl-pyrrolidin-2-one (Example 50) (15.0 g, 43.9 mmol) in $CCl_4$ (500 mL). Stir at room temp overnight. Filter the suspension. Concentrate the filtrate. Form a suspension in $CH_2Cl_2$ and filter. Dissolve the solid in $CH_2Cl_2$ and wash several times with water. Dry, filter and concentrate. Concentrate the filtrate. Purify the combined residue by a plug of silica gel eluting with a mixture of EtOAc and hexanes (20:80) to give the title compound (17.6 g, 96%): Mass spectrum (apci) m/z=421.1 (M+H).

Example 194

3-(2,4-dichlorobenzyl)-1-cyclohexylpiperidin-2-one

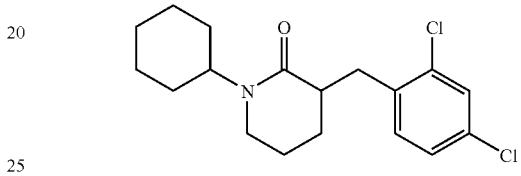

Add 1.8 M LDA (0.9 mL, 1.7 mmol) to solution of 1-cyclohexylpiperidin-2-one (300 mg, 1.7 mmol) in THF (5 mL) at −78° C. and stir for 15 minutes. Add 2,4-dichloro-1-(chloromethyl)benzene (640 mg, 3.3 mmol) and warm the reaction to room temperature. Quench the reaction with water and dilute with ethyl acetate. Dry the organic layer with sodium sulfate, filter and concentrate. Purify the residue by biotage chromatography to afford the title compound as a white solid (1.4 g, 81%): MS (APCI-pos mode) m/z (rel intensity): 340.2 (M+H).

Example 195

2-[3',5'-Dichloro-4'-(1-cyclohexyl-2-oxo-pyrrolidin-3-ylmethyl)-biphenyl-4-yloxy]-2-methyl-propionic acid ethyl ester

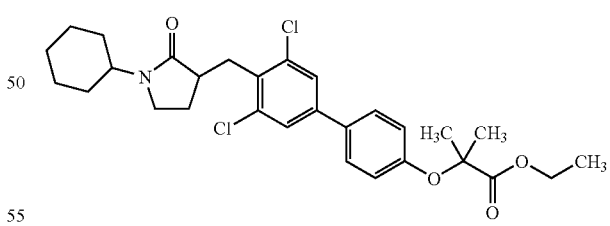

Combine 1-Cyclohexyl-3-(3,5-dichloro-4'-hydroxy-biphenyl-4-ylmethyl)-pyrrolidin-2-one (prep 55) (0.15 g, 0.36 mmol), ethyl 2-bromoisobutyrate (0.28 g, 1.43 mmol) and $Cs_2CO_3$ (0.35 g, 1.07 mmol) in DMF (7 mL) and heat to 60° C. for 16 hours. Cool the reaction, extract with diethyl ether and water, dry ($Na_2SO_4$) and then purify by normal phase chromatography (30 to 80% gradient of ethyl acetate in hexanes) to afford 200 mg (100%) of the title compound: LC-MS (ES +) m/z=exact mass calcd for $C_{29}H_{35}Cl_2NO_4$ 531, found 532 and 534 (M+1 and M+3, 100%).

Example 196

2-[3',5'-Dichloro-4'-(1-cyclohexyl-2-oxo-pyrrolidin-3-ylmethyl)-biphenyl-4-yloxy]-2-methyl-propionic acid

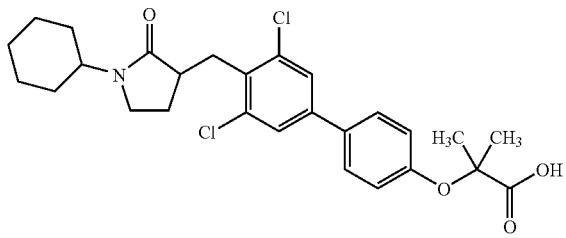

Dissolve 2-[3',5'-Dichloro-4'-(1-cyclohexyl-2-oxo-pyrrolidin-3-ylmethyl)-biphenyl-4-yloxy]-2-methyl-propionic acid ethyl ester (Example 195) (0.20 g, 0.37 mmol) in ethanol (10 mL) and treat with 5 N NaOH (0.4 mL). Heat the reaction to reflux for 1 hour, cool to room temperature and remove the solvent in vacuo. Aqueous 1 N HCl is added to adjust the pH to pH ~1 and the mixture is extracted with ethyl acetate and water. The organic layer is dried ($Na_2SO_4$) to afford 136 mg (72%) of the title compound: LC-MS (ES+) m/z=exact mass calcd for $C_{27}H_{31}Cl_2NO_4$ 503, found 504 and 506 (M+1 and M+3, 100%) and $R_t$ (Purity at 214 nm)=6.03 min (96.7%).

Example 197

[3',5'-Dichloro-4'-(1-cyclohexyl-2-oxo-pyrrolidin-3-ylmethyl)-biphenyl-4-yloxy]-acetic acid ethyl ester

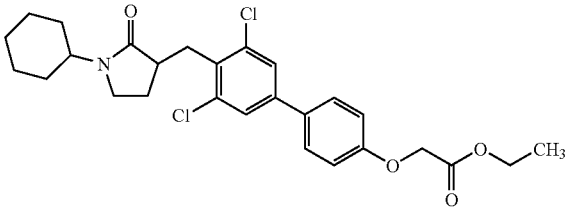

Combine 1-cyclohexyl-3-(3,5-dichloro-4'-hydroxy-biphenyl-4-ylmethyl)-pyrrolidin-2-one (Preparation 52) (0.15 g, 0.36 mmol), ethyl bromoacetate (0.12 g, 0.718 mmol) and $Cs_2CO_3$ (0.29 g, 0.89 mmol) in DMF (6 mL) and heat to 60° C. for 16 hours. Cool the reaction, extract with diethyl ether and water, dry the organic layer ($Na_2SO_4$) and then purify by normal phase chromatography (30 to 80% gradient of ethyl acetate in hexanes) to afford 159 mg (88%) of the title compound: LC-MS (ES+) m/z=exact mass calcd for $C_{27}H_{31}Cl_2NO_4$ 503, found 504 and 506 (M+1 and M+3, 100%).

Example 198

[3',5'-Dichloro-4'-(1-cyclohexyl-2-oxo-pyrrolidin-3-ylmethyl)-biphenyl-4-yloxy]-acetic acid

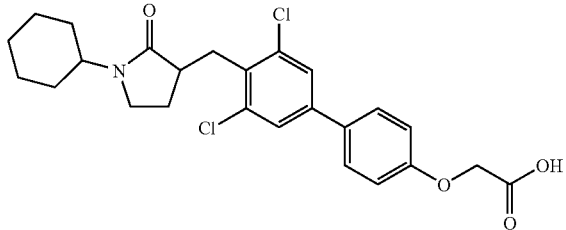

[3',5'-Dichloro-4'-(1-cyclohexyl-2-oxo-pyrrolidin-3-ylmethyl)-biphenyl-4-yloxy]-acetic acid ethyl ester (ex 206) (0.159 g, 0.315 mmol) is saponified as described in example 196 to afford 132 mg (88%) of the title compound: LC-MS (ES+) m/z=exact mass calcd for $C_{25}H_{27}Cl_2NO_4$ 475, found 476 and 478 (M+1 and M+3, 100%) and $R_t$ (Purity at 214 nm)=5.43 min (97.2%).

Example 199

3-[3',5'-Dichloro-4'-(1-cyclohexyl-2-oxo-pyrrolidin-3-ylmethyl)-biphenyl-4-yloxy]-propionic acid

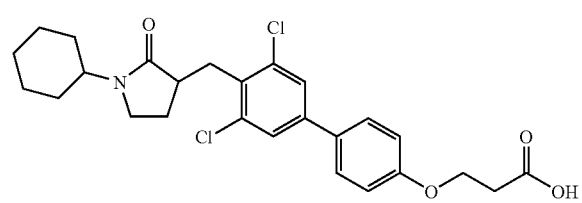

Treat a solution of 1-cyclohexyl-3-(3,5-dichloro-4'-hydroxy-biphenyl-4-ylmethyl)-pyrrolidin-2-one (55) (0.20 g, 0.47 mmol) in THF (3 mL) with a 1 molar solution of potassium tert-butoxide in THF (0.50 mL, 0.49 mmol) and stir for 5 minutes at room temperature. Add dropwise a solution of beta-propiolactone (0.038 g, 0.527 mmol) in THF (3 mL) and stir the reaction at room temperature for 16 hours under $N_2$. Quench the reaction with 1 N HCl, extract with ethyl acetate and water, dry the organic layer ($Na_2SO_4$) and purify by normal phase chromatography (30 to 100% gradient of ethyl acetate in hexanes) to afford 26 mg (11%) of the title compound: LC-MS (ES+) m/z=exact mass calcd for $C_{26}H_{29}Cl_2NO_4$ 489, found 490 and 492 (M+1 and M+3, 100%).

Example 200

3-[3',5'-Dichloro-4'-(1-cyclohexyl-2-oxo-pyrrolidin-3-ylmethyl)-biphenyl-4-yl]-propionic acid

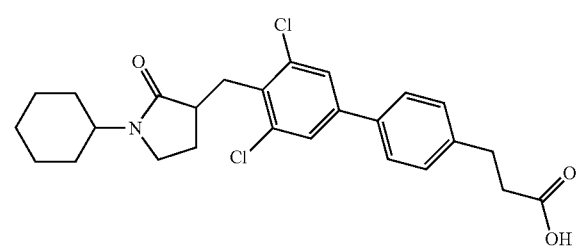

Charge a vial with 3,5-dichloro-4-((1-cyclohexyl-2-oxopyrrolidin-3-yl)methyl)phenyl trifluoromethanesulfonate (Example 240) (0.30 g, 0.63 mmol), 4-(2-carboxyethyl)benzene boronic acid (0.123 g, 0.634 mmol) and $Pd(Ph_3)_4$ (0.073 g, 0.063 mmol) in 1,4-dioxane (5 mL) and 2 M $Na_2CO_3$ (1 mL) and heat to 95° C. for 16 hours. Cool the reaction, extract with ethyl acetate and water, dry the organic layer ($Na_2SO_4$) and purify by HPLC (5 to 95% acetonitrile in water with 0.1% trifluroacetic acid buffer) to afford 373 mg (62%) of the title compound: LC-MS (ES +) m/z=exact mass calcd for $C_{26}H_{29}Cl_2NO_3$ 473, found 474 and 476 (M+1 and M+3, 100%).

Example 201

3,5-Dichloro-4-(1-cyclohexyl-2-oxo-pyrrolidin-3-ylmethyl)-benzoic acid methyl ester

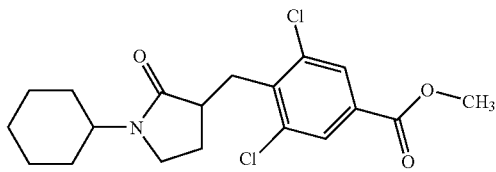

Heat a mixture of 3,5-dichloro-4-((1-cyclohexyl-2-oxopyrrolidin-3-yl)methyl)phenyl trifluoromethanesulfonate (Example 240) (2.0 g, 4.2 mmol), anhydrous sodium acetate (1.04 g, 12.7 mmol) and dichloro[1,1'-bis(diphenylphosphino)ferrocene]palladium (II) dichloromethane adduct (34 mg, 0.042 mmol) in methanol (60 mL) to 120° C. under 60 psi of carbon monoxide for 5 hours. Cool the reaction, extract with ethyl acetate and water and dry the organic layer ($Na_2SO_4$). The crude product is purified by normal phase chromatography (0 to 100% gradient of ethyl acetate in hexanes) to afford 1.21 g (75%) of the title compound: LC-MS (ES+) m/z=exact mass calcd for $C_{19}H_{23}Cl_2NO_3$ 383, found 384 and 386 (M+1 and M+3, 100%).

Example 202

3-(4-tert-butyl-benzyl)-1-(cis-4-hydroxy-cyclohexyl)-pyrrolidin-2-one

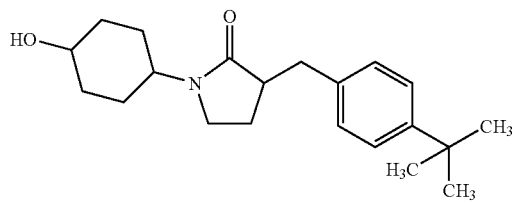

Dissolve 1.0 equivalent of cis-1-[4-(tert-butyl-dimethyl-silanoxy)-cyclohexyl]-pyrrolidin-2-one (Preparation 17) in THF, cool to −78° C. and treat with 1.1 equivalent of LDA. Allow reaction to warm to −40° C., re-cool to −78° C. and treat resulting anion with 1.1 equivalent of 4-tert-butylbenzyl bromide. Warm reaction to room temperature, quench with $NH_4Cl$ (sat), dilute with diethyl ether, wash with brine, dry over sodium sulfate, filter and evaporate to an oil. Chromatography (silica, 4:1 hexanes/EtoAc) yields 3-(4-tert-butyl-benzyl)-1-[4-(tert-butyl-dimethyl-silanyloxy)-cyclohexyl]-pyrrolidin-2-one in 29% yield. The silylether is dissolved in THF, treated with 3.0 equivalents of TBAF and allowed to stir at room temperature overnight. Quench reaction with water, dilute with methylene chloride, separate, dry over sodium sulfate, filter and evaporate. Chromatography (silica, 4:6 hexanes/EtoAc) provides the titled compound in 57% yield: Mass spectrum (API-ES positive) m/z=330.2 (M+H).

Example 203

1-(cis-4-hydroxy-cyclohexyl)-3-(4-trifluoromethyl-benzyl)-pyrrolidin-2-one

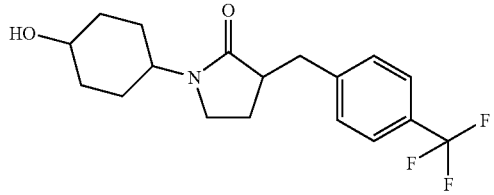

Using the procedure to synthesize Example 202 and using cis-1-[4-(tert-butyl-dimethyl-silanyloxy)-cyclohexyl]-pyrrolidin-2-one (Preparation 17), 4-trifluoromethyl benzylbromide and 1.5 equivalents of LDA affords an oil. Chromatography (silica, 4:1 hexanes/EtoAc) yields 4-[4-tert-butyl dimethyl-silanyloxy)-cyclohexyl]-3-(4-trifluoromethyl-benzyl)-pyrrolidin-2-one in 39% yield. The silylether is dissolved in THF, treated with 5.0 equivalents of TBAF and allowed to stir at room temperature overnight. Quench reaction with water, dilute with methylene chloride, separate, dry over sodium sulfate, filter and evaporate. Chromatography (silica, 4:6 hexanes/EtoAc) provides the titled compound in 21% yield: Mass spectrum (API-ES positive) m/z=342.3 (M+H).

Example 204

3-[1-(2,4-Dichloro-phenyl)-1-methyl-ethyl]-1-(trans-4-hydroxy-cyclohexyl)-pyrrolidin-2-one

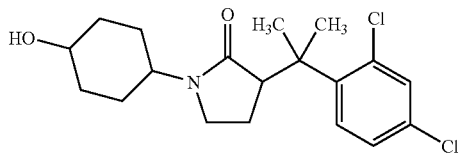

Dissolve 3-(2,4-Dichloro-phenyl)-3-methyl-2-(2-oxoethyl)-butyric acid ethyl ester (Preparation 61) in THF and treat with trans-4-Amino-cyclohexan-1-ol (2.0 eq), acetic acid (6.0 eq) and NaBH(OAc)3 (4.0 eq). Allow reaction to stir at room temperature for 17 h and heat to 60° C. for six hours. Cool to room temperature, filter, dilute filtrate with EtOAc, wash with 0.1 N HCl, brine, dry over sodium sulfate and filter. Chromatography (silica, 1:1 to 3:7 hexanes/EtoAc) yields the titled compound in 53% yield: Mass spectrum (API-ES positive) m/z=372.0 (M+H).

Example 205 b 1-Cyclohexyl-3-[1-(2,4-dichloro-phenyl)-1-methyl-ethyl]-pyrrolidin-2-one

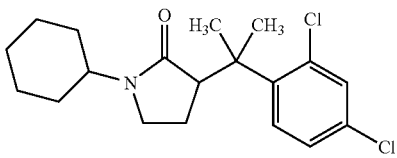

Using the procedure to prepare Example 204 and using the reagent Amino-cyclohexane yields the titled compound in 33% yield: Mass spectrum (API-ES positive) m/z=355 (M+H).

Example 206

3-(2,6-Dichloro-4-methoxy-benzyl)-1-(cis-4-hydroxy-cyclohexyl)-pyrrolidin-2-one

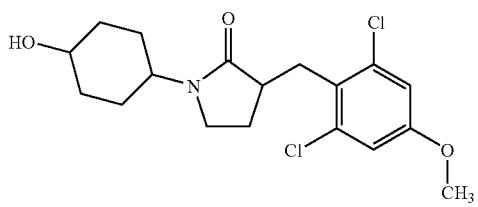

Using the procedure to synthesize Example 202 and using the reagents of cis-1-[4-(tert-butyl-dimethyl-silanoxy)-cyclohexyl]-pyrrolidin-2-one (Preparation 17) and 2-Bromomethyl-1,3-dichloro-5-methoxy-benzene (Preparation 62). Warm reaction to room temperature, quench with NH$_4$Cl (sat), dilute with diethyl ether, wash with brine, dry over sodium sulfate, filter and evaporate to an oil. Chromatography (silica, 100% hexanes to 75:25 hexanes/EtoAc) yields 1-[4-(tert-Butyl-dimethyl-silanyloxy)-cyclohexyl]-3-(2,6-dichloro-4-methoxy-benzyl)-pyrrolidin-2-one in 49% yield. The silylether is dissolved in THF, treated with 10.0 equivalents of HCl (conc) and allowed to stir at room temperature for 3 h, quench reaction with water, dilute with EtOAc, adjust pH to 7.0, separate, dry over sodium sulfate, filter and evaporate provides the titled compound in 84% yield: Mass spectrum (API-ES positive) m/z=372 (M+H).

Example 207

3-Chloro-N-[3,5-dichloro-4-(1-cyclohexyl-2-oxo-pyrrolidin-3-ylmethyl)-phenyl]-2-methyl-benzenesulfonamide

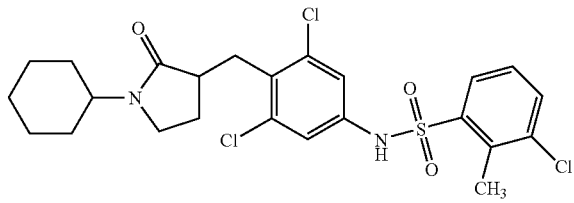

Place 3-Chloro-2-methyl-benzenesulfonyl chloride (160 mg, 0.70 mmol) in CH$_2$Cl$_2$ (10 mL) and cool to 0° C. Slowly add pyridine (0.06 mL, 0.70 mmol) and stir for 15 minutes. Add 3-(4-Amino-2,6-dichloro-benzyl)-1-cyclohexyl-pyrrolidin-2-one (Example 183), 200 mg, 0.59 mmol) and stir for 12 hours. Quench with 1N HCl and extract with dichloromethane. Wash the extract with NaHCO$_3$, brine. Dry over sodium sulfate, filter, and concentrate. Purify by silica gel (10-80% ethyl acetate in hexanes) to afford 181 mg (58%) of the title compound: Mass spectrum (apci) m/z=529.05 (M+H).

Example 208

3-Chloro-N-[2,4-dichloro-3-(1-cyclohexyl-2-oxo-pyrrolidin-3-ylmethyl)-phenyl]-2-methyl-benzenesulfonamide

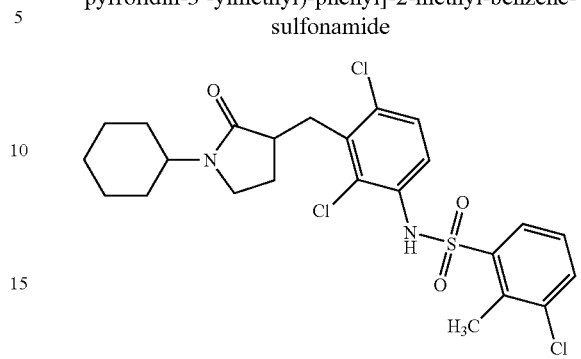

Using the procedure to synthesize Example 207 and using reagents 3-Chloro-2-methyl-benzenesulfonyl chloride (194 mg, 0.84 mmol), pyridine (0.07 mL, 0.84 mmol), and 3-(3-Amino-2,6-dichloro-benzyl)-1-cyclohexyl-pyrrolidin-2-one (Example 192) (240 mg, 0.70 mmol) affords 175 mg (47%) of the title compound: Mass spectrum (apci) m/z=529.05 (M+H).

Example 209

Trans-3-(4-chloro-6-fluoro-benzyl)-1-(4-hydroxy-cyclohexyl)-piperidin-2-one

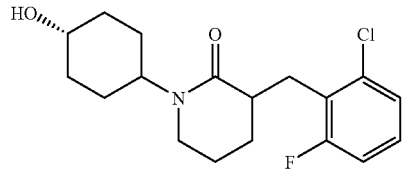

Dissolve trans-1-(4-[tert-butyl-dimethyl-silanyloxy)-cyclohexyl]-piperidin-2-one (0.3 g, 0.96 mmol) in anhydrous THF (6 mL) under nitrogen, cool to −78° C. and add LDA (2M solution in THF) (0.72 mL, 1.44 mmol) dropwise. Stir the reaction mixture for 5 minutes and add 2-bromomethyl-1-chloro-3-fluoro-benzene (0.3 g, 1.44 mmol) in anhydrous THF (2 mL) dropwise. Stir the reaction mixture at −78° C. for 3 hours, slowly warm to room temperature, quench with saturated aqueous NH$_4$Cl (5 mL) and extract with DCM (3×10 mL). Dry the organic layer over Na$_2$SO$_4$, remove the solvent and purify the residue by chromatography over silica gel (eluting with 0 to 20% EtOAc in hexane) to obtain trans-3-(-2-chloro-6-fluoro-benzyl)-1-(4-[tert-butyl-dimethyl-silanyloxy]-cyclohexyl)-piperidin-2-one as a white solid (0.2 g). Dissolve the trans-3-(-2-chloro-6-fluoro-benzyl)-1-(4-[tert-butyl-dimethyl-silanyloxy]-cyclohexyl)-piperedin-2-one in methanol containing concentrated hydrochloric acid (5% v/v) and heat at 40° C. for 1 hour. Evaporate the solvent, dissolve the residue in DCM (10 mL) and wash with saturated aqueous NaHCO$_3$ (5 mL). Dry the organic layer over anhydrous Na$_2$SO$_4$, remove the solvent and purify the residue by chromatography over silica gel (eluting with 0 to 50% EtOAc in hexane) to obtain the title compound as a clear oil (110 mg, 34%): MS (ES+) m/z=340 (M+H)$^+$.

Example 210

Trans-3-(2-chloro-4-pyridin-3-yl-benzyl)-1-(4-hydroxy-cyclohexyl)-piperidin-2-one

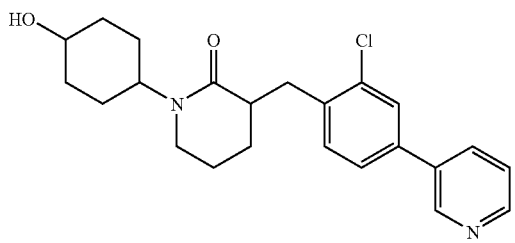

Combine trans-3-(4 bromo-2-chloro-benzyl)-1-[4-(tert-butyl-dimethyl-silanyloxy)-cyclohexyl]-piperidin-2-one (Preparation 65) (0.2 g, 0.49 mmol), 3-pyridine boronic acid (0.2 g, 1.49 mmol), tetrakis(triphenylphosphine)palladium (0) (0.06 g, 0.05 mmol), $Na_2CO_3$ (1.1 g, 9.95 mmols), water (1.5 mL), 1,2-dimethoxy-ethane (7 mL) and heat at 80° C. for 24 hours. Cool the reaction mixture to room temperature, add saturated aqueous $NaHCO_3$ (5 mL) and extract with EtOAc (3×10 mL). Dry the organic layer over anhydrous $Na_2SO_4$, remove the solvent and purify the residue by chromatography over silica gel (eluting with 50 to 100% EtOAc in hexane) to obtain trans-1-[4-(tert-butyl-dimethyl-silanyloxy)-cyclohexyl]-3-(2-chloro-4-pyridine-3-yl-benzyl)-piperidin-2-one as a white solid (0.2 g, 80%).

Dissolve trans-1-[4-(tert-butyl-dimethyl-silanyloxy)-cyclohexyl]-3-(2-chloro-4-pyridine-3-yl-benzyl)-piperidin-2-one (0.2 g, 0.39 mmol) in methanol containing concentrated hydrochloric acid (5% v/v) and heat at 40° C. for 1 hour. Evaporate the solvent, dissolve the residue in DCM (10 mL) and wash with saturated aqueous $NaHCO_3$ (5 mL). Dry the organic layer over anhydrous $Na_2SO_4$, remove the solvent and purify the residue by chromatography over silica gel eluting with EtOAc to obtain the title compound as a white solid (131.4 mg, 84%): MS (ES+) m/z=399 $(M+H)^+$.

Examples 211 and 212 may be prepared essentially as described in Example 210, using cis-1-(4-[tert-butyl-dimethyl-silanyloxy)-cyclohexyl]-piperidin-$^2$-one and the appropriate boronic acid.

Example 213

3-(4-Bromo-2-chloro-benzyl)-1-cyclohex-3-enyl-pyrrolidin-2-one

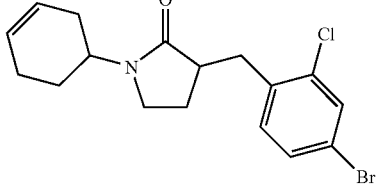

Dissolve 1-cyclohex-3-enyl-pyrrolidin-2-one (Preparation 66) (300 mg, 1.82 mmol) in anhydrous THF (8 mL), cool to −78° C. and add LDA (2M in THF, 1.36 mL, 2.72 mmol) dropwise. After 10 minutes add 4-bromo-1-bromomethyl-2-chloro-benzene (512 mg, 1.82 mmol) and allow the mixture to warm to room temperature over 16 h. Quench with saturated aqueous ammonium chloride, extract with dichloromethane, dry the organic layer over sodium sulfate and evaporate. Purify the residue by chromatography on silica gel (eluting 0 to 50% ethyl acetate in hexane) to give the title compound as a clear oil (370 mg, 56%): MS (EI) m/z=367, 369 (M+).

Example 214

3-(2-Chloro-4-pyridin-3-yl-benzyl)-1-cyclohex-3-enyl-pyrrolidin-2-one

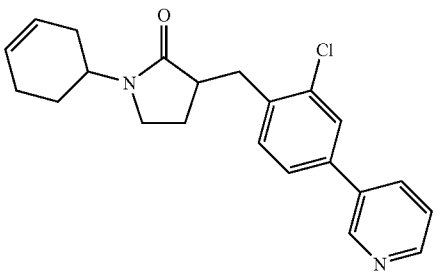

Combine 3-(4-bromo-2-chloro-benzyl)-1-cyclohex-3-enyl-pyrrolidin-2-one (370 mg, 1.01 mmol), 3-pyridine

TABLE 9

| Example | Structure | Compound | MS (ES+) m/z |
|---|---|---|---|
| 211 | 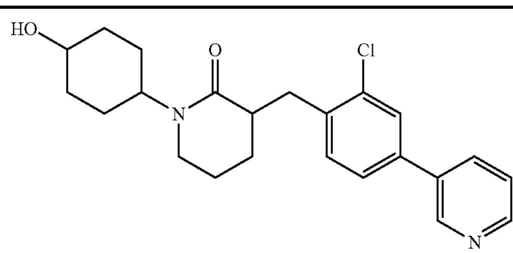 | Cis-3-(2-chloro-4-pyridin-3-yl-benzyl)-1-(4-hydroxy-cyclohexyl)-piperidine-2-one | 399 $(M + H)^+$ |
| 212 | | Cis-3-(2-chloro-4-pyridin-4-yl-benzyl)-1-(4-hydroxy-cyclohexyl)-piperidine-2-one | 399 $(M + H)^+$ | boronic acid (372 mg, 3.03 mmol), tetrakis(triphenylphosphine)palladium(0) (116 mg, 0.10 mmol), Na₂CO₃ (2.14 g, 20.2 mmols), water (1.5 mL), 1,2-dimethoxy-ethane (8 mL) and heat at 80° C. for 20 hours. Cool the reaction mixture to room temperature, add saturated aqueous NaHCO₃ (5 mL) and extract with EtOAc (3×10 mL). Dry the organic layer over anhydrous Na₂SO₄, remove the solvent and purify the residue by chromatography over silica gel eluting with EtOAc in hexane (0 to 100%) to obtain 3-(2-chloro-4-pyridin-3-yl-benzyl)-1-cyclohex-3-enyl-pyrrolidin-2-one as a clear oil (60 mg, 16%): MS (ES+) m/z=367 (M+H)⁺.

Example 215

3-(2-Chloro-6-fluoro-benzyl)-1-cyclohexyl-piperidin-2-one

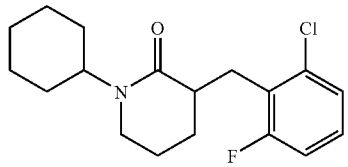

Dissolve 1-cyclohexyl-piperidin-2-one (0.2 g, 1.10 mmol) in dry THF (11 mL) cool to −78° C. and add lithium bis(trimethylsilyl)amide (1.66 mL of 1.0 M solution in THF, 1.66 mmol). After 15 min add 1-bromomethyl-2-chloro-6-fluorobenzene (0.49 g, 2.21 mmol), and allow the mixture to warm to room temperature over 15 h. Wash the mixture with brine, dry the organic layer over sodium sulfate and evaporate. Purify the residue by chromatography on silica gel (eluting 0% to 100% ethyl acetate in hexane) to give the desired product (0.21 g, 59%). MS (ES+) m/z=324 (M+H)⁺.

Example 216

3-(4-Bromo-2-chloro-benzyl)-1-cyclohexyl-piperidin-2-one

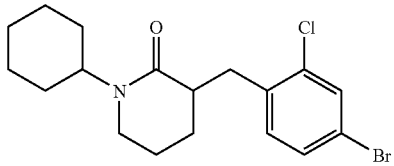

Dissolve 1-cyclohexyl-piperidin-2-one (0.2 g, 1.10 mmol) in dry DMF (11 mL) cool to −78° C. and add lithium bis(trimethylsilyl)amide (1.66 mL of 1.0 M solution in THF, 1.66 mmol). After 15 min add 1-bromomethyl-2-chloro-4-bromobenzene (0.63 g, 2.21 mmol), and allow the mixture to warm to room temperature over 15 h. Partition the mixture between ether and brine, dry the organic layer over sodium sulfate and evaporate. Purify the residue by chromatography on silica gel (eluting 0% to 100% ethyl acetate in hexane) to give the desired product (0.16 g, 38%). MS (ES+) m/z=384, 386 (M+H)⁺.

Example 217

3-(2-Chloro-4-pyridin-3-yl-benzyl)-1-cyclohexyl-piperidin-2-one, ammonium chloride salt

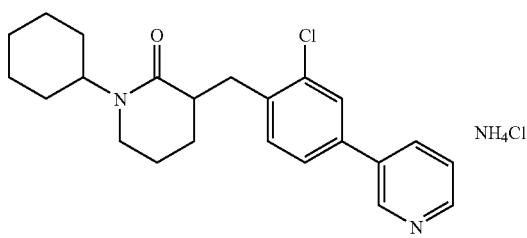

Dissolve 3-(4-bromo-2-chloro-benzyl)-1-cyclohexyl-piperidin-2-one (98 mg, 0.26 mmol), tetrakis(triphenylphosphine)palladium(0) (30 mg, 0.03 mmol), and pyridine-3-boronic acid (96 mg, 0.78 mmol) in ethylene glycol dimethyl ether (2.6 mL) and 2 M aqueous sodium carbonate (2.6 mL) and heat at 75° C. 16 h. Partition the mixture between ethyl acetate and brine, dry the organic layer over sodium sulfate and evaporate. Purify the residue by chromatography on silica gel (eluting 0% to 100% ethyl acetate in hexane) and then by prep HPLC (10% to 90% acetonitrile in 0.1% aqueous trifluoroacetic acid over 30 min, Sorbax SB-Phenyl 21.2 mm×25 cm, 22 mL/min) to give the trifluoroacetic acid salt. Free the base by passing the residue in methanol through an SCX column eluting with methanol and then 1M ammonia in methanol to obtain the free base (32 mg, 0.085 mmol). Add ammonium chloride (4.5 mg, 0.085 mmol) and evaporate methanol out of the mixture 3 times to give the desired product (37 mg, 33%). MS (ES+) n/z=383 (M+H)⁺.

Example 218

3-(2,4-Dichloro-benzyl)-1-(cis-4-hydroxy-cyclohexyl)-3-methyl-pyrrolidin-2-one

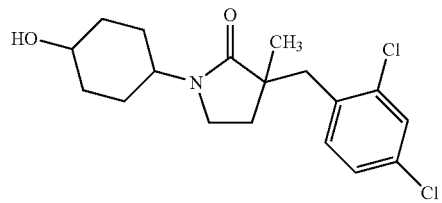

Dissolve 3-(2,4-dichloro-benzyl)-1-(cis-4-t-butyldimethylsilyloxy-cyclohexyl)-3-methyl-pyrrolidin-2-one and 3-(2,4-dichloro-3-methyl-benzyl)-1-(cis-4-t-butyldimethylsilyloxy-cyclohexyl)-3-methyl-pyrrolidin-2-one (0.42 g, 0.89 mmol) in ethanol-2N HCl (1:1, 9 mL) and stir at 70° C. 2 h. Cool the mixture and partition between dichloromethane and saturated aqueous sodium bicarbonate and brine, dry the organic layer over sodium sulfate and evaporate. Purify the residue by column chromatography on silica gel (eluting 0% to 100% ethyl acetate in hexane) to give the desired product (97 mg, 31%). MS(ES+) m/z=356.

Example 219

3-(2,4-Dichloro-3-methyl-benzyl)-1-(cis-4-hydroxycyclohexyl)-3-methyl-pyrrolidin-2-one

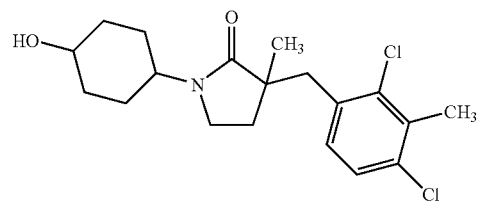

Also isolate from the alkylation mixture of 3-(2,4-dichloro-benzyl)-1-(cis-4-hydroxy-cyclohexyl)-3-methyl-pyrrolidin-2-one, the title compound (63 mg, 19%). MS(ES+) m/z=370.

Example 220 and 221

3-(2-Chloro-4-pyridin-3-yl-benzyl)-1-cyclohexyl-3-methyl-pyrrolidin-2-one and 3-[1-(2-chloro-4-pyridin-3-yl-phenyl)-ethyl]-1-cyclohexyl-pyrrolidin-2-one, isomers 1 and 2

Isomers 1 and 2

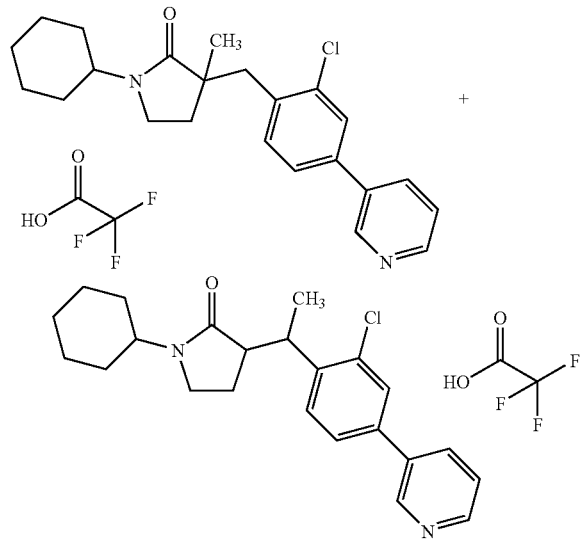

Dissolve 3-(2-chloro-4-pyridin-3-yl-benzyl)-1-cyclohexyl-pyrrolidin-2-one (300 mg, 0.82 mmol) in THF (8.2 mL), cool to −78° C. and add lithium diisopropylamide mono (tetrahydrofuran) (1.09 mL of 1.5 M solution in cyclohexanes, 1.63 mmol). After 6 minutes, add iodomethane (0.15 mL, 2.45 mmol) and stir 2.5 h. Wash the mixture with brine, dry the organic layer over sodium sulfate and evaporate. Purify the residue by HPLC (Zorbax SB-Phenyl 21.2 mm×25 cm, 22 mL/min of 10% to 90% acetonitrile in 0.1% aqueous TFA over 30 min) to obtain first a mixture of 3-(2-chloro-4-pyridin-3-yl-benzyl)-1-cyclohexyl-3-methyl-pyrrolidin-2-one and 3-[1-(2-chloro-4-pyridin-3-yl-phenyl)-ethyl]-1-cyclohexyl-pyrrolidin-2-one, isomer 1 (130 mg) and second 3-[1-(2-chloro-4-pyridin-3-yl-phenyl)-ethyl]-1-cyclohexyl-pyrrolidin-2-one, isomer 2 (36 mg, 12%) as their TFA salts.

Example 222

3-(2-Chloro-4-pyridin-3-yl-benzyl)-1-cyclohexyl-3-methyl-pyrrolidin-2-one ammonium chloride salt

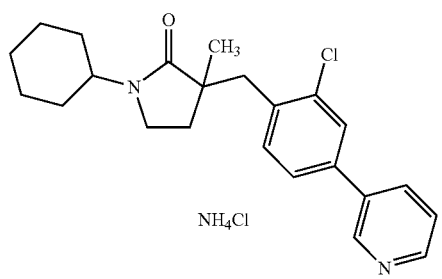

Free the bases in the mixture of 3-(2-chloro-4-pyridin-3-yl-benzyl)-1-cyclohexyl-3-methyl-pyrrolidin-2-one and 3-[1-(2-chloro-4-pyridin-3-yl-phenyl)-ethyl]-1-cyclohexyl-pyrrolidin-2-one, isomer 1 trifluoroacetic acid salts by passage through an SCX column eluting with methanol followed by 1N ammonia in methanol and evaporate. Further purify the residue by chromatography on silica gel (eluting with 15% acetonitrile in dichloromethane) to give first 3-[1-(2-chloro-4-pyridin-3-yl-phenyl)-ethyl]-1-cyclohexyl-pyrrolidin-2-one, isomer 1 (40 mg, 13%), and second 3-(2-chloro-4-pyridin-3-yl-benzyl)-1-cyclohexyl-3-methyl-pyrrolidin-2-one.
To a solution of 3-(2-chloro-4-pyridin-3-yl-benzyl)-1-cyclohexyl-3-methyl-pyrrolidin-2-one in methanol, add ammonium chloride (11.7 mg, 0.22 mmol) and evaporate methanol out of the mixture three times to give the desired title compound (94 mg, 27%). MS (ES+) m/z=383.

Example 223

3-[1-(2-Chloro-4-pyridin-3-yl-phenyl)-ethyl]-1-cyclohexyl-pyrrolidin-2-one, isomer 1 ammonium chloride salt

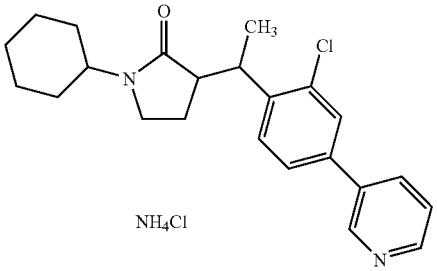

Also obtain from the methylation step of the synthesis of 3-(2-chloro-4-pyridin-3-yl-benzyl)-1-cyclohexyl-3-methyl-pyrrolidin-2-one ammonium chloride (Example 222), 3-[1-(2-chloro-4-pyridin-3-yl-phenyl)-ethyl]-1-cyclohexyl-pyrrolidin-2-one, isomer 1 (40 mg, 0.10 mmol). Take up the residue in methanol and add ammonium chloride (5.5 mg, 0.10 mmol) and evaporate methanol out of the mixture three times to obtain the title compound (42 mg, 100%). HRMS (ES+) calcd for $C_{23}H_{27}ClN_2O$ 383.1890, found 383.1915.

Example 224

3-[1-(2-Chloro-4-pyridin-3-yl-phenyl)-ethyl]-1-cyclohexyl-pyrrolidin-2-one, isomer 2 ammonium chloride salt

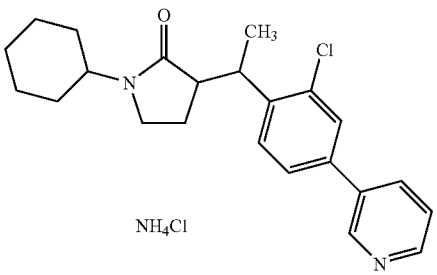

Also obtain from the methylation step of the synthesis of 3-(2-chloro-4-pyridin-3-yl-benzyl)-1-cyclohexyl-3-methyl-pyrrolidin-2-one hydrochloride (Ex 230), 3-[1-(2-chloro-4- pyridin-3-yl-phenyl)-ethyl]-1-cyclohexyl-pyrrolidin-2-one trifluoroacetic acid salt, isomer 2 (36 mg, 0.095 mmol). Free the base by passage through an SCX column eluting with methanol followed by 1N ammonia in methanol. Take up the residue in methanol and add ammonium chloride (5.0 mg, 0.09 mmol) and evaporate methanol out of the mixture three times to obtain the title compound (40 mg, 100%). HRMS (ES+) calcd for $C_{23}H_{27}ClN_2O$ 383.1890, found 383.1912.

Example 225

3-Chloro-4-(1-cyclohexyl-2-oxo-pyrrolidin-3-ylmethyl)-benzoic acid methyl ester

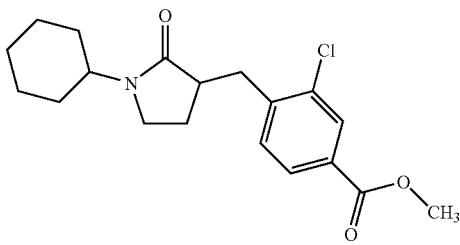

Dissolve 3-(4-bromo-2-chloro-benzyl)-1-cyclohexyl-piperidin-2-one (Example 55) (2.0 g, 5.41 mmol) and dichloro [1,1'-bis(diphenylphosphino)ferrocene]palladium (II) dichloromethane adduct (220 mg, 0.27 mmol) in DMF (11 mL) and methanol (4.5 mL) with triethylamine (15.2 mL, 10.8 mmol), purge the flask with carbon monoxide and heat at 70° C. for 16 h under a balloon of carbon monoxide. Evaporate the methanol and wash the mixture with brine, dry the organic layer over sodium sulfate and evaporate. Purify the residue by chromatography on silica gel (eluting 10% to 100% ethyl acetate in hexane) to give the desired product (1.44 g, 76%). MS (ES+) m/z=350.

Example 226

3-(2-Chloro-4-phenoxy-benzyl)-1-cyclohexyl-pyrrolidin-2-one

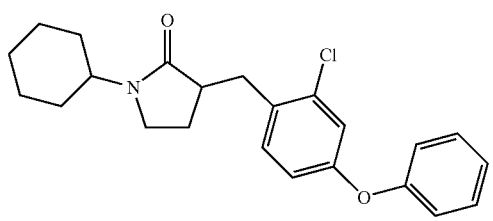

Dissolve 3-(4-bromo-2-chloro-benzyl)-1-cyclohexyl-piperidin-2-one (Example 55) (0.2 g, 0.54 mmol), copper (I) iodide (10.5 mg, 0.05 mmol), N,N-dimethylglycine hydrochloride (22.6 mg, 0.16 mmol) in dioxane (3 mL) with cesium carbonate (0.53 g, 1.62 mmol), and heat at 90° C. 24 h. Evaporate and purify the residue by chromatography on silica gel (eluting 10% to 100% ethyl acetate in hexane) to give the desired product (17 mg, 8%). MS (ES+) n/z=384 (M+H)⁺.

Example 227

3-[2-Chloro-4-(3-hydroxy-pyrrolidin-1-yl)-benzyl]-1-cyclohexyl-pyrrolidin-2-one

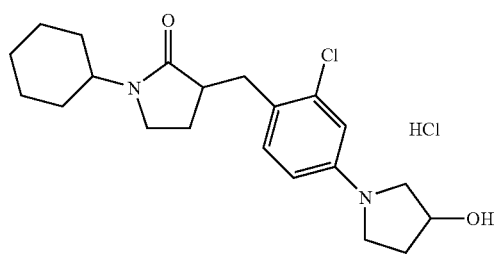

Dissolve 3-(4-bromo-2-chloro-benzyl)-1-cyclohexyl-piperidin-2-one (Example 55) (0.2 g, 0.54 mmol), rac-3-hydroxy-pyrrolidine (0.053 mL, 0.64 mmol), copper (I) iodide (10.5 mg, 0.05 mmol), in dimethylacetamide (1 mL) with potassium carbonate (0.13 g, 0.95 mmol), and heat at 90° C. 48 h. Evaporate and purify the residue by chromatography on silica gel (eluting 10% to 100% ethyl acetate in hexane) to give the desired product (39 mg, 19%). MS (ES+) m/z=377 (M+H)⁺.

Example 228

3-(2-Chloro-4-piperidin-1-yl-benzyl)-1-cyclohexyl-pyrrolidin-2-one

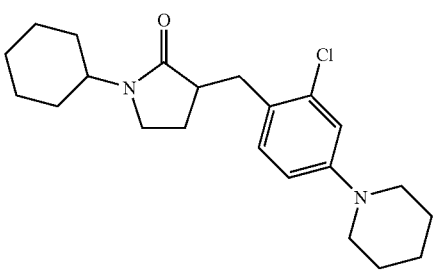

Dissolve 3-(4-bromo-2-chloro-benzyl)-1-cyclohexyl-piperidin-2-one (Example 55) (0.20 g, 0.54 mmol), piperidine (0.21 mL, 2.16 mmol), palladium (II) acetate (12 mg, 0.05 mmol) and rac-2,2'-bis(diphenylphosphino)-1,1'-binaphthyl (67 mg, 0.11 mmol) in toluene (1 mL) with cesium carbonate (264 mg, 0.81 mmol) and heat at 90° C. 16 h. Pass the mixture through an SCX ion exchange column washing with methanol and eluting with 1N ammonia in methanol and evaporate. Purify the residue by preparative reversed phase HPLC chromatography to give the title compound (98 mg, 48%). MS (ES+) nz/z=376 (M+H)⁺.

Examples 229 and 230 may be prepared essentially as described in Example 228, using 3-(4-bromo-2-chloro-benzyl)-1-cyclohexyl-piperidin-2-one and the appropriate amine. MS (ES+) data are shown in the Table below.

TABLE 10

| Example | Structure | Compound | MS (ES+) m/z |
|---|---|---|---|
| 229 | 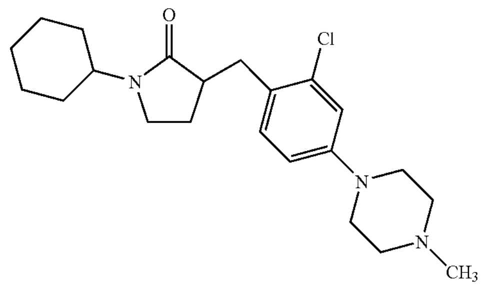 | 3-[2-Chloro-4-(4-methyl-piperazin-1-yl)-benzyl]-1-cyclohexyl-pyrrolidin-2-one | 391 (M + H)+ |
| 230 | 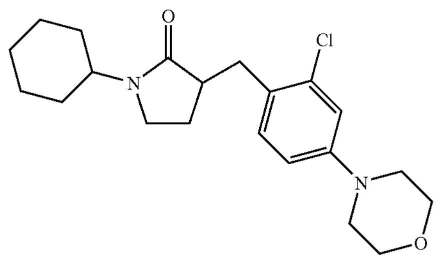 | 3-(2-Chloro-4-morpholin-4-yl-benzyl)-1-cyclohexyl-pyrrolidin-2-one | 378 (M + H)+ |

Example 231

3-(2-Chloro-4-phenylamino-benzyl)-1-cyclohexyl-pyrrolidin-2-one

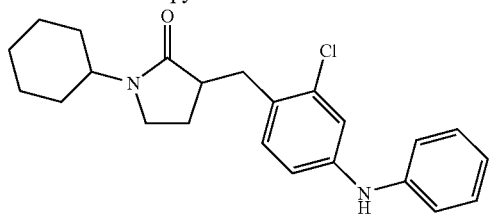

Prepare essentially as described in Example 228, using 3-(4-bromo-2-chloro-benzyl)-1-cyclohexyl-piperidin-2-one and aniline. Evaporate the crude reaction mixture and purify by chromatography on silica gel to give the title compound (127 mg, 61%). MS (ES+) m/z=383 (M+H)+.

Example 232

3-(4-Benzyloxy-2,6-dichloro-benzyl)-1-(cis-4-hydroxy-cyclohexyl)-pyrrolidin-2-one

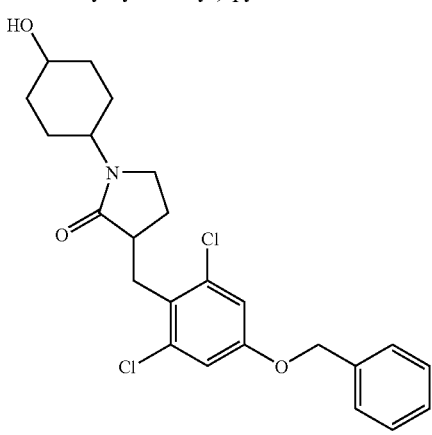

Combine 0.5 g (0.9 mmol) 3-(4-benzyloxy-2,6-dichloro-benzyl)-1-[cis-4-(tert-butyl-dimethyl-silanyloxy)-cyclohexyl]-pyrrolidin-2-one (Preparation 71) with 25 mL THF and treat with 0.5 mL 1 M TBAF in THF. Reflux for 2 hours, concentrate under vacuum and purify by chromatography using a gradient (CHCl3>10% MeOH) to recover 145 mg (36%) of a foam. Mass spectrum (apci) m/z=448 (M+). HPLC (5 to 95) R$_t$ (Purity at 214 nm)=4.703 min (99%).

Example 233

3-[2,6-Dichloro-4-(pyridin-3-ylmethoxy)-benzyl]-1-(cis-4-hydroxy-cyclohexyl)-pyrrolidin-2-one hydrochloride

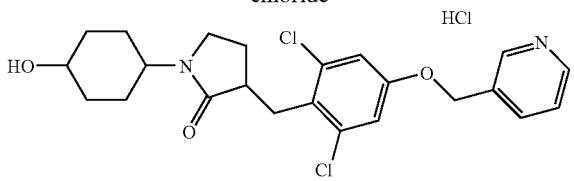

Combine 500 mg (1.1 mmol) of 1-[cis-4-(tert-butyl-dimethyl-silanyloxy)-cyclohexyl]-3-(2,6-dichloro-4-hydroxy-benzyl)-pyrrolidin-2-one (Preparation 72) with 540 mg of 3-pyridyl methyl bromide hydrobromide, 1.4 g Cs$_2$CO$_3$ and 10 mL dry DMF. Stir at ambient temperature for 72 hour, dilute with 25 mL brine and extract 3 times with 30 mL EtOAc. Wash the combined organic layer with brine (50 mL), dry with MgSO$_4$ and concentrate under vacuum to an oil. Purify by radial chromatography using Hex/EtOAc 50/50 to recover 0.37 g of an oil.

Dissolve the resulting oil in 20 mL MeOH and treat with 3 mL 1 N HCl at 40° C. for 12 hour. Concentrate under vacuum, partition the residue between 50 nL CH$_2$Cl$_2$ and saturated aqueous NaHCO$_3$. Dry the organic layer over MgSO$_4$, concentrate under vacuum and purify by radial chromatography using 5% MeOH in CHCl$_3$ to recover 160 mg of an oil.

Dissolve the oil in 25 mnL EtOAc and treat with 1 equivalent of 1 N HCl in Ether. Concentrate to dryness to get 168 mg solid. Mass spectrum (api-es) m/z 449 (M+H).

Example 234

4-{3,5-Dichloro-4-[1-(4-hydroxy-cyclohexyl)-2-oxo-pyrrolidin-3-ylmethyl]-phenoxy}-benzoic acid methyl ester

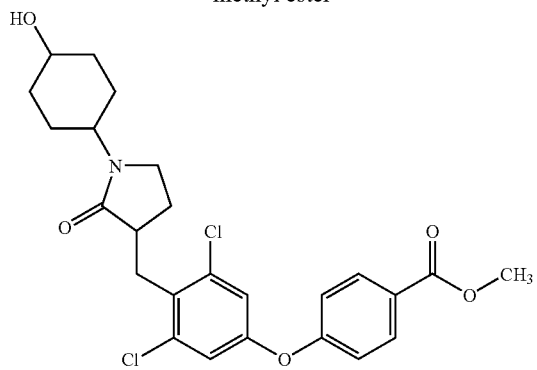

Dissolve 90 mg of 4-(4-{1-[cis-4-(tert-butyl-dimethyl-silanyloxy)-cyclohexyl]-2-oxo-pyrrolidin-3-ylmethyl}-3,5-dichloro-phenoxy)-benzoic acid methy ester (Preparation 73) in 10 mL EtOH and treat with 1 mL 1 N aqueous HCl. Heat at 60° C. for 2 hours. Concentrate to dryness under vacuum and purify by radial chromatography using 5% MeOH in CHCl₃ to recover 73 mg of product. Mass spectrum (api-es) m/z 492 (M+H).

Example 235

3-(2,6-Dichloro-4-pyridin-3-yl-benzyl)-1-(cis-4-hydroxy-cyclohexyl)-pyrrolidin-2-one hydrochloride

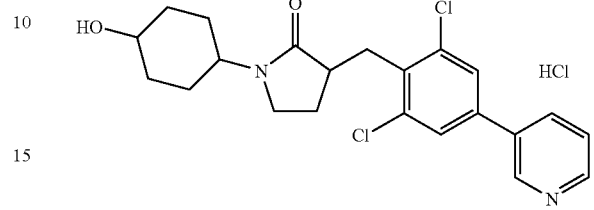

Add HCl (0.015 mL) to 1-[cis-4-(tert-butyl-dimethyl-silanyloxy)-cyclohexyl]-3-(2,6-dichloro-4-pyridin-3-yl-benzyl)-pyrrolidin-2-one (Preparation 75) (0.027 G, 0.0506 mmol) in methanol (2 mL) and heat to 40° C. for 1 hour. Concentrate under reduced pressure to give the title compound (0.017 g): mass spectrum (m/z):420(M+1).

TABLE 11

The following compounds are prepared essentially as described in Example 236 except using the reagents in the "Reagents used" column.

| Example | Structure and name | Reagents used | Mass spec |
|---------|---------------------|---------------|-----------|
| 236 | 3-(2,6-Dichloro-4-hydroxy-benzyl)-1-(cis-4-hydroxy-cyclohexyl)-pyrrolidin-2-one | 1-[cis-4-(tert-butyl-dimethyl-silanyloxy)-cyclohexyl]-3-(2,6-dichloro-4-hydroxy-benzyl)-pyrrolidin-2-one (0.094 g, 0.199 mmol) | (m/z): 359 (M + 1) |
| 237 | 3-(2,6-Dichloro-4-pyridin-4-yl-benzyl)-1-(cis-4-hydroxy-cyclohexyl)-pyrrolidin-2-one hydrochloride | 1-[cis-4-(tert-butyl-dimethyl-silanyloxy)-cyclohexyl]-3-(2,6-dichloro-4-pyridin-4-yl-benzyl)-pyrrolidin-2-one (0.189 g, 0.355 mmol) | (m/z): 420 (M + 1) |
| 238 | 3-[2,6-Dichloro-4-(1-methyl-1H-pyrazol-4-yl)-benzyl]-1-(cis-4-hydroxy-cyclohexyl)-pyrrolidin-2-one hydrochloride | 1-[cis-4-(tert-butyl-dimethyl-silanyloxy)-cyclohexyl]-3-[2,6-dichloro-4-(1-methyl-1H-pyrazol-4-yl)-benzyl]-pyrrolidin-2-one (0.300 g, 0.559 mmol) | (m/z): 424 (M + 1) |

TABLE 11-continued

The following compounds are prepared essentially as described in Example 236 except using the reagents in the "Reagents used" column.

| Example | Structure and name | Reagents used | Mass spec |
|---|---|---|---|
| 239 | 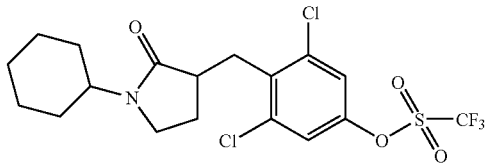<br>3-(2,6-Dichloro-4-isopropoxy-benzyl)-1-(cis-4-hydroxy-cyclohexyl)-pyrrolidin-2-one | 1-[cis-4-(tert-butyl-dimethyl-silanyloxy)-cyclohexyl]-3-(2,6-dichloro-4-isopropoxy-benzyl)-pyrrolidin-2-one (0.0.08 g, 0.155 mmol) | (m/z): 401 (M + 1) |

Example 240

3,5-dichloro-4-((1-cyclohexyl-2-oxopyrrolidin-3-yl)methyl)phenyl trifluoromethanesulfonate

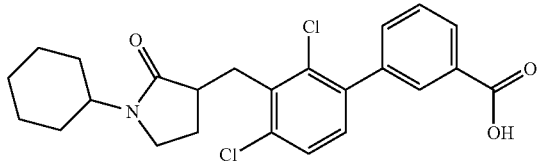

Charge a flask with 3-(2,6-dichloro-4-hydroxybenzyl)-1-cyclohexylpyrrolidin-2-one (Example 175) (7.5 g, 22 mmol) dissolve with pyridine (200 mL) and cool to 0° C. under nitrogen. Add $Tf_2O$ (10 mL, 26 mmol) slowly and warm to room temperature. Stir at room temperature for 30 minutes. Pour into water (1 L) and extract with ether. Wash ether layer twice with water. Dry over sodium sulfate, filter and concentrate. Purify over silica gel (10% ethyl acetate in hexanes) to yield 8.5 g (82%) of the title compound as a white solid. Mass spectrum (apci) rn/z=474.1 (M+H).

Example 241

2',4'-Dichloro-3'-(1-cyclohexyl-2-oxo-pyrrolidin-3-ylmethyl)-biphenyl-3-carboxylic acid

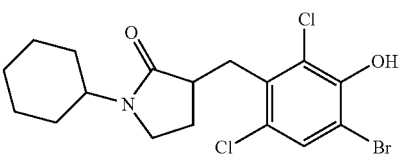

Place 3-(ethoxycarbonyl)phenylboronic acid (670 mg, 3.46 mmol), 3-(3-bromo-2,6-dichlorobenzyl)-1-cyclohexylpyrrolidin-2-one (Example 50) (700 mg, 1.73 mmol), and Pd(PPh3)4 (173 mg, 0.173 mmol) into a flask and purge with nitrogen. Add DME (50 mL) and 2M sodium carbonate (5 mL) and heat to 75° C. for 24 hr. Cool reaction, add DCM and wash with saturated sodium bicarbonate. Dry, filter, and concentrate organic layer. Purify by silica gel (30-45% EtOAc in Hex). Dissolve ester in ethanol (3 mL) and water (1 mL) and add KOH (291 mg, 5.18 mmol). Stir for 1 hour at room temperature. Strip off solvent and add water. Bring to a pH of 2 with 1M HCl. Filter precipitate to give 727 mg (94%) of title compound as a white solid. Mass spectrum (apci) m/z=446.2 (M+H).

Example 242

1-Cyclohexyl-3-[2,4-dichloro-4'-(3-dimethylamino-propoxy)-biphenyl-3-ylmethyl]-pyrrolidin-2-one hydrochloride

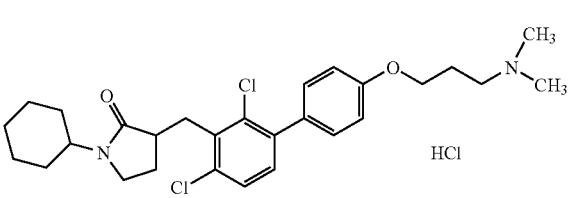

Place 3-(3-(4-hydroxyphenyl)-2,6-dichlorobenzyl)-1-cyclohexylpyrrolidin-2-one (0.200 g, 0.478 mmol), sodium iodide (0.072 g, 0.478 mmol, and cesium carbonate (1.25 g, 3.82 mmol) in acetone (lOmL). Add 3-bromo-N,N-dimethylpropan-1-amine hydrochloride (0.194 g, 0.956 mmol) and stir at room temperature for 3 hours. Add water and extract with DCM. Dry, filter, and concentrate. Purify by silica gel to give the free base. Dissolve in DCM and add 2M HCl in ether. Concentrate to give 84 mg (33%) of the title compound as a tan solid. Mass spectrum (apci) m/z=503.3 (M+H).

Example 243

3-(4-bromo-2,6-dichloro-3-hydroxybenzyl)-1-cyclohexylpyrrolidin-2-one

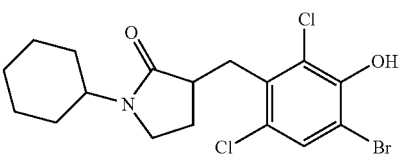

Place 3-(2,6-dichloro-3-hydroxybenzyl)-1-cyclohexylpyrrolidin-2-one (1.116 g, 3.26 mmol) in acetic acid (5 mL). Add NBS (0.609 g, 3.42 mmol) and stir at room temperature for 2 hours. Pour reaction mixture onto water, filter, and dry to give 1.165 g (85%) of the title compound. Mass spectrum (apci) m/z=422.1 (M+H).

Example 244

3-(2,4-Dichloro-benzyl)-1-(cis-4-hydroxy-cis-3-methyl-cyclohexyl)-pyrrolidin-2-one

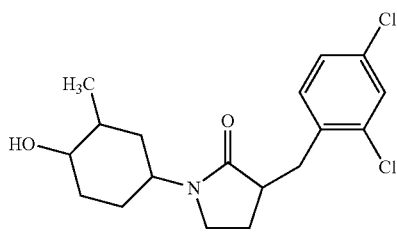

Step 1: 3-(2,4-Dichloro-benzyl)-1-(trans-4-hydroxy-trans-2-methyl-cyclohexyl)-pyrrolidin-2-one Dissolve 3-(2,4-dichloro-benzyl)-1-(2-methyl-4-oxo-cyclohexyl)-pyrrolidin-2-one (0.063 g, 0.18 mmol) in MeOH (10 mL) and cool the solution to 0° C. under $N_2$. Add $Et_4NBH_4$ (0.026 g, 0.18 mmol) under $N_2$. Stir the reaction mixture for four hours and warm the reaction to room temperature. Add water (10 mL), and extract the aqueous layer with dichloromethane (3×50 mL). Combine the organic layers and dry with $Na_2SO_4$, filter, concentrate and purify by flash column chromatography (silica gel, 50-80% of EtOAc/Hexane) to give the compound as a white solid (0.044 g, 69%): MS (APCI-pos mode) m/z (rel intensity) 356.1 (100), 358.1 (60).

Step 2: 3-(2,4-Dichloro-benzyl)-1-(cis-4-hydroxy-cis-3-methyl-cyclohexyl)-pyrrolidin-2-one Also isolated in step 1 above from 3-(2,4-dichloro-benzyl)-4-oxo-4-(2-oxo-oxazolidin-3-yl)-butyraldehyde (0.54 g, 1.64 mmol) and cis-4-amino-cis-2-methyl-cyclohexanol (Preparation 56) (0.25 g, 1.94 mmol) was 0.11 g (20%) of the title compound (as the minor product) as a white solid: MS (APCI-pos mode) m/z (rel intensity) 356.0 (100), 358.1 (40).

Example 245

3-(2,6-Dichloro-3-hydroxy-4-iodobenzyl)-1-cyclohexylpyrrolidin-2-one

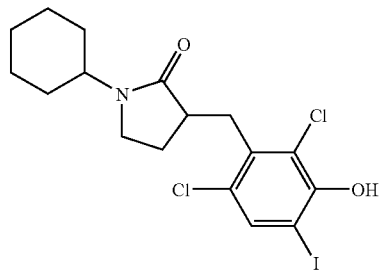

Slowly add a solution of 1-cyclohexyl-3-(2,6-dichloro-3-hydroxy-benzyl)-pyrrolidin-2-one (1.0 g, 2.9 mmol) in a minimal amount of ammonium hydroxide (with N,N-dimethylformamide added to aid in dissolution) to a stirred solution of iodine (74 mg, 2.9 mmol) in aqueous potassium iodide at 0° C. Stir over night warming to room temperature. Acidify with conc. HCl to pH less than 2, collect the precipitate, wash with water and ether, and dry under vacuum to yield the title compound 1.2 g (88%) Mass Spectrum (apci) 468 (M+H).

Example 246

1-Cyclohexyl-3-(2,4-dichloro-phenylsulfanyl)-4,4-dimethyl-pyrrolidin-2-one

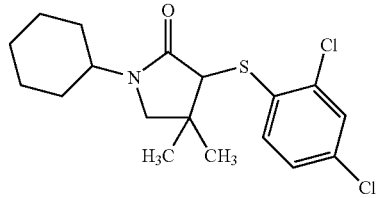

Place toluene-4-sulfonic acid 1-cyclohexyl-4,4-dimethyl-2-oxo-pyrrolidin-3-yl ester (0.102 g, 0.28 mmol), 2,4-dichloro-benzenethiol (0.073 ml, 0.56 mmol) and DBU (0.130 ml, 0.84 mmol) in DMF (3 mL). Stir for 5 hours at 50° C. Quench with water and extract with ethyl acetate. Wash the extract brine and dry over magnesium sulfate, filter, and concentrate. Flash chromatography affords 0.030 g (29%) of the title compound: Mass spectrum (apci) m/z=372 (M+H).

Example 247

3',5'-Dichloro-4'-(1-cyclohexyl-2-oxo-pyrrolidin-3-ylmethyl)-biphenyl-4-carboxylic acid

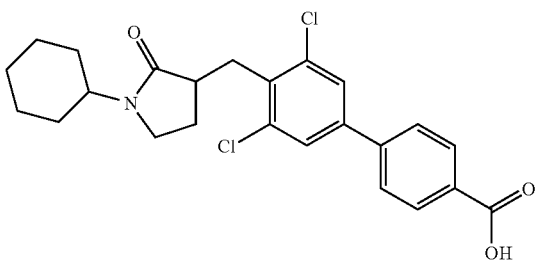

Combine trifluoro-methanesulfonic acid 3,5-dichloro-4-(1-cyclohexyl-2-oxo-pyrrolidin-3-ylmethyl)-phenyl ester (5.0 g, 10.54 mmol) and 4-methoxycarbonyl-phenylboronic acid (2.85 g, 15.81 mmol) in toluene (50 mL) and sodium carbonate (25 mL). After degassing with nitrogen, add Pd(PPh$_3$)$_4$ and heat to reflux for 17 h. Cool to room temperature, dilute with ethyl acetate, wash with water, dry over sodium sulfate, filter and concentrate to a foam. Chromatography (silica, 25% EtOAc/hexanes) yields 4.2 g (87%) of a solid. Dissolve the solid in EtOH, treat with KOH (5.0 eq) and heat to 50° C. for 4 h. Filter through celite, dilute the filtrate with water and acidify to pH 2. Collect the resulting solid, rinse with water and dry to yield 96% of a light-tan solid: Mass spectrum (API-ES positive) m/z=448 (M +H).

Example 248

5-[3,5-Dichloro-4-(1-cyclohexyl-2-oxo-pyrrolidin-3-ylmethyl)-phenyl]-thiophene-2-carboxylic acid methyl ester

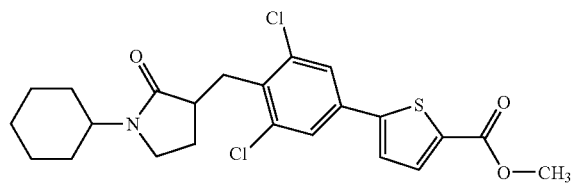

To a solution of 5-bromo-thiophene-2-carboxylic acid methyl ester (Preparation 86) (552.5 mg, 2.5 mmol) in 5 mL of THF, add n-butyl lithium (1.6 M, 1.56 mL, 2.5 mmol) at −78° C. and stir at that temperature for 30 min. Add anhydrous zinc chloride (455 mg, 4.0 mmol) and keep in −78° C. for 30 min, and then warm up to room temp. After stirring at room temp for 30 min, add 3,5-dichloro-4-((1-cyclohexyl-2-oxopyrrolidin-3-yl)methyl)phenyl trifluoromethanesulfonate (593 mg, 1.25 mmol). Add 1,1'-bis(diphenylphosphino) ferrocene)dichloroplladium and complex with dichloromethane (102 mg, 0.125 mmol) with 1.0 mL of THF. After heating to reflux for 5 hours. cool the reaction to room temp. Dilute with ethyl acetate, wash with water, separate the organic layer, and dry over anhydrous sodium sulfate. Purify the crude material by flash chromatography on silica gel using hexane:ethyl acetate (10:1.5) as eluent to give 94 mg of the title compound LC/MS (API) m/z: 466.0 (M+1).

Example 249

5-[3,5-Dichloro-4-(1-cyclohexyl-2-oxo-pyrrolidin-3-ylmethyl)-phenyl]-thiophene-2-carboxylic acid

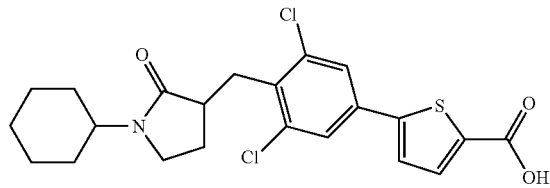

Add 1.0 mL of LiOH (2.0 N aq.) to a solution of 5-[3,5-Dichloro-4-(1-cyclohexyl-2-oxo-pyrrolidin-3-ylmethyl)-phenyl]-thiophene-2-carboxylic acid methyl ester (85 mg, 0.182 mmol) in 3.0 mL of dioxane and heat to 50° C. After 3 hours, a TLC shows the reaction to be complete. Dilute the reaction with DCM /H$_2$O (50/50), acidify with 1.0N HCl, extract with ethyl acetate, and dry the combined organic layers with sodium sulfate. Filter off the sodium sulfate and concentrate to give the title compound. LC/MS (API) m/z: 452.0 (M+1).

Examiple 250

N-(3,5-dichloro-4-((1-cyclohexyl-2-oxopyrrolidin-3-yl)methyl)phenyl)methanesulfonamide

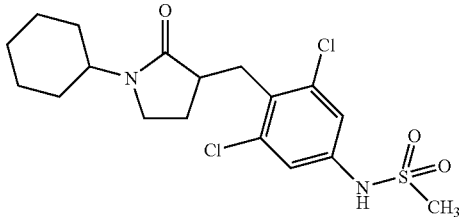

Charge a flask with 3-(4-amino-2,6-dichlorobenzyl)-1-cyclohexylpyrrolidin-2-one (250 mg, 0.73 mmol) and dissolve in methylene chloride (3 mL). Add triethylamine (0.16 ml) followed by sulfonyl chloride (0.11 ml, 1.5 mmol) and stir at room temperature for 1 hour. Pour into saturated aqueous bicarbonate and extract with methylene chloride. Dry over soium sulfate, filter and concentrate in vacuo. Purify residue over silica gel (30% ethyl acetate in hexanes) to afford 184 mg (60%) of the title compound. Mass spectrum (apci) m/z=419.1 (M+H).

Example 251

N-(3,5-dichloro-4-((1-cyclohexyl-2-oxopyrrolidin-3-yl)methyl)phenyl)benzenesulfonamide

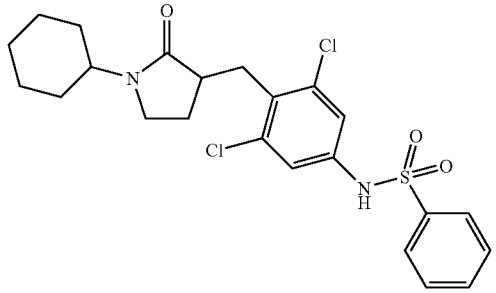

Using the procedure to synthesize Example 250 and using reagents 3-(4-amino-2,6-dichlorobenzyl)-1-cyclohexylpyrrolidin-2-one (250 mg, 0.73 mmol) and benzene sulfonyl chloride (0.19 mL, 1.5 mmol) affords 229 mg (65%) of the title compound. Mass spectrum (apci) m/z=481.1 (M+H).

Example 252

1-Cyclohexyl-3-[2,6-dichloro-4-(1-methyl-1H-pyrazol-4-yl)-benzyl]-pyrrolidin-2-one

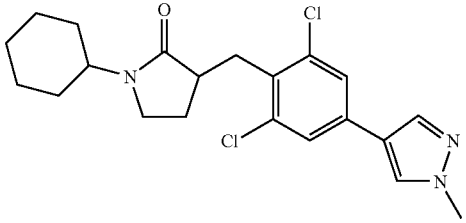

Using the method of Example 81 and using 3,5-dichloro-4-((1-cyclohexyl-2-oxopyrrolidin-3-yl)methyl)phenyl trifluoromethanesulfonate (Example 240) (1.673 g, 3.53 mmol), 1-methyl-4-(4,4,5,5-tetramethyl-1,3,2-dioxaborolan-2-yl)-1H-pyrazole (2.2 g, 10.6 mmol), tetrakis(triphenylphosphine)palladium (0.408 g, 0.353 mmol), dimethoxyethane (16 mL) and sodium carbonate (2M, 6.2 mL) gives the title compound. Purify the crude material over silica gel (1/1 hexane in ethyl acetate to 1/3 hexane in ethyl acetate) to yield 0.873 g (61%) of the title compound: mass spectrum (m/z): 408(M+2).

Example 253

1-Cyclohexyl-3-[2,6-dichloro-4-(1-isobutyl-1H-pyrazol-4-yl)-benzyl]-pyrrolidin-2-one

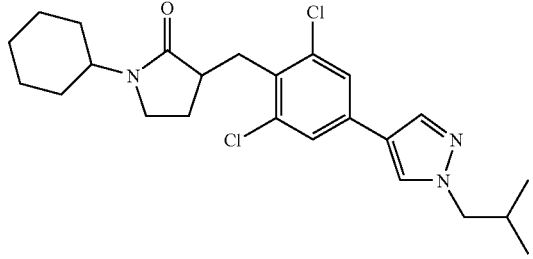

Using the method of Example 81 and using 3,5-dichloro-4-((1-cyclohexyl-2-oxopyrrolidin-3-yl)methyl)phenyl trifluoromethanesulfonate (Example 240) (1.459 g, 3.07 mmol), 1-isobutyl-4-(4,4,5,5-tetramethyl-1,3,2-dioxaborolan-2-yl)-1H-pyrazole (2.3 g, 9.23 mmol) tetrakis(triphenylphosphine) palladium (0.355 g, 0.307 mmol), dimethoxyethane (15 mL) and sodium carbonate (2M, 5.4 mL) gives the title compound. Purify the crude material over silica gel (1/1 hexane in ethyl acetate) to yield 1.047 g (76%) of the title compound: mass spectrum (m/z): 450(M+2).

Example 254

1-Cyclohexyl-3-[2,6-dichloro-4-(1H-pyrazol-4-yl)-benzyl]-pyrrolidin-2-one

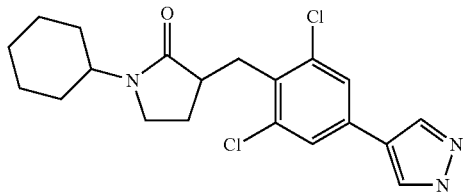

Using the method of Example 81 and using 3,5-dichloro-4-((1-cyclohexyl-2-oxopyrrolidin-3-yl)methyl)phenyl trifluoromethanesulfonate (Example 240) (1.238 g, 2.61 mmol), 1-boc-4-(4,4,5,5-tetramethyl-1,3,2-dioxaborolan-2-yl)pyrazole (2.3 g, 7.83 mmol) tetrakis(triphenylphosphine)palladium (0.302 g, 0.261 mmol), dimethoxyethane (15 mL) and sodium carbonate (2M, 4.6 mL) gives the title compound. Purify the crude material over silica gel (1/1 hexane in ethyl acetate to 1/3 hexane in ethyl acetate) to yield 0.545 g (53%) of the title compound: mass spectrum (m/z): 394(M+2).

Example 255

1-Cyclohexyl-3-(2,6-dichloro-4-thiophen-3-yl-benzyl)-pyrrolidin-2-one

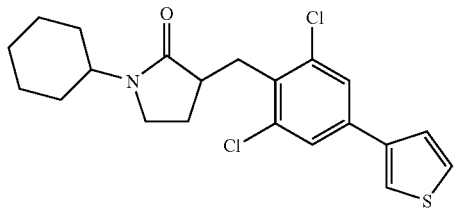

Using the method of Example 81 and using 3,5-dichloro-4-((1-cyclohexyl-2-oxopyrrolidin-3-yl)methyl)phenyl trifluoromethanesulfonate (Example 240) (1.485 g, 3.31 mmol), thiophene-3-boronic acid (1.2 g, 9.39 mmol) tetrakis(triphenylphosphine)palladium (0.362 g, 0.3.13 mmol), dimethoxyethane (15 mL) and sodium carbonate (2M, 5.5 mL) gives the title compound. Purify the crude material over silica gel (4/1 hexane in ethyl acetate) to yield 1.109 g (87%) of the title compound: mass spectrum (m/z): 410(M+2).

Example 256

3',5'-Dichloro-4'-(1-cyclohexyl-2-oxo-pyrrolidin-3-ylmethyl)-4-fluoro-biphenyl-3-carbonitrile

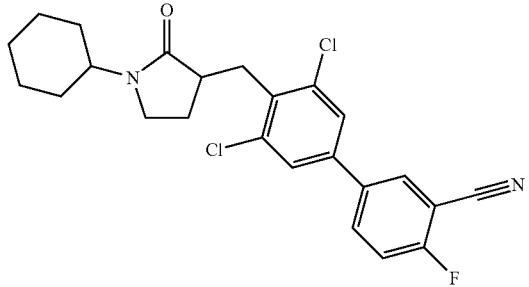

To a solution of 3,5-dichloro-4-((1-cyclohexyl-2-oxopyrrolidin-3-yl)methyl)phenyl trifluoromethanesulfonate (Example 240) (1.34 g, 2.83 mmol) in THF (30 mL) in a round bottom flask was added 3-cyano-4-fluorophenylboronic acid (560 mg, 3.39 mmol), sodium carbonate (900 mg, 8.48 mmol) and water (10 mL). The mixture was stirred at 60° C. for 5 minutes, palladium tetrakis (163 mg, 0.14 mmol) was added. Reaction mixture was brought to 80° C. and stirred for 3 hours. Cooled and partitioned between ethyl acetate and HCL(1 N). Organic was separated, wash with water, brine; dry over sodium sulfate, filter, and concentrate. Purify by silica gel (25-50% ethyl acetate in hexane) to afford 1.10 g (88%) of the title compound: Mass spectrum (LCMS) m/z=445.0 (M+H).

Pharmacological Methods

In the following section binding assays as well as functional assays useful for evaluating the efficiency of the compounds of the invention are described.

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 µL/well capacity) in the following fashion: 9 µL/well of substrate (2.22 mM NADP, 55.5 µM Cortisol, 10 mM Tris, 0.25% Prionex, 0.1% Triton X100), 3 µL/well of water to compound wells or 3 µL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male $C_{57}BL/6$ mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 µl per animal, followed by a subcutaneous dose, 200 µl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Coming Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d4-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer. All of the examples disclosed herein demonstrate activity in the 11β-HSD type 1 enzyme assay with $IC_{50}$ of less than 20 um. Examples 91, 135, 119, 15, and 99 were active in the Acute In Vivo Cortisone Conversion Assay. Some examples were inactive in in the Acute In Vivo Cortisone Conversion Assay including 65, and 69.

The assay results are given below for the indicated compound in the 11β-HSD type 1 enzyme assay.

| Example | 11β-HSD type 1 enzyme assay $IC_{50}$ (nM) |
|---|---|
| 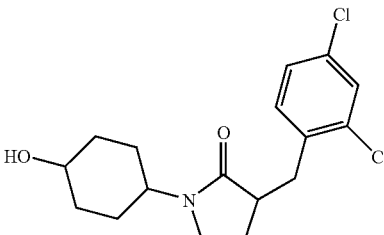 | 230 |
| 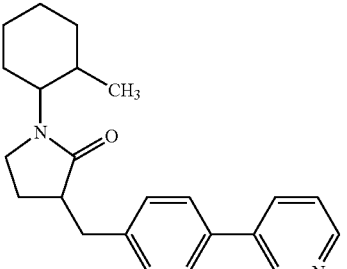 | 384 |
| 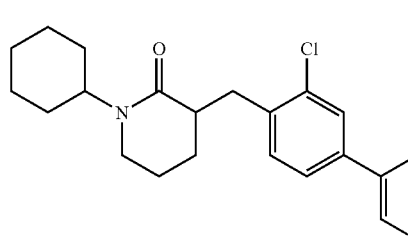 | 565 |

-continued

| Example | 11β-HSD type 1 enzyme assay $IC_{50}$ (nM) |
|---|---|
| 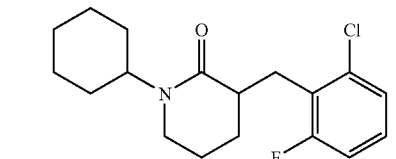 | 378 |
| 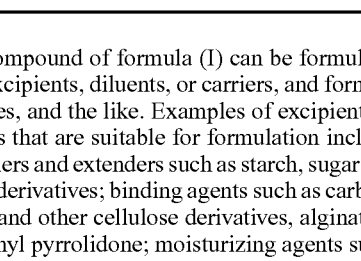 | 273 |
| 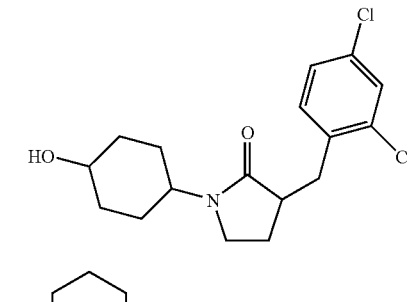 | 494 |
| 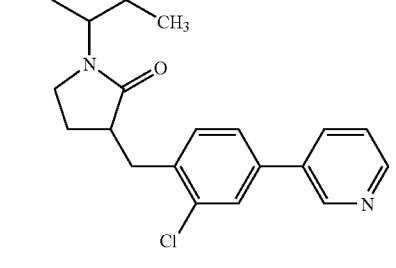 | 879 |

A compound of formula (I) can be formulated with common excipients, diluents, or carriers, and formed into tablets, capsules, and the like. Examples of excipients, diluents, and carriers that are suitable for formulation include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, a compound of formula (I) or a pharmaceutically acceptable salt thereof, is suited to formulation as sustained release dosage forms. The formulations can also be so constituted that they release the active ingredient only or preferably in a particular part of the intestinal tract, possibly over a period of time. Such formulations would involve coatings, envelopes, or protective matrices that may be made from polymeric substances or waxes.

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from (1) to (20) above.

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, occular, topical, sublingual, buccal, or other routes. Oral administration may be preferred for treatment of the disorders described herein. However, oral administration is the preferred route. Other routes include the intravenous route as a matter of convenience or to avoid potential complications related to oral administration.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

For the purpose of oral therapeutic administration, the compounds may be incorporated with excipients and used in the form of tablets, troches, capsules, elixirs, suspensions, syrups, wafers, chewing gums and the like. These preparations should contain at least 4% of the active ingredients, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, hydrogenated vegetable oil, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used. In those instances where oral administration is impossible or not preferred, the composition may be made available in a form suitable for parenteral administration, e.g., intravenous, intraperitoneal or intramuscular.

We claim:

1. A compound structurally represented by formula (I):

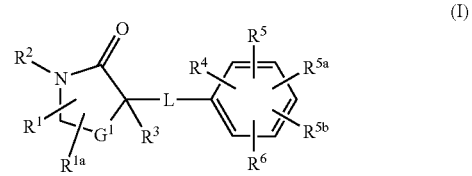

or a pharmaceutically acceptable salt thereof, wherein
$G^1$ is methylene;
L is methylene;
$R^1$ is hydrogen,
$R^{1a}$ is hydrogen;
$R^2$ is

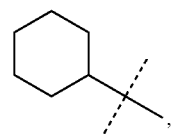

wherein the dashed line represents the point of attachment to the $R^2$ position in formula I;
$R^3$ is hydrogen,
$R^4$ and $R^5$ are each independently hydrogen, hydroxy, —C(O)OH, —(C$_1$-C$_4$)alkyl (optionally substituted with one to three halogens), —(C$_1$-C$_6$)alkoxy (optionally substituted with one to three halogens), halogen, cyano, —OCF$_3$, —(C$_1$-C$_4$) alkyl-C(O)OH, —(C$_1$-C$_4$)alkyl-C(O)O(C$_1$-C$_4$)alkyl, or —(C$_1$-C$_4$)alkyl-OH;

R$^{5a}$ and R$^{5b}$ are independently hydrogen or halogen;

R$^6$ is hydrogen, hydroxy, —(C$_1$-C$_4$)alkyl (optionally substituted with one to three halogens), —(C$_1$-C$_6$)alkoxy (optionally substituted with one to three halogens), —O—(C$_2$-C$_6$)alkynyl, halogen, cyano, —NH$_2$, —SCF$_3$, —C(O)O(C$_1$-C$_4$)alkyl, —(C$_3$-C$_8$)cycloalkyl, —O—SO$_2$—(C$_1$-C$_4$)alkyl, —O—SO$_2$—CF$_3$, —O-phenyl, —O—(C$_1$-C$_4$)alkyl-phenyl, —O-phenyl-C(O)O—(C$_1$-C$_4$)alkyl, —O—(C$_1$-C$_4$)alkyl-phenyl-C(O)O—(C$_1$-C$_4$)alkyl, —NH-phenyl, —CH$_2$-phenyl, —O-(C$_1$-C$_4$)alkyl-pyridinyl, Ar$^1$, Het$^1$, Ar$^2$, Het$^2$, —C(O)(C$_1$-C$_4$)alkyl, —C(O)—Ar$^2$, —C(O)-Het$^2$, —NHSO$_2$—(C$_1$-C$_4$)alkyl, —NHSO$_2$-phenyl(R$^{19}$)(R$^{19}$), —(C$_1$-C$_4$)alkyl-C(O)N(R$^{11}$)(R$^{12}$), or —(C$_1$-C$_4$)alkyl-N(R$^{13}$)(R$^{14}$);

wherein R$^{11}$ and R$^{12}$ are each independently hydrogen or —(C$_1$-C$_4$)alkyl, or R$^{11}$ and R$^{12}$ taken together with the nitrogen to which they are attached form piperidinyl, piperazinyl, or pyrrolidinyl (wherein optionally the piperidinyl, piperazinyl, or pyrrolidinyl ring is substituted once with —(C$_1$-C$_4$)alkyl); wherein R$^{13}$ and R$^{14}$ are each independently hydrogen or —(C$_1$-C$_4$)alkyl (optionally substituted with one to three halogens), or R$^{13}$ and R$^{14}$ taken together with the nitrogen to which they are attached form piperidinyl, pyrrolidinyl, or piperazinyl; provided that when L is —O— or —S—, then R$^6$ is not hydrogen;

Ar$^1$ is phenyl or naphthyl;

Ar$^2$ is Ar$^1$ optionally and independently substituted one to three times with halogen, hydroxy, —C(O)OH, —(C$_1$-C$_6$)alkoxy, cyano, —CF$_3$, —(C$_1$-C$_4$)alkyl, —(C$_1$-C$_4$)alkyl-C(O)OH, —O(C$_1$-C$_4$)alkyl-C(O)OH, —(C$_1$-C$_4$)alkyl-N(R$^{15}$)(R$^{16}$), —O—(C$_1$-C$_4$)alkyl-N(R$^{15}$)(R$^{16}$), —O—(C$_1$-C$_4$)alkyl-C(O)O—(C$_1$-C$_4$)alkyl, —O—(C$_1$-C$_4$)alkyl-piperidinyl, imidazolyl, pyridinyl, or —(C$_1$-C$_4$)alkyl-imidazolyl;

wherein R$^{15}$ and R$^{16}$ are each independently hydrogen or —(C$_1$-C$_4$)alkyl, or R$^{15}$ and R$^{16}$ taken together with the nitrogen to which they are attached form piperidinyl, pyrrolidinyl, morpholinyl, or imidazolyl;

Het$^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl, indolyl, isoindolyl, indolinyl, benzofuranyl, benzothiophenyl, quinolinyl, isoquinolinyl, quinoxalinyl, quinazolinyl, or phthalazinyl;

Het$^2$ is Het$^1$ optionally and independently substituted one to three times with halogen, hydroxy, —(C$_1$-C$_6$)alkoxy (optionally substituted with one to three halogens), —C(O)OH, —NH$_2$, cyano, —CF$_3$, —(C$_1$-C$_4$)alkyl (optionally substituted with one to three halogens), —(C$_1$-C$_4$)alkyl-C(O)OH, —O(C$_1$-C$_4$)alkyl-C(O)OH, —C(O)O—(C$_1$-C$_4$)alkyl, —(C$_1$-C$_4$)alkyl-N(R$^{17}$)(R$^{18}$), —O(C$_1$-C$_4$)alkyl-N(R$^{17}$)(R$^{18}$), imidazolyl, pyridinyl, or —(C$_1$-C$_4$)alkyl-imidazolyl; wherein R$^{17}$ and R$^{18}$ are each independently hydrogen or —(C$_1$-C$_4$)alkyl (optionally substituted with one to three halogens), or R$^{17}$ and R$^{18}$ taken together with the nitrogen to which they are attached form piperidinyl or pyrrolidinyl;

R$^{19}$ is hydrogen, halogen, or —(C$_1$-C$_4$)alkyl (optionally substituted with one to three halogens).

2. A compound of claim 1 or a pharmaceutically acceptable salt thereof wherein R$^2$ is

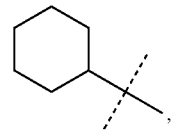

wherein the dashed line represents the point of attachment to the R$^2$ position in formula I.

3. A compound of claim 2 or a pharmaceutically acceptable salt thereof wherein R$^6$ is hydroxy, —(C$_1$-C$_4$)alkyl, —(C$_1$-C$_6$)alkoxy, —O—(C$_2$-C$_6$)alkynyl, halogen, cyano, —NH$_2$, —CF$_3$, —SCF$_3$, —C(O)O(C$_1$-C$_4$)alkyl, —(C$_3$-C$_8$)cycloalkyl, —O—SO$_2$—(C$_1$-C$_4$)alkyl, —O—SO$_2$—CF$_3$, —O-phenyl, —O—(C$_1$-C$_4$)alkyl-phenyl, —O-phenyl-C(O)O—(C$_1$-C$_4$)alkyl, —O—(C$_1$-C$_4$)alkyl-phenyl-C(O)O—(C$_1$-C$_4$)alkyl, —NH-phenyl, —CH$_2$-phenyl, —O—(C$_1$-C$_4$)alkyl-pyridinyl, Ar$^1$, Ar$^2$, Het$^1$, Het$^2$, —C(O)(C$_1$-C$_4$)alkyl, —C(O)—Ar$^2$, —C(O)-Het$^2$, —NHSO$_2$—(C$_1$-C$_4$)alkyl, —NHSO$_2$-phenyl(R$^{19}$)(R$^{19}$), —(C$_1$-C$_4$)alkyl-C(O)N(R$^{11}$)(R$^{12}$), or —(C$_1$-C$_4$)alkyl-N(R$^{13}$)(R$^{14}$);

wherein R$^{11}$ and R$^{12}$ are each independently hydrogen or C$_1$-C$_4$ alkyl, or R$^{11}$ and R$^{12}$ taken together with the nitrogen to which they are attached form piperidinyl, piperazinyl, or pyrrolidinyl (wherein optionally the piperidinyl, piperazinyl, or pyrrolidinyl ring is substituted once with —(C$_1$-C$_4$)alkyl); wherein R$^{13}$ and R$^{14}$ are each independently hydrogen or —(C$_1$-C$_4$)alkyl, or R$^{13}$ and R$^{14}$ taken together with the nitrogen to which they are attached form piperidinyl, pyrrolidinyl, or piperazinyl;

Ar$^1$ is phenyl;

Ar$^2$ is Ar$^1$ optionally and independently substituted one or times with halogen, hydroxy, —C(O)OH, —(C$_1$-C$_6$)alkoxy, cyano, —CF$_3$, —(C$_1$-C$_4$)alkyl, —(C$_1$-C$_4$)alkyl-C(O)OH, —O(C$_1$-C$_4$)alkyl-C(O)OH, —(C$_1$-C$_4$)alkyl-N(R$^{15}$)(R$^{16}$), —O—(C$_1$-C$_4$)alkyl-N(R$^{15}$)(R$^{16}$), —O—(C$_1$-C$_4$)alkyl-C(O)O—(C$_1$-C$_4$)alkyl, —O—(C$_1$-C$_4$)alkyl-piperidinyl, imidazolyl, pyridinyl, or —(C$_1$-C$_4$)alkyl-imidazolyl; wherein R$^{15}$ and R$^{16}$ are each independently hydrogen or —(C$_1$-C$_4$)alkyl, or R$^{15}$ and R$^{16}$ taken together with the nitrogen to which they are attached form piperidinyl, pyrrolidinyl, morpholinyl, or imidazolyl;

Het$^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

Het$^2$ is Het$^1$ optionally and independently substituted once with halogen, hydroxy, —(C$_1$-C$_6$)alkoxy, —C(O)OH, —NH$_2$, cyano, —CF$_3$, —(C$_1$-C$_4$)alkyl, —(C$_1$-C$_4$)alkyl- C(O)OH, —O($C_1$-$C_4$ alkyl)C(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$)($R^{18}$);

wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl.

4. A compound of claim 1 structurally represented by formula (Ia),

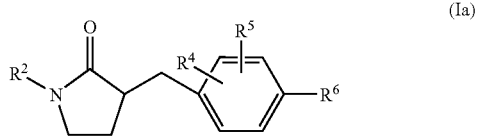

(Ia)

or a pharmaceutically acceptable salt thereof, wherein $R^2$ is

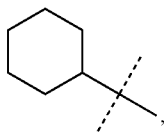

wherein the dashed line represents the point of attachment to the $R^2$ positon in formula I;

$R^4$ and $R^5$ are each independently hydrogen, halogen, or hydroxy;

$R^{5a}$ and $R^{5b}$ are hydrogen, $R^6$ is hydroxy, —($C_1$-$C_4$)alkyl (optionally substituted with one to three halogens), —($C_1$-$C_6$)alkoxy (optionally substituted with one to three halogens), —O—($C_2$-$C_6$)alkynyl, halogen, cyano, —$NH_2$, —$CF_3$, —$SCF_3$, —C(O)O($C_1$-$C_4$)alkyl, —($C_3$-$C_8$)cycloalkyl, —O—$SO_2$—($C_1$-$C_4$)alkyl, —O—$SO_2$—$CF_3$, —O-phenyl, —O—($C_1$-$C_4$)alkyl-phenyl, —O-phenyl-C(O)O—($C_1$-$C_4$)alkyl, —O—($C_1$-$C_4$)alkyl-phenyl-C(O)O—($C_1$-$C_4$)alkyl, —NH-phenyl, —$CH_2$-phenyl, —O—($C_1$-$C_4$)alkyl-pyridinyl, $Ar^1$, $Het^1$, $Ar^2$, $Het^2$, —C(O)($C_1$-$C_4$)alkyl, —C(O)—$Ar^2$, —C(O)-$Het^2$, —$NHSO_2$—($C_1$-$C_4$)alkyl, —$NHSO_2$-phenyl ($R^{19}$)($R^{19}$), —($C_1$-$C_4$)alkyl-C(O)N($R^{11}$)($R^{12}$), or —($C_1$-$C_4$)alkyl-N($R^{13}$)($R^{14}$);

wherein $R^{11}$ and $R^{12}$ are each independently hydrogen or $C_1$-$C_4$ alkyl, or $R^{11}$ and $R^{12}$ taken together with the nitrogen to which they are attached form piperidinyl, piperazinyl, or pyrrolidinyl (wherein optionally the piperidinyl, piperazinyl, or pyrrolidinyl ring is substituted once with —($C_1$-$C_4$)alkyl); and wherein $R^{13}$ and $R^{14}$ are each independently hydrogen or —($C_1$-$C_4$)alkyl (optionally substituted with one to three halogens,), or $R^{13}$ and $R^{14}$ taken together with the nitrogen to which they are attached form piperidinyl, pyrrolidinyl, or piperazinyl;

$Ar^1$ is phenyl;

$Ar^2$ is $Ar^1$ optionally and independently substituted one or two times with halogen, hydroxy, —C(O)OH, —($C_1$-$C_6$)alkoxy, cyano, —$CF_3$, —($C_1$-$C_4$)alkyl, —($C_1$-$C_4$)alkyl-C(O)OH, —O($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$), —O—($C_1$-$C_4$)alkyl-C(O)O—($C_1$-$C_4$)alkyl;

wherein $R^{15}$ and $R^{16}$ are each independently hydrogen or —($C_1$-$C_4$)alkyl, or $R^{15}$ and $R^{16}$ taken together with the nitrogen to which they are attached form piperidinyl, pyrrolidinyl, morpholinyl, or imidazolyl;

$Het^1$ is independently imidazolyl, oxadiazolyl, pyrazolyl, pyrrolyl, tetrazolyl, thiadiazolyl, triazolyl, pyrrolidinyl, morpholinyl, pyridinyl, piperidinyl, pyrimidinyl, pyrazinyl, piperazinyl, pyridazinyl, furanyl, thiophenyl, thiazolyl, oxazolyl, isoxazolyl, isothiazolyl;

$Het^2$ is $Het^1$ optionally and independently substituted one or two times with halogen, hydroxy, —($C_1$-$C_6$)alkoxy(optionally substituted with one to three halogens), —C(O)OH, —$NH_2$, cyano, —$CF_3$, —($C_1$-$C_4$)alkyl (optionally substituted with one to three halogens), —($C_1$-$C_4$)alkyl-C(O)OH, —O($C_1$-$C_4$)alkylC(O)OH, —C(O)O—($C_1$-$C_4$)alkyl, —($C_1$-$C_4$)alkyl-N($R^{17}$)($R^{18}$), —O($C_1$-$C_4$)alkyl-N($R^{17}$)($R^{18}$);

wherein $R^{17}$ and $R^{18}$ are each independently hydrogen or —($C_1$-$C_4$)alkyl (optionally substituted with one to three halogens), or $R^{17}$ and $R^{18}$ taken together with the nitrogen to which they are attached form piperidinyl or pyrrolidinyl;

$R^{19}$ is hydrogen, halogen, or —($C_1$-$C_4$)alkyl (optionally substituted with one to three halogens); and $R^{20}$ is hydroxy, —($C_1$-$C_4$)alkyl (optionally substituted with one to three halogens), or —$CH_2OH$.

5. A compound of claim 1 structurally represented by formula I, or a pharmaceutically acceptable salt thereof, wherein $G^1$ is methylene; L is —$CH_2$; $R^1$ is —H; $R^2$ is Cyclohexyl $R^3$ is —H; $R^4$ and $R^5$ are each independently hydrogen, —F, —Cl, —Br, —I, hydroxy, or —$CH_3$; $R^{5a}$ and $R^{5b}$ are hydrogen; $R^6$ is —H, —F, —Cl, —Br, —I, —$CH_3$, —$SCF_3$, —OH, —$OCF_3$, —$CF_3$, —$OCH_3$, —CN, —C(O)OH, —$CH_2CH_2CH_2$C(O)-(4-methyl-piperazin-1-yl), benzyl, tert-butyl, nicotinonitrile, nicotinic acid, —$OCH_2$CCH, —$NH_2$, cyclohexyl, —C(O)-phenyl, —C(O)$OCH_3$, —$NHSO_2$-phenyl (wherein the phenyl is optionally substituted by —$CH_3$, —Cl), —NH-phenyl, —$OCH_2$-phenyl, —$OCH_2$-pyridinyl, phenoxy (optionally optionally substituted with —C(O)$OCH_3$), isopropoxy, —$OSO_2CF_3$, —$NSO_2CH_3$, —$NSO_2$-phenyl, phenyl (optionally substituted by one or two moieties independently selected from —F, —COOH, —OH, —$CH_3$, —$OCH_3$, —$OCH_2CH_2$-piperidinyl, —$OCH_2CH_2N(CH_3)_2$, —$OCH_2CH_2CH_2N(CH_3)_2$, —$OCH_2CH_2CH_2$COOH, —$OCH_2$-piperidinyl, —$OCH_2CH_2$-imidazolyl, —$OCH_2CH_2CH_2$-piperidinyl, —$OCH_2CH_2$-morpholinyl, —$OC(CH_3)_2$$COOCH_2CH_3$, —$OC(CH_3)_2$COOH, —$OCH_2COOCH_2CH_3$, —$OCH_2$COOH, —$OCH_2CH_2$COOH, and —$CH_2CH_2$COOH), pyridinyl (optionally substituted once with Cl, CN, COOH, $NH_2$, Br, $CH_3$, $OCH_3$, or OH,), pyrazinyl, pyrimidinyl, 1,3-dihydro-benzoimidazol-2-one, pyrrolidinyl (optionally substituted once with with —OH), piperidinyl, piperazinyl (optionally substituted once with with —$CH_3$), morpholinyl, pyrazolyl (optionally substituted once —$CH_3$), thiophenyl, —$CH_2$-pyrrolidinyl, or thiophenyl (optionally substituted once with —C(O)$OCH_3$, or —C(O)OH); provided that when L is —O— or —S— then $R^6$ is not hydrogen.

6. A compound of claim 1 selected from the group consisting of

3-Benzyl-1-cyclohexyl-pyrrolidin-2-one;
3-[2-Chloro-4-(2-chloro-pyridin-3-yl)-benzyl]-1-cyclohexyl-pyrrolidin-2-one;
5-[3-Chloro-4-(1-cyclohexyl-2-oxo-pyrrolidin-3-ylmethyl)-phenyl]-pyridine-2-carbonitrile;
3-[3-Chloro-4-(1-cyclohexyl-2-oxo-pyrrolidin-3-ylmethyl)-phenyl]-pyridine-2-carbonitrile;
3-[2-Chloro-4-(6-chloro-pyridin-3-yl)-benzyl]-1-cyclohexyl-pyrrolidin-2-one;
5-[3-Chloro-4-(1-cyclohexyl-2-oxo-pyrrolidin-3-ylmethyl)-phenyl]-nicotinonitrile hydrochloride salt;
5-[3-Chloro-4-(1-cyclohexyl-2-oxo-pyrrolidin-3-ylmethyl)-phenyl]-nicotinonitrile;
3-(2-Chloro-4-pyrimidin-2-yl-benzyl)-1-cyclohexyl-pyrrolidin-2-one;
3-(2-Chloro-4-pyrazin-2-yl-benzyl)-1-cyclohexyl-pyrrolidin-2-one;
5-[3-Chloro-4-(1-cyclohexyl-2-oxo-pyrrolidin-3-ylmethyl)-phenyl]-nicotinic acid;
3-(3-bromo-6-chloro-2-fluoro-benzyl)-1-cyclohexyl-pyrrolidin-2-one;
3-{6-Chloro-2-fluoro-3-[4-(4-methyl-piperazin-1-yl)-4-oxo-butyl]-benzyl}-1-cyclohexyl-pyrrolidin-2-one;
3-(2-Chloro-6-fluoro-benzyl)-1-cyclohexyl-pyrrolidin-2-one;
1-Cyclohexyl-3-(2-fluoro-benzyl)-pyrrolidin-2-one;
1-Cyclohexyl-3-(2-chloro-benzyl)-pyrrolidin-2-one;
1-Cyclohexyl-3-(2-trifluoromethyl-benzyl)-pyrrolidin-2-one;
1-Cyclohexyl-3-(2,6-dichloro-benzyl)-pyrrolidin-2-one;
1-Cyclohexyl-3-(2-methoxy-benzyl)-pyrrolidin-2-one;
3-Biphenyl-2-ylmethyl-1-cyclohexyl-pyrrolidin-2-one;
2-(1-Cyclohexyl-2-oxo-pyrrolidin-3-ylmethyl)-benzonitrile;
3-(4-tert-Butyl-benzyl)-1-cyclohexyl-pyrrolidin-2-one;
1-Cyclohexyl-3-(2-methyl-benzyl)-pyrrolidin-2-one;
1-Cyclohexyl-3-(2-hydroxy-benzyl)-pyrrolidin-2-one;
1-Cyclohexyl-3-(4-methoxy-benzyl)-pyrrolidin-2-one;
1-Cyclohexyl-3-(2,6-difluoro-benzyl)-pyrrolidin-2-one;
3-Biphenyl-4-ylmethyl-1-cyclohexyl-pyrrolidin-2-one;
1-Cyclohexyl-3-(4-trifluoromethyl-benzyl)-pyrrolidin-2-one;
1-Cyclohexyl-3-(3-trifluoromethyl-benzyl)-pyrrolidin-2-one;
1-Cyclohexyl-3-(3-methyl-benzyl)-pyrrolidin-2-one;
1-Cyclohexyl-3-(4-methyl-benzyl)-pyrrolidin-2-one;
1-Cyclohexyl-3-(3-chloro-benzyl)-pyrrolidin-2-one;
3-(3-Bromo-2,6-dichloro-benzyl)-1-cyclohexyl-pyrrolidin-2-one;
1-Cyclohexyl-3-(2-trifluoromethoxy-benzyl)-pyrrolidin-2-one;
3-(2-Bromo-benzyl)-1-cyclohexyl-pyrrolidin-2-one;
1-Cyclohexyl-3-(2,4-dichloro-benzyl)-pyrrolidin-2-one;
3-(4-Bromo-2-chloro-benzyl)-1-cyclohexyl-pyrrolidin-2-one;
3-(2-Bromo-6-chloro-benzyl)-1-cyclohexyl-pyrrolidin-2-one;
1-Cyclohexyl-3-[(2,4-dichloro-phenyl)-hydroxy-methyl]-pyrrolidin-2-one;
1-Cyclohexyl-3-[(2,4-dichloro-phenyl)-hydroxy-methyl]-pyrrolidin-2-one, Isomer 1;
1-Cyclohexyl-3-[(2,4-dichloro-phenyl)-hydroxy-methyl]-pyrrolidin-2-one, Isomer 2;
3-(3-Chloro-biphenyl-2-ylmethyl)-1-cyclohexyl-pyrrolidin-2-one;
3-(2-Chloro-6-pyridin-3-yl-benzyl)-1-cyclohexyl-pyrrolidin-2-one;
3-(2-Chloro-4-pyridin-4-yl-benzyl)-1-cyclohexyl-pyrrolidin-2-one;
3-(2-Chloro-4-pyridin-3-yl-benzyl)-1-cyclohexyl-pyrrolidin-2-one;
3-(3-Chloro-biphenyl-4-ylmethyl)-1-cyclohexyl-pyrrolidin-2-one;
3-(3-Chloro-4'-hydroxy-biphenyl-4-ylmethyl)-1-cyclohexyl-pyrrolidin-2-one;
3-(3-Chloro-4'-methoxy-2'-methyl-biphenyl-4-ylmethyl)-1-cyclohexyl-pyrrolidin-2-one;
3'-Chloro-4'-(1-cyclohexyl-2-oxo-pyrrolidin-3-ylmethyl)-biphenyl-2-carboxylic acid;
3'-Chloro-4'-(1-cyclohexyl-2-oxo-pyrrolidin-3-ylmethyl)-biphenyl-3-carboxylic acid;
3'-Chloro-4'-(1-cyclohexyl-2-oxo-pyrrolidin-3-ylmethyl)-biphenyl-4-carboxylic acid;
3-(2-Benzyl-6-chloro-benzyl)-1-cyclohexyl-pyrrolidin-2-one;
3-(4-Benzyl-2-chloro-benzyl)-1-cyclohexyl-pyrrolidin-2-one;
3-(2-Chloro-6-hydroxy-benzyl)-1-cyclohexyl-pyrrolidin-2-one;
3-[3-Chloro-4'-(4-methyl-piperazine-1-carbonyl)-biphenyl-4-ylmethyl]-1-cyclohexyl-pyrrolidin-2-one;
3-[3-Chloro-4'-(2-piperidin-1-yl-ethoxy)-biphenyl-4-ylmethyl]-1-cyclohexyl-pyrrolidin-2-one;
3-[3-Chloro-4'-(2-piperidin-1-yl-ethoxy)-biphenyl-4-ylmethyl]-1-cyclohexyl-pyrrolidin-2-one;
3-[3-Chloro-4'-(2-dimethylamino-ethoxy)-biphenyl-4-ylmethyl]-1-cyclohexyl-pyrrolidin-2-one;
3-[3-Chloro-4'-(2-dimethylamino-ethoxy)-biphenyl-4-ylmethyl]-1-cyclohexyl-pyrrolidin-2-one;
3-[3-Chloro-4'-(3-dimethylamino-propoxy)-biphenyl-4-ylmethyl]-1-cyclohexyl-pyrrolidin-2-one;
3-[3-Chloro-4'-(3-dimethylamino-propoxy)-biphenyl-4-ylmethyl]-1-cyclohexyl-pyrrolidin-2-one;
4-[3'-Chloro-4'-(1-cyclohexyl-2-oxo-pyrrolidin-3-ylmethyl)-biphenyl-4-yloxy]-butyric acid;
3-(R)-(2-Chloro-6-fluoro-benzyl)-1-cyclohexyl-pyrrolidin-2-one;
3-(2-Chloro-4-pyrimidin-5-yl-benzyl)-1-cyclohexyl-pyrrolidin-2-one;
(S)-3-(2-Chloro-6-fluoro-benzyl)-1-cyclohexyl-pyrrolidin-2-one;
3-(2-Chloro-6-fluoro-benzyl)-1-cyclohexyl-pyrrolidin-2-one;
1-Cyclohexyl-3-(3-methoxy-benzyl)-pyrrolidin-2-one;
1-Cyclohexyl-3-(3-hydroxy-benzyl)-pyrrolidin-2-one;
3-(4-Chloro-benzyl)-1-cyclohexyl-pyrrolidin-2-one;
1-Cyclohexyl-3-(2,6-dichloro-3-methoxy-benzyl)-pyrrolidin-2-one;
1-Cyclohexyl-3-(2,6-dichloro-3-hydroxy-benzyl)-pyrrolidin-2-one;
5-[3-Chloro-4-(1-cyclohexyl-2-oxo-pyrrolidin-3-ylmethyl)-phenyl]-pyridine-2-carboxylic acid;
3-(4-(3-Bromo-4-methylpyridin-2-yl)-2-chlorobenzyl)-1-cyclohexylpyrrolidin-2-one;
3-(2-Chloro-4-(2-methoxypyridin-3-yl)benzyl)-1-cyclohexylpyrrolidin-2-one;
3-(2-Chloro-4-(6-methoxy-4-methylpyridin-3-yl)benzyl)-1-cyclohexylpyrrolidin-2-one;
3-(2-Chloro-4-(2,6-dimethylpyridin-3-yl)benzyl)-1-cyclohexylpyrrolidin-2-one;
3-(2-Chloro-4-(4-methylpyridin-3-yl)benzyl)-1-cyclohexylpyrrolidin-2-one;

3-(2-Chloro-4-(2-hydroxypyridin-3-yl)benzyl)-1-cyclohexylpyrrolidin-2-one;
3-(2-Chloro-4-(6-methylpyridin-3-yl)benzyl)-1-cyclohexylpyrrolidin-2-one;
3-(2,6-Dichloro-3-(pyridin-3-yl)benzyl)-1-cyclohexylpyrrolidin-2-one;
3-(2-Chloro-4-(2-chloropyridin-4-yl)benzyl)-1-cyclohexylpyrrolidin-2-one;
3-(2-Chloro-4-(6-(piperidin-1-ylmethyl)pyridin-3-yl)benzyl)-1-cyclohexylpyrrolidin-2-one;
3-(2,6-Dichloro-3-(pyridin-4-yl)benzyl)-1-cyclohexylpyrrolidin-2-one hydrochloride;
3-(2,6-Dichloro-3-(pyridin-4-yl)benzyl)-1-cyclohexylpyrrolidin-2-one;
1-Cyclohexyl-3-(2,4-dichloro-4'-hydroxy-biphenyl-3-ylmethyl)-pyrrolidin-2-one;
4-[2',4'-Dichloro-3'-(1-cyclohexyl-2-oxo-pyrrolidin-3-ylmethyl)-biphenyl-4-yloxy]-butyric acid;
3-(3-Bromo-2,4-dichlorobenzyl)-1-cyclohexylpyrrolidin-2-one;
3-(2,4-Dichloro-3-(pyridin-4-yl)benzyl)-1-cyclohexylpyrrolidin-2-one;
3-(2,4-Dichloro-3-(pyridin-3-yl)benzyl)-1-cyclohexylpyrrolidin-2-one;
3-(2-Chloro-4-fluorobenzyl)-1-cyclohexylpyrrolidin-2-one;
3-(3-Chloro-4'-hydroxy-2'-methyl-biphenyl-4-ylmethyl)-1-cyclohexyl-pyrrolidin-2-one;
3-[3-Chloro-4'-(2-dimethylamino-ethoxy)-2'-methyl-biphenyl-4-ylmethyl]-1-cyclohexyl-pyrrolidin-2-one;
3-[3-Chloro-4'-(3-dimethylamino-propoxy)-2'-methyl-biphenyl-4-ylmethyl]-1-cyclohexyl-pyrrolidin-2-one;
3-[3-Chloro-2'-methyl-4'-(2-piperidin-1-yl-ethoxy)-biphenyl-4-ylmethyl]-1-cyclohexyl-pyrrolidin-2-one;
3-[3-Chloro-2'-methyl-4'-(2-piperidin-1-yl-ethoxy)-biphenyl-4-ylmethyl]-1-cyclohexyl-pyrrolidin-2-one;
4-[3'-Chloro-4'-(1-cyclohexyl-2-oxo-pyrrolidin-3-ylmethyl)-2-methyl-biphenyl-4-yloxy]-butyric acid;
3-(2,6-Dichloro-4-methoxybenzyl)-1-cyclohexylpyrrolidin-2-one;
3-(2,4-dichloro-6-methoxybenzyl)-1-cyclohexylpyrrolidin-2-one;
3-(2,6-Dichloro-4-hydroxybenzyl)-1-cyclohexylpyrrolidin-2-one;
3-(2,4-Dichloro-6-hydroxybenzyl)-1-cyclohexylpyrrolidin-2-one;
3-(2,6-Dichloro-4-(prop-2-ynyloxy)benzyl)-1-cyclohexylpyrrolidin-2-one;
3-(2,6-dichloro-4-(pyridin-3-yl)benzyl)-1-cyclohexylpyrrolidin-2-one;
3-(2,6-dichloro-4-(pyridin-4-yl)benzyl)-1-cyclohexylpyrrolidin-2-one;
4-[3',5'-Dichloro-4'-(1-cyclohexyl-2-oxo-pyrrolidin-3-ylmethyl)-biphenyl-4-yloxy]-butyric acid;
1-Cyclohexyl-3-[3,5-dichloro-4'-(3-dimethylamino-propoxy)-biphenyl-4-ylmethyl]-pyrrolidin-2-one;
1-Cyclohexyl-3-[3,5-dichloro-4'-(2-piperidin-1-yl-ethoxy)-biphenyl-4-ylmethyl]-pyrrolidin-2-one;
1-Cyclohexyl-3-[3,5-dichloro-4'-(piperidin-4-ylmethoxy)-biphenyl-4-ylmethyl]-pyrrolidin-2-one;
1-Cyclohexyl-3-[3,5-dichloro-4'-(2-imidazol-1-yl-ethoxy)-biphenyl-4-ylmethyl]-pyrrolidin-2-one;
1-Cyclohexyl-3-[3,5-dichloro-4'-(3-piperidin-1-yl-propoxy)-biphenyl-4-ylmethyl]-pyrrolidin-2-one;
1-Cyclohexyl-3-[3,5-dichloro-4'-(2-morpholin-4-yl-ethoxy)-biphenyl-4-ylmethyl]-pyrrolidin-2-one;
1-Cyclohexyl-3-[3,5-dichloro-2',6'-difluoro-4'-(2-piperidin-1-yl-ethoxy)-biphenyl-4-ylmethyl]-pyrrolidin-2-one;
1-Cyclohexyl-3-[3,5-dichloro-2',6'-difluoro-4'-(2-imidazol-1-yl-ethoxy)-biphenyl-4-ylmethyl]-pyrrolidin-2-one;
3-(4-Amino-2,6-dichlorobenzyl)-1-cyclohexylpyrrolidin-2-one;
3-(3,5-dibromo-2,6-dichloro-4-hydroxybenzyl)-1cyclohexylpyrrolidin-2-one;
3-(2-Chloro-4-(6-methoxypyridin-3-yl)benzyl)-1-cyclohexylpyrrolidin-2-one;
3-(2-Chloro-4-(5-methoxypyridin-3-yl)benzyl)-1-cyclohexylpyrrolidin-2-one;
3-(2-Chloro-4-cyclohexylbenzyl)-1-cyclohexylpyrrolidin-2-one;
3-Chloro-4-((1-cyclohexyl-2-oxopyrrolidin-3-yl)methyl)benzonitrile;
3-(4-Benzoyl-2-chlorobenzyl)-1-cyclohexylpyrrolidin-2-one;
3-(3-Amino-2,6-dichlorobenzyl)-1-cyclohexylpyrrolidin-2-one;
3-(3-Amino-4-bromo-2,6-dichlorobenzyl)-1-cyclohexylpyrrolidin-2-one;
2-[3',5'-Dichloro-4'-(1-cyclohexyl-2-oxo-pyrrolidin-3-ylmethyl)-biphenyl-4-yloxy]-2-methyl-propionic acid ethyl ester;
2-[3',5'-Dichloro-4'-(1-cyclohexyl-2-oxo-pyrrolidin-3-ylmethyl)-biphenyl-4-yloxy]-2-methyl-propionic acid;
[3',5'-Dichloro-4'-(1-cyclohexyl-2-oxo-pyrrolidin-3-ylmethyl)-biphenyl-4-yloxy]-acetic acid ethyl ester;
[3',5'-Dichloro-4'-(1-cyclohexyl-2-oxo-pyrrolidin-3-ylmethyl)-biphenyl-4-yloxy]-acetic acid;
3-[3',5'-Dichloro-4'-(1-cyclohexyl-2-oxo-pyrrolidin-3-ylmethyl)-biphenyl-4-yloxy]-propionic acid;
3-[3',5'-Dichloro-4'-(1-cyclohexyl-2-oxo-pyrrolidin-3-ylmethyl)-biphenyl-4-yl]-propionic acid;
3,5-Dichloro-4-(1-cyclohexyl-2-oxo-pyrrolidin-3-ylmethyl)-benzoic acid methyl ester;
3-Chloro-N-[3,5-dichloro-4-(1-cyclohexyl-2-oxo-pyrrolidin-3-ylmethyl)-phenyl]-2-methyl-benzenesulfonamide;
3-Chloro-N-[2,4-dichloro-3-(1-cyclohexyl-2-oxo-pyrrolidin-3-ylmethyl)-phenyl]-2-methyl-benzenesulfonamide;
3-[1-(2-Chloro-4-pyridin-3-yl-phenyl)-ethyl]-1-cyclohexyl-pyrrolidin-2-one;
3-Chloro-4-(1-cyclohexyl-2-oxo-pyrrolidin-3-ylmethyl)-benzoic acid methyl ester;
3-(2-Chloro-4-phenoxy-benzyl)-1-cyclohexyl-pyrrolidin-2-one;
3-[2-Chloro-4-(3-hydroxy-pyrrolidin-1-yl)-benzyl]-1-cyclohexyl-pyrrolidin-2-one;
3-(2-Chloro-4-piperidin-1-yl-benzyl)-1-cyclohexyl-pyrrolidin-2-one;
3-[2-Chloro-4-(4-methyl-piperazin-1-yl)-benzyl]-1-cyclohexyl-pyrrolidin-2-one;
3-(2-Chloro-4-morpholin-4-yl-benzyl)-1-cyclohexyl-pyrrolidin-2-one;
3-(2-Chloro-4-phenylamino-benzyl)-1-cyclohexyl-pyrrolidin-2-one;
3,5-dichloro-4-((1-cyclohexyl-2-oxopyrrolidin-3-yl)methyl)phenyl trifluoromethanesulfonate;
2',4'-Dichloro-3'-(1-cyclohexyl-2-oxo-pyrrolidin-3-ylmethyl)-biphenyl-3-carboxylic acid;
1-Cyclohexyl-3-[2,4-dichloro-4'-(3-dimethylamino-propoxy)-biphenyl-3-ylmethyl]-pyrrolidin-2-one;

3-(4-bromo-2,6-dichloro-3-hydroxybenzyl)-1-cyclohexylpyrrolidin-2-one;

3-(2,6-Dichloro-3-hydroxy-4-iodobenzyl)-1-cyclohexylpyrrolidin-2-one

3',5'-Dichloro-4'-(1-cyclohexyl-2-oxo-pyrrolidin-3-ylmethyl)-biphenyl-4-carboxylic acid;

5-[3,5-Dichloro-4-(1-cyclohexyl-2-oxo-pyrrolidin-3-ylmethyl)-phenyl]-thiophene-2-carboxylic acid methyl ester;

5-[3,5-Dichloro-4-(1-cyclohexyl-2-oxo-pyrrolidin-3-ylmethyl)-phenyl]-thiophene-2-carboxylic acid;

N-(3,5-dichloro-4-((1-cyclohexyl-2-oxopyrrolidin-3-yl)methyl)phenyl)methanesulfonamide;

N-(3,5-dichloro-4-((1-cyclohexyl-2-oxopyrrolidin-3-yl)methyl)phenyl)benzenesulfonamide;

1-Cyclohexyl-3-[2,6-dichloro-4-(1-methyl-1H-pyrazol-4-yl)-benzyl]-pyrrolidin-2-one;

1-Cyclohexyl-3-[2,6-dichloro-4-(1-isobutyl-1H-pyrazol-4-yl)-benzyl]-pyrrolidin-2-one;

1-Cyclohexyl-3-[2,6-dichloro-4-(1H-pyrazol-4-yl)-benzyl]-pyrrolidin-2-one;

1-Cyclohexyl-3-(2,6-dichloro-4-thiophen-3-yl-benzyl)-pyrrolidin-2-one; and

3',5'-Dichloro-4'-(1-cyclohexyl-2-oxo-pyrrolidin-3-ylmethyl)-4-fluoro-biphenyl-3-carbonitrile, or a pharmaceutically acceptable salt thereof.

7. A pharmaceutical composition which comprises a compound of claim 6 and a pharmaceutically acceptable carrier.

\* \* \* \* \*